(12) United States Patent
Chien et al.

(10) Patent No.: US 7,270,987 B1
(45) Date of Patent: Sep. 18, 2007

(54) CRYSTALLIZATION OF FMS-LIKE TYROSINE KINASE 3

(75) Inventors: Ellen Chien, La Jolla, CA (US); Ciaran N. Cronin, San Diego, CA (US); Douglas R. Dougan, Calgary (CA); Kheng Lim, San Diego, CA (US); Clifford D. Mol, San Diego, CA (US); Bi Ching Sang, San Diego, CA (US); Garret Textor, San Diego, CA (US)

(73) Assignee: Takeda San Diego, Inc., San Diego, CA (US)

( * ) Notice: Subject to any disclaimer, the term of this patent is extended or adjusted under 35 U.S.C. 154(b) by 361 days.

(21) Appl. No.: 11/000,639

(22) Filed: Nov. 30, 2004

(51) Int. Cl.
*C12N 9/00* (2006.01)
*G01N 31/00* (2006.01)

(52) U.S. Cl. .......................................... 435/183; 436/4
(58) Field of Classification Search ................. 435/183
See application file for complete search history.

(56) References Cited

U.S. PATENT DOCUMENTS

2005/0181975 A1* 8/2005 Griffith et al. ................. 514/2

OTHER PUBLICATIONS

Griffith et al. The Structural Basis for Autoinhibition of FLT3 by the Juxtamembrane Domain. Molecular Cell. Jan. 2004, vol. 13, pp. 169-178.*

* cited by examiner

*Primary Examiner*—Kathleen Kerr Bragdon
*Assistant Examiner*—Suzanne M. Noakes
(74) *Attorney, Agent, or Firm*—David J. Weitz

(57) ABSTRACT

Provided are crystals and structure coordinates relating to FMS-like tyrosine kinase 3 and its various uses.

10 Claims, 100 Drawing Sheets

FIGURE 1A

SEQ ID NO:1 Amino acid sequence for full-length human wild type FLT3

(Residues 564-713 and 778-954 are underlined)

```
  1 MPALARDAGT VPLLVVFSAM IFGTITNQDL PVIKCVLINH KNNDSSVGKS
 51 SSYPMVSESP EDLGCALRPQ SSGTVYEAAA VEVDVSASIT LQVLVDAPGN
101 ISCLWVFKHS SLNCQPHFDL QNRGVVSMVI LKMTETQAGE YLLFIQSEAT
151 NYTILFTVSI RNTLLYTLRR PYFRKMENQD ALVCISESVP EPIVEWVLCD
201 SQGESCKEES PAVVKKEEKV LHELFGTDIR CCARNELGRE CTRLFTIDLN
251 QTPQTTLPQL FLKVGEPLWI RCKAVHVNHG FGLTWELENK ALEEGNYFEM
301 STYSTNRTMI RILFAFVSSV ARNDTGYYTC SSSKHPSQSA LVTIVGKGFI
351 NATNSSEDYE IDQYEEFCFS VRFKAYPQIR CTWTFSRKSF PCEQKGLDNG
401 YSISKFCNHK HQPGEYIFHA ENDDAQFTKM FTLNIRRKPQ VLAEASASQA
451 SCFSDGYPLP SWTWKKCSDK SPNCTEEITE GVWNRKANRK VFGQWVSSST
501 LNMSEAIKGF LVKCCAYNSL GTSCETILLN SPGPFPFIQD NISFYATIGV
551 CLLFIVVLTL LICHKYKKQF RYESQLQMVQ VTGSSDNEYF YVDFREYEYD
601 LKWEFPRENL EFGKVLGSGA FGKVMNATAY GISKTGVSIQ VAVKMLKEKA
651 DSSEREALMS ELKMMTQLGS HENIVNLLGA CTLSGPIYLI FEYCCYGDLL
701 NYLRSKREKF HRTWTEIFKE HNFSFYPTFQ SHPNSSMPGS REVQIHPDSD
751 QISGLHGNSF HSEDEIEYEN QKRLEEEEDL NVLTFEDLLC FAYQVAKGME
801 FLEFKSCVHR DLAARNVLVT HGKVVKICDF GLARDIMSDS NYVVRGNARL
851 PVKWMAPESL FEGIYTIKSD VWSYGILLWE IFSLGVNPYP GIPVDANFYK
901 LIQNGFKMDQ PFYATEEIYI IMQSCWAFDS RKRPSFPNLT SFLGCQLADA
951 EEAMYQNVDG RVSECPHTYQ NRRPFSREMD LGLLSPQAQV EDS
```

SEQ ID NO: 2 Human cDNA sequence encoding of residues 564-713, and 778-954 of FLT3

```
  1 CACAAGTACA AAAAGCAATT TAGGTATGAA AGCCAGCTAC AGATGGTACA GGTGACCGGC
 61 TCCTCAGATA ATGAGTACTT CTACGTTGAT TTCAGAGAAT ATGAATATGA TCTCAAATGG
121 GAGTTTCCAA GAGAAAATTT AGAGTTTGGG AAGGTACTAG GATCAGGTGC TTTTGGAAAA
181 GTGATGAACG CAACAGCTTA TGGAATTAGC AAAACAGGAG TCTCAATCCA GGTTGCCGTC
241 AAAATGCTGA AGAAAAAGC AGACAGCTCT GAAAGAGAGG CACTCATGTC AGAACTCAAG
301 ATGATGACCC AGCTGGGAAG CCACGAGAAT ATTGTGAACC TGCTGGGGGC GTGCACACTG
361 TCAGGACCAA TTTACTTGAT TTTTGAATAC TGTTGCTATG GTGATCTTCT CAACTATCTA
421 AGAAGTAAAA GAGAAAAATT TCACAGGACT GCTAGCGAGG ACTTGAATGT GCTTACATTT
481 GAAGATCTTC TTTGCTTTGC ATATCAAGTT GCCAAAGGAA TGGAATTTCT GGAATTTAAG
541 TCGTGTGTTC ACAGAGACCT GGCCGCCAGG AACGTGCTTG TCACCCACGG GAAAGTGGTG
601 AAGATATGTG ACTTTGGATT GGCTCGAGAT ATCATGAGTG ATTCCAACTA TGTTGTCAGG
661 GGCAATGCCC GTCTGCCTGT AAAATGGATG GCCCCCGAAA GCCTGTTTGA AGGCATCTAC
721 ACCATTAAGA GTGATGTCTG GTCATATGGA ATATTACTGT GGGAAATCTT CTCACTTGGT
781 GTGAATCCTT ACCCTGGCAT TCCGGTTGAT GCTAACTTCT ACAAACTGAT TCAAAATGGA
841 TTTAAAATGG ATCAGCCATT TTATGCTACA GAAGAAATAT ACATTATAAT GCAATCCTGC
901 TGGGCTTTTG ACTCAAGGAA ACGGCCATCC TTCCCTAATT TGACTTCGTT TTTAGGATGT
961 CAGCTGGCAG ATGCAGAAGA AGCGATG
```

FIGURE 1B

SEQ ID NO:3 Amino acid sequence for residues 564-713, and 778-954 of FLT3 with a N-terminal 6x-histidine tag, spacer region and rTEV cleavage site (6x-histidine tag, spacer region, and rTEV cleavage site, Tyr to Phe mutations and Ala-Ser dipeptide inserted in place of the Kinase Insertion Domain (KID; residues 714-777) are underlined)

```
  1 MSYYHHHHHH DYDIPTTENLY FQGAMEPGGS HKYKKQFRYE SQLQMVQVTGS
 51 SDNEFFFVDF REYEYDLKWEF PRENLEFGKV LGSGAFGKVM NATAYGISKTG
101 VSIQVAVKML KEKADSSEREA LMSELKMMTQ LGSHENIVNL LGACTLSGPIY
151 LIFEYCCYGD LLNYLRSKREK FHRTASEDLN VLTFEDLLCF AYQVAKGMEFL
201 EFKSCVHRDL AARNVLVTHGK VVKICDFGLA RDIMSDSNYV VRGNARLPVKW
251 MAPESLFEGI YTIKSDVWSYG ILLWEIFSLG VNPYPGIPVD ANFYKLIQNGF
301 KMDQPFYATE EIYIIMQSCWA FDSRKRPSFP NLTSFLGCQL ADAEEAM
```

FIGURE 3AA

LEGEND

Column headings from left to right are (A)'Atom Number', (B)'Atom Type', (C)'Amino Acid', (D)'Chain Identifier', (E)'Amino Acid Number', (F)'X Coordinate', (G)'Y Coordinate', (H)'Z Coordinate', (I)'Occupancy' (OCC) and (J)'B factor'.

FLT3 Coordinates corresponding to [SEQ. ID No. 3]

Molecule A

|      | A | B | C | D | E | F | G | H | I | J |
|------|---|---|---|---|---|---|---|---|---|---|
| ATOM | 1  | C   | TYR | A | 599 | 88.358 | 32.530 | -18.838 | 1.00 | 33.83 |
| ATOM | 2  | N   | TYR | A | 599 | 87.248 | 30.431 | -19.489 | 1.00 | 33.78 |
| ATOM | 3  | O   | TYR | A | 599 | 88.580 | 33.022 | -19.947 | 1.00 | 33.96 |
| ATOM | 4  | CA  | TYR | A | 599 | 88.268 | 31.022 | -18.630 | 1.00 | 33.53 |
| ATOM | 5  | CB  | TYR | A | 599 | 89.629 | 30.372 | -18.891 | 1.00 | 33.32 |
| ATOM | 6  | CD1 | TYR | A | 599 | 91.840 | 31.570 | -19.105 | 1.00 | 32.65 |
| ATOM | 7  | CD2 | TYR | A | 599 | 90.845 | 31.416 | -16.942 | 1.00 | 32.90 |
| ATOM | 8  | CE1 | TYR | A | 599 | 92.908 | 32.266 | -18.574 | 1.00 | 32.26 |
| ATOM | 9  | CE2 | TYR | A | 599 | 91.905 | 32.112 | -16.393 | 1.00 | 31.73 |
| ATOM | 10 | CG  | TYR | A | 599 | 90.794 | 31.135 | -18.301 | 1.00 | 33.10 |
| ATOM | 11 | OH  | TYR | A | 599 | 93.996 | 33.229 | -16.675 | 1.00 | 31.88 |
| ATOM | 12 | CZ  | TYR | A | 599 | 92.935 | 32.536 | -17.211 | 1.00 | 32.17 |
| ATOM | 13 | N   | ASP | A | 600 | 88.202 | 33.276 | -17.735 | 1.00 | 33.77 |
| ATOM | 14 | CA  | ASP | A | 600 | 88.269 | 34.735 | -17.752 | 1.00 | 32.87 |
| ATOM | 15 | CB  | ASP | A | 600 | 87.595 | 35.310 | -16.503 | 1.00 | 33.31 |
| ATOM | 16 | CG  | ASP | A | 600 | 86.925 | 36.650 | -16.760 | 1.00 | 32.94 |
| ATOM | 17 | OD1 | ASP | A | 600 | 87.631 | 37.622 | -17.113 | 1.00 | 31.94 |
| ATOM | 18 | OD2 | ASP | A | 600 | 85.696 | 36.824 | -16.622 | 1.00 | 33.13 |
| ATOM | 19 | C   | ASP | A | 600 | 89.711 | 35.229 | -17.839 | 1.00 | 32.31 |
| ATOM | 20 | O   | ASP | A | 600 | 90.608 | 34.685 | -17.190 | 1.00 | 32.34 |
| ATOM | 21 | N   | LEU | A | 601 | 89.917 | 36.269 | -18.641 | 1.00 | 31.24 |
| ATOM | 22 | CA  | LEU | A | 601 | 91.236 | 36.872 | -18.824 | 1.00 | 30.32 |
| ATOM | 23 | CB  | LEU | A | 601 | 91.280 | 37.675 | -20.128 | 1.00 | 30.79 |
| ATOM | 24 | CG  | LEU | A | 601 | 91.642 | 36.906 | -21.398 | 1.00 | 31.53 |
| ATOM | 25 | CD1 | LEU | A | 601 | 90.383 | 36.412 | -22.102 | 1.00 | 32.23 |
| ATOM | 26 | CD2 | LEU | A | 601 | 92.481 | 37.776 | -22.332 | 1.00 | 32.40 |
| ATOM | 27 | C   | LEU | A | 601 | 91.627 | 37.767 | -17.650 | 1.00 | 28.67 |
| ATOM | 28 | O   | LEU | A | 601 | 92.810 | 38.054 | -17.454 | 1.00 | 27.84 |
| ATOM | 29 | N   | LYS | A | 602 | 90.633 | 38.202 | -16.875 | 1.00 | 27.06 |
| ATOM | 30 | CA  | LYS | A | 602 | 90.868 | 39.061 | -15.714 | 1.00 | 25.85 |
| ATOM | 31 | CB  | LYS | A | 602 | 89.538 | 39.515 | -15.094 | 1.00 | 27.16 |
| ATOM | 32 | CG  | LYS | A | 602 | 88.849 | 38.474 | -14.213 | 1.00 | 28.93 |
| ATOM | 33 | CD  | LYS | A | 602 | 87.406 | 38.857 | -13.922 | 1.00 | 30.45 |
| ATOM | 34 | CE  | LYS | A | 602 | 87.100 | 38.764 | -12.436 | 1.00 | 31.23 |
| ATOM | 35 | NZ  | LYS | A | 602 | 85.994 | 37.806 | -12.153 | 1.00 | 31.90 |
| ATOM | 36 | C   | LYS | A | 602 | 91.750 | 38.374 | -14.668 | 1.00 | 23.85 |
| ATOM | 37 | O   | LYS | A | 602 | 92.263 | 39.023 | -13.760 | 1.00 | 25.06 |
| ATOM | 38 | N   | TRP | A | 603 | 91.921 | 37.062 | -14.824 | 1.00 | 20.75 |

FIGURE 3AB

|  | A | B | C | D | E | F | G | H | I | J |
|---|---|---|---|---|---|---|---|---|---|---|
| ATOM | 39 | CA | TRP | A | 603 | 92.703 | 36.237 | -13.913 | 1.00 | 17.89 |
| ATOM | 40 | CB | TRP | A | 603 | 92.093 | 34.836 | -13.821 | 1.00 | 16.20 |
| ATOM | 41 | CG | TRP | A | 603 | 90.883 | 34.794 | -12.964 | 1.00 | 14.18 |
| ATOM | 42 | CD1 | TRP | A | 603 | 89.594 | 34.673 | -13.379 | 1.00 | 14.05 |
| ATOM | 43 | NE1 | TRP | A | 603 | 88.743 | 34.686 | -12.300 | 1.00 | 14.10 |
| ATOM | 44 | CE2 | TRP | A | 603 | 89.481 | 34.826 | -11.155 | 1.00 | 14.69 |
| ATOM | 45 | CD2 | TRP | A | 603 | 90.839 | 34.898 | -11.539 | 1.00 | 14.50 |
| ATOM | 46 | CE3 | TRP | A | 603 | 91.811 | 35.044 | -10.540 | 1.00 | 14.20 |
| ATOM | 47 | CZ3 | TRP | A | 603 | 91.402 | 35.110 | -9.209 | 1.00 | 15.44 |
| ATOM | 48 | CH2 | TRP | A | 603 | 90.043 | 35.029 | -8.863 | 1.00 | 15.65 |
| ATOM | 49 | CZ2 | TRP | A | 603 | 89.070 | 34.889 | -9.820 | 1.00 | 15.71 |
| ATOM | 50 | C | TRP | A | 603 | 94.157 | 36.116 | -14.330 | 1.00 | 17.90 |
| ATOM | 51 | O | TRP | A | 603 | 95.001 | 35.718 | -13.526 | 1.00 | 17.63 |
| ATOM | 52 | N | GLU | A | 604 | 94.442 | 36.452 | -15.585 | 1.00 | 18.40 |
| ATOM | 53 | CA | GLU | A | 604 | 95.781 | 36.306 | -16.146 | 1.00 | 19.51 |
| ATOM | 54 | CB | GLU | A | 604 | 95.767 | 36.540 | -17.670 | 1.00 | 20.15 |
| ATOM | 55 | CG | GLU | A | 604 | 96.949 | 35.935 | -18.427 | 1.00 | 20.71 |
| ATOM | 56 | CD | GLU | A | 604 | 96.951 | 34.395 | -18.447 | 1.00 | 21.25 |
| ATOM | 57 | OE1 | GLU | A | 604 | 98.035 | 33.816 | -18.684 | 1.00 | 21.65 |
| ATOM | 58 | OE2 | GLU | A | 604 | 95.886 | 33.757 | -18.230 | 1.00 | 21.12 |
| ATOM | 59 | C | GLU | A | 604 | 96.791 | 37.225 | -15.454 | 1.00 | 19.30 |
| ATOM | 60 | O | GLU | A | 604 | 96.573 | 38.431 | -15.324 | 1.00 | 18.65 |
| ATOM | 61 | N | PHE | A | 605 | 97.888 | 36.620 | -15.009 | 1.00 | 20.72 |
| ATOM | 62 | CA | PHE | A | 605 | 98.979 | 37.310 | -14.298 | 1.00 | 22.73 |
| ATOM | 63 | CB | PHE | A | 605 | 99.070 | 36.756 | -12.837 | 1.00 | 25.36 |
| ATOM | 64 | CG | PHE | A | 605 | 100.077 | 37.484 | -11.936 | 1.00 | 28.67 |
| ATOM | 65 | CD1 | PHE | A | 605 | 101.329 | 36.929 | -11.670 | 1.00 | 29.86 |
| ATOM | 66 | CE1 | PHE | A | 605 | 102.260 | 37.591 | -10.845 | 1.00 | 32.45 |
| ATOM | 67 | CZ | PHE | A | 605 | 101.932 | 38.819 | -10.254 | 1.00 | 33.96 |
| ATOM | 68 | CE2 | PHE | A | 605 | 100.679 | 39.379 | -10.496 | 1.00 | 32.68 |
| ATOM | 69 | CD2 | PHE | A | 605 | 99.759 | 38.707 | -11.326 | 1.00 | 30.57 |
| ATOM | 70 | C | PHE | A | 605 | 100.260 | 37.024 | -15.081 | 1.00 | 21.70 |
| ATOM | 71 | O | PHE | A | 605 | 100.518 | 35.865 | -15.415 | 1.00 | 20.71 |
| ATOM | 72 | N | PRO | A | 606 | 101.043 | 38.058 | -15.405 | 1.00 | 21.59 |
| ATOM | 73 | CA | PRO | A | 606 | 102.251 | 37.865 | -16.226 | 1.00 | 22.40 |
| ATOM | 74 | CB | PRO | A | 606 | 102.765 | 39.297 | -16.454 | 1.00 | 21.72 |
| ATOM | 75 | CG | PRO | A | 606 | 101.586 | 40.179 | -16.157 | 1.00 | 21.67 |
| ATOM | 76 | CD | PRO | A | 606 | 100.852 | 39.472 | -15.033 | 1.00 | 21.50 |
| ATOM | 77 | C | PRO | A | 606 | 103.268 | 37.024 | -15.460 | 1.00 | 23.20 |
| ATOM | 78 | O | PRO | A | 606 | 103.507 | 37.307 | -14.266 | 1.00 | 24.04 |
| ATOM | 79 | N | ARG | A | 607 | 103.833 | 36.000 | -16.119 | 1.00 | 23.01 |
| ATOM | 80 | CA | ARG | A | 607 | 104.771 | 35.085 | -15.455 | 1.00 | 23.07 |
| ATOM | 81 | CB | ARG | A | 607 | 104.935 | 33.763 | -16.227 | 1.00 | 22.09 |
| ATOM | 82 | CG | ARG | A | 607 | 105.356 | 33.886 | -17.687 | 1.00 | 21.11 |
| ATOM | 83 | CD | ARG | A | 607 | 105.375 | 32.556 | -18.438 | 1.00 | 20.17 |
| ATOM | 84 | NE | ARG | A | 607 | 104.028 | 32.021 | -18.638 | 1.00 | 20.03 |
| ATOM | 85 | CZ | ARG | A | 607 | 103.571 | 30.891 | -18.103 | 1.00 | 18.82 |
| ATOM | 86 | NH1 | ARG | A | 607 | 102.330 | 30.500 | -18.351 | 1.00 | 18.00 |
| ATOM | 87 | NH2 | ARG | A | 607 | 104.349 | 30.145 | -17.330 | 1.00 | 18.50 |
| ATOM | 88 | C | ARG | A | 607 | 106.135 | 35.719 | -15.149 | 1.00 | 24.05 |
| ATOM | 89 | O | ARG | A | 607 | 106.890 | 35.207 | -14.317 | 1.00 | 24.61 |
| ATOM | 90 | N | GLU | A | 608 | 106.433 | 36.838 | -15.811 | 1.00 | 23.52 |

FIGURE 3AC

| | A | B | C | D | E | F | G | H | I | J |
|---|---|---|---|---|---|---|---|---|---|---|
| ATOM | 91 | CA | GLU | A | 608 | 107.637 | 37.609 | -15.523 | 1.00 | 24.20 |
| ATOM | 92 | CB | GLU | A | 608 | 107.993 | 38.507 | -16.704 | 1.00 | 25.79 |
| ATOM | 93 | CG | GLU | A | 608 | 109.408 | 38.286 | -17.210 | 1.00 | 28.94 |
| ATOM | 94 | CD | GLU | A | 608 | 109.488 | 37.256 | -18.326 | 1.00 | 30.29 |
| ATOM | 95 | OE1 | GLU | A | 608 | 110.129 | 37.560 | -19.363 | 1.00 | 30.35 |
| ATOM | 96 | OE2 | GLU | A | 608 | 108.921 | 36.148 | -18.169 | 1.00 | 30.49 |
| ATOM | 97 | C | GLU | A | 608 | 107.500 | 38.437 | -14.242 | 1.00 | 22.90 |
| ATOM | 98 | O | GLU | A | 608 | 108.493 | 38.954 | -13.714 | 1.00 | 23.33 |
| ATOM | 99 | N | ASN | A | 609 | 106.265 | 38.550 | -13.750 | 1.00 | 20.69 |
| ATOM | 100 | CA | ASN | A | 609 | 105.976 | 39.234 | -12.486 | 1.00 | 18.13 |
| ATOM | 101 | CB | ASN | A | 609 | 104.651 | 40.010 | -12.584 | 1.00 | 15.65 |
| ATOM | 102 | CG | ASN | A | 609 | 104.785 | 41.289 | -13.434 | 1.00 | 15.44 |
| ATOM | 103 | OD1 | ASN | A | 609 | 105.792 | 41.501 | -14.115 | 1.00 | 12.68 |
| ATOM | 104 | ND2 | ASN | A | 609 | 103.767 | 42.143 | -13.389 | 1.00 | 16.48 |
| ATOM | 105 | C | ASN | A | 609 | 106.018 | 38.312 | -11.261 | 1.00 | 17.10 |
| ATOM | 106 | O | ASN | A | 609 | 105.628 | 38.707 | -10.145 | 1.00 | 18.14 |
| ATOM | 107 | N | LEU | A | 610 | 106.524 | 37.086 | -11.485 | 1.00 | 14.97 |
| ATOM | 108 | CA | LEU | A | 610 | 106.811 | 36.148 | -10.410 | 1.00 | 14.34 |
| ATOM | 109 | CB | LEU | A | 610 | 106.159 | 34.793 | -10.698 | 1.00 | 13.69 |
| ATOM | 110 | CG | LEU | A | 610 | 104.630 | 34.694 | -10.734 | 1.00 | 12.92 |
| ATOM | 111 | CD1 | LEU | A | 610 | 104.216 | 33.338 | -11.291 | 1.00 | 12.89 |
| ATOM | 112 | CD2 | LEU | A | 610 | 104.009 | 34.925 | -9.360 | 1.00 | 11.02 |
| ATOM | 113 | C | LEU | A | 610 | 108.313 | 35.951 | -10.198 | 1.00 | 16.28 |
| ATOM | 114 | O | LEU | A | 610 | 109.043 | 35.598 | -11.128 | 1.00 | 17.43 |
| ATOM | 115 | N | GLU | A | 611 | 108.772 | 36.199 | -8.974 | 1.00 | 18.38 |
| ATOM | 116 | CA | GLU | A | 611 | 110.121 | 35.813 | -8.562 | 1.00 | 19.63 |
| ATOM | 117 | CB | GLU | A | 611 | 110.837 | 36.936 | -7.794 | 1.00 | 20.62 |
| ATOM | 118 | CG | GLU | A | 611 | 110.865 | 38.290 | -8.494 | 1.00 | 23.05 |
| ATOM | 119 | CD | GLU | A | 611 | 111.822 | 38.334 | -9.674 | 1.00 | 24.70 |
| ATOM | 120 | OE1 | GLU | A | 611 | 111.357 | 38.536 | -10.819 | 1.00 | 25.40 |
| ATOM | 121 | OE2 | GLU | A | 611 | 113.042 | 38.171 | -9.458 | 1.00 | 26.01 |
| ATOM | 122 | C | GLU | A | 611 | 109.990 | 34.564 | -7.695 | 1.00 | 19.11 |
| ATOM | 123 | O | GLU | A | 611 | 109.420 | 34.612 | -6.605 | 1.00 | 18.88 |
| ATOM | 124 | N | PHE | A | 612 | 110.513 | 33.448 | -8.187 | 1.00 | 18.37 |
| ATOM | 125 | CA | PHE | A | 612 | 110.364 | 32.172 | -7.503 | 1.00 | 18.73 |
| ATOM | 126 | CB | PHE | A | 612 | 110.459 | 31.014 | -8.498 | 1.00 | 17.92 |
| ATOM | 127 | CG | PHE | A | 612 | 109.223 | 30.841 | -9.325 | 1.00 | 18.17 |
| ATOM | 128 | CD1 | PHE | A | 612 | 109.179 | 31.305 | -10.637 | 1.00 | 17.29 |
| ATOM | 129 | CE1 | PHE | A | 612 | 108.031 | 31.157 | -11.407 | 1.00 | 17.53 |
| ATOM | 130 | CZ | PHE | A | 612 | 106.902 | 30.543 | -10.854 | 1.00 | 19.12 |
| ATOM | 131 | CE2 | PHE | A | 612 | 106.932 | 30.081 | -9.538 | 1.00 | 17.43 |
| ATOM | 132 | CD2 | PHE | A | 612 | 108.088 | 30.236 | -8.781 | 1.00 | 17.38 |
| ATOM | 133 | C | PHE | A | 612 | 111.333 | 31.985 | -6.343 | 1.00 | 19.52 |
| ATOM | 134 | O | PHE | A | 612 | 112.547 | 32.089 | -6.507 | 1.00 | 20.49 |
| ATOM | 135 | N | GLY | A | 613 | 110.767 | 31.718 | -5.170 | 1.00 | 20.68 |
| ATOM | 136 | CA | GLY | A | 613 | 111.530 | 31.446 | -3.968 | 1.00 | 21.67 |
| ATOM | 137 | C | GLY | A | 613 | 111.670 | 29.956 | -3.743 | 1.00 | 22.26 |
| ATOM | 138 | O | GLY | A | 613 | 111.985 | 29.215 | -4.670 | 1.00 | 22.43 |
| ATOM | 139 | N | LYS | A | 614 | 111.427 | 29.519 | -2.512 | 1.00 | 23.20 |
| ATOM | 140 | CA | LYS | A | 614 | 111.608 | 28.118 | -2.139 | 1.00 | 24.89 |
| ATOM | 141 | CB | LYS | A | 614 | 111.782 | 27.985 | -0.616 | 1.00 | 27.40 |
| ATOM | 142 | CG | LYS | A | 614 | 110.596 | 28.478 | 0.222 | 1.00 | 30.09 |

FIGURE 3AD

|   | A | B | C | D | E | F | G | H | I | J |
|---|---|---|---|---|---|---|---|---|---|---|
| ATOM | 143 | CD | LYS | A | 614 | 110.946 | 28.558 | 1.710 | 1.00 | 31.84 |
| ATOM | 144 | CE | LYS | A | 614 | 110.115 | 29.624 | 2.428 | 1.00 | 33.10 |
| ATOM | 145 | NZ | LYS | A | 614 | 108.918 | 29.047 | 3.124 | 1.00 | 34.53 |
| ATOM | 146 | C | LYS | A | 614 | 110.480 | 27.203 | -2.637 | 1.00 | 24.29 |
| ATOM | 147 | O | LYS | A | 614 | 109.353 | 27.654 | -2.882 | 1.00 | 23.83 |
| ATOM | 148 | N | VAL | A | 615 | 110.806 | 25.921 | -2.796 | 1.00 | 22.73 |
| ATOM | 149 | CA | VAL | A | 615 | 109.811 | 24.879 | -3.041 | 1.00 | 21.68 |
| ATOM | 150 | CB | VAL | A | 615 | 110.473 | 23.557 | -3.526 | 1.00 | 21.85 |
| ATOM | 151 | CG1 | VAL | A | 615 | 109.425 | 22.494 | -3.840 | 1.00 | 21.35 |
| ATOM | 152 | CG2 | VAL | A | 615 | 111.368 | 23.803 | -4.744 | 1.00 | 22.20 |
| ATOM | 153 | C | VAL | A | 615 | 109.054 | 24.640 | -1.732 | 1.00 | 21.48 |
| ATOM | 154 | O | VAL | A | 615 | 109.659 | 24.289 | -0.715 | 1.00 | 22.22 |
| ATOM | 155 | N | LEU | A | 616 | 107.741 | 24.848 | -1.752 | 1.00 | 19.64 |
| ATOM | 156 | CA | LEU | A | 616 | 106.933 | 24.742 | -0.536 | 1.00 | 19.81 |
| ATOM | 157 | CB | LEU | A | 616 | 105.704 | 25.668 | -0.597 | 1.00 | 17.56 |
| ATOM | 158 | CG | LEU | A | 616 | 105.924 | 27.184 | -0.508 | 1.00 | 16.65 |
| ATOM | 159 | CD1 | LEU | A | 616 | 104.622 | 27.922 | -0.752 | 1.00 | 16.65 |
| ATOM | 160 | CD2 | LEU | A | 616 | 106.533 | 27.614 | 0.823 | 1.00 | 15.62 |
| ATOM | 161 | C | LEU | A | 616 | 106.509 | 23.304 | -0.248 | 1.00 | 20.45 |
| ATOM | 162 | O | LEU | A | 616 | 106.560 | 22.848 | 0.898 | 1.00 | 20.91 |
| ATOM | 163 | N | GLY | A | 617 | 106.093 | 22.598 | -1.295 | 1.00 | 20.53 |
| ATOM | 164 | CA | GLY | A | 617 | 105.686 | 21.212 | -1.180 | 1.00 | 20.65 |
| ATOM | 165 | C | GLY | A | 617 | 105.662 | 20.551 | -2.539 | 1.00 | 21.13 |
| ATOM | 166 | O | GLY | A | 617 | 105.480 | 21.222 | -3.556 | 1.00 | 20.50 |
| ATOM | 167 | N | SER | A | 618 | 105.852 | 19.235 | -2.553 | 1.00 | 22.62 |
| ATOM | 168 | CA | SER | A | 618 | 105.846 | 18.466 | -3.793 | 1.00 | 24.65 |
| ATOM | 169 | CB | SER | A | 618 | 107.230 | 18.477 | -4.452 | 1.00 | 24.37 |
| ATOM | 170 | OG | SER | A | 618 | 108.217 | 17.946 | -3.585 | 1.00 | 24.90 |
| ATOM | 171 | C | SER | A | 618 | 105.372 | 17.034 | -3.572 | 1.00 | 26.04 |
| ATOM | 172 | O | SER | A | 618 | 105.567 | 16.456 | -2.501 | 1.00 | 27.00 |
| ATOM | 173 | N | GLY | A | 619 | 104.746 | 16.475 | -4.602 | 1.00 | 27.06 |
| ATOM | 174 | CA | GLY | A | 619 | 104.242 | 15.116 | -4.573 | 1.00 | 27.97 |
| ATOM | 175 | C | GLY | A | 619 | 103.742 | 14.720 | -5.946 | 1.00 | 28.90 |
| ATOM | 176 | O | GLY | A | 619 | 103.937 | 15.454 | -6.918 | 1.00 | 29.33 |
| ATOM | 177 | N | ALA | A | 620 | 103.094 | 13.560 | -6.025 | 1.00 | 29.67 |
| ATOM | 178 | CA | ALA | A | 620 | 102.518 | 13.071 | -7.277 | 1.00 | 29.68 |
| ATOM | 179 | CB | ALA | A | 620 | 101.856 | 11.712 | -7.064 | 1.00 | 29.31 |
| ATOM | 180 | C | ALA | A | 620 | 101.525 | 14.074 | -7.879 | 1.00 | 29.74 |
| ATOM | 181 | O | ALA | A | 620 | 101.297 | 14.076 | -9.090 | 1.00 | 30.74 |
| ATOM | 182 | N | PHE | A | 621 | 100.949 | 14.923 | -7.027 | 1.00 | 28.54 |
| ATOM | 183 | CA | PHE | A | 621 | 100.044 | 15.986 | -7.458 | 1.00 | 27.86 |
| ATOM | 184 | CB | PHE | A | 621 | 99.395 | 16.657 | -6.241 | 1.00 | 26.73 |
| ATOM | 185 | CG | PHE | A | 621 | 100.303 | 17.623 | -5.519 | 1.00 | 25.93 |
| ATOM | 186 | CD1 | PHE | A | 621 | 100.356 | 18.963 | -5.894 | 1.00 | 25.71 |
| ATOM | 187 | CE1 | PHE | A | 621 | 101.196 | 19.863 | -5.234 | 1.00 | 24.34 |
| ATOM | 188 | CZ | PHE | A | 621 | 101.996 | 19.422 | -4.190 | 1.00 | 24.35 |
| ATOM | 189 | CE2 | PHE | A | 621 | 101.953 | 18.086 | -3.801 | 1.00 | 24.78 |
| ATOM | 190 | CD2 | PHE | A | 621 | 101.109 | 17.193 | -4.469 | 1.00 | 25.86 |
| ATOM | 191 | C | PHE | A | 621 | 100.759 | 17.046 | -8.298 | 1.00 | 28.02 |
| ATOM | 192 | O | PHE | A | 621 | 100.149 | 17.677 | -9.165 | 1.00 | 29.85 |
| ATOM | 193 | N | GLY | A | 622 | 102.049 | 17.237 | -8.023 | 1.00 | 26.22 |
| ATOM | 194 | CA | GLY | A | 622 | 102.836 | 18.294 | -8.635 | 1.00 | 22.99 |

FIGURE 3AE

| | A | B | C | D | E | F | G | H | I | J |
|---|---|---|---|---|---|---|---|---|---|---|
| ATOM | 195 | C | GLY | A | 622 | 103.715 | 18.991 | -7.614 | 1.00 | 19.86 |
| ATOM | 196 | O | GLY | A | 622 | 104.254 | 18.354 | -6.706 | 1.00 | 18.32 |
| ATOM | 197 | N | LYS | A | 623 | 103.867 | 20.302 | -7.765 | 1.00 | 18.12 |
| ATOM | 198 | CA | LYS | A | 623 | 104.649 | 21.086 | -6.810 | 1.00 | 16.99 |
| ATOM | 199 | CB | LYS | A | 623 | 106.138 | 21.138 | -7.204 | 1.00 | 16.70 |
| ATOM | 200 | CG | LYS | A | 623 | 106.495 | 22.095 | -8.330 | 1.00 | 16.48 |
| ATOM | 201 | CD | LYS | A | 623 | 107.935 | 22.563 | -8.197 | 1.00 | 16.42 |
| ATOM | 202 | CE | LYS | A | 623 | 108.705 | 22.392 | -9.490 | 1.00 | 16.25 |
| ATOM | 203 | NZ | LYS | A | 623 | 110.173 | 22.535 | -9.277 | 1.00 | 16.56 |
| ATOM | 204 | C | LYS | A | 623 | 104.076 | 22.477 | -6.564 | 1.00 | 14.71 |
| ATOM | 205 | O | LYS | A | 623 | 103.407 | 23.054 | -7.424 | 1.00 | 14.16 |
| ATOM | 206 | N | VAL | A | 624 | 104.336 | 22.988 | -5.367 | 1.00 | 13.72 |
| ATOM | 207 | CA | VAL | A | 624 | 103.903 | 24.318 | -4.961 | 1.00 | 13.84 |
| ATOM | 208 | CB | VAL | A | 624 | 102.907 | 24.259 | -3.771 | 1.00 | 13.67 |
| ATOM | 209 | CG1 | VAL | A | 624 | 102.591 | 25.654 | -3.235 | 1.00 | 12.52 |
| ATOM | 210 | CG2 | VAL | A | 624 | 101.625 | 23.537 | -4.187 | 1.00 | 11.38 |
| ATOM | 211 | C | VAL | A | 624 | 105.144 | 25.107 | -4.585 | 1.00 | 14.33 |
| ATOM | 212 | O | VAL | A | 624 | 105.954 | 24.654 | -3.777 | 1.00 | 13.36 |
| ATOM | 213 | N | MET | A | 625 | 105.301 | 26.278 | -5.193 | 1.00 | 16.27 |
| ATOM | 214 | CA | MET | A | 625 | 106.477 | 27.109 | -4.950 | 1.00 | 17.62 |
| ATOM | 215 | CB | MET | A | 625 | 107.250 | 27.354 | -6.245 | 1.00 | 18.54 |
| ATOM | 216 | CG | MET | A | 625 | 107.593 | 26.097 | -7.001 | 1.00 | 21.18 |
| ATOM | 217 | SD | MET | A | 625 | 109.349 | 25.891 | -7.175 | 1.00 | 27.00 |
| ATOM | 218 | CE | MET | A | 625 | 109.531 | 25.976 | -8.954 | 1.00 | 26.19 |
| ATOM | 219 | C | MET | A | 625 | 106.092 | 28.438 | -4.335 | 1.00 | 17.49 |
| ATOM | 220 | O | MET | A | 625 | 105.048 | 29.008 | -4.658 | 1.00 | 17.55 |
| ATOM | 221 | N | ASN | A | 626 | 106.935 | 28.921 | -3.431 | 1.00 | 17.33 |
| ATOM | 222 | CA | ASN | A | 626 | 106.802 | 30.276 | -2.939 | 1.00 | 16.56 |
| ATOM | 223 | CB | ASN | A | 626 | 107.594 | 30.462 | -1.650 | 1.00 | 17.73 |
| ATOM | 224 | CG | ASN | A | 626 | 107.678 | 31.909 | -1.228 | 1.00 | 17.85 |
| ATOM | 225 | OD1 | ASN | A | 626 | 108.705 | 32.566 | -1.426 | 1.00 | 19.73 |
| ATOM | 226 | ND2 | ASN | A | 626 | 106.593 | 32.425 | -0.661 | 1.00 | 16.70 |
| ATOM | 227 | C | ASN | A | 626 | 107.304 | 31.236 | -4.009 | 1.00 | 16.17 |
| ATOM | 228 | O | ASN | A | 626 | 108.264 | 30.936 | -4.729 | 1.00 | 13.77 |
| ATOM | 229 | N | ALA | A | 627 | 106.638 | 32.379 | -4.121 | 1.00 | 14.42 |
| ATOM | 230 | CA | ALA | A | 627 | 107.047 | 33.405 | -5.062 | 1.00 | 13.69 |
| ATOM | 231 | CB | ALA | A | 627 | 106.477 | 33.117 | -6.456 | 1.00 | 12.11 |
| ATOM | 232 | C | ALA | A | 627 | 106.623 | 34.784 | -4.581 | 1.00 | 12.97 |
| ATOM | 233 | O | ALA | A | 627 | 105.795 | 34.914 | -3.679 | 1.00 | 12.94 |
| ATOM | 234 | N | THR | A | 628 | 107.215 | 35.810 | -5.179 | 1.00 | 12.14 |
| ATOM | 235 | CA | THR | A | 628 | 106.752 | 37.170 | -4.987 | 1.00 | 13.27 |
| ATOM | 236 | CB | THR | A | 628 | 107.924 | 38.096 | -4.609 | 1.00 | 13.86 |
| ATOM | 237 | OG1 | THR | A | 628 | 108.607 | 37.556 | -3.465 | 1.00 | 12.94 |
| ATOM | 238 | CG2 | THR | A | 628 | 107.402 | 39.429 | -4.092 | 1.00 | 13.78 |
| ATOM | 239 | C | THR | A | 628 | 106.070 | 37.609 | -6.274 | 1.00 | 14.54 |
| ATOM | 240 | O | THR | A | 628 | 106.672 | 37.573 | -7.351 | 1.00 | 17.05 |
| ATOM | 241 | N | ALA | A | 629 | 104.801 | 37.988 | -6.159 | 1.00 | 14.61 |
| ATOM | 242 | CA | ALA | A | 629 | 104.021 | 38.446 | -7.300 | 1.00 | 14.97 |
| ATOM | 243 | CB | ALA | A | 629 | 102.620 | 37.870 | -7.251 | 1.00 | 14.98 |
| ATOM | 244 | C | ALA | A | 629 | 103.961 | 39.958 | -7.293 | 1.00 | 16.51 |
| ATOM | 245 | O | ALA | A | 629 | 103.484 | 40.555 | -6.330 | 1.00 | 15.30 |
| ATOM | 246 | N | TYR | A | 630 | 104.446 | 40.573 | -8.366 | 1.00 | 18.38 |

FIGURE 3AF

|      | A | B | C | D | E | F | G | H | I | J |
|---|---|---|---|---|---|---|---|---|---|---|
| ATOM | 247 | CA  | TYR | A | 630 | 104.374 | 42.018 | -8.478  | 1.00 | 22.56 |
| ATOM | 248 | CB  | TYR | A | 630 | 105.678 | 42.608 | -9.100  | 1.00 | 23.99 |
| ATOM | 249 | CG  | TYR | A | 630 | 106.909 | 42.402 | -8.207  | 1.00 | 25.83 |
| ATOM | 250 | CD1 | TYR | A | 630 | 107.544 | 43.491 | -7.575  | 1.00 | 26.24 |
| ATOM | 251 | CE1 | TYR | A | 630 | 108.667 | 43.306 | -6.744  | 1.00 | 25.52 |
| ATOM | 252 | CZ  | TYR | A | 630 | 109.157 | 42.022 | -6.538  | 1.00 | 25.71 |
| ATOM | 253 | OH  | TYR | A | 630 | 110.244 | 41.826 | -5.712  | 1.00 | 25.59 |
| ATOM | 254 | CE2 | TYR | A | 630 | 108.545 | 40.925 | -7.149  | 1.00 | 26.76 |
| ATOM | 255 | CD2 | TYR | A | 630 | 107.426 | 41.117 | -7.979  | 1.00 | 26.36 |
| ATOM | 256 | C   | TYR | A | 630 | 103.070 | 42.394 | -9.236  | 1.00 | 24.16 |
| ATOM | 257 | O   | TYR | A | 630 | 102.747 | 41.876 | -10.441 | 1.00 | 27.03 |
| ATOM | 258 | N   | GLY | A | 631 | 102.302 | 43.261 | -8.503  | 1.00 | 25.41 |
| ATOM | 259 | CA  | GLY | A | 631 | 101.127 | 43.906 | -9.062  | 1.00 | 28.08 |
| ATOM | 260 | C   | GLY | A | 631 | 99.874  | 43.055 | -9.194  | 1.00 | 29.76 |
| ATOM | 261 | O   | GLY | A | 631 | 98.956  | 43.431 | -9.921  | 1.00 | 30.90 |
| ATOM | 262 | N   | ILE | A | 632 | 99.821  | 41.925 | -8.496  | 1.00 | 30.35 |
| ATOM | 263 | CA  | ILE | A | 632 | 98.675  | 41.019 | -8.614  | 1.00 | 33.16 |
| ATOM | 264 | CB  | ILE | A | 632 | 99.008  | 39.580 | -8.083  | 1.00 | 31.12 |
| ATOM | 265 | CG1 | ILE | A | 632 | 97.982  | 38.553 | -8.604  | 1.00 | 30.49 |
| ATOM | 266 | CD1 | ILE | A | 632 | 98.568  | 37.160 | -8.787  | 1.00 | 29.60 |
| ATOM | 267 | CG2 | ILE | A | 632 | 99.063  | 39.538 | -6.566  | 1.00 | 30.39 |
| ATOM | 268 | C   | ILE | A | 632 | 97.379  | 41.578 | -8.001  | 1.00 | 35.59 |
| ATOM | 269 | O   | ILE | A | 632 | 96.301  | 41.411 | -8.579  | 1.00 | 36.69 |
| ATOM | 270 | N   | SER | A | 633 | 97.491  | 42.255 | -6.858  | 1.00 | 37.73 |
| ATOM | 271 | CA  | SER | A | 633 | 96.319  | 42.753 | -6.137  | 1.00 | 40.19 |
| ATOM | 272 | CB  | SER | A | 633 | 96.342  | 42.283 | -4.679  | 1.00 | 40.25 |
| ATOM | 273 | OG  | SER | A | 633 | 96.043  | 40.896 | -4.591  | 1.00 | 38.64 |
| ATOM | 274 | C   | SER | A | 633 | 96.169  | 44.273 | -6.218  | 1.00 | 42.25 |
| ATOM | 275 | O   | SER | A | 633 | 95.055  | 44.791 | -6.294  | 1.00 | 43.59 |
| ATOM | 276 | N   | LYS | A | 634 | 97.291  | 44.983 | -6.196  | 1.00 | 43.92 |
| ATOM | 277 | CA  | LYS | A | 634 | 97.289  | 46.424 | -6.431  | 1.00 | 45.52 |
| ATOM | 278 | CB  | LYS | A | 634 | 97.462  | 47.195 | -5.119  | 1.00 | 47.26 |
| ATOM | 279 | CG  | LYS | A | 634 | 96.169  | 47.382 | -4.325  | 1.00 | 48.20 |
| ATOM | 280 | CD  | LYS | A | 634 | 95.956  | 48.847 | -3.954  | 1.00 | 48.86 |
| ATOM | 281 | CE  | LYS | A | 634 | 96.251  | 49.101 | -2.480  | 1.00 | 48.88 |
| ATOM | 282 | NZ  | LYS | A | 634 | 96.959  | 50.395 | -2.274  | 1.00 | 48.45 |
| ATOM | 283 | C   | LYS | A | 634 | 98.395  | 46.773 | -7.419  | 1.00 | 45.01 |
| ATOM | 284 | O   | LYS | A | 634 | 99.512  | 46.262 | -7.310  | 1.00 | 45.34 |
| ATOM | 285 | N   | THR | A | 635 | 98.076  | 47.633 | -8.386  | 1.00 | 44.19 |
| ATOM | 286 | CA  | THR | A | 635 | 99.006  | 47.974 | -9.466  | 1.00 | 43.12 |
| ATOM | 287 | CB  | THR | A | 635 | 98.297  | 48.822 | -10.560 | 1.00 | 43.20 |
| ATOM | 288 | OG1 | THR | A | 635 | 97.126  | 48.133 | -11.017 | 1.00 | 43.25 |
| ATOM | 289 | CG2 | THR | A | 635 | 99.152  | 48.920 | -11.824 | 1.00 | 43.02 |
| ATOM | 290 | C   | THR | A | 635 | 100.259 | 48.672 | -8.932  | 1.00 | 41.98 |
| ATOM | 291 | O   | THR | A | 635 | 100.265 | 49.887 | -8.713  | 1.00 | 42.88 |
| ATOM | 292 | N   | GLY | A | 636 | 101.310 | 47.883 | -8.715  | 1.00 | 40.24 |
| ATOM | 293 | CA  | GLY | A | 636 | 102.582 | 48.394 | -8.231  | 1.00 | 38.99 |
| ATOM | 294 | C   | GLY | A | 636 | 102.957 | 47.944 | -6.829  | 1.00 | 37.67 |
| ATOM | 295 | O   | GLY | A | 636 | 103.954 | 48.408 | -6.272  | 1.00 | 37.42 |
| ATOM | 296 | N   | VAL | A | 637 | 102.159 | 47.044 | -6.259  | 1.00 | 35.85 |
| ATOM | 297 | CA  | VAL | A | 637 | 102.415 | 46.511 | -4.923  | 1.00 | 34.31 |
| ATOM | 298 | CB  | VAL | A | 637 | 101.234 | 46.794 | -3.945  | 1.00 | 35.14 |

FIGURE 3AG

|  | A | B | C | D | E | F | G | H | I | J |
|---|---|---|---|---|---|---|---|---|---|---|
| ATOM | 299 | CG1 | VAL | A | 637 | 101.540 | 46.276 | -2.537 | 1.00 | 35.54 |
| ATOM | 300 | CG2 | VAL | A | 637 | 100.905 | 48.288 | -3.902 | 1.00 | 35.77 |
| ATOM | 301 | C | VAL | A | 637 | 102.690 | 45.010 | -5.010 | 1.00 | 32.61 |
| ATOM | 302 | O | VAL | A | 637 | 101.881 | 44.247 | -5.547 | 1.00 | 33.41 |
| ATOM | 303 | N | SER | A | 638 | 103.838 | 44.596 | -4.482 | 1.00 | 29.73 |
| ATOM | 304 | CA | SER | A | 638 | 104.217 | 43.188 | -4.481 | 1.00 | 26.87 |
| ATOM | 305 | CB | SER | A | 638 | 105.736 | 43.055 | -4.617 | 1.00 | 26.85 |
| ATOM | 306 | OG | SER | A | 638 | 106.326 | 42.570 | -3.419 | 1.00 | 28.44 |
| ATOM | 307 | C | SER | A | 638 | 103.727 | 42.461 | -3.227 | 1.00 | 24.34 |
| ATOM | 308 | O | SER | A | 638 | 103.666 | 43.045 | -2.147 | 1.00 | 25.02 |
| ATOM | 309 | N | ILE | A | 639 | 103.380 | 41.186 | -3.377 | 1.00 | 22.70 |
| ATOM | 310 | CA | ILE | A | 639 | 103.017 | 40.344 | -2.231 | 1.00 | 22.63 |
| ATOM | 311 | CB | ILE | A | 639 | 101.481 | 40.360 | -1.943 | 1.00 | 24.05 |
| ATOM | 312 | CG1 | ILE | A | 639 | 100.675 | 40.016 | -3.197 | 1.00 | 23.88 |
| ATOM | 313 | CD1 | ILE | A | 639 | 99.556 | 39.058 | -2.919 | 1.00 | 23.42 |
| ATOM | 314 | CG2 | ILE | A | 639 | 101.036 | 41.690 | -1.305 | 1.00 | 25.51 |
| ATOM | 315 | C | ILE | A | 639 | 103.509 | 38.906 | -2.383 | 1.00 | 20.42 |
| ATOM | 316 | O | ILE | A | 639 | 103.903 | 38.479 | -3.467 | 1.00 | 20.36 |
| ATOM | 317 | N | GLN | A | 640 | 103.479 | 38.165 | -1.282 | 1.00 | 18.69 |
| ATOM | 318 | CA | GLN | A | 640 | 103.872 | 36.765 | -1.288 | 1.00 | 17.55 |
| ATOM | 319 | CB | GLN | A | 640 | 104.303 | 36.325 | 0.109 | 1.00 | 18.57 |
| ATOM | 320 | CG | GLN | A | 640 | 105.623 | 36.935 | 0.569 | 1.00 | 19.88 |
| ATOM | 321 | CD | GLN | A | 640 | 106.783 | 36.502 | -0.293 | 1.00 | 20.33 |
| ATOM | 322 | OE1 | GLN | A | 640 | 107.214 | 35.350 | -0.230 | 1.00 | 20.47 |
| ATOM | 323 | NE2 | GLN | A | 640 | 107.290 | 37.420 | -1.110 | 1.00 | 21.67 |
| ATOM | 324 | C | GLN | A | 640 | 102.739 | 35.879 | -1.796 | 1.00 | 17.07 |
| ATOM | 325 | O | GLN | A | 640 | 101.566 | 36.078 | -1.452 | 1.00 | 16.22 |
| ATOM | 326 | N | VAL | A | 641 | 103.100 | 34.902 | -2.621 | 1.00 | 14.70 |
| ATOM | 327 | CA | VAL | A | 641 | 102.129 | 33.984 | -3.190 | 1.00 | 14.07 |
| ATOM | 328 | CB | VAL | A | 641 | 101.738 | 34.372 | -4.636 | 1.00 | 13.68 |
| ATOM | 329 | CG1 | VAL | A | 641 | 100.993 | 35.704 | -4.670 | 1.00 | 13.53 |
| ATOM | 330 | CG2 | VAL | A | 641 | 102.960 | 34.380 | -5.564 | 1.00 | 13.07 |
| ATOM | 331 | C | VAL | A | 641 | 102.635 | 32.545 | -3.176 | 1.00 | 15.01 |
| ATOM | 332 | O | VAL | A | 641 | 103.837 | 32.292 | -3.057 | 1.00 | 14.86 |
| ATOM | 333 | N | ALA | A | 642 | 101.699 | 31.609 | -3.289 | 1.00 | 14.30 |
| ATOM | 334 | CA | ALA | A | 642 | 102.032 | 30.211 | -3.484 | 1.00 | 14.93 |
| ATOM | 335 | CB | ALA | A | 642 | 101.311 | 29.355 | -2.476 | 1.00 | 16.41 |
| ATOM | 336 | C | ALA | A | 642 | 101.639 | 29.819 | -4.899 | 1.00 | 14.35 |
| ATOM | 337 | O | ALA | A | 642 | 100.512 | 30.058 | -5.333 | 1.00 | 16.18 |
| ATOM | 338 | N | VAL | A | 643 | 102.575 | 29.225 | -5.625 | 1.00 | 12.56 |
| ATOM | 339 | CA | VAL | A | 643 | 102.345 | 28.927 | -7.026 | 1.00 | 11.90 |
| ATOM | 340 | CB | VAL | A | 643 | 103.431 | 29.535 | -7.950 | 1.00 | 10.84 |
| ATOM | 341 | CG1 | VAL | A | 643 | 102.946 | 29.522 | -9.388 | 1.00 | 10.52 |
| ATOM | 342 | CG2 | VAL | A | 643 | 103.766 | 30.954 | -7.535 | 1.00 | 7.97 |
| ATOM | 343 | C | VAL | A | 643 | 102.243 | 27.434 | -7.244 | 1.00 | 12.80 |
| ATOM | 344 | O | VAL | A | 643 | 103.185 | 26.686 | -6.979 | 1.00 | 14.30 |
| ATOM | 345 | N | LYS | A | 644 | 101.086 | 27.005 | -7.724 | 1.00 | 13.65 |
| ATOM | 346 | CA | LYS | A | 644 | 100.864 | 25.598 | -7.999 | 1.00 | 14.71 |
| ATOM | 347 | CB | LYS | A | 644 | 99.441 | 25.180 | -7.626 | 1.00 | 14.22 |
| ATOM | 348 | CG | LYS | A | 644 | 99.172 | 23.692 | -7.828 | 1.00 | 14.69 |
| ATOM | 349 | CD | LYS | A | 644 | 98.254 | 23.129 | -6.754 | 1.00 | 15.03 |
| ATOM | 350 | CE | LYS | A | 644 | 98.279 | 21.619 | -6.758 | 1.00 | 14.57 |

FIGURE 3AH

|  | A | B | C | D | E | F | G | H | I | J |
|---|---|---|---|---|---|---|---|---|---|---|
| ATOM | 351 | NZ | LYS | A | 644 | 97.510 | 21.023 | -7.882 | 1.00 | 14.39 |
| ATOM | 352 | C | LYS | A | 644 | 101.136 | 25.327 | -9.464 | 1.00 | 15.06 |
| ATOM | 353 | O | LYS | A | 644 | 100.612 | 26.015 | -10.340 | 1.00 | 14.22 |
| ATOM | 354 | N | MET | A | 645 | 101.968 | 24.323 | -9.712 | 1.00 | 16.90 |
| ATOM | 355 | CA | MET | A | 645 | 102.346 | 23.927 | -11.062 | 1.00 | 19.40 |
| ATOM | 356 | CB | MET | A | 645 | 103.579 | 24.710 | -11.522 | 1.00 | 19.25 |
| ATOM | 357 | CG | MET | A | 645 | 104.895 | 24.196 | -10.946 | 1.00 | 20.46 |
| ATOM | 358 | SD | MET | A | 645 | 106.230 | 25.397 | -10.979 | 1.00 | 22.00 |
| ATOM | 359 | CE | MET | A | 645 | 105.501 | 26.737 | -10.027 | 1.00 | 21.31 |
| ATOM | 360 | C | MET | A | 645 | 102.619 | 22.426 | -11.109 | 1.00 | 20.50 |
| ATOM | 361 | O | MET | A | 645 | 102.726 | 21.772 | -10.069 | 1.00 | 21.04 |
| ATOM | 362 | N | LEU | A | 646 | 102.742 | 21.889 | -12.316 | 1.00 | 21.63 |
| ATOM | 363 | CA | LEU | A | 646 | 103.030 | 20.474 | -12.491 | 1.00 | 23.46 |
| ATOM | 364 | CB | LEU | A | 646 | 102.520 | 19.984 | -13.845 | 1.00 | 23.13 |
| ATOM | 365 | CG | LEU | A | 646 | 101.000 | 19.935 | -13.997 | 1.00 | 23.57 |
| ATOM | 366 | CD1 | LEU | A | 646 | 100.635 | 19.517 | -15.405 | 1.00 | 24.48 |
| ATOM | 367 | CD2 | LEU | A | 646 | 100.363 | 19.000 | -12.968 | 1.00 | 23.92 |
| ATOM | 368 | C | LEU | A | 646 | 104.512 | 20.179 | -12.356 | 1.00 | 24.19 |
| ATOM | 369 | O | LEU | A | 646 | 105.355 | 21.043 | -12.606 | 1.00 | 23.76 |
| ATOM | 370 | N | LYS | A | 647 | 104.810 | 18.948 | -11.950 | 1.00 | 26.36 |
| ATOM | 371 | CA | LYS | A | 647 | 106.180 | 18.451 | -11.861 | 1.00 | 28.83 |
| ATOM | 372 | CB | LYS | A | 647 | 106.218 | 17.110 | -11.109 | 1.00 | 30.65 |
| ATOM | 373 | CG | LYS | A | 647 | 105.432 | 15.964 | -11.768 | 1.00 | 32.44 |
| ATOM | 374 | CD | LYS | A | 647 | 104.142 | 15.645 | -11.012 | 1.00 | 33.78 |
| ATOM | 375 | CE | LYS | A | 647 | 102.922 | 16.218 | -11.729 | 1.00 | 34.52 |
| ATOM | 376 | NZ | LYS | A | 647 | 101.629 | 15.755 | -11.154 | 1.00 | 35.24 |
| ATOM | 377 | C | LYS | A | 647 | 106.808 | 18.330 | -13.255 | 1.00 | 28.77 |
| ATOM | 378 | O | LYS | A | 647 | 106.098 | 18.309 | -14.263 | 1.00 | 28.87 |
| ATOM | 379 | N | GLU | A | 648 | 108.137 | 18.254 | -13.298 | 1.00 | 29.17 |
| ATOM | 380 | CA | GLU | A | 648 | 108.889 | 18.221 | -14.554 | 1.00 | 29.89 |
| ATOM | 381 | CB | GLU | A | 648 | 110.364 | 17.892 | -14.278 | 1.00 | 30.70 |
| ATOM | 382 | CG | GLU | A | 648 | 111.279 | 17.923 | -15.499 | 1.00 | 31.81 |
| ATOM | 383 | CD | GLU | A | 648 | 111.768 | 19.319 | -15.861 | 1.00 | 32.32 |
| ATOM | 384 | OE1 | GLU | A | 648 | 111.437 | 20.288 | -15.140 | 1.00 | 32.37 |
| ATOM | 385 | OE2 | GLU | A | 648 | 112.490 | 19.445 | -16.876 | 1.00 | 32.31 |
| ATOM | 386 | C | GLU | A | 648 | 108.297 | 17.255 | -15.587 | 1.00 | 29.79 |
| ATOM | 387 | O | GLU | A | 648 | 107.958 | 16.114 | -15.259 | 1.00 | 29.29 |
| ATOM | 388 | N | LYS | A | 649 | 108.157 | 17.747 | -16.820 | 1.00 | 30.01 |
| ATOM | 389 | CA | LYS | A | 649 | 107.725 | 16.963 | -17.991 | 1.00 | 30.21 |
| ATOM | 390 | CB | LYS | A | 649 | 108.934 | 16.286 | -18.662 | 1.00 | 29.63 |
| ATOM | 391 | CG | LYS | A | 649 | 109.707 | 17.192 | -19.616 | 1.00 | 29.28 |
| ATOM | 392 | CD | LYS | A | 649 | 110.880 | 16.462 | -20.261 | 1.00 | 29.13 |
| ATOM | 393 | CE | LYS | A | 649 | 111.893 | 17.441 | -20.844 | 1.00 | 29.08 |
| ATOM | 394 | NZ | LYS | A | 649 | 112.356 | 17.046 | -22.209 | 1.00 | 28.63 |
| ATOM | 395 | C | LYS | A | 649 | 106.593 | 15.952 | -17.737 | 1.00 | 30.25 |
| ATOM | 396 | O | LYS | A | 649 | 106.605 | 14.842 | -18.278 | 1.00 | 30.24 |
| ATOM | 397 | N | ALA | A | 650 | 105.617 | 16.348 | -16.922 | 1.00 | 30.07 |
| ATOM | 398 | CA | ALA | A | 650 | 104.484 | 15.487 | -16.581 | 1.00 | 29.83 |
| ATOM | 399 | CB | ALA | A | 650 | 103.865 | 15.942 | -15.274 | 1.00 | 29.22 |
| ATOM | 400 | C | ALA | A | 650 | 103.425 | 15.451 | -17.687 | 1.00 | 29.76 |
| ATOM | 401 | O | ALA | A | 650 | 102.836 | 14.401 | -17.956 | 1.00 | 28.47 |
| ATOM | 402 | N | ASP | A | 651 | 103.204 | 16.613 | -18.306 | 1.00 | 30.26 |

FIGURE 3AI

|  | A | B | C | D | E | F | G | H | I | J |
|---|---|---|---|---|---|---|---|---|---|---|
| ATOM | 403 | CA | ASP | A | 651 | 102.204 | 16.848 | -19.359 | 1.00 | 29.89 |
| ATOM | 404 | CB | ASP | A | 651 | 102.878 | 17.473 | -20.590 | 1.00 | 30.00 |
| ATOM | 405 | CG | ASP | A | 651 | 103.119 | 18.970 | -20.442 | 1.00 | 30.06 |
| ATOM | 406 | OD1 | ASP | A | 651 | 102.814 | 19.539 | -19.372 | 1.00 | 29.61 |
| ATOM | 407 | OD2 | ASP | A | 651 | 103.619 | 19.664 | -21.355 | 1.00 | 30.43 |
| ATOM | 408 | C | ASP | A | 651 | 101.349 | 15.642 | -19.772 | 1.00 | 29.93 |
| ATOM | 409 | O | ASP | A | 651 | 101.683 | 14.922 | -20.719 | 1.00 | 31.09 |
| ATOM | 410 | N | SER | A | 652 | 100.246 | 15.436 | -19.057 | 1.00 | 28.83 |
| ATOM | 411 | CA | SER | A | 652 | 99.316 | 14.347 | -19.355 | 1.00 | 28.21 |
| ATOM | 412 | CB | SER | A | 652 | 99.763 | 13.063 | -18.643 | 1.00 | 27.99 |
| ATOM | 413 | OG | SER | A | 652 | 98.968 | 11.954 | -19.022 | 1.00 | 27.38 |
| ATOM | 414 | C | SER | A | 652 | 97.894 | 14.741 | -18.943 | 1.00 | 27.92 |
| ATOM | 415 | O | SER | A | 652 | 97.458 | 15.870 | -19.195 | 1.00 | 27.34 |
| ATOM | 416 | N | SER | A | 653 | 97.180 | 13.809 | -18.313 | 1.00 | 27.03 |
| ATOM | 417 | CA | SER | A | 653 | 95.898 | 14.098 | -17.675 | 1.00 | 26.94 |
| ATOM | 418 | CB | SER | A | 653 | 95.303 | 12.822 | -17.077 | 1.00 | 26.93 |
| ATOM | 419 | OG | SER | A | 653 | 94.342 | 12.249 | -17.947 | 1.00 | 27.27 |
| ATOM | 420 | C | SER | A | 653 | 96.075 | 15.151 | -16.579 | 1.00 | 26.50 |
| ATOM | 421 | O | SER | A | 653 | 95.126 | 15.846 | -16.210 | 1.00 | 26.17 |
| ATOM | 422 | N | GLU | A | 654 | 97.306 | 15.258 | -16.080 | 1.00 | 25.98 |
| ATOM | 423 | CA | GLU | A | 654 | 97.686 | 16.214 | -15.043 | 1.00 | 25.96 |
| ATOM | 424 | CB | GLU | A | 654 | 99.146 | 15.989 | -14.638 | 1.00 | 26.93 |
| ATOM | 425 | CG | GLU | A | 654 | 99.369 | 14.841 | -13.662 | 1.00 | 27.88 |
| ATOM | 426 | CD | GLU | A | 654 | 100.210 | 13.718 | -14.249 | 1.00 | 28.74 |
| ATOM | 427 | OE1 | GLU | A | 654 | 99.723 | 12.567 | -14.289 | 1.00 | 29.82 |
| ATOM | 428 | OE2 | GLU | A | 654 | 101.359 | 13.978 | -14.667 | 1.00 | 28.84 |
| ATOM | 429 | C | GLU | A | 654 | 97.485 | 17.672 | -15.465 | 1.00 | 25.10 |
| ATOM | 430 | O | GLU | A | 654 | 97.202 | 18.527 | -14.627 | 1.00 | 25.06 |
| ATOM | 431 | N | ARG | A | 655 | 97.641 | 17.945 | -16.760 | 1.00 | 24.95 |
| ATOM | 432 | CA | ARG | A | 655 | 97.464 | 19.291 | -17.308 | 1.00 | 24.45 |
| ATOM | 433 | CB | ARG | A | 655 | 98.109 | 19.411 | -18.701 | 1.00 | 25.53 |
| ATOM | 434 | CG | ARG | A | 655 | 98.452 | 20.846 | -19.122 | 1.00 | 27.43 |
| ATOM | 435 | CD | ARG | A | 655 | 99.912 | 21.086 | -19.527 | 1.00 | 29.44 |
| ATOM | 436 | NE | ARG | A | 655 | 100.817 | 21.188 | -18.374 | 1.00 | 32.22 |
| ATOM | 437 | CZ | ARG | A | 655 | 101.400 | 22.312 | -17.935 | 1.00 | 32.36 |
| ATOM | 438 | NH1 | ARG | A | 655 | 101.192 | 23.476 | -18.533 | 1.00 | 33.15 |
| ATOM | 439 | NH2 | ARG | A | 655 | 102.204 | 22.272 | -16.884 | 1.00 | 32.39 |
| ATOM | 440 | C | ARG | A | 655 | 95.988 | 19.693 | -17.338 | 1.00 | 22.77 |
| ATOM | 441 | O | ARG | A | 655 | 95.638 | 20.820 | -16.994 | 1.00 | 21.92 |
| ATOM | 442 | N | GLU | A | 656 | 95.127 | 18.761 | -17.734 | 1.00 | 22.77 |
| ATOM | 443 | CA | GLU | A | 656 | 93.683 | 18.998 | -17.743 | 1.00 | 22.42 |
| ATOM | 444 | CB | GLU | A | 656 | 92.965 | 17.930 | -18.573 | 1.00 | 23.44 |
| ATOM | 445 | CG | GLU | A | 656 | 93.641 | 17.634 | -19.909 | 1.00 | 25.84 |
| ATOM | 446 | CD | GLU | A | 656 | 92.663 | 17.330 | -21.037 | 1.00 | 27.37 |
| ATOM | 447 | OE1 | GLU | A | 656 | 91.445 | 17.572 | -20.871 | 1.00 | 28.69 |
| ATOM | 448 | OE2 | GLU | A | 656 | 93.116 | 16.847 | -22.102 | 1.00 | 26.87 |
| ATOM | 449 | C | GLU | A | 656 | 93.129 | 19.066 | -16.314 | 1.00 | 20.99 |
| ATOM | 450 | O | GLU | A | 656 | 92.132 | 19.747 | -16.052 | 1.00 | 19.79 |
| ATOM | 451 | N | ALA | A | 657 | 93.796 | 18.366 | -15.398 | 1.00 | 19.67 |
| ATOM | 452 | CA | ALA | A | 657 | 93.480 | 18.428 | -13.976 | 1.00 | 18.79 |
| ATOM | 453 | CB | ALA | A | 657 | 94.221 | 17.332 | -13.224 | 1.00 | 18.17 |
| ATOM | 454 | C | ALA | A | 657 | 93.819 | 19.806 | -13.402 | 1.00 | 18.66 |

FIGURE 3AJ

|  | A | B | C | D | E | F | G | H | I | J |
|---|---|---|---|---|---|---|---|---|---|---|
| ATOM | 455 | O | ALA | A | 657 | 93.025 | 20.392 | -12.664 | 1.00 | 19.15 |
| ATOM | 456 | N | LEU | A | 658 | 94.992 | 20.328 | -13.747 | 1.00 | 18.54 |
| ATOM | 457 | CA | LEU | A | 658 | 95.380 | 21.669 | -13.315 | 1.00 | 18.71 |
| ATOM | 458 | CB | LEU | A | 658 | 96.816 | 21.987 | -13.739 | 1.00 | 17.99 |
| ATOM | 459 | CG | LEU | A | 658 | 97.572 | 23.092 | -12.994 | 1.00 | 17.97 |
| ATOM | 460 | CD1 | LEU | A | 658 | 97.526 | 22.912 | -11.472 | 1.00 | 18.86 |
| ATOM | 461 | CD2 | LEU | A | 658 | 99.011 | 23.154 | -13.483 | 1.00 | 17.13 |
| ATOM | 462 | C | LEU | A | 658 | 94.408 | 22.713 | -13.862 | 1.00 | 19.03 |
| ATOM | 463 | O | LEU | A | 658 | 94.039 | 23.655 | -13.155 | 1.00 | 19.43 |
| ATOM | 464 | N | MET | A | 659 | 93.984 | 22.519 | -15.112 | 1.00 | 18.09 |
| ATOM | 465 | CA | MET | A | 659 | 92.996 | 23.384 | -15.755 | 1.00 | 17.49 |
| ATOM | 466 | CB | MET | A | 659 | 92.872 | 23.051 | -17.241 | 1.00 | 17.83 |
| ATOM | 467 | CG | MET | A | 659 | 93.963 | 23.676 | -18.102 | 1.00 | 20.14 |
| ATOM | 468 | SD | MET | A | 659 | 94.111 | 25.475 | -17.892 | 1.00 | 21.26 |
| ATOM | 469 | CE | MET | A | 659 | 93.422 | 26.034 | -19.510 | 1.00 | 21.89 |
| ATOM | 470 | C | MET | A | 659 | 91.632 | 23.313 | -15.074 | 1.00 | 16.74 |
| ATOM | 471 | O | MET | A | 659 | 90.961 | 24.338 | -14.914 | 1.00 | 17.05 |
| ATOM | 472 | N | SER | A | 660 | 91.236 | 22.102 | -14.674 | 1.00 | 16.05 |
| ATOM | 473 | CA | SER | A | 660 | 90.021 | 21.885 | -13.890 | 1.00 | 15.33 |
| ATOM | 474 | CB | SER | A | 660 | 89.823 | 20.399 | -13.620 | 1.00 | 15.87 |
| ATOM | 475 | OG | SER | A | 660 | 88.768 | 19.886 | -14.407 | 1.00 | 21.40 |
| ATOM | 476 | C | SER | A | 660 | 90.075 | 22.633 | -12.562 | 1.00 | 14.33 |
| ATOM | 477 | O | SER | A | 660 | 89.121 | 23.314 | -12.184 | 1.00 | 12.44 |
| ATOM | 478 | N | GLU | A | 661 | 91.202 | 22.503 | -11.867 | 1.00 | 13.97 |
| ATOM | 479 | CA | GLU | A | 661 | 91.401 | 23.171 | -10.590 | 1.00 | 16.15 |
| ATOM | 480 | CB | GLU | A | 661 | 92.770 | 22.807 | -10.006 | 1.00 | 17.17 |
| ATOM | 481 | CG | GLU | A | 661 | 93.019 | 23.298 | -8.588 | 1.00 | 18.47 |
| ATOM | 482 | CD | GLU | A | 661 | 94.433 | 23.004 | -8.101 | 1.00 | 21.28 |
| ATOM | 483 | OE1 | GLU | A | 661 | 94.913 | 23.695 | -7.173 | 1.00 | 22.03 |
| ATOM | 484 | OE2 | GLU | A | 661 | 95.072 | 22.074 | -8.641 | 1.00 | 22.43 |
| ATOM | 485 | C | GLU | A | 661 | 91.246 | 24.683 | -10.762 | 1.00 | 15.79 |
| ATOM | 486 | O | GLU | A | 661 | 90.545 | 25.329 | -9.981 | 1.00 | 13.88 |
| ATOM | 487 | N | LEU | A | 662 | 91.880 | 25.226 | -11.804 | 1.00 | 16.41 |
| ATOM | 488 | CA | LEU | A | 662 | 91.813 | 26.655 | -12.111 | 1.00 | 17.01 |
| ATOM | 489 | CB | LEU | A | 662 | 92.626 | 26.986 | -13.368 | 1.00 | 16.54 |
| ATOM | 490 | CG | LEU | A | 662 | 92.519 | 28.414 | -13.919 | 1.00 | 16.70 |
| ATOM | 491 | CD1 | LEU | A | 662 | 92.934 | 29.462 | -12.891 | 1.00 | 16.96 |
| ATOM | 492 | CD2 | LEU | A | 662 | 93.360 | 28.548 | -15.164 | 1.00 | 17.83 |
| ATOM | 493 | C | LEU | A | 662 | 90.375 | 27.129 | -12.291 | 1.00 | 17.48 |
| ATOM | 494 | O | LEU | A | 662 | 89.953 | 28.092 | -11.645 | 1.00 | 17.91 |
| ATOM | 495 | N | LYS | A | 663 | 89.633 | 26.449 | -13.165 | 1.00 | 15.75 |
| ATOM | 496 | CA | LYS | A | 663 | 88.239 | 26.793 | -13.431 | 1.00 | 16.56 |
| ATOM | 497 | CB | LYS | A | 663 | 87.621 | 25.842 | -14.466 | 1.00 | 17.35 |
| ATOM | 498 | CG | LYS | A | 663 | 88.154 | 26.042 | -15.892 | 1.00 | 19.18 |
| ATOM | 499 | CD | LYS | A | 663 | 87.099 | 25.706 | -16.945 | 1.00 | 19.99 |
| ATOM | 500 | CE | LYS | A | 663 | 87.163 | 26.662 | -18.136 | 1.00 | 20.51 |
| ATOM | 501 | NZ | LYS | A | 663 | 86.140 | 26.325 | -19.179 | 1.00 | 19.99 |
| ATOM | 502 | C | LYS | A | 663 | 87.416 | 26.817 | -12.140 | 1.00 | 15.77 |
| ATOM | 503 | O | LYS | A | 663 | 86.596 | 27.713 | -11.938 | 1.00 | 15.54 |
| ATOM | 504 | N | MET | A | 664 | 87.656 | 25.843 | -11.267 | 1.00 | 14.68 |
| ATOM | 505 | CA | MET | A | 664 | 86.978 | 25.770 | -9.978 | 1.00 | 15.58 |
| ATOM | 506 | CB | MET | A | 664 | 87.342 | 24.466 | -9.269 | 1.00 | 14.82 |

FIGURE 3AK

|  | A | B | C | D | E | F | G | H | I | J |
|---|---|---|---|---|---|---|---|---|---|---|
| ATOM | 507 | CG | MET | A | 664 | 86.923 | 24.396 | -7.804 | 1.00 | 16.22 |
| ATOM | 508 | SD | MET | A | 664 | 87.395 | 22.846 | -7.006 | 1.00 | 16.91 |
| ATOM | 509 | CE | MET | A | 664 | 86.873 | 21.657 | -8.219 | 1.00 | 19.32 |
| ATOM | 510 | C | MET | A | 664 | 87.325 | 26.975 | -9.096 | 1.00 | 15.77 |
| ATOM | 511 | O | MET | A | 664 | 86.441 | 27.653 | -8.576 | 1.00 | 17.04 |
| ATOM | 512 | N | MET | A | 665 | 88.615 | 27.242 | -8.945 | 1.00 | 14.94 |
| ATOM | 513 | CA | MET | A | 665 | 89.076 | 28.301 | -8.059 | 1.00 | 14.77 |
| ATOM | 514 | CB | MET | A | 665 | 90.577 | 28.153 | -7.796 | 1.00 | 14.91 |
| ATOM | 515 | CG | MET | A | 665 | 90.948 | 26.868 | -7.054 | 1.00 | 14.88 |
| ATOM | 516 | SD | MET | A | 665 | 89.888 | 26.506 | -5.625 | 1.00 | 15.82 |
| ATOM | 517 | CE | MET | A | 665 | 90.442 | 27.779 | -4.492 | 1.00 | 15.53 |
| ATOM | 518 | C | MET | A | 665 | 88.728 | 29.712 | -8.546 | 1.00 | 15.23 |
| ATOM | 519 | O | MET | A | 665 | 88.598 | 30.626 | -7.731 | 1.00 | 15.00 |
| ATOM | 520 | N | THR | A | 666 | 88.563 | 29.884 | -9.860 | 1.00 | 14.07 |
| ATOM | 521 | CA | THR | A | 666 | 88.139 | 31.170 | -10.419 | 1.00 | 14.63 |
| ATOM | 522 | CB | THR | A | 666 | 88.415 | 31.272 | -11.949 | 1.00 | 13.65 |
| ATOM | 523 | OG1 | THR | A | 666 | 88.047 | 30.052 | -12.600 | 1.00 | 14.16 |
| ATOM | 524 | CG2 | THR | A | 666 | 89.897 | 31.397 | -12.244 | 1.00 | 11.61 |
| ATOM | 525 | C | THR | A | 666 | 86.662 | 31.430 | -10.156 | 1.00 | 16.28 |
| ATOM | 526 | O | THR | A | 666 | 86.255 | 32.582 | -9.990 | 1.00 | 18.39 |
| ATOM | 527 | N | GLN | A | 667 | 85.870 | 30.358 | -10.128 | 1.00 | 17.58 |
| ATOM | 528 | CA | GLN | A | 667 | 84.419 | 30.459 | -9.992 | 1.00 | 18.27 |
| ATOM | 529 | CB | GLN | A | 667 | 83.706 | 29.382 | -10.828 | 1.00 | 21.34 |
| ATOM | 530 | CG | GLN | A | 667 | 84.013 | 29.386 | -12.331 | 1.00 | 25.41 |
| ATOM | 531 | CD | GLN | A | 667 | 83.459 | 30.601 | -13.068 | 1.00 | 27.48 |
| ATOM | 532 | OE1 | GLN | A | 667 | 82.347 | 30.557 | -13.599 | 1.00 | 28.24 |
| ATOM | 533 | NE2 | GLN | A | 667 | 84.241 | 31.679 | -13.115 | 1.00 | 26.60 |
| ATOM | 534 | C | GLN | A | 667 | 83.971 | 30.350 | -8.542 | 1.00 | 17.30 |
| ATOM | 535 | O | GLN | A | 667 | 82.805 | 30.597 | -8.228 | 1.00 | 18.32 |
| ATOM | 536 | N | LEU | A | 668 | 84.896 | 29.978 | -7.663 | 1.00 | 15.51 |
| ATOM | 537 | CA | LEU | A | 668 | 84.571 | 29.731 | -6.262 | 1.00 | 13.67 |
| ATOM | 538 | CB | LEU | A | 668 | 85.736 | 29.018 | -5.562 | 1.00 | 13.34 |
| ATOM | 539 | CG | LEU | A | 668 | 85.470 | 28.416 | -4.178 | 1.00 | 12.59 |
| ATOM | 540 | CD1 | LEU | A | 668 | 84.436 | 27.305 | -4.270 | 1.00 | 11.89 |
| ATOM | 541 | CD2 | LEU | A | 668 | 86.755 | 27.895 | -3.566 | 1.00 | 10.63 |
| ATOM | 542 | C | LEU | A | 668 | 84.201 | 31.009 | -5.505 | 1.00 | 13.20 |
| ATOM | 543 | O | LEU | A | 668 | 83.244 | 31.020 | -4.729 | 1.00 | 14.05 |
| ATOM | 544 | N | GLY | A | 669 | 84.952 | 32.080 | -5.747 | 1.00 | 10.39 |
| ATOM | 545 | CA | GLY | A | 669 | 84.834 | 33.291 | -4.959 | 1.00 | 10.10 |
| ATOM | 546 | C | GLY | A | 669 | 85.756 | 33.203 | -3.754 | 1.00 | 10.88 |
| ATOM | 547 | O | GLY | A | 669 | 86.098 | 32.109 | -3.296 | 1.00 | 11.45 |
| ATOM | 548 | N | SER | A | 670 | 86.157 | 34.355 | -3.235 | 1.00 | 9.00 |
| ATOM | 549 | CA | SER | A | 670 | 87.082 | 34.396 | -2.118 | 1.00 | 8.91 |
| ATOM | 550 | CB | BSER | A | 670 | 87.903 | 35.687 | -2.149 | 0.35 | 9.26 |
| ATOM | 551 | CB | ASER | A | 670 | 87.881 | 35.697 | -2.139 | 0.65 | 8.57 |
| ATOM | 552 | OG | BSER | A | 670 | 88.716 | 35.743 | -3.308 | 0.35 | 10.01 |
| ATOM | 553 | OG | ASER | A | 670 | 87.023 | 36.810 | -1.961 | 0.65 | 8.47 |
| ATOM | 554 | C | SER | A | 670 | 86.357 | 34.263 | -0.784 | 1.00 | 9.46 |
| ATOM | 555 | O | SER | A | 670 | 85.193 | 34.640 | -0.650 | 1.00 | 9.72 |
| ATOM | 556 | N | HIS | A | 671 | 87.066 | 33.722 | 0.198 | 1.00 | 8.37 |
| ATOM | 557 | CA | HIS | A | 671 | 86.597 | 33.696 | 1.573 | 1.00 | 9.61 |
| ATOM | 558 | CB | HIS | A | 671 | 85.860 | 32.386 | 1.878 | 1.00 | 6.09 |

FIGURE 3AL

| | A | B | C | D | E | F | G | H | I | J |
|---|---|---|---|---|---|---|---|---|---|---|
| ATOM | 559 | CG | HIS | A | 671 | 85.182 | 32.377 | 3.210 | 1.00 | 4.99 |
| ATOM | 560 | ND1 | HIS | A | 671 | 85.789 | 31.895 | 4.350 | 1.00 | 4.51 |
| ATOM | 561 | CE1 | HIS | A | 671 | 84.960 | 32.018 | 5.372 | 1.00 | 4.74 |
| ATOM | 562 | NE2 | HIS | A | 671 | 83.841 | 32.574 | 4.938 | 1.00 | 3.98 |
| ATOM | 563 | CD2 | HIS | A | 671 | 83.957 | 32.813 | 3.591 | 1.00 | 4.10 |
| ATOM | 564 | C | HIS | A | 671 | 87.802 | 33.850 | 2.482 | 1.00 | 10.05 |
| ATOM | 565 | O | HIS | A | 671 | 88.899 | 33.429 | 2.125 | 1.00 | 11.95 |
| ATOM | 566 | N | GLU | A | 672 | 87.588 | 34.458 | 3.647 | 1.00 | 11.78 |
| ATOM | 567 | CA | GLU | A | 672 | 88.622 | 34.650 | 4.671 | 1.00 | 14.19 |
| ATOM | 568 | CB | GLU | A | 672 | 88.011 | 35.274 | 5.939 | 1.00 | 17.50 |
| ATOM | 569 | CG | GLU | A | 672 | 87.002 | 36.401 | 5.703 | 1.00 | 23.53 |
| ATOM | 570 | CD | GLU | A | 672 | 85.609 | 35.899 | 5.302 | 1.00 | 27.08 |
| ATOM | 571 | OE1 | GLU | A | 672 | 85.303 | 35.883 | 4.080 | 1.00 | 25.36 |
| ATOM | 572 | OE2 | GLU | A | 672 | 84.815 | 35.525 | 6.209 | 1.00 | 28.36 |
| ATOM | 573 | C | GLU | A | 672 | 89.339 | 33.343 | 5.043 | 1.00 | 14.37 |
| ATOM | 574 | O | GLU | A | 672 | 90.548 | 33.335 | 5.275 | 1.00 | 15.50 |
| ATOM | 575 | N | ASN | A | 673 | 88.592 | 32.241 | 5.081 | 1.00 | 12.01 |
| ATOM | 576 | CA | ASN | A | 673 | 89.118 | 30.976 | 5.572 | 1.00 | 10.75 |
| ATOM | 577 | CB | ASN | A | 673 | 88.197 | 30.414 | 6.656 | 1.00 | 8.76 |
| ATOM | 578 | CG | ASN | A | 673 | 87.974 | 31.401 | 7.785 | 1.00 | 7.87 |
| ATOM | 579 | OD1 | ASN | A | 673 | 86.859 | 31.855 | 8.019 | 1.00 | 8.65 |
| ATOM | 580 | ND2 | ASN | A | 673 | 89.046 | 31.756 | 8.477 | 1.00 | 7.73 |
| ATOM | 581 | C | ASN | A | 673 | 89.412 | 29.942 | 4.486 | 1.00 | 11.69 |
| ATOM | 582 | O | ASN | A | 673 | 89.480 | 28.736 | 4.753 | 1.00 | 10.75 |
| ATOM | 583 | N | ILE | A | 674 | 89.606 | 30.433 | 3.266 | 1.00 | 11.89 |
| ATOM | 584 | CA | ILE | A | 674 | 90.008 | 29.595 | 2.146 | 1.00 | 11.26 |
| ATOM | 585 | CB | ILE | A | 674 | 88.897 | 29.581 | 1.057 | 1.00 | 11.82 |
| ATOM | 586 | CG1 | ILE | A | 674 | 87.568 | 29.035 | 1.619 | 1.00 | 11.78 |
| ATOM | 587 | CD1 | ILE | A | 674 | 87.596 | 27.580 | 2.114 | 1.00 | 12.89 |
| ATOM | 588 | CG2 | ILE | A | 674 | 89.341 | 28.821 | -0.197 | 1.00 | 11.61 |
| ATOM | 589 | C | ILE | A | 674 | 91.294 | 30.186 | 1.604 | 1.00 | 11.10 |
| ATOM | 590 | O | ILE | A | 674 | 91.469 | 31.405 | 1.623 | 1.00 | 12.80 |
| ATOM | 591 | N | VAL | A | 675 | 92.207 | 29.322 | 1.168 | 1.00 | 11.10 |
| ATOM | 592 | CA | VAL | A | 675 | 93.363 | 29.740 | 0.377 | 1.00 | 12.16 |
| ATOM | 593 | CB | VAL | A | 675 | 94.421 | 28.613 | 0.235 | 1.00 | 11.38 |
| ATOM | 594 | CG1 | VAL | A | 675 | 95.600 | 29.075 | -0.607 | 1.00 | 12.48 |
| ATOM | 595 | CG2 | VAL | A | 675 | 94.896 | 28.138 | 1.595 | 1.00 | 8.31 |
| ATOM | 596 | C | VAL | A | 675 | 92.839 | 30.135 | -0.999 | 1.00 | 13.85 |
| ATOM | 597 | O | VAL | A | 675 | 92.631 | 29.293 | -1.867 | 1.00 | 14.12 |
| ATOM | 598 | N | ASN | A | 676 | 92.602 | 31.428 | -1.171 | 1.00 | 17.30 |
| ATOM | 599 | CA | ASN | A | 676 | 92.033 | 31.953 | -2.406 | 1.00 | 17.66 |
| ATOM | 600 | CB | ASN | A | 676 | 91.404 | 33.323 | -2.149 | 1.00 | 17.39 |
| ATOM | 601 | CG | ASN | A | 676 | 90.443 | 33.312 | -0.975 | 1.00 | 16.53 |
| ATOM | 602 | OD1 | ASN | A | 676 | 89.394 | 32.671 | -1.027 | 1.00 | 16.17 |
| ATOM | 603 | ND2 | ASN | A | 676 | 90.800 | 34.015 | 0.093 | 1.00 | 14.44 |
| ATOM | 604 | C | ASN | A | 676 | 93.051 | 32.060 | -3.534 | 1.00 | 19.00 |
| ATOM | 605 | O | ASN | A | 676 | 94.232 | 32.374 | -3.308 | 1.00 | 17.53 |
| ATOM | 606 | N | LEU | A | 677 | 92.574 | 31.795 | -4.748 | 1.00 | 18.97 |
| ATOM | 607 | CA | LEU | A | 677 | 93.338 | 32.033 | -5.964 | 1.00 | 17.50 |
| ATOM | 608 | CB | LEU | A | 677 | 92.688 | 31.310 | -7.142 | 1.00 | 17.37 |
| ATOM | 609 | CG | LEU | A | 677 | 93.376 | 31.356 | -8.511 | 1.00 | 18.51 |
| ATOM | 610 | CD1 | LEU | A | 677 | 94.274 | 30.147 | -8.725 | 1.00 | 19.13 |

FIGURE 3AM

| | A | B | C | D | E | F | G | H | I | J |
|---|---|---|---|---|---|---|---|---|---|---|
| ATOM | 611 | CD2 | LEU | A | 677 | 92.330 | 31.442 | -9.602 | 1.00 | 16.90 |
| ATOM | 612 | C | LEU | A | 677 | 93.425 | 33.539 | -6.223 | 1.00 | 18.16 |
| ATOM | 613 | O | LEU | A | 677 | 92.431 | 34.267 | -6.094 | 1.00 | 18.41 |
| ATOM | 614 | N | LEU | A | 678 | 94.620 | 34.003 | -6.575 | 1.00 | 16.79 |
| ATOM | 615 | CA | LEU | A | 678 | 94.846 | 35.428 | -6.807 | 1.00 | 15.44 |
| ATOM | 616 | CB | LEU | A | 678 | 96.070 | 35.917 | -6.026 | 1.00 | 15.37 |
| ATOM | 617 | CG | LEU | A | 678 | 95.930 | 35.848 | -4.500 | 1.00 | 14.27 |
| ATOM | 618 | CD1 | LEU | A | 678 | 97.190 | 36.347 | -3.839 | 1.00 | 13.99 |
| ATOM | 619 | CD2 | LEU | A | 678 | 94.701 | 36.623 | -4.002 | 1.00 | 13.49 |
| ATOM | 620 | C | LEU | A | 678 | 94.978 | 35.772 | -8.282 | 1.00 | 13.99 |
| ATOM | 621 | O | LEU | A | 678 | 94.701 | 36.905 | -8.690 | 1.00 | 11.84 |
| ATOM | 622 | N | GLY | A | 679 | 95.396 | 34.781 | -9.065 | 1.00 | 13.27 |
| ATOM | 623 | CA | GLY | A | 679 | 95.587 | 34.934 | -10.494 | 1.00 | 13.91 |
| ATOM | 624 | C | GLY | A | 679 | 96.155 | 33.673 | -11.110 | 1.00 | 14.81 |
| ATOM | 625 | O | GLY | A | 679 | 96.326 | 32.666 | -10.421 | 1.00 | 15.66 |
| ATOM | 626 | N | ALA | A | 680 | 96.454 | 33.723 | -12.408 | 1.00 | 15.19 |
| ATOM | 627 | CA | ALA | A | 680 | 96.981 | 32.556 | -13.114 | 1.00 | 14.92 |
| ATOM | 628 | CB | ALA | A | 680 | 95.838 | 31.617 | -13.525 | 1.00 | 13.39 |
| ATOM | 629 | C | ALA | A | 680 | 97.804 | 32.933 | -14.331 | 1.00 | 13.75 |
| ATOM | 630 | O | ALA | A | 680 | 97.543 | 33.953 | -14.970 | 1.00 | 14.28 |
| ATOM | 631 | N | CYS | A | 681 | 98.799 | 32.103 | -14.641 | 1.00 | 14.77 |
| ATOM | 632 | CA | CYS | A | 681 | 99.503 | 32.174 | -15.924 | 1.00 | 14.94 |
| ATOM | 633 | CB | CYS | A | 681 | 101.025 | 32.287 | -15.743 | 1.00 | 15.20 |
| ATOM | 634 | SG | CYS | A | 681 | 101.615 | 33.183 | -14.287 | 1.00 | 17.50 |
| ATOM | 635 | C | CYS | A | 681 | 99.173 | 30.928 | -16.749 | 1.00 | 15.43 |
| ATOM | 636 | O | CYS | A | 681 | 99.531 | 29.811 | -16.367 | 1.00 | 15.91 |
| ATOM | 637 | N | THR | A | 682 | 98.489 | 31.127 | -17.873 | 1.00 | 15.44 |
| ATOM | 638 | CA | THR | A | 682 | 98.097 | 30.028 | -18.759 | 1.00 | 15.28 |
| ATOM | 639 | CB | THR | A | 682 | 96.561 | 29.966 | -18.892 | 1.00 | 14.92 |
| ATOM | 640 | OG1 | THR | A | 682 | 96.058 | 31.252 | -19.276 | 1.00 | 13.92 |
| ATOM | 641 | CG2 | THR | A | 682 | 95.906 | 29.718 | -17.529 | 1.00 | 15.07 |
| ATOM | 642 | C | THR | A | 682 | 98.737 | 30.158 | -20.142 | 1.00 | 15.95 |
| ATOM | 643 | O | THR | A | 682 | 98.815 | 29.183 | -20.903 | 1.00 | 16.34 |
| ATOM | 644 | N | LEU | A | 683 | 99.191 | 31.368 | -20.459 | 1.00 | 15.86 |
| ATOM | 645 | CA | LEU | A | 683 | 99.785 | 31.660 | -21.764 | 1.00 | 16.32 |
| ATOM | 646 | CB | LEU | A | 683 | 99.193 | 32.952 | -22.344 | 1.00 | 15.96 |
| ATOM | 647 | CG | LEU | A | 683 | 97.688 | 33.212 | -22.135 | 1.00 | 16.59 |
| ATOM | 648 | CD1 | LEU | A | 683 | 97.307 | 34.598 | -22.637 | 1.00 | 17.45 |
| ATOM | 649 | CD2 | LEU | A | 683 | 96.819 | 32.145 | -22.805 | 1.00 | 16.82 |
| ATOM | 650 | C | LEU | A | 683 | 101.305 | 31.757 | -21.677 | 1.00 | 16.19 |
| ATOM | 651 | O | LEU | A | 683 | 101.858 | 32.043 | -20.613 | 1.00 | 17.01 |
| ATOM | 652 | N | SER | A | 684 | 101.969 | 31.495 | -22.798 | 1.00 | 16.85 |
| ATOM | 653 | CA | SER | A | 684 | 103.423 | 31.654 | -22.931 | 1.00 | 18.68 |
| ATOM | 654 | CB | SER | A | 684 | 103.834 | 33.130 | -22.795 | 1.00 | 18.71 |
| ATOM | 655 | OG | SER | A | 684 | 102.949 | 33.976 | -23.506 | 1.00 | 19.58 |
| ATOM | 656 | C | SER | A | 684 | 104.256 | 30.771 | -21.992 | 1.00 | 19.47 |
| ATOM | 657 | O | SER | A | 684 | 105.389 | 31.122 | -21.643 | 1.00 | 20.94 |
| ATOM | 658 | N | GLY | A | 685 | 103.703 | 29.627 | -21.596 | 1.00 | 18.34 |
| ATOM | 659 | CA | GLY | A | 685 | 104.452 | 28.673 | -20.798 | 1.00 | 18.95 |
| ATOM | 660 | C | GLY | A | 685 | 103.608 | 27.783 | -19.905 | 1.00 | 19.45 |
| ATOM | 661 | O | GLY | A | 685 | 102.386 | 27.724 | -20.062 | 1.00 | 19.73 |
| ATOM | 662 | N | PRO | A | 686 | 104.262 | 27.099 | -18.963 | 1.00 | 19.72 |

FIGURE 3AN

|  | A | B | C | D | E | F | G | H | I | J |
|---|---|---|---|---|---|---|---|---|---|---|
| ATOM | 663 | CA | PRO | A | 686 | 103.589 | 26.138 | -18.080 | 1.00 | 19.50 |
| ATOM | 664 | CB | PRO | A | 686 | 104.733 | 25.592 | -17.217 | 1.00 | 19.80 |
| ATOM | 665 | CG | PRO | A | 686 | 105.795 | 26.636 | -17.280 | 1.00 | 20.40 |
| ATOM | 666 | CD | PRO | A | 686 | 105.703 | 27.209 | -18.662 | 1.00 | 20.27 |
| ATOM | 667 | C | PRO | A | 686 | 102.526 | 26.800 | -17.207 | 1.00 | 19.16 |
| ATOM | 668 | O | PRO | A | 686 | 102.720 | 27.932 | -16.751 | 1.00 | 18.20 |
| ATOM | 669 | N | ILE | A | 687 | 101.414 | 26.095 | -16.997 | 1.00 | 18.85 |
| ATOM | 670 | CA | ILE | A | 687 | 100.290 | 26.614 | -16.224 | 1.00 | 18.24 |
| ATOM | 671 | CB | ILE | A | 687 | 99.060 | 25.679 | -16.323 | 1.00 | 18.03 |
| ATOM | 672 | CG1 | ILE | A | 687 | 98.640 | 25.501 | -17.782 | 1.00 | 19.14 |
| ATOM | 673 | CD1 | ILE | A | 687 | 97.742 | 24.295 | -18.021 | 1.00 | 20.59 |
| ATOM | 674 | CG2 | ILE | A | 687 | 97.893 | 26.236 | -15.516 | 1.00 | 16.79 |
| ATOM | 675 | C | ILE | A | 687 | 100.686 | 26.840 | -14.769 | 1.00 | 17.49 |
| ATOM | 676 | O | ILE | A | 687 | 101.201 | 25.937 | -14.107 | 1.00 | 16.97 |
| ATOM | 677 | N | TYR | A | 688 | 100.462 | 28.063 | -14.301 | 1.00 | 17.22 |
| ATOM | 678 | CA | TYR | A | 688 | 100.704 | 28.432 | -12.914 | 1.00 | 17.46 |
| ATOM | 679 | CB | TYR | A | 688 | 101.705 | 29.590 | -12.827 | 1.00 | 16.34 |
| ATOM | 680 | CG | TYR | A | 688 | 103.139 | 29.261 | -13.201 | 1.00 | 16.76 |
| ATOM | 681 | CD1 | TYR | A | 688 | 104.043 | 30.281 | -13.501 | 1.00 | 16.67 |
| ATOM | 682 | CE1 | TYR | A | 688 | 105.362 | 29.998 | -13.846 | 1.00 | 16.69 |
| ATOM | 683 | CZ | TYR | A | 688 | 105.796 | 28.683 | -13.887 | 1.00 | 16.74 |
| ATOM | 684 | OH | TYR | A | 688 | 107.103 | 28.403 | -14.228 | 1.00 | 16.59 |
| ATOM | 685 | CE2 | TYR | A | 688 | 104.921 | 27.649 | -13.592 | 1.00 | 16.40 |
| ATOM | 686 | CD2 | TYR | A | 688 | 103.599 | 27.942 | -13.248 | 1.00 | 17.05 |
| ATOM | 687 | C | TYR | A | 688 | 99.387 | 28.856 | -12.273 | 1.00 | 17.53 |
| ATOM | 688 | O | TYR | A | 688 | 98.647 | 29.667 | -12.843 | 1.00 | 18.74 |
| ATOM | 689 | N | LEU | A | 689 | 99.090 | 28.293 | -11.103 | 1.00 | 16.80 |
| ATOM | 690 | CA | LEU | A | 689 | 97.973 | 28.759 | -10.285 | 1.00 | 16.08 |
| ATOM | 691 | CB | LEU | A | 689 | 97.106 | 27.597 | -9.790 | 1.00 | 16.26 |
| ATOM | 692 | CG | LEU | A | 689 | 96.420 | 26.677 | -10.811 | 1.00 | 16.61 |
| ATOM | 693 | CD1 | LEU | A | 689 | 95.236 | 25.942 | -10.174 | 1.00 | 17.41 |
| ATOM | 694 | CD2 | LEU | A | 689 | 95.982 | 27.415 | -12.069 | 1.00 | 16.56 |
| ATOM | 695 | C | LEU | A | 689 | 98.544 | 29.532 | -9.116 | 1.00 | 15.50 |
| ATOM | 696 | O | LEU | A | 689 | 99.315 | 28.988 | -8.323 | 1.00 | 14.84 |
| ATOM | 697 | N | ILE | A | 690 | 98.182 | 30.810 | -9.032 | 1.00 | 15.66 |
| ATOM | 698 | CA | ILE | A | 690 | 98.739 | 31.708 | -8.027 | 1.00 | 14.76 |
| ATOM | 699 | CB | ILE | A | 690 | 99.088 | 33.077 | -8.637 | 1.00 | 14.42 |
| ATOM | 700 | CG1 | ILE | A | 690 | 100.016 | 32.919 | -9.846 | 1.00 | 13.02 |
| ATOM | 701 | CD1 | ILE | A | 690 | 100.097 | 34.161 | -10.707 | 1.00 | 11.53 |
| ATOM | 702 | CG2 | ILE | A | 690 | 99.740 | 33.968 | -7.584 | 1.00 | 13.08 |
| ATOM | 703 | C | ILE | A | 690 | 97.793 | 31.878 | -6.847 | 1.00 | 15.36 |
| ATOM | 704 | O | ILE | A | 690 | 96.760 | 32.558 | -6.945 | 1.00 | 16.11 |
| ATOM | 705 | N | PHE | A | 691 | 98.160 | 31.247 | -5.737 | 1.00 | 14.97 |
| ATOM | 706 | CA | PHE | A | 691 | 97.364 | 31.266 | -4.515 | 1.00 | 15.56 |
| ATOM | 707 | CB | PHE | A | 691 | 97.321 | 29.870 | -3.908 | 1.00 | 16.87 |
| ATOM | 708 | CG | PHE | A | 691 | 96.497 | 28.886 | -4.681 | 1.00 | 17.92 |
| ATOM | 709 | CD1 | PHE | A | 691 | 97.114 | 27.897 | -5.444 | 1.00 | 18.82 |
| ATOM | 710 | CE1 | PHE | A | 691 | 96.358 | 26.964 | -6.147 | 1.00 | 19.45 |
| ATOM | 711 | CZ | PHE | A | 691 | 94.964 | 27.015 | -6.087 | 1.00 | 18.94 |
| ATOM | 712 | CE2 | PHE | A | 691 | 94.340 | 27.997 | -5.320 | 1.00 | 17.76 |
| ATOM | 713 | CD2 | PHE | A | 691 | 95.106 | 28.925 | -4.626 | 1.00 | 17.72 |
| ATOM | 714 | C | PHE | A | 691 | 97.936 | 32.225 | -3.475 | 1.00 | 16.07 |

FIGURE 3AO

|  | A | B | C | D | E | F | G | H | I | J |
|---|---|---|---|---|---|---|---|---|---|---|
| ATOM | 715 | O | PHE | A | 691 | 99.111 | 32.606 | -3.536 | 1.00 | 16.69 |
| ATOM | 716 | N | GLU | A | 692 | 97.095 | 32.606 | -2.515 | 1.00 | 17.88 |
| ATOM | 717 | CA | GLU | A | 692 | 97.543 | 33.323 | -1.324 | 1.00 | 17.37 |
| ATOM | 718 | CB | GLU | A | 692 | 96.392 | 33.536 | -0.344 | 1.00 | 17.79 |
| ATOM | 719 | CG | GLU | A | 692 | 95.356 | 34.556 | -0.778 | 1.00 | 22.24 |
| ATOM | 720 | CD | GLU | A | 692 | 94.078 | 34.471 | 0.046 | 1.00 | 25.41 |
| ATOM | 721 | OE1 | GLU | A | 692 | 93.766 | 33.380 | 0.577 | 1.00 | 27.06 |
| ATOM | 722 | OE2 | GLU | A | 692 | 93.375 | 35.496 | 0.160 | 1.00 | 27.08 |
| ATOM | 723 | C | GLU | A | 692 | 98.609 | 32.497 | -0.626 | 1.00 | 16.87 |
| ATOM | 724 | O | GLU | A | 692 | 98.535 | 31.264 | -0.601 | 1.00 | 18.30 |
| ATOM | 725 | N | TYR | A | 693 | 99.595 | 33.186 | -0.066 | 1.00 | 15.92 |
| ATOM | 726 | CA | TYR | A | 693 | 100.628 | 32.556 | 0.741 | 1.00 | 14.39 |
| ATOM | 727 | CB | TYR | A | 693 | 101.977 | 33.217 | 0.459 | 1.00 | 12.34 |
| ATOM | 728 | CG | TYR | A | 693 | 103.140 | 32.623 | 1.210 | 1.00 | 12.75 |
| ATOM | 729 | CD1 | TYR | A | 693 | 103.813 | 33.367 | 2.188 | 1.00 | 11.67 |
| ATOM | 730 | CE1 | TYR | A | 693 | 104.888 | 32.836 | 2.879 | 1.00 | 10.92 |
| ATOM | 731 | CZ | TYR | A | 693 | 105.305 | 31.543 | 2.611 | 1.00 | 12.71 |
| ATOM | 732 | OH | TYR | A | 693 | 106.374 | 31.019 | 3.308 | 1.00 | 14.95 |
| ATOM | 733 | CE2 | TYR | A | 693 | 104.658 | 30.777 | 1.644 | 1.00 | 11.51 |
| ATOM | 734 | CD2 | TYR | A | 693 | 103.582 | 31.323 | 0.945 | 1.00 | 11.20 |
| ATOM | 735 | C | TYR | A | 693 | 100.274 | 32.650 | 2.228 | 1.00 | 14.68 |
| ATOM | 736 | O | TYR | A | 693 | 99.843 | 33.697 | 2.720 | 1.00 | 14.73 |
| ATOM | 737 | N | CYS | A | 694 | 100.442 | 31.540 | 2.933 | 1.00 | 14.52 |
| ATOM | 738 | CA | CYS | A | 694 | 100.217 | 31.497 | 4.371 | 1.00 | 12.60 |
| ATOM | 739 | CB | CYS | A | 694 | 99.112 | 30.494 | 4.716 | 1.00 | 12.69 |
| ATOM | 740 | SG | CYS | A | 694 | 97.593 | 30.641 | 3.735 | 1.00 | 15.41 |
| ATOM | 741 | C | CYS | A | 694 | 101.538 | 31.103 | 5.004 | 1.00 | 12.79 |
| ATOM | 742 | O | CYS | A | 694 | 101.985 | 29.968 | 4.868 | 1.00 | 14.61 |
| ATOM | 743 | N | CYS | A | 695 | 102.168 | 32.044 | 5.692 | 1.00 | 12.66 |
| ATOM | 744 | CA | CYS | A | 695 | 103.581 | 31.900 | 6.024 | 1.00 | 14.08 |
| ATOM | 745 | CB | CYS | A | 695 | 104.153 | 33.228 | 6.514 | 1.00 | 14.77 |
| ATOM | 746 | SG | CYS | A | 695 | 103.260 | 33.952 | 7.898 | 1.00 | 18.02 |
| ATOM | 747 | C | CYS | A | 695 | 103.909 | 30.786 | 7.012 | 1.00 | 13.33 |
| ATOM | 748 | O | CYS | A | 695 | 105.031 | 30.280 | 7.031 | 1.00 | 14.03 |
| ATOM | 749 | N | TYR | A | 696 | 102.940 | 30.401 | 7.828 | 1.00 | 13.17 |
| ATOM | 750 | CA | TYR | A | 696 | 103.198 | 29.403 | 8.855 | 1.00 | 14.08 |
| ATOM | 751 | CB | TYR | A | 696 | 102.340 | 29.679 | 10.083 | 1.00 | 14.61 |
| ATOM | 752 | CG | TYR | A | 696 | 102.797 | 30.875 | 10.872 | 1.00 | 16.01 |
| ATOM | 753 | CD1 | TYR | A | 696 | 104.125 | 31.001 | 11.278 | 1.00 | 17.33 |
| ATOM | 754 | CE1 | TYR | A | 696 | 104.549 | 32.103 | 12.016 | 1.00 | 18.08 |
| ATOM | 755 | CZ | TYR | A | 696 | 103.637 | 33.092 | 12.350 | 1.00 | 17.84 |
| ATOM | 756 | OH | TYR | A | 696 | 104.047 | 34.182 | 13.078 | 1.00 | 19.09 |
| ATOM | 757 | CE2 | TYR | A | 696 | 102.314 | 32.989 | 11.958 | 1.00 | 17.68 |
| ATOM | 758 | CD2 | TYR | A | 696 | 101.901 | 31.882 | 11.221 | 1.00 | 17.35 |
| ATOM | 759 | C | TYR | A | 696 | 103.025 | 27.966 | 8.362 | 1.00 | 13.00 |
| ATOM | 760 | O | TYR | A | 696 | 103.240 | 27.010 | 9.115 | 1.00 | 15.03 |
| ATOM | 761 | N | GLY | A | 697 | 102.651 | 27.820 | 7.096 | 1.00 | 10.63 |
| ATOM | 762 | CA | GLY | A | 697 | 102.513 | 26.516 | 6.489 | 1.00 | 11.37 |
| ATOM | 763 | C | GLY | A | 697 | 101.280 | 25.796 | 6.982 | 1.00 | 12.51 |
| ATOM | 764 | O | GLY | A | 697 | 100.328 | 26.426 | 7.451 | 1.00 | 14.55 |
| ATOM | 765 | N | ASP | A | 698 | 101.290 | 24.472 | 6.885 | 1.00 | 11.85 |
| ATOM | 766 | CA | ASP | A | 698 | 100.090 | 23.721 | 7.212 | 1.00 | 12.64 |

FIGURE 3AP

|       | A   | B   | C    | D | E   | F       | G      | H      | I    | J     |
|-------|-----|-----|------|---|-----|---------|--------|--------|------|-------|
| ATOM  | 767 | CB  | ASP  | A | 698 | 100.076 | 22.333 | 6.555  | 1.00 | 14.34 |
| ATOM  | 768 | CG  | ASP  | A | 698 | 101.166 | 21.429 | 7.069  | 1.00 | 17.16 |
| ATOM  | 769 | OD1 | ASP  | A | 698 | 102.204 | 21.333 | 6.397  | 1.00 | 21.70 |
| ATOM  | 770 | OD2 | ASP  | A | 698 | 101.087 | 20.775 | 8.130  | 1.00 | 18.35 |
| ATOM  | 771 | C   | ASP  | A | 698 | 99.873  | 23.652 | 8.714  | 1.00 | 11.99 |
| ATOM  | 772 | O   | ASP  | A | 698 | 100.828 | 23.645 | 9.505  | 1.00 | 11.14 |
| ATOM  | 773 | N   | LEU  | A | 699 | 98.599  | 23.608 | 9.087  | 1.00 | 13.90 |
| ATOM  | 774 | CA  | LEU  | A | 699 | 98.184  | 23.597 | 10.477 | 1.00 | 12.04 |
| ATOM  | 775 | CB  | LEU  | A | 699 | 96.661  | 23.515 | 10.566 | 1.00 | 9.71  |
| ATOM  | 776 | CG  | LEU  | A | 699 | 96.037  | 23.428 | 11.962 | 1.00 | 10.18 |
| ATOM  | 777 | CD1 | LEU  | A | 699 | 96.306  | 24.700 | 12.761 | 1.00 | 8.08  |
| ATOM  | 778 | CD2 | LEU  | A | 699 | 94.531  | 23.133 | 11.868 | 1.00 | 9.36  |
| ATOM  | 779 | C   | LEU  | A | 699 | 98.853  | 22.476 | 11.264 | 1.00 | 11.80 |
| ATOM  | 780 | O   | LEU  | A | 699 | 99.284  | 22.695 | 12.394 | 1.00 | 11.61 |
| ATOM  | 781 | N   | LEU  | A | 700 | 98.961  | 21.293 | 10.659 | 1.00 | 13.82 |
| ATOM  | 782 | CA  | LEU  | A | 700 | 99.583  | 20.137 | 11.327 | 1.00 | 17.84 |
| ATOM  | 783 | CB  | LEU  | A | 700 | 99.571  | 18.885 | 10.435 | 1.00 | 18.78 |
| ATOM  | 784 | CG  | LEU  | A | 700 | 100.146 | 17.622 | 11.089 | 1.00 | 19.90 |
| ATOM  | 785 | CD1 | LEU  | A | 700 | 99.277  | 17.179 | 12.252 | 1.00 | 18.63 |
| ATOM  | 786 | CD2 | LEU  | A | 700 | 100.313 | 16.495 | 10.074 | 1.00 | 20.74 |
| ATOM  | 787 | C   | LEU  | A | 700 | 101.008 | 20.427 | 11.789 | 1.00 | 17.86 |
| ATOM  | 788 | O   | LEU  | A | 700 | 101.344 | 20.245 | 12.967 | 1.00 | 17.92 |
| ATOM  | 789 | N   | ASN  | A | 701 | 101.834 | 20.885 | 10.856 | 1.00 | 17.57 |
| ATOM  | 790 | CA  | ASN  | A | 701 | 103.196 | 21.264 | 11.169 | 1.00 | 18.03 |
| ATOM  | 791 | CB  | BASN | A | 701 | 103.919 | 21.662 | 9.872  | 0.35 | 17.23 |
| ATOM  | 792 | CB  | AASN | A | 701 | 103.985 | 21.586 | 9.903  | 0.65 | 22.78 |
| ATOM  | 793 | CG  | BASN | A | 701 | 105.274 | 22.319 | 10.114 | 0.35 | 15.93 |
| ATOM  | 794 | CG  | AASN | A | 701 | 104.592 | 20.347 | 9.272  | 0.65 | 25.88 |
| ATOM  | 795 | OD1 | BASN | A | 701 | 105.390 | 23.546 | 10.154 | 0.35 | 14.68 |
| ATOM  | 796 | OD1 | AASN | A | 701 | 104.221 | 19.952 | 8.161  | 0.65 | 27.09 |
| ATOM  | 797 | ND2 | BASN | A | 701 | 106.305 | 21.501 | 10.250 | 0.35 | 16.33 |
| ATOM  | 798 | ND2 | AASN | A | 701 | 105.526 | 19.718 | 9.984  | 0.65 | 27.10 |
| ATOM  | 799 | C   | ASN  | A | 701 | 103.224 | 22.410 | 12.175 | 1.00 | 17.67 |
| ATOM  | 800 | O   | ASN  | A | 701 | 104.018 | 22.390 | 13.122 | 1.00 | 19.80 |
| ATOM  | 801 | N   | TYR  | A | 702 | 102.337 | 23.386 | 11.982 | 1.00 | 14.72 |
| ATOM  | 802 | CA  | TYR  | A | 702 | 102.218 | 24.522 | 12.888 | 1.00 | 11.75 |
| ATOM  | 803 | CB  | TYR  | A | 702 | 101.114 | 25.463 | 12.415 | 1.00 | 10.86 |
| ATOM  | 804 | CG  | TYR  | A | 702 | 100.946 | 26.673 | 13.296 | 1.00 | 12.60 |
| ATOM  | 805 | CD1 | TYR  | A | 702 | 99.964  | 26.705 | 14.294 | 1.00 | 12.34 |
| ATOM  | 806 | CE1 | TYR  | A | 702 | 99.814  | 27.825 | 15.118 | 1.00 | 12.51 |
| ATOM  | 807 | CZ  | TYR  | A | 702 | 100.646 | 28.915 | 14.939 | 1.00 | 13.58 |
| ATOM  | 808 | OH  | TYR  | A | 702 | 100.499 | 30.018 | 15.749 | 1.00 | 17.74 |
| ATOM  | 809 | CE2 | TYR  | A | 702 | 101.635 | 28.905 | 13.959 | 1.00 | 12.09 |
| ATOM  | 810 | CD2 | TYR  | A | 702 | 101.780 | 27.790 | 13.146 | 1.00 | 11.40 |
| ATOM  | 811 | C   | TYR  | A | 702 | 101.941 | 24.081 | 14.326 | 1.00 | 11.78 |
| ATOM  | 812 | O   | TYR  | A | 702 | 102.649 | 24.478 | 15.249 | 1.00 | 10.10 |
| ATOM  | 813 | N   | LEU  | A | 703 | 100.911 | 23.257 | 14.500 | 1.00 | 11.52 |
| ATOM  | 814 | CA  | LEU  | A | 703 | 100.538 | 22.749 | 15.814 | 1.00 | 12.23 |
| ATOM  | 815 | CB  | LEU  | A | 703 | 99.310  | 21.835 | 15.711 | 1.00 | 11.51 |
| ATOM  | 816 | CG  | LEU  | A | 703 | 97.949  | 22.458 | 15.374 | 1.00 | 10.86 |
| ATOM  | 817 | CD1 | LEU  | A | 703 | 96.952  | 21.358 | 15.005 | 1.00 | 10.63 |
| ATOM  | 818 | CD2 | LEU  | A | 703 | 97.407  | 23.304 | 16.524 | 1.00 | 9.94  |

FIGURE 3AQ

|      | A   | B   | C   | D | E   | F       | G      | H      | I    | J     |
|------|-----|-----|-----|---|-----|---------|--------|--------|------|-------|
| ATOM | 819 | C   | LEU | A | 703 | 101.694 | 22.011 | 16.484 | 1.00 | 12.72 |
| ATOM | 820 | O   | LEU | A | 703 | 101.935 | 22.193 | 17.672 | 1.00 | 14.10 |
| ATOM | 821 | N   | ARG | A | 704 | 102.413 | 21.196 | 15.712 | 1.00 | 13.91 |
| ATOM | 822 | CA  | ARG | A | 704 | 103.547 | 20.425 | 16.224 | 1.00 | 14.88 |
| ATOM | 823 | CB  | ARG | A | 704 | 104.018 | 19.407 | 15.184 | 1.00 | 14.60 |
| ATOM | 824 | CG  | ARG | A | 704 | 103.105 | 18.195 | 15.058 | 1.00 | 15.38 |
| ATOM | 825 | CD  | ARG | A | 704 | 103.457 | 17.261 | 13.922 | 1.00 | 14.57 |
| ATOM | 826 | NE  | ARG | A | 704 | 102.538 | 16.132 | 13.894 | 1.00 | 17.43 |
| ATOM | 827 | CZ  | ARG | A | 704 | 102.639 | 15.076 | 13.090 | 1.00 | 17.76 |
| ATOM | 828 | NH1 | ARG | A | 704 | 101.730 | 14.113 | 13.164 | 1.00 | 16.50 |
| ATOM | 829 | NH2 | ARG | A | 704 | 103.632 | 14.974 | 12.215 | 1.00 | 17.65 |
| ATOM | 830 | C   | ARG | A | 704 | 104.717 | 21.307 | 16.663 | 1.00 | 16.11 |
| ATOM | 831 | O   | ARG | A | 704 | 105.404 | 20.990 | 17.629 | 1.00 | 17.40 |
| ATOM | 832 | N   | SER | A | 705 | 104.942 | 22.404 | 15.946 | 1.00 | 15.71 |
| ATOM | 833 | CA  | SER | A | 705 | 106.006 | 23.343 | 16.284 | 1.00 | 16.67 |
| ATOM | 834 | CB  | SER | A | 705 | 106.329 | 24.250 | 15.093 | 1.00 | 16.67 |
| ATOM | 835 | OG  | SER | A | 705 | 105.282 | 25.177 | 14.869 | 1.00 | 19.70 |
| ATOM | 836 | C   | SER | A | 705 | 105.666 | 24.191 | 17.509 | 1.00 | 17.09 |
| ATOM | 837 | O   | SER | A | 705 | 106.557 | 24.795 | 18.104 | 1.00 | 18.27 |
| ATOM | 838 | N   | LYS | A | 706 | 104.386 | 24.221 | 17.880 | 1.00 | 17.19 |
| ATOM | 839 | CA  | LYS | A | 706 | 103.901 | 25.009 | 19.014 | 1.00 | 17.90 |
| ATOM | 840 | CB  | LYS | A | 706 | 102.567 | 25.683 | 18.665 | 1.00 | 17.48 |
| ATOM | 841 | CG  | LYS | A | 706 | 102.644 | 26.755 | 17.591 | 1.00 | 17.52 |
| ATOM | 842 | CD  | LYS | A | 706 | 103.852 | 27.655 | 17.759 | 1.00 | 16.26 |
| ATOM | 843 | CE  | LYS | A | 706 | 103.503 | 29.079 | 17.424 | 1.00 | 16.92 |
| ATOM | 844 | NZ  | LYS | A | 706 | 104.661 | 29.985 | 17.699 | 1.00 | 20.41 |
| ATOM | 845 | C   | LYS | A | 706 | 103.727 | 24.193 | 20.295 | 1.00 | 19.22 |
| ATOM | 846 | O   | LYS | A | 706 | 103.432 | 24.747 | 21.353 | 1.00 | 20.73 |
| ATOM | 847 | N   | ARG | A | 707 | 103.901 | 22.879 | 20.191 | 1.00 | 21.27 |
| ATOM | 848 | CA  | ARG | A | 707 | 103.702 | 21.964 | 21.314 | 1.00 | 23.57 |
| ATOM | 849 | CB  | ARG | A | 707 | 104.122 | 20.554 | 20.908 | 1.00 | 22.51 |
| ATOM | 850 | CG  | ARG | A | 707 | 102.982 | 19.609 | 20.784 | 1.00 | 20.69 |
| ATOM | 851 | CD  | ARG | A | 707 | 103.388 | 18.191 | 20.508 | 1.00 | 20.45 |
| ATOM | 852 | NE  | ARG | A | 707 | 102.554 | 17.602 | 19.463 | 1.00 | 20.10 |
| ATOM | 853 | CZ  | ARG | A | 707 | 102.862 | 16.499 | 18.802 | 1.00 | 20.62 |
| ATOM | 854 | NH1 | ARG | A | 707 | 102.048 | 16.043 | 17.857 | 1.00 | 19.44 |
| ATOM | 855 | NH2 | ARG | A | 707 | 103.990 | 15.850 | 19.080 | 1.00 | 20.62 |
| ATOM | 856 | C   | ARG | A | 707 | 104.443 | 22.369 | 22.589 | 1.00 | 26.41 |
| ATOM | 857 | O   | ARG | A | 707 | 103.842 | 22.472 | 23.658 | 1.00 | 28.29 |
| ATOM | 858 | N   | GLU | A | 708 | 105.746 | 22.607 | 22.464 | 1.00 | 29.71 |
| ATOM | 859 | CA  | GLU | A | 708 | 106.600 | 22.896 | 23.611 | 1.00 | 31.81 |
| ATOM | 860 | CB  | GLU | A | 708 | 108.070 | 22.606 | 23.269 | 1.00 | 36.37 |
| ATOM | 861 | CG  | GLU | A | 708 | 108.465 | 21.134 | 23.344 | 1.00 | 41.46 |
| ATOM | 862 | CD  | GLU | A | 708 | 108.312 | 20.401 | 22.013 | 1.00 | 44.70 |
| ATOM | 863 | OE1 | GLU | A | 708 | 109.173 | 20.599 | 21.124 | 1.00 | 45.87 |
| ATOM | 864 | OE2 | GLU | A | 708 | 107.338 | 19.621 | 21.851 | 1.00 | 45.06 |
| ATOM | 865 | C   | GLU | A | 708 | 106.428 | 24.333 | 24.106 | 1.00 | 30.78 |
| ATOM | 866 | O   | GLU | A | 708 | 107.089 | 24.752 | 25.051 | 1.00 | 32.20 |
| ATOM | 867 | N   | LYS | A | 709 | 105.542 | 25.088 | 23.467 | 1.00 | 29.54 |
| ATOM | 868 | CA  | LYS | A | 709 | 105.249 | 26.452 | 23.904 | 1.00 | 29.10 |
| ATOM | 869 | CB  | LYS | A | 709 | 106.094 | 27.491 | 23.136 | 1.00 | 32.20 |
| ATOM | 870 | CG  | LYS | A | 709 | 105.992 | 27.422 | 21.604 | 1.00 | 35.56 |

FIGURE 3AR

|      | A    | B   | C   | D | E   | F       | G      | H      | I    | J     |
|------|------|-----|-----|---|-----|---------|--------|--------|------|-------|
| ATOM | 871  | CD  | LYS | A | 709 | 106.320 | 28.769 | 20.953 | 1.00 | 38.03 |
| ATOM | 872  | CE  | LYS | A | 709 | 107.530 | 28.676 | 20.020 | 1.00 | 39.13 |
| ATOM | 873  | NZ  | LYS | A | 709 | 107.147 | 28.365 | 18.606 | 1.00 | 38.61 |
| ATOM | 874  | C   | LYS | A | 709 | 103.750 | 26.744 | 23.827 | 1.00 | 26.31 |
| ATOM | 875  | O   | LYS | A | 709 | 103.322 | 27.828 | 23.423 | 1.00 | 28.47 |
| ATOM | 876  | N   | PHE | A | 710 | 102.954 | 25.752 | 24.207 | 1.00 | 22.11 |
| ATOM | 877  | CA  | PHE | A | 710 | 101.520 | 25.934 | 24.346 | 1.00 | 19.08 |
| ATOM | 878  | CB  | PHE | A | 710 | 100.778 | 24.641 | 24.030 | 1.00 | 16.76 |
| ATOM | 879  | CG  | PHE | A | 710 | 99.294  | 24.735 | 24.230 | 1.00 | 14.88 |
| ATOM | 880  | CD1 | PHE | A | 710 | 98.720  | 24.404 | 25.459 | 1.00 | 13.04 |
| ATOM | 881  | CE1 | PHE | A | 710 | 97.350  | 24.503 | 25.652 | 1.00 | 12.55 |
| ATOM | 882  | CZ  | PHE | A | 710 | 96.531  | 24.932 | 24.604 | 1.00 | 11.50 |
| ATOM | 883  | CE2 | PHE | A | 710 | 97.094  | 25.269 | 23.380 | 1.00 | 12.34 |
| ATOM | 884  | CD2 | PHE | A | 710 | 98.470  | 25.178 | 23.198 | 1.00 | 13.03 |
| ATOM | 885  | C   | PHE | A | 710 | 101.179 | 26.394 | 25.759 | 1.00 | 19.99 |
| ATOM | 886  | O   | PHE | A | 710 | 101.717 | 25.878 | 26.743 | 1.00 | 19.72 |
| ATOM | 887  | N   | HIS | A | 711 | 100.270 | 27.356 | 25.843 | 1.00 | 20.50 |
| ATOM | 888  | CA  | HIS | A | 711 | 99.849  | 27.947 | 27.105 | 1.00 | 23.09 |
| ATOM | 889  | CB  | HIS | A | 711 | 100.408 | 29.368 | 27.212 | 1.00 | 25.54 |
| ATOM | 890  | CG  | HIS | A | 711 | 100.084 | 30.073 | 28.493 | 1.00 | 28.97 |
| ATOM | 891  | ND1 | HIS | A | 711 | 99.361  | 31.248 | 28.529 | 1.00 | 29.44 |
| ATOM | 892  | CE1 | HIS | A | 711 | 99.248  | 31.654 | 29.782 | 1.00 | 30.42 |
| ATOM | 893  | NE2 | HIS | A | 711 | 99.881  | 30.793 | 30.559 | 1.00 | 30.83 |
| ATOM | 894  | CD2 | HIS | A | 711 | 100.420 | 29.798 | 29.777 | 1.00 | 30.91 |
| ATOM | 895  | C   | HIS | A | 711 | 98.336  | 27.952 | 27.059 | 1.00 | 23.26 |
| ATOM | 896  | O   | HIS | A | 711 | 97.750  | 28.331 | 26.053 | 1.00 | 24.79 |
| ATOM | 897  | N   | ARG | A | 712 | 97.700  | 27.508 | 28.135 | 1.00 | 23.25 |
| ATOM | 898  | CA  | ARG | A | 712 | 96.253  | 27.380 | 28.149 | 1.00 | 22.04 |
| ATOM | 899  | CB  | ARG | A | 712 | 95.795  | 26.574 | 29.361 | 1.00 | 22.17 |
| ATOM | 900  | CG  | ARG | A | 712 | 94.388  | 26.036 | 29.215 | 1.00 | 23.89 |
| ATOM | 901  | CD  | ARG | A | 712 | 93.807  | 25.496 | 30.485 | 1.00 | 24.73 |
| ATOM | 902  | NE  | ARG | A | 712 | 93.755  | 26.522 | 31.511 | 1.00 | 27.95 |
| ATOM | 903  | CZ  | ARG | A | 712 | 92.875  | 26.546 | 32.497 | 1.00 | 29.65 |
| ATOM | 904  | NH1 | ARG | A | 712 | 92.914  | 27.538 | 33.386 | 1.00 | 29.11 |
| ATOM | 905  | NH2 | ARG | A | 712 | 91.960  | 25.582 | 32.597 | 1.00 | 29.21 |
| ATOM | 906  | C   | ARG | A | 712 | 95.531  | 28.727 | 28.082 | 1.00 | 22.36 |
| ATOM | 907  | O   | ARG | A | 712 | 94.794  | 28.986 | 27.131 | 1.00 | 23.88 |
| ATOM | 908  | N   | THR | A | 713 | 95.743  | 29.577 | 29.083 | 1.00 | 23.40 |
| ATOM | 909  | CA  | THR | A | 713 | 95.044  | 30.857 | 29.163 | 1.00 | 24.75 |
| ATOM | 910  | CB  | THR | A | 713 | 95.003  | 31.378 | 30.619 | 1.00 | 24.42 |
| ATOM | 911  | OG1 | THR | A | 713 | 96.336  | 31.604 | 31.090 | 1.00 | 23.73 |
| ATOM | 912  | CG2 | THR | A | 713 | 94.466  | 30.309 | 31.564 | 1.00 | 25.37 |
| ATOM | 913  | C   | THR | A | 713 | 95.684  | 31.892 | 28.242 | 1.00 | 26.24 |
| ATOM | 914  | O   | THR | A | 713 | 96.785  | 31.678 | 27.736 | 1.00 | 25.99 |
| ATOM | 915  | N   | ALA | A | 776 | 94.980  | 33.005 | 28.033 | 1.00 | 29.23 |
| ATOM | 916  | CA  | ALA | A | 776 | 95.470  | 34.137 | 27.240 | 1.00 | 31.98 |
| ATOM | 917  | CB  | ALA | A | 776 | 94.496  | 35.307 | 27.338 | 1.00 | 31.39 |
| ATOM | 918  | C   | ALA | A | 776 | 96.872  | 34.591 | 27.637 | 1.00 | 34.00 |
| ATOM | 919  | O   | ALA | A | 776 | 97.199  | 34.662 | 28.827 | 1.00 | 34.79 |
| ATOM | 920  | N   | SER | A | 777 | 97.694  | 34.895 | 26.634 | 1.00 | 37.31 |
| ATOM | 921  | CA  | SER | A | 777 | 99.034  | 35.441 | 26.868 | 1.00 | 41.08 |
| ATOM | 922  | CB  | SER | A | 777 | 100.107 | 34.370 | 26.641 | 1.00 | 41.03 |

FIGURE 3AS

| | A | B | C | D | E | F | G | H | I | J |
|---|---|---|---|---|---|---|---|---|---|---|
| ATOM | 923 | OG | SER | A | 777 | 101.165 | 34.503 | 27.580 | 1.00 | 40.97 |
| ATOM | 924 | C | SER | A | 777 | 99.324 | 36.671 | 26.004 | 1.00 | 42.87 |
| ATOM | 925 | O | SER | A | 777 | 98.849 | 36.769 | 24.871 | 1.00 | 43.01 |
| ATOM | 926 | N | GLU | A | 778 | 100.104 | 37.603 | 26.551 | 1.00 | 45.95 |
| ATOM | 927 | CA | GLU | A | 778 | 100.546 | 38.794 | 25.817 | 1.00 | 48.58 |
| ATOM | 928 | CB | GLU | A | 778 | 101.326 | 39.737 | 26.745 | 1.00 | 49.56 |
| ATOM | 929 | CG | GLU | A | 778 | 101.757 | 41.053 | 26.106 | 1.00 | 51.69 |
| ATOM | 930 | CD | GLU | A | 778 | 101.119 | 42.275 | 26.750 | 1.00 | 52.34 |
| ATOM | 931 | OE1 | GLU | A | 778 | 99.918 | 42.527 | 26.501 | 1.00 | 53.07 |
| ATOM | 932 | OE2 | GLU | A | 778 | 101.820 | 42.992 | 27.497 | 1.00 | 52.01 |
| ATOM | 933 | C | GLU | A | 778 | 101.386 | 38.417 | 24.586 | 1.00 | 49.07 |
| ATOM | 934 | O | GLU | A | 778 | 101.311 | 39.079 | 23.544 | 1.00 | 49.30 |
| ATOM | 935 | N | ASP | A | 779 | 102.166 | 37.344 | 24.724 | 1.00 | 48.91 |
| ATOM | 936 | CA | ASP | A | 779 | 103.022 | 36.812 | 23.661 | 1.00 | 47.73 |
| ATOM | 937 | CB | ASP | A | 779 | 103.951 | 35.734 | 24.240 | 1.00 | 47.66 |
| ATOM | 938 | CG | ASP | A | 779 | 105.150 | 35.433 | 23.348 | 1.00 | 47.17 |
| ATOM | 939 | OD1 | ASP | A | 779 | 105.076 | 35.648 | 22.118 | 1.00 | 46.68 |
| ATOM | 940 | OD2 | ASP | A | 779 | 106.213 | 34.957 | 23.801 | 1.00 | 46.45 |
| ATOM | 941 | C | ASP | A | 779 | 102.197 | 36.228 | 22.515 | 1.00 | 46.47 |
| ATOM | 942 | O | ASP | A | 779 | 101.323 | 35.387 | 22.734 | 1.00 | 47.63 |
| ATOM | 943 | N | LEU | A | 780 | 102.490 | 36.676 | 21.295 | 1.00 | 45.06 |
| ATOM | 944 | CA | LEU | A | 780 | 101.786 | 36.210 | 20.096 | 1.00 | 43.23 |
| ATOM | 945 | CB | LEU | A | 780 | 101.745 | 37.309 | 19.025 | 1.00 | 43.81 |
| ATOM | 946 | CG | LEU | A | 780 | 101.118 | 38.651 | 19.435 | 1.00 | 44.21 |
| ATOM | 947 | CD1 | LEU | A | 780 | 102.192 | 39.716 | 19.681 | 1.00 | 43.89 |
| ATOM | 948 | CD2 | LEU | A | 780 | 100.103 | 39.132 | 18.400 | 1.00 | 43.61 |
| ATOM | 949 | C | LEU | A | 780 | 102.386 | 34.912 | 19.534 | 1.00 | 40.62 |
| ATOM | 950 | O | LEU | A | 780 | 101.743 | 34.216 | 18.744 | 1.00 | 39.68 |
| ATOM | 951 | N | ASN | A | 781 | 103.614 | 34.598 | 19.955 | 1.00 | 38.34 |
| ATOM | 952 | CA | ASN | A | 781 | 104.270 | 33.328 | 19.619 | 1.00 | 35.20 |
| ATOM | 953 | CB | ASN | A | 781 | 105.785 | 33.416 | 19.836 | 1.00 | 36.60 |
| ATOM | 954 | CG | ASN | A | 781 | 106.573 | 33.355 | 18.533 | 1.00 | 38.62 |
| ATOM | 955 | OD1 | ASN | A | 781 | 106.068 | 32.915 | 17.494 | 1.00 | 39.55 |
| ATOM | 956 | ND2 | ASN | A | 781 | 107.822 | 33.803 | 18.585 | 1.00 | 38.72 |
| ATOM | 957 | C | ASN | A | 781 | 103.708 | 32.152 | 20.414 | 1.00 | 30.80 |
| ATOM | 958 | O | ASN | A | 781 | 103.870 | 30.988 | 20.031 | 1.00 | 30.83 |
| ATOM | 959 | N | VAL | A | 782 | 103.056 | 32.464 | 21.528 | 1.00 | 24.13 |
| ATOM | 960 | CA | VAL | A | 782 | 102.415 | 31.449 | 22.349 | 1.00 | 18.56 |
| ATOM | 961 | CB | VAL | A | 782 | 102.215 | 31.965 | 23.800 | 1.00 | 17.76 |
| ATOM | 962 | CG1 | VAL | A | 782 | 101.255 | 31.097 | 24.571 | 1.00 | 16.14 |
| ATOM | 963 | CG2 | VAL | A | 782 | 103.553 | 32.039 | 24.528 | 1.00 | 18.46 |
| ATOM | 964 | C | VAL | A | 782 | 101.090 | 31.017 | 21.709 | 1.00 | 14.18 |
| ATOM | 965 | O | VAL | A | 782 | 100.271 | 31.853 | 21.340 | 1.00 | 12.32 |
| ATOM | 966 | N | LEU | A | 783 | 100.910 | 29.709 | 21.556 | 1.00 | 12.03 |
| ATOM | 967 | CA | LEU | A | 783 | 99.623 | 29.147 | 21.173 | 1.00 | 10.85 |
| ATOM | 968 | CB | LEU | A | 783 | 99.804 | 27.827 | 20.415 | 1.00 | 8.86 |
| ATOM | 969 | CG | LEU | A | 783 | 98.595 | 27.262 | 19.655 | 1.00 | 10.07 |
| ATOM | 970 | CD1 | LEU | A | 783 | 98.151 | 28.168 | 18.527 | 1.00 | 9.78 |
| ATOM | 971 | CD2 | LEU | A | 783 | 98.883 | 25.871 | 19.109 | 1.00 | 10.97 |
| ATOM | 972 | C | LEU | A | 783 | 98.799 | 28.945 | 22.436 | 1.00 | 11.95 |
| ATOM | 973 | O | LEU | A | 783 | 99.323 | 28.489 | 23.459 | 1.00 | 14.22 |
| ATOM | 974 | N | THR | A | 784 | 97.516 | 29.301 | 22.368 | 1.00 | 10.86 |

FIGURE 3AT

|  | A | B | C | D | E | F | G | H | I | J |
|---|---|---|---|---|---|---|---|---|---|---|
| ATOM | 975 | CA | THR | A | 784 | 96.624 | 29.218 | 23.523 | 1.00 | 9.00 |
| ATOM | 976 | CB | THR | A | 784 | 96.145 | 30.618 | 23.979 | 1.00 | 9.96 |
| ATOM | 977 | OG1 | THR | A | 784 | 95.276 | 31.179 | 22.982 | 1.00 | 9.43 |
| ATOM | 978 | CG2 | THR | A | 784 | 97.316 | 31.616 | 24.092 | 1.00 | 5.75 |
| ATOM | 979 | C | THR | A | 784 | 95.417 | 28.371 | 23.201 | 1.00 | 10.79 |
| ATOM | 980 | O | THR | A | 784 | 95.179 | 28.035 | 22.041 | 1.00 | 12.29 |
| ATOM | 981 | N | PHE | A | 785 | 94.650 | 28.035 | 24.233 | 1.00 | 10.88 |
| ATOM | 982 | CA | PHE | A | 785 | 93.410 | 27.302 | 24.044 | 1.00 | 10.39 |
| ATOM | 983 | CB | PHE | A | 785 | 92.758 | 26.966 | 25.383 | 1.00 | 11.22 |
| ATOM | 984 | CG | PHE | A | 785 | 91.488 | 26.189 | 25.237 | 1.00 | 11.86 |
| ATOM | 985 | CD1 | PHE | A | 785 | 91.525 | 24.844 | 24.879 | 1.00 | 9.98 |
| ATOM | 986 | CE1 | PHE | A | 785 | 90.346 | 24.111 | 24.726 | 1.00 | 11.84 |
| ATOM | 987 | CZ | PHE | A | 785 | 89.120 | 24.731 | 24.917 | 1.00 | 12.82 |
| ATOM | 988 | CE2 | PHE | A | 785 | 89.073 | 26.086 | 25.270 | 1.00 | 13.80 |
| ATOM | 989 | CD2 | PHE | A | 785 | 90.254 | 26.806 | 25.426 | 1.00 | 12.23 |
| ATOM | 990 | C | PHE | A | 785 | 92.417 | 28.056 | 23.171 | 1.00 | 10.29 |
| ATOM | 991 | O | PHE | A | 785 | 91.769 | 27.467 | 22.306 | 1.00 | 11.46 |
| ATOM | 992 | N | GLU | A | 786 | 92.296 | 29.354 | 23.419 | 1.00 | 12.56 |
| ATOM | 993 | CA | GLU | A | 786 | 91.460 | 30.242 | 22.625 | 1.00 | 16.29 |
| ATOM | 994 | CB | GLU | A | 786 | 91.578 | 31.681 | 23.155 | 1.00 | 21.67 |
| ATOM | 995 | CG | GLU | A | 786 | 90.623 | 32.694 | 22.531 | 1.00 | 29.22 |
| ATOM | 996 | CD | GLU | A | 786 | 89.191 | 32.184 | 22.431 | 1.00 | 33.88 |
| ATOM | 997 | OE1 | GLU | A | 786 | 88.718 | 31.937 | 21.286 | 1.00 | 34.36 |
| ATOM | 998 | OE2 | GLU | A | 786 | 88.541 | 32.031 | 23.499 | 1.00 | 35.94 |
| ATOM | 999 | C | GLU | A | 786 | 91.853 | 30.167 | 21.150 | 1.00 | 14.81 |
| ATOM | 1000 | O | GLU | A | 786 | 90.995 | 30.202 | 20.274 | 1.00 | 15.02 |
| ATOM | 1001 | N | ASP | A | 787 | 93.150 | 30.047 | 20.883 | 1.00 | 14.25 |
| ATOM | 1002 | CA | ASP | A | 787 | 93.641 | 29.894 | 19.516 | 1.00 | 13.54 |
| ATOM | 1003 | CB | ASP | A | 787 | 95.173 | 29.925 | 19.471 | 1.00 | 13.09 |
| ATOM | 1004 | CG | ASP | A | 787 | 95.733 | 31.279 | 19.844 | 1.00 | 15.27 |
| ATOM | 1005 | OD1 | ASP | A | 787 | 96.839 | 31.341 | 20.432 | 1.00 | 15.21 |
| ATOM | 1006 | OD2 | ASP | A | 787 | 95.126 | 32.344 | 19.601 | 1.00 | 16.23 |
| ATOM | 1007 | C | ASP | A | 787 | 93.109 | 28.619 | 18.888 | 1.00 | 12.55 |
| ATOM | 1008 | O | ASP | A | 787 | 92.663 | 28.623 | 17.738 | 1.00 | 13.74 |
| ATOM | 1009 | N | LEU | A | 788 | 93.140 | 27.529 | 19.647 | 1.00 | 10.69 |
| ATOM | 1010 | CA | LEU | A | 788 | 92.608 | 26.263 | 19.151 | 1.00 | 11.20 |
| ATOM | 1011 | CB | LEU | A | 788 | 92.876 | 25.126 | 20.139 | 1.00 | 8.89 |
| ATOM | 1012 | CG | LEU | A | 788 | 94.308 | 24.901 | 20.626 | 1.00 | 8.39 |
| ATOM | 1013 | CD1 | LEU | A | 788 | 94.340 | 23.674 | 21.529 | 1.00 | 9.71 |
| ATOM | 1014 | CD2 | LEU | A | 788 | 95.288 | 24.746 | 19.465 | 1.00 | 7.35 |
| ATOM | 1015 | C | LEU | A | 788 | 91.117 | 26.378 | 18.831 | 1.00 | 10.51 |
| ATOM | 1016 | O | LEU | A | 788 | 90.663 | 25.871 | 17.804 | 1.00 | 13.09 |
| ATOM | 1017 | N | LEU | A | 789 | 90.372 | 27.051 | 19.708 | 1.00 | 10.34 |
| ATOM | 1018 | CA | LEU | A | 789 | 88.960 | 27.335 | 19.485 | 1.00 | 11.02 |
| ATOM | 1019 | CB | LEU | A | 789 | 88.379 | 28.127 | 20.654 | 1.00 | 11.62 |
| ATOM | 1020 | CG | LEU | A | 789 | 87.955 | 27.343 | 21.899 | 1.00 | 13.62 |
| ATOM | 1021 | CD1 | LEU | A | 789 | 87.367 | 28.286 | 22.948 | 1.00 | 13.17 |
| ATOM | 1022 | CD2 | LEU | A | 789 | 86.971 | 26.239 | 21.542 | 1.00 | 14.74 |
| ATOM | 1023 | C | LEU | A | 789 | 88.756 | 28.107 | 18.180 | 1.00 | 11.93 |
| ATOM | 1024 | O | LEU | A | 789 | 87.928 | 27.724 | 17.359 | 1.00 | 13.00 |
| ATOM | 1025 | N | CYS | A | 790 | 89.526 | 29.180 | 18.002 | 1.00 | 12.01 |
| ATOM | 1026 | CA | CYS | A | 790 | 89.532 | 29.960 | 16.771 | 1.00 | 15.16 |

FIGURE 3AU

|      | A    | B    | C   | D | E   | F      | G      | H      | I    | J     |
|------|------|------|-----|---|-----|--------|--------|--------|------|-------|
| ATOM | 1027 | CB   | CYS | A | 790 | 90.580 | 31.063 | 16.837 | 1.00 | 17.36 |
| ATOM | 1028 | SG   | CYS | A | 790 | 90.002 | 32.440 | 17.800 | 1.00 | 29.56 |
| ATOM | 1029 | C    | CYS | A | 790 | 89.778 | 29.118 | 15.528 | 1.00 | 12.39 |
| ATOM | 1030 | O    | CYS | A | 790 | 89.020 | 29.222 | 14.565 | 1.00 | 12.69 |
| ATOM | 1031 | N    | PHE | A | 791 | 90.841 | 28.312 | 15.549 | 1.00 | 8.44  |
| ATOM | 1032 | CA   | PHE | A | 791 | 91.148 | 27.416 | 14.441 | 1.00 | 9.33  |
| ATOM | 1033 | CB   | PHE | A | 791 | 92.320 | 26.488 | 14.784 | 1.00 | 8.65  |
| ATOM | 1034 | CG   | PHE | A | 791 | 93.649 | 27.194 | 14.943 | 1.00 | 5.88  |
| ATOM | 1035 | CD1  | PHE | A | 791 | 94.701 | 26.560 | 15.582 | 1.00 | 5.72  |
| ATOM | 1036 | CE1  | PHE | A | 791 | 95.936 | 27.199 | 15.732 | 1.00 | 6.26  |
| ATOM | 1037 | CZ   | PHE | A | 791 | 96.118 | 28.485 | 15.239 | 1.00 | 5.32  |
| ATOM | 1038 | CE2  | PHE | A | 791 | 95.068 | 29.128 | 14.595 | 1.00 | 4.82  |
| ATOM | 1039 | CD2  | PHE | A | 791 | 93.848 | 28.483 | 14.449 | 1.00 | 5.57  |
| ATOM | 1040 | C    | PHE | A | 791 | 89.920 | 26.586 | 14.110 | 1.00 | 11.34 |
| ATOM | 1041 | O    | PHE | A | 791 | 89.519 | 26.508 | 12.952 | 1.00 | 15.54 |
| ATOM | 1042 | N    | ALA | A | 792 | 89.309 | 25.994 | 15.133 | 1.00 | 11.63 |
| ATOM | 1043 | CA   | ALA | A | 792 | 88.120 | 25.165 | 14.953 | 1.00 | 13.36 |
| ATOM | 1044 | CB   | ALA | A | 792 | 87.676 | 24.586 | 16.295 | 1.00 | 12.31 |
| ATOM | 1045 | C    | ALA | A | 792 | 86.977 | 25.960 | 14.311 | 1.00 | 13.90 |
| ATOM | 1046 | O    | ALA | A | 792 | 86.296 | 25.489 | 13.392 | 1.00 | 12.87 |
| ATOM | 1047 | N    | TYR | A | 793 | 86.774 | 27.169 | 14.810 | 1.00 | 12.70 |
| ATOM | 1048 | CA   | TYR | A | 793 | 85.745 | 28.040 | 14.288 | 1.00 | 14.67 |
| ATOM | 1049 | CB   | TYR | A | 793 | 85.650 | 29.292 | 15.153 | 1.00 | 12.73 |
| ATOM | 1050 | CG   | TYR | A | 793 | 84.609 | 30.260 | 14.684 | 1.00 | 13.88 |
| ATOM | 1051 | CD1  | TYR | A | 793 | 84.937 | 31.586 | 14.436 | 1.00 | 15.64 |
| ATOM | 1052 | CE1  | TYR | A | 793 | 83.984 | 32.491 | 14.009 | 1.00 | 17.94 |
| ATOM | 1053 | CZ   | TYR | A | 793 | 82.687 | 32.064 | 13.809 | 1.00 | 18.49 |
| ATOM | 1054 | OH   | TYR | A | 793 | 81.743 | 32.967 | 13.381 | 1.00 | 21.37 |
| ATOM | 1055 | CE2  | TYR | A | 793 | 82.333 | 30.745 | 14.051 | 1.00 | 16.61 |
| ATOM | 1056 | CD2  | TYR | A | 793 | 83.293 | 29.853 | 14.483 | 1.00 | 14.00 |
| ATOM | 1057 | C    | TYR | A | 793 | 86.017 | 28.407 | 12.819 | 1.00 | 14.95 |
| ATOM | 1058 | O    | TYR | A | 793 | 85.128 | 28.294 | 11.962 | 1.00 | 15.14 |
| ATOM | 1059 | N    | GLN | A | 794 | 87.253 | 28.816 | 12.548 | 1.00 | 12.14 |
| ATOM | 1060 | CA   | GLN | A | 794 | 87.669 | 29.257 | 11.226 | 1.00 | 12.77 |
| ATOM | 1061 | CB   | GLN | A | 794 | 89.090 | 29.825 | 11.289 | 1.00 | 12.34 |
| ATOM | 1062 | CG   | GLN | A | 794 | 89.166 | 31.212 | 11.949 | 1.00 | 13.72 |
| ATOM | 1063 | CD   | GLN | A | 794 | 90.549 | 31.560 | 12.474 | 1.00 | 16.70 |
| ATOM | 1064 | OE1  | GLN | A | 794 | 91.551 | 31.111 | 11.938 | 1.00 | 19.46 |
| ATOM | 1065 | NE2  | GLN | A | 794 | 90.601 | 32.372 | 13.519 | 1.00 | 20.54 |
| ATOM | 1066 | C    | GLN | A | 794 | 87.545 | 28.160 | 10.162 | 1.00 | 12.62 |
| ATOM | 1067 | O    | GLN | A | 794 | 87.089 | 28.419 | 9.040  | 1.00 | 10.94 |
| ATOM | 1068 | N    | VAL | A | 795 | 87.922 | 26.936 | 10.523 | 1.00 | 10.15 |
| ATOM | 1069 | CA   | VAL | A | 795 | 87.807 | 25.818 | 9.601  | 1.00 | 12.03 |
| ATOM | 1070 | CB   | VAL | A | 795 | 88.538 | 24.548 | 10.110 | 1.00 | 11.74 |
| ATOM | 1071 | CG1  | VAL | A | 795 | 88.253 | 23.362 | 9.190  | 1.00 | 9.27  |
| ATOM | 1072 | CG2  | VAL | A | 795 | 90.065 | 24.803 | 10.225 | 1.00 | 9.07  |
| ATOM | 1073 | C    | VAL | A | 795 | 86.334 | 25.520 | 9.324  | 1.00 | 13.88 |
| ATOM | 1074 | O    | VAL | A | 795 | 85.957 | 25.186 | 8.195  | 1.00 | 14.57 |
| ATOM | 1075 | N    | ALA | A | 796 | 85.497 | 25.669 | 10.344 | 1.00 | 13.17 |
| ATOM | 1076 | CA   | ALA | A | 796 | 84.077 | 25.439 | 10.153 | 1.00 | 14.47 |
| ATOM | 1077 | CB   | ALA | A | 796 | 83.355 | 25.366 | 11.489 | 1.00 | 12.36 |
| ATOM | 1078 | C    | ALA | A | 796 | 83.481 | 26.523 | 9.244  | 1.00 | 16.33 |

FIGURE 3AV

|  | A | B | C | D | E | F | G | H | I | J |
|---|---|---|---|---|---|---|---|---|---|---|
| ATOM | 1079 | O | ALA | A | 796 | 82.596 | 26.233 | 8.435 | 1.00 | 17.19 |
| ATOM | 1080 | N | LYS | A | 797 | 83.980 | 27.758 | 9.365 | 1.00 | 14.53 |
| ATOM | 1081 | CA | LYS | A | 797 | 83.507 | 28.861 | 8.532 | 1.00 | 15.04 |
| ATOM | 1082 | CB | LYS | A | 797 | 84.031 | 30.210 | 9.032 | 1.00 | 17.48 |
| ATOM | 1083 | CG | LYS | A | 797 | 83.236 | 30.827 | 10.168 | 1.00 | 20.57 |
| ATOM | 1084 | CD | LYS | A | 797 | 83.530 | 32.327 | 10.298 | 1.00 | 26.00 |
| ATOM | 1085 | CE | LYS | A | 797 | 84.945 | 32.604 | 10.850 | 1.00 | 27.79 |
| ATOM | 1086 | NZ | LYS | A | 797 | 85.604 | 33.801 | 10.230 | 1.00 | 29.30 |
| ATOM | 1087 | C | LYS | A | 797 | 83.898 | 28.647 | 7.073 | 1.00 | 14.04 |
| ATOM | 1088 | O | LYS | A | 797 | 83.115 | 28.934 | 6.163 | 1.00 | 13.86 |
| ATOM | 1089 | N | GLY | A | 798 | 85.110 | 28.146 | 6.857 | 1.00 | 14.90 |
| ATOM | 1090 | CA | GLY | A | 798 | 85.573 | 27.800 | 5.523 | 1.00 | 15.24 |
| ATOM | 1091 | C | GLY | A | 798 | 84.723 | 26.694 | 4.922 | 1.00 | 15.19 |
| ATOM | 1092 | O | GLY | A | 798 | 84.258 | 26.798 | 3.778 | 1.00 | 14.85 |
| ATOM | 1093 | N | MET | A | 799 | 84.509 | 25.638 | 5.702 | 1.00 | 13.84 |
| ATOM | 1094 | CA | MET | A | 799 | 83.682 | 24.516 | 5.265 | 1.00 | 13.93 |
| ATOM | 1095 | CB | MET | A | 799 | 83.667 | 23.400 | 6.303 | 1.00 | 13.52 |
| ATOM | 1096 | CG | MET | A | 799 | 84.899 | 22.510 | 6.293 | 1.00 | 13.50 |
| ATOM | 1097 | SD | MET | A | 799 | 85.562 | 22.100 | 4.635 | 1.00 | 18.66 |
| ATOM | 1098 | CE | MET | A | 799 | 84.126 | 21.345 | 3.801 | 1.00 | 14.83 |
| ATOM | 1099 | C | MET | A | 799 | 82.264 | 24.958 | 4.941 | 1.00 | 13.90 |
| ATOM | 1100 | O | MET | A | 799 | 81.691 | 24.529 | 3.934 | 1.00 | 15.16 |
| ATOM | 1101 | N | GLU | A | 800 | 81.722 | 25.837 | 5.780 | 1.00 | 12.17 |
| ATOM | 1102 | CA | GLU | A | 800 | 80.410 | 26.417 | 5.555 | 1.00 | 13.49 |
| ATOM | 1103 | CB | GLU | A | 800 | 80.050 | 27.353 | 6.708 | 1.00 | 14.63 |
| ATOM | 1104 | CG | GLU | A | 800 | 78.631 | 27.893 | 6.648 | 1.00 | 16.19 |
| ATOM | 1105 | CD | GLU | A | 800 | 78.330 | 28.845 | 7.782 | 1.00 | 19.73 |
| ATOM | 1106 | OE1 | GLU | A | 800 | 77.475 | 28.515 | 8.624 | 1.00 | 21.51 |
| ATOM | 1107 | OE2 | GLU | A | 800 | 78.955 | 29.925 | 7.839 | 1.00 | 23.47 |
| ATOM | 1108 | C | GLU | A | 800 | 80.364 | 27.171 | 4.223 | 1.00 | 14.26 |
| ATOM | 1109 | O | GLU | A | 800 | 79.398 | 27.055 | 3.468 | 1.00 | 14.61 |
| ATOM | 1110 | N | PHE | A | 801 | 81.410 | 27.947 | 3.947 | 1.00 | 12.80 |
| ATOM | 1111 | CA | PHE | A | 801 | 81.530 | 28.652 | 2.681 | 1.00 | 11.73 |
| ATOM | 1112 | CB | PHE | A | 801 | 82.828 | 29.467 | 2.648 | 1.00 | 8.49 |
| ATOM | 1113 | CG | PHE | A | 801 | 83.100 | 30.128 | 1.327 | 1.00 | 6.53 |
| ATOM | 1114 | CD1 | PHE | A | 801 | 84.009 | 29.571 | 0.432 | 1.00 | 5.18 |
| ATOM | 1115 | CE1 | PHE | A | 801 | 84.272 | 30.186 | -0.796 | 1.00 | 5.74 |
| ATOM | 1116 | CZ | PHE | A | 801 | 83.626 | 31.375 | -1.135 | 1.00 | 5.48 |
| ATOM | 1117 | CE2 | PHE | A | 801 | 82.716 | 31.940 | -0.245 | 1.00 | 7.08 |
| ATOM | 1118 | CD2 | PHE | A | 801 | 82.456 | 31.313 | 0.979 | 1.00 | 6.19 |
| ATOM | 1119 | C | PHE | A | 801 | 81.483 | 27.670 | 1.510 | 1.00 | 12.52 |
| ATOM | 1120 | O | PHE | A | 801 | 80.776 | 27.897 | 0.526 | 1.00 | 14.25 |
| ATOM | 1121 | N | LEU | A | 802 | 82.236 | 26.583 | 1.633 | 1.00 | 12.79 |
| ATOM | 1122 | CA | LEU | A | 802 | 82.343 | 25.588 | 0.579 | 1.00 | 14.93 |
| ATOM | 1123 | CB | LEU | A | 802 | 83.442 | 24.576 | 0.917 | 1.00 | 14.07 |
| ATOM | 1124 | CG | LEU | A | 802 | 84.864 | 25.144 | 0.874 | 1.00 | 13.33 |
| ATOM | 1125 | CD1 | LEU | A | 802 | 85.890 | 24.104 | 1.323 | 1.00 | 13.68 |
| ATOM | 1126 | CD2 | LEU | A | 802 | 85.185 | 25.667 | -0.514 | 1.00 | 12.17 |
| ATOM | 1127 | C | LEU | A | 802 | 81.009 | 24.889 | 0.343 | 1.00 | 15.77 |
| ATOM | 1128 | O | LEU | A | 802 | 80.664 | 24.572 | -0.797 | 1.00 | 13.75 |
| ATOM | 1129 | N | GLU | A | 803 | 80.267 | 24.669 | 1.430 | 1.00 | 16.55 |
| ATOM | 1130 | CA | GLU | A | 803 | 78.912 | 24.127 | 1.378 | 1.00 | 15.10 |

FIGURE 3AW

|  | A | B | C | D | E | F | G | H | I | J |
|---|---|---|---|---|---|---|---|---|---|---|
| ATOM | 1131 | CB | GLU | A | 803 | 78.337 | 24.023 | 2.790 | 1.00 | 16.50 |
| ATOM | 1132 | CG | GLU | A | 803 | 76.988 | 23.326 | 2.896 | 1.00 | 18.58 |
| ATOM | 1133 | CD | GLU | A | 803 | 76.405 | 23.395 | 4.298 | 1.00 | 19.26 |
| ATOM | 1134 | OE1 | GLU | A | 803 | 77.151 | 23.153 | 5.262 | 1.00 | 19.10 |
| ATOM | 1135 | OE2 | GLU | A | 803 | 75.205 | 23.708 | 4.444 | 1.00 | 20.53 |
| ATOM | 1136 | C | GLU | A | 803 | 78.041 | 25.023 | 0.508 | 1.00 | 14.15 |
| ATOM | 1137 | O | GLU | A | 803 | 77.331 | 24.550 | -0.380 | 1.00 | 14.73 |
| ATOM | 1138 | N | PHE | A | 804 | 78.133 | 26.325 | 0.738 | 1.00 | 12.05 |
| ATOM | 1139 | CA | PHE | A | 804 | 77.303 | 27.283 | 0.016 | 1.00 | 10.76 |
| ATOM | 1140 | CB | BPHE | A | 804 | 77.294 | 28.589 | 0.839 | 0.35 | 8.43 |
| ATOM | 1141 | CB | APHE | A | 804 | 76.970 | 28.507 | 0.869 | 0.65 | 13.26 |
| ATOM | 1142 | CG | BPHE | A | 804 | 76.767 | 29.801 | 0.111 | 0.35 | 5.67 |
| ATOM | 1143 | CG | APHE | A | 804 | 76.015 | 28.173 | 1.987 | 0.65 | 14.80 |
| ATOM | 1144 | CD1 | BPHE | A | 804 | 77.643 | 30.714 | -0.472 | 0.35 | 5.09 |
| ATOM | 1145 | CD1 | APHE | A | 804 | 74.637 | 28.256 | 1.793 | 0.65 | 14.42 |
| ATOM | 1146 | CE1 | BPHE | A | 804 | 77.163 | 31.843 | -1.138 | 0.35 | 3.25 |
| ATOM | 1147 | CE1 | APHE | A | 804 | 73.757 | 27.900 | 2.812 | 0.65 | 14.44 |
| ATOM | 1148 | CZ | BPHE | A | 804 | 75.797 | 32.077 | -1.204 | 0.35 | 3.37 |
| ATOM | 1149 | CZ | APHE | A | 804 | 74.256 | 27.433 | 4.030 | 0.65 | 13.34 |
| ATOM | 1150 | CE2 | BPHE | A | 804 | 74.913 | 31.184 | -0.613 | 0.35 | 4.06 |
| ATOM | 1151 | CE2 | APHE | A | 804 | 75.618 | 27.330 | 4.225 | 0.65 | 12.86 |
| ATOM | 1152 | CD2 | BPHE | A | 804 | 75.402 | 30.054 | 0.048 | 0.35 | 4.90 |
| ATOM | 1153 | CD2 | APHE | A | 804 | 76.490 | 27.684 | 3.206 | 0.65 | 14.10 |
| ATOM | 1154 | C | PHE | A | 804 | 77.791 | 27.541 | -1.412 | 1.00 | 11.50 |
| ATOM | 1155 | O | PHE | A | 804 | 77.029 | 27.993 | -2.269 | 1.00 | 10.81 |
| ATOM | 1156 | N | LYS | A | 805 | 79.046 | 27.180 | -1.673 | 1.00 | 11.51 |
| ATOM | 1157 | CA | LYS | A | 805 | 79.589 | 27.179 | -3.028 | 1.00 | 11.74 |
| ATOM | 1158 | CB | LYS | A | 805 | 81.015 | 27.727 | -3.021 | 1.00 | 11.43 |
| ATOM | 1159 | CG | LYS | A | 805 | 81.109 | 29.189 | -2.646 | 1.00 | 13.40 |
| ATOM | 1160 | CD | LYS | A | 805 | 80.376 | 30.062 | -3.648 | 1.00 | 15.16 |
| ATOM | 1161 | CE | LYS | A | 805 | 80.128 | 31.448 | -3.085 | 1.00 | 17.18 |
| ATOM | 1162 | NZ | LYS | A | 805 | 80.667 | 32.502 | -3.993 | 1.00 | 19.25 |
| ATOM | 1163 | C | LYS | A | 805 | 79.540 | 25.797 | -3.706 | 1.00 | 12.55 |
| ATOM | 1164 | O | LYS | A | 805 | 80.256 | 25.557 | -4.677 | 1.00 | 13.65 |
| ATOM | 1165 | N | SER | A | 806 | 78.700 | 24.896 | -3.190 | 1.00 | 11.97 |
| ATOM | 1166 | CA | SER | A | 806 | 78.465 | 23.580 | -3.804 | 1.00 | 11.17 |
| ATOM | 1167 | CB | SER | A | 806 | 77.738 | 23.718 | -5.147 | 1.00 | 9.99 |
| ATOM | 1168 | OG | SER | A | 806 | 76.506 | 24.395 | -5.000 | 1.00 | 12.14 |
| ATOM | 1169 | C | SER | A | 806 | 79.746 | 22.756 | -3.983 | 1.00 | 10.88 |
| ATOM | 1170 | O | SER | A | 806 | 80.020 | 22.212 | -5.056 | 1.00 | 10.99 |
| ATOM | 1171 | N | CYS | A | 807 | 80.527 | 22.670 | -2.923 | 1.00 | 10.85 |
| ATOM | 1172 | CA | CYS | A | 807 | 81.766 | 21.915 | -2.965 | 1.00 | 13.15 |
| ATOM | 1173 | CB | CYS | A | 807 | 82.986 | 22.840 | -2.909 | 1.00 | 12.08 |
| ATOM | 1174 | SG | CYS | A | 807 | 83.208 | 23.834 | -4.392 | 1.00 | 16.25 |
| ATOM | 1175 | C | CYS | A | 807 | 81.805 | 20.943 | -1.813 | 1.00 | 15.01 |
| ATOM | 1176 | O | CYS | A | 807 | 81.139 | 21.131 | -0.796 | 1.00 | 15.84 |
| ATOM | 1177 | N | VAL | A | 808 | 82.580 | 19.887 | -2.000 | 1.00 | 17.74 |
| ATOM | 1178 | CA | VAL | A | 808 | 82.857 | 18.931 | -0.944 | 1.00 | 19.17 |
| ATOM | 1179 | CB | VAL | A | 808 | 82.226 | 17.551 | -1.247 | 1.00 | 19.34 |
| ATOM | 1180 | CG1 | VAL | A | 808 | 82.635 | 16.510 | -0.207 | 1.00 | 23.15 |
| ATOM | 1181 | CG2 | VAL | A | 808 | 80.708 | 17.663 | -1.297 | 1.00 | 20.83 |
| ATOM | 1182 | C | VAL | A | 808 | 84.363 | 18.843 | -0.936 | 1.00 | 19.10 |

FIGURE 3AX

|  | A | B | C | D | E | F | G | H | I | J |
|---|---|---|---|---|---|---|---|---|---|---|
| ATOM | 1183 | O | VAL | A | 808 | 85.000 | 18.850 | -1.994 | 1.00 | 19.99 |
| ATOM | 1184 | N | HIS | A | 809 | 84.939 | 18.807 | 0.253 | 1.00 | 18.18 |
| ATOM | 1185 | CA | HIS | A | 809 | 86.372 | 18.633 | 0.360 | 1.00 | 17.47 |
| ATOM | 1186 | CB | HIS | A | 809 | 86.930 | 19.470 | 1.497 | 1.00 | 16.31 |
| ATOM | 1187 | CG | HIS | A | 809 | 88.353 | 19.860 | 1.286 | 1.00 | 17.62 |
| ATOM | 1188 | ND1 | HIS | A | 809 | 89.379 | 18.938 | 1.273 | 1.00 | 15.93 |
| ATOM | 1189 | CE1 | HIS | A | 809 | 90.519 | 19.563 | 1.052 | 1.00 | 16.42 |
| ATOM | 1190 | NE2 | HIS | A | 809 | 90.269 | 20.852 | 0.911 | 1.00 | 17.40 |
| ATOM | 1191 | CD2 | HIS | A | 809 | 88.920 | 21.064 | 1.046 | 1.00 | 16.24 |
| ATOM | 1192 | C | HIS | A | 809 | 86.676 | 17.168 | 0.593 | 1.00 | 17.95 |
| ATOM | 1193 | O | HIS | A | 809 | 86.236 | 16.591 | 1.585 | 1.00 | 16.19 |
| ATOM | 1194 | N | ARG | A | 810 | 87.415 | 16.558 | -0.324 | 1.00 | 17.74 |
| ATOM | 1195 | CA | ARG | A | 810 | 87.653 | 15.122 | -0.230 | 1.00 | 20.66 |
| ATOM | 1196 | CB | ARG | A | 810 | 87.685 | 14.481 | -1.621 | 1.00 | 23.15 |
| ATOM | 1197 | CG | ARG | A | 810 | 86.318 | 14.403 | -2.309 | 1.00 | 26.65 |
| ATOM | 1198 | CD | ARG | A | 810 | 86.351 | 13.712 | -3.667 | 1.00 | 33.45 |
| ATOM | 1199 | NE | ARG | A | 810 | 85.195 | 12.838 | -3.874 | 1.00 | 37.96 |
| ATOM | 1200 | CZ | ARG | A | 810 | 84.352 | 12.922 | -4.903 | 1.00 | 40.98 |
| ATOM | 1201 | NH1 | ARG | A | 810 | 84.521 | 13.850 | -5.846 | 1.00 | 41.78 |
| ATOM | 1202 | NH2 | ARG | A | 810 | 83.328 | 12.076 | -4.989 | 1.00 | 41.34 |
| ATOM | 1203 | C | ARG | A | 810 | 88.912 | 14.797 | 0.568 | 1.00 | 20.43 |
| ATOM | 1204 | O | ARG | A | 810 | 89.330 | 13.653 | 0.625 | 1.00 | 21.05 |
| ATOM | 1205 | N | ASP | A | 811 | 89.499 | 15.810 | 1.198 | 1.00 | 21.24 |
| ATOM | 1206 | CA | ASP | A | 811 | 90.749 | 15.647 | 1.927 | 1.00 | 20.37 |
| ATOM | 1207 | CB | ASP | A | 811 | 91.920 | 15.662 | 0.942 | 1.00 | 21.20 |
| ATOM | 1208 | CG | ASP | A | 811 | 93.182 | 15.016 | 1.496 | 1.00 | 21.46 |
| ATOM | 1209 | OD1 | ASP | A | 811 | 94.196 | 15.061 | 0.770 | 1.00 | 24.64 |
| ATOM | 1210 | OD2 | ASP | A | 811 | 93.281 | 14.464 | 2.614 | 1.00 | 19.15 |
| ATOM | 1211 | C | ASP | A | 811 | 90.906 | 16.726 | 3.007 | 1.00 | 19.98 |
| ATOM | 1212 | O | ASP | A | 811 | 91.929 | 17.410 | 3.083 | 1.00 | 21.77 |
| ATOM | 1213 | N | LEU | A | 812 | 89.878 | 16.881 | 3.835 | 1.00 | 17.84 |
| ATOM | 1214 | CA | LEU | A | 812 | 89.938 | 17.819 | 4.943 | 1.00 | 18.16 |
| ATOM | 1215 | CB | LEU | A | 812 | 88.544 | 18.207 | 5.429 | 1.00 | 16.29 |
| ATOM | 1216 | CG | LEU | A | 812 | 88.497 | 19.254 | 6.546 | 1.00 | 18.02 |
| ATOM | 1217 | CD1 | LEU | A | 812 | 88.970 | 20.648 | 6.051 | 1.00 | 16.32 |
| ATOM | 1218 | CD2 | LEU | A | 812 | 87.095 | 19.336 | 7.132 | 1.00 | 16.60 |
| ATOM | 1219 | C | LEU | A | 812 | 90.746 | 17.214 | 6.081 | 1.00 | 19.61 |
| ATOM | 1220 | O | LEU | A | 812 | 90.354 | 16.192 | 6.660 | 1.00 | 20.51 |
| ATOM | 1221 | N | ALA | A | 813 | 91.867 | 17.862 | 6.396 | 1.00 | 17.57 |
| ATOM | 1222 | CA | ALA | A | 813 | 92.813 | 17.378 | 7.392 | 1.00 | 14.21 |
| ATOM | 1223 | CB | ALA | A | 813 | 93.612 | 16.234 | 6.810 | 1.00 | 12.83 |
| ATOM | 1224 | C | ALA | A | 813 | 93.737 | 18.538 | 7.752 | 1.00 | 17.16 |
| ATOM | 1225 | O | ALA | A | 813 | 93.921 | 19.455 | 6.935 | 1.00 | 17.03 |
| ATOM | 1226 | N | ALA | A | 814 | 94.337 | 18.496 | 8.946 | 1.00 | 15.05 |
| ATOM | 1227 | CA | ALA | A | 814 | 95.231 | 19.576 | 9.377 | 1.00 | 14.99 |
| ATOM | 1228 | CB | ALA | A | 814 | 95.788 | 19.313 | 10.773 | 1.00 | 12.73 |
| ATOM | 1229 | C | ALA | A | 814 | 96.359 | 19.885 | 8.375 | 1.00 | 15.31 |
| ATOM | 1230 | O | ALA | A | 814 | 96.743 | 21.050 | 8.207 | 1.00 | 16.89 |
| ATOM | 1231 | N | ARG | A | 815 | 96.869 | 18.855 | 7.700 | 1.00 | 14.78 |
| ATOM | 1232 | CA | ARG | A | 815 | 97.929 | 19.034 | 6.694 | 1.00 | 14.25 |
| ATOM | 1233 | CB | ARG | A | 815 | 98.495 | 17.681 | 6.251 | 1.00 | 15.70 |
| ATOM | 1234 | CG | ARG | A | 815 | 97.510 | 16.846 | 5.457 | 1.00 | 17.40 |

FIGURE 3AY

| | A | B | C | D | E | F | G | H | I | J |
|---|---|---|---|---|---|---|---|---|---|---|
| ATOM | 1235 | CD | ARG | A | 815 | 97.991 | 15.472 | 5.016 | 1.00 | 18.83 |
| ATOM | 1236 | NE | ARG | A | 815 | 96.852 | 14.742 | 4.454 | 1.00 | 20.24 |
| ATOM | 1237 | CZ | ARG | A | 815 | 96.006 | 13.994 | 5.159 | 1.00 | 19.41 |
| ATOM | 1238 | NH1 | ARG | A | 815 | 94.987 | 13.399 | 4.548 | 1.00 | 21.31 |
| ATOM | 1239 | NH2 | ARG | A | 815 | 96.176 | 13.833 | 6.464 | 1.00 | 17.90 |
| ATOM | 1240 | C | ARG | A | 815 | 97.470 | 19.830 | 5.465 | 1.00 | 14.19 |
| ATOM | 1241 | O | ARG | A | 815 | 98.298 | 20.369 | 4.740 | 1.00 | 15.27 |
| ATOM | 1242 | N | ASN | A | 816 | 96.157 | 19.892 | 5.236 | 1.00 | 15.33 |
| ATOM | 1243 | CA | ASN | A | 816 | 95.589 | 20.634 | 4.105 | 1.00 | 17.77 |
| ATOM | 1244 | CB | ASN | A | 816 | 94.616 | 19.744 | 3.315 | 1.00 | 17.64 |
| ATOM | 1245 | CG | ASN | A | 816 | 95.324 | 18.575 | 2.644 | 1.00 | 18.36 |
| ATOM | 1246 | OD1 | ASN | A | 816 | 96.497 | 18.679 | 2.289 | 1.00 | 18.65 |
| ATOM | 1247 | ND2 | ASN | A | 816 | 94.621 | 17.463 | 2.476 | 1.00 | 16.33 |
| ATOM | 1248 | C | ASN | A | 816 | 94.957 | 21.985 | 4.491 | 1.00 | 17.31 |
| ATOM | 1249 | O | ASN | A | 816 | 94.326 | 22.661 | 3.680 | 1.00 | 18.72 |
| ATOM | 1250 | N | VAL | A | 817 | 95.156 | 22.370 | 5.741 | 1.00 | 17.89 |
| ATOM | 1251 | CA | VAL | A | 817 | 94.728 | 23.665 | 6.238 | 1.00 | 16.77 |
| ATOM | 1252 | CB | VAL | A | 817 | 93.883 | 23.509 | 7.517 | 1.00 | 16.74 |
| ATOM | 1253 | CG1 | VAL | A | 817 | 93.630 | 24.854 | 8.183 | 1.00 | 16.70 |
| ATOM | 1254 | CG2 | VAL | A | 817 | 92.550 | 22.820 | 7.170 | 1.00 | 19.38 |
| ATOM | 1255 | C | VAL | A | 817 | 96.007 | 24.440 | 6.504 | 1.00 | 16.41 |
| ATOM | 1256 | O | VAL | A | 817 | 96.975 | 23.890 | 7.033 | 1.00 | 16.52 |
| ATOM | 1257 | N | LEU | A | 818 | 96.020 | 25.705 | 6.108 | 1.00 | 14.80 |
| ATOM | 1258 | CA | LEU | A | 818 | 97.211 | 26.526 | 6.253 | 1.00 | 14.67 |
| ATOM | 1259 | CB | LEU | A | 818 | 97.626 | 27.099 | 4.905 | 1.00 | 15.58 |
| ATOM | 1260 | CG | LEU | A | 818 | 97.847 | 26.093 | 3.768 | 1.00 | 16.54 |
| ATOM | 1261 | CD1 | LEU | A | 818 | 97.988 | 26.890 | 2.519 | 1.00 | 18.60 |
| ATOM | 1262 | CD2 | LEU | A | 818 | 99.097 | 25.253 | 3.979 | 1.00 | 15.59 |
| ATOM | 1263 | C | LEU | A | 818 | 96.999 | 27.636 | 7.269 | 1.00 | 14.24 |
| ATOM | 1264 | O | LEU | A | 818 | 95.859 | 28.002 | 7.583 | 1.00 | 12.53 |
| ATOM | 1265 | N | VAL | A | 819 | 98.107 | 28.149 | 7.792 | 1.00 | 12.13 |
| ATOM | 1266 | CA | VAL | A | 819 | 98.083 | 29.152 | 8.845 | 1.00 | 10.40 |
| ATOM | 1267 | CB | VAL | A | 819 | 98.718 | 28.613 | 10.157 | 1.00 | 10.07 |
| ATOM | 1268 | CG1 | VAL | A | 819 | 98.551 | 29.600 | 11.314 | 1.00 | 7.08 |
| ATOM | 1269 | CG2 | VAL | A | 819 | 98.111 | 27.261 | 10.525 | 1.00 | 8.00 |
| ATOM | 1270 | C | VAL | A | 819 | 98.814 | 30.392 | 8.369 | 1.00 | 12.29 |
| ATOM | 1271 | O | VAL | A | 819 | 99.964 | 30.315 | 7.920 | 1.00 | 11.54 |
| ATOM | 1272 | N | THR | A | 820 | 98.127 | 31.529 | 8.448 | 1.00 | 14.80 |
| ATOM | 1273 | CA | THR | A | 820 | 98.726 | 32.826 | 8.142 | 1.00 | 17.18 |
| ATOM | 1274 | CB | THR | A | 820 | 97.688 | 33.780 | 7.516 | 1.00 | 19.78 |
| ATOM | 1275 | OG1 | THR | A | 820 | 96.716 | 34.134 | 8.511 | 1.00 | 21.82 |
| ATOM | 1276 | CG2 | THR | A | 820 | 96.859 | 33.090 | 6.434 | 1.00 | 19.32 |
| ATOM | 1277 | C | THR | A | 820 | 99.218 | 33.474 | 9.421 | 1.00 | 17.87 |
| ATOM | 1278 | O | THR | A | 820 | 98.936 | 32.991 | 10.528 | 1.00 | 16.18 |
| ATOM | 1279 | N | HIS | A | 821 | 99.951 | 34.575 | 9.252 | 1.00 | 19.93 |
| ATOM | 1280 | CA | HIS | A | 821 | 100.160 | 35.555 | 10.311 | 1.00 | 21.07 |
| ATOM | 1281 | CB | HIS | A | 821 | 100.945 | 36.755 | 9.768 | 1.00 | 23.24 |
| ATOM | 1282 | CG | HIS | A | 821 | 102.117 | 37.130 | 10.617 | 1.00 | 23.98 |
| ATOM | 1283 | ND1 | HIS | A | 821 | 103.314 | 36.449 | 10.574 | 1.00 | 23.49 |
| ATOM | 1284 | CE1 | HIS | A | 821 | 104.148 | 36.976 | 11.453 | 1.00 | 25.18 |
| ATOM | 1285 | NE2 | HIS | A | 821 | 103.536 | 37.977 | 12.065 | 1.00 | 25.64 |
| ATOM | 1286 | CD2 | HIS | A | 821 | 102.259 | 38.086 | 11.569 | 1.00 | 24.72 |

FIGURE 3AZ

|      | A    | B    | C   | D   | E   | F      | G      | H      | I    | J     |
|------|------|------|-----|-----|-----|--------|--------|--------|------|-------|
| ATOM | 1287 | C    | HIS | A   | 821 | 98.792 | 36.010 | 10.832 | 1.00 | 22.60 |
| ATOM | 1288 | O    | HIS | A   | 821 | 97.799 | 36.011 | 10.097 | 1.00 | 25.24 |
| ATOM | 1289 | N    | GLY | A   | 822 | 98.727 | 36.371 | 12.105 | 1.00 | 22.12 |
| ATOM | 1290 | CA   | GLY | A   | 822 | 97.458 | 36.741 | 12.706 | 1.00 | 20.46 |
| ATOM | 1291 | C    | GLY | A   | 822 | 96.662 | 35.535 | 13.162 | 1.00 | 20.44 |
| ATOM | 1292 | O    | GLY | A   | 822 | 95.556 | 35.688 | 13.684 | 1.00 | 20.60 |
| ATOM | 1293 | N    | LYS | A   | 823 | 97.235 | 34.344 | 12.971 | 1.00 | 19.47 |
| ATOM | 1294 | CA   | LYS | A   | 823 | 96.634 | 33.071 | 13.389 | 1.00 | 19.88 |
| ATOM | 1295 | CB   | LYS | A   | 823 | 96.548 | 32.966 | 14.914 | 1.00 | 20.06 |
| ATOM | 1296 | CG   | LYS | A   | 823 | 97.747 | 32.273 | 15.529 | 1.00 | 20.98 |
| ATOM | 1297 | CD   | LYS | A   | 823 | 98.386 | 33.124 | 16.605 | 1.00 | 21.24 |
| ATOM | 1298 | CE   | LYS | A   | 823 | 98.551 | 32.344 | 17.890 | 1.00 | 20.29 |
| ATOM | 1299 | NZ   | LYS | A   | 823 | 98.916 | 33.225 | 19.030 | 1.00 | 20.26 |
| ATOM | 1300 | C    | LYS | A   | 823 | 95.285 | 32.772 | 12.729 | 1.00 | 19.04 |
| ATOM | 1301 | O    | LYS | A   | 823 | 94.389 | 32.189 | 13.335 | 1.00 | 19.90 |
| ATOM | 1302 | N    | VAL | A   | 824 | 95.159 | 33.177 | 11.474 | 1.00 | 17.00 |
| ATOM | 1303 | CA   | VAL | A   | 824 | 94.002 | 32.836 | 10.682 | 1.00 | 15.92 |
| ATOM | 1304 | CB   | VAL | A   | 824 | 93.616 | 33.987 | 9.738  | 1.00 | 16.78 |
| ATOM | 1305 | CG1  | VAL | A   | 824 | 92.559 | 33.536 | 8.721  | 1.00 | 16.64 |
| ATOM | 1306 | CG2  | VAL | A   | 824 | 93.128 | 35.196 | 10.551 | 1.00 | 13.96 |
| ATOM | 1307 | C    | VAL | A   | 824 | 94.328 | 31.561 | 9.912  | 1.00 | 16.29 |
| ATOM | 1308 | O    | VAL | A   | 824 | 95.455 | 31.385 | 9.432  | 1.00 | 16.54 |
| ATOM | 1309 | N    | VAL | A   | 825 | 93.351 | 30.663 | 9.823  | 1.00 | 15.45 |
| ATOM | 1310 | CA   | VAL | A   | 825 | 93.523 | 29.432 | 9.066  | 1.00 | 15.97 |
| ATOM | 1311 | CB   | VAL | A   | 825 | 93.241 | 28.165 | 9.911  | 1.00 | 18.01 |
| ATOM | 1312 | CG1  | VAL | A   | 825 | 94.301 | 28.006 | 11.006 | 1.00 | 17.53 |
| ATOM | 1313 | CG2  | VAL | A   | 825 | 91.854 | 28.199 | 10.500 | 1.00 | 17.23 |
| ATOM | 1314 | C    | VAL | A   | 825 | 92.701 | 29.430 | 7.777  | 1.00 | 15.89 |
| ATOM | 1315 | O    | VAL | A   | 825 | 91.612 | 30.007 | 7.707  | 1.00 | 15.21 |
| ATOM | 1316 | N    | LYS | A   | 826 | 93.249 | 28.782 | 6.755  | 1.00 | 16.12 |
| ATOM | 1317 | CA   | LYS | A   | 826 | 92.647 | 28.752 | 5.428  | 1.00 | 14.06 |
| ATOM | 1318 | CB   | LYS | A   | 826 | 93.375 | 29.719 | 4.496  | 1.00 | 13.25 |
| ATOM | 1319 | CG   | LYS | A   | 826 | 93.122 | 31.194 | 4.795  | 1.00 | 11.86 |
| ATOM | 1320 | CD   | LYS | A   | 826 | 94.082 | 32.085 | 4.036  | 1.00 | 11.49 |
| ATOM | 1321 | CE   | LYS | A   | 826 | 93.704 | 33.549 | 4.191  | 1.00 | 12.93 |
| ATOM | 1322 | NZ   | LYS | A   | 826 | 92.494 | 33.896 | 3.376  | 1.00 | 14.47 |
| ATOM | 1323 | C    | LYS | A   | 826 | 92.727 | 27.340 | 4.883  | 1.00 | 14.63 |
| ATOM | 1324 | O    | LYS | A   | 826 | 93.798 | 26.732 | 4.878  | 1.00 | 14.62 |
| ATOM | 1325 | N    | ILE | A   | 827 | 91.583 | 26.806 | 4.464  | 1.00 | 15.09 |
| ATOM | 1326 | CA   | ILE | A   | 827 | 91.528 | 25.488 | 3.835  | 1.00 | 13.46 |
| ATOM | 1327 | CB   | ILE | A   | 827 | 90.075 | 24.956 | 3.826  | 1.00 | 14.97 |
| ATOM | 1328 | CG1  | ILE | A   | 827 | 89.439 | 25.113 | 5.216  | 1.00 | 15.64 |
| ATOM | 1329 | CD1  | ILE | A   | 827 | 87.949 | 24.780 | 5.269  | 1.00 | 14.48 |
| ATOM | 1330 | CG2  | ILE | A   | 827 | 90.043 | 23.497 | 3.395  | 1.00 | 15.43 |
| ATOM | 1331 | C    | ILE | A   | 827 | 92.067 | 25.610 | 2.415  | 1.00 | 13.72 |
| ATOM | 1332 | O    | ILE | A   | 827 | 91.638 | 26.497 | 1.663  | 1.00 | 11.75 |
| ATOM | 1333 | N    | CYS | A   | 828 | 93.026 | 24.756 | 2.051  | 1.00 | 13.52 |
| ATOM | 1334 | CA   | CYS | A   | 828 | 93.485 | 24.732 | 0.663  | 1.00 | 14.95 |
| ATOM | 1335 | CB   | CYS | A   | 828 | 94.977 | 24.424 | 0.548  | 1.00 | 17.40 |
| ATOM | 1336 | SG   | CYS | A   | 828 | 95.407 | 22.676 | 0.632  | 1.00 | 24.91 |
| ATOM | 1337 | C    | CYS | A   | 828 | 92.640 | 23.776 | -0.181 | 1.00 | 16.38 |
| ATOM | 1338 | O    | CYS | A   | 828 | 91.911 | 22.929 | 0.349  | 1.00 | 15.68 |

FIGURE 3BA

|      | A    | B    | C   | D   | E   | F      | G      | H       | I    | J     |
|------|------|------|-----|-----|-----|--------|--------|---------|------|-------|
| ATOM | 1339 | N    | ASP | A   | 829 | 92.757 | 23.912 | -1.496  | 1.00 | 16.79 |
| ATOM | 1340 | CA   | ASP | A   | 829 | 91.901 | 23.199 | -2.426  | 1.00 | 17.98 |
| ATOM | 1341 | CB   | ASP | A   | 829 | 91.692 | 24.039 | -3.693  | 1.00 | 17.14 |
| ATOM | 1342 | CG   | ASP | A   | 829 | 92.906 | 24.058 | -4.600  | 1.00 | 19.54 |
| ATOM | 1343 | OD1  | ASP | A   | 829 | 94.008 | 23.621 | -4.186  | 1.00 | 19.76 |
| ATOM | 1344 | OD2  | ASP | A   | 829 | 92.849 | 24.505 | -5.765  | 1.00 | 20.79 |
| ATOM | 1345 | C    | ASP | A   | 829 | 92.397 | 21.790 | -2.767  | 1.00 | 18.65 |
| ATOM | 1346 | O    | ASP | A   | 829 | 91.873 | 21.153 | -3.685  | 1.00 | 18.10 |
| ATOM | 1347 | N    | PHE | A   | 830 | 93.402 | 21.311 | -2.035  | 1.00 | 19.20 |
| ATOM | 1348 | CA   | PHE | A   | 830 | 93.910 | 19.959 | -2.243  | 1.00 | 20.14 |
| ATOM | 1349 | CB   | PHE | A   | 830 | 95.227 | 19.735 | -1.502  | 1.00 | 22.72 |
| ATOM | 1350 | CG   | PHE | A   | 830 | 95.956 | 18.495 | -1.928  | 1.00 | 25.97 |
| ATOM | 1351 | CD1  | PHE | A   | 830 | 96.159 | 17.451 | -1.028  | 1.00 | 29.56 |
| ATOM | 1352 | CE1  | PHE | A   | 830 | 96.838 | 16.283 | -1.415  | 1.00 | 30.65 |
| ATOM | 1353 | CZ   | PHE | A   | 830 | 97.311 | 16.163 | -2.716  | 1.00 | 30.27 |
| ATOM | 1354 | CE2  | PHE | A   | 830 | 97.108 | 17.207 | -3.624  | 1.00 | 29.69 |
| ATOM | 1355 | CD2  | PHE | A   | 830 | 96.434 | 18.360 | -3.226  | 1.00 | 27.63 |
| ATOM | 1356 | C    | PHE | A   | 830 | 92.864 | 18.920 | -1.843  | 1.00 | 20.01 |
| ATOM | 1357 | O    | PHE | A   | 830 | 92.747 | 18.541 | -0.675  | 1.00 | 20.74 |
| ATOM | 1358 | N    | GLY | A   | 831 | 92.101 | 18.472 | -2.834  | 1.00 | 18.50 |
| ATOM | 1359 | CA   | GLY | A   | 831 | 91.031 | 17.522 | -2.614  | 1.00 | 18.13 |
| ATOM | 1360 | C    | GLY | A   | 831 | 89.666 | 18.178 | -2.714  | 1.00 | 18.32 |
| ATOM | 1361 | O    | GLY | A   | 831 | 88.648 | 17.520 | -2.497  | 1.00 | 17.58 |
| ATOM | 1362 | N    | LEU | A   | 832 | 89.639 | 19.472 | -3.033  | 1.00 | 17.18 |
| ATOM | 1363 | CA   | LEU | A   | 832 | 88.376 | 20.174 | -3.199  | 1.00 | 17.14 |
| ATOM | 1364 | CB   | LEU | A   | 832 | 88.567 | 21.694 | -3.156  | 1.00 | 17.07 |
| ATOM | 1365 | CG   | LEU | A   | 832 | 87.282 | 22.537 | -3.111  | 1.00 | 17.13 |
| ATOM | 1366 | CD1  | LEU | A   | 832 | 86.494 | 22.270 | -1.830  | 1.00 | 18.02 |
| ATOM | 1367 | CD2  | LEU | A   | 832 | 87.588 | 24.013 | -3.242  | 1.00 | 16.41 |
| ATOM | 1368 | C    | LEU | A   | 832 | 87.728 | 19.765 | -4.514  | 1.00 | 18.90 |
| ATOM | 1369 | O    | LEU | A   | 832 | 88.384 | 19.729 | -5.554  | 1.00 | 17.43 |
| ATOM | 1370 | N    | ALA | A   | 833 | 86.437 | 19.456 | -4.454  | 1.00 | 20.22 |
| ATOM | 1371 | CA   | ALA | A   | 833 | 85.677 | 19.092 | -5.640  | 1.00 | 21.46 |
| ATOM | 1372 | CB   | ALA | A   | 833 | 85.461 | 17.584 | -5.679  | 1.00 | 21.09 |
| ATOM | 1373 | C    | ALA | A   | 833 | 84.344 | 19.820 | -5.653  | 1.00 | 21.44 |
| ATOM | 1374 | O    | ALA | A   | 833 | 83.716 | 19.992 | -4.611  | 1.00 | 21.46 |
| ATOM | 1375 | N    | ARG | A   | 834 | 83.926 | 20.250 | -6.837  | 1.00 | 24.50 |
| ATOM | 1376 | CA   | ARG | A   | 834 | 82.598 | 20.820 | -7.044  | 1.00 | 28.72 |
| ATOM | 1377 | CB   | ARG | A   | 834 | 82.593 | 21.728 | -8.269  | 1.00 | 30.42 |
| ATOM | 1378 | CG   | ARG | A   | 834 | 83.307 | 23.028 | -8.080  | 1.00 | 33.57 |
| ATOM | 1379 | CD   | ARG | A   | 834 | 83.564 | 23.773 | -9.381  | 1.00 | 37.86 |
| ATOM | 1380 | NE   | ARG | A   | 834 | 84.164 | 22.923 | -10.413 | 1.00 | 39.52 |
| ATOM | 1381 | CZ   | ARG | A   | 834 | 84.333 | 23.288 | -11.682 | 1.00 | 40.45 |
| ATOM | 1382 | NH1  | ARG | A   | 834 | 83.957 | 24.494 | -12.091 | 1.00 | 40.22 |
| ATOM | 1383 | NH2  | ARG | A   | 834 | 84.889 | 22.448 | -12.543 | 1.00 | 40.99 |
| ATOM | 1384 | C    | ARG | A   | 834 | 81.572 | 19.714 | -7.258  | 1.00 | 28.87 |
| ATOM | 1385 | O    | ARG | A   | 834 | 81.862 | 18.728 | -7.941  | 1.00 | 31.38 |
| ATOM | 1386 | N    | ASP | A   | 835 | 80.375 | 19.901 | -6.698  | 1.00 | 28.27 |
| ATOM | 1387 | CA   | ASP | A   | 835 | 79.262 | 18.942 | -6.806  | 1.00 | 27.61 |
| ATOM | 1388 | CB   | ASP | A   | 835 | 78.045 | 19.453 | -6.028  | 1.00 | 26.50 |
| ATOM | 1389 | CG   | ASP | A   | 835 | 78.307 | 19.555 | -4.534  | 1.00 | 26.48 |
| ATOM | 1390 | OD1  | ASP | A   | 835 | 79.240 | 18.884 | -4.051  | 1.00 | 26.77 |

FIGURE 3BB

|      | A    | B    | C   | D | E   | F      | G      | H      | I    | J     |
|------|------|------|-----|---|-----|--------|--------|--------|------|-------|
| ATOM | 1391 | OD2  | ASP | A | 835 | 77.634 | 20.276 | -3.764 | 1.00 | 26.18 |
| ATOM | 1392 | C    | ASP | A | 835 | 78.850 | 18.597 | -8.242 | 1.00 | 26.39 |
| ATOM | 1393 | O    | ASP | A | 835 | 78.665 | 19.482 | -9.076 | 1.00 | 27.64 |
| TER  | 1393 |      | ASP | A | 835 |        |        |        |      |       |
| ATOM | 1394 | N    | PRO | A | 851 | 93.882 | 8.042  | 2.678  | 1.00 | 30.98 |
| ATOM | 1395 | CD   | PRO | A | 851 | 93.709 | 8.395  | 1.259  | 1.00 | 31.04 |
| ATOM | 1396 | CA   | PRO | A | 851 | 93.609 | 9.178  | 3.564  | 1.00 | 30.22 |
| ATOM | 1397 | CB   | PRO | A | 851 | 93.090 | 10.248 | 2.601  | 1.00 | 31.69 |
| ATOM | 1398 | CG   | PRO | A | 851 | 92.778 | 9.564  | 1.337  | 1.00 | 32.71 |
| ATOM | 1399 | C    | PRO | A | 851 | 92.588 | 8.825  | 4.640  | 1.00 | 27.25 |
| ATOM | 1400 | O    | PRO | A | 851 | 91.748 | 9.650  | 5.021  | 1.00 | 27.66 |
| ATOM | 1401 | N    | VAL | A | 852 | 92.689 | 7.356  | 4.859  | 1.00 | 24.41 |
| ATOM | 1402 | CA   | VAL | A | 852 | 91.601 | 6.566  | 5.427  | 1.00 | 22.41 |
| ATOM | 1403 | CB   | VAL | A | 852 | 91.974 | 5.071  | 5.384  | 1.00 | 23.88 |
| ATOM | 1404 | CG1  | VAL | A | 852 | 91.264 | 4.284  | 6.447  | 1.00 | 24.44 |
| ATOM | 1405 | CG2  | VAL | A | 852 | 91.695 | 4.497  | 3.988  | 1.00 | 22.52 |
| ATOM | 1406 | C    | VAL | A | 852 | 91.154 | 7.033  | 6.822  | 1.00 | 22.36 |
| ATOM | 1407 | O    | VAL | A | 852 | 89.955 | 7.025  | 7.132  | 1.00 | 21.59 |
| ATOM | 1408 | N    | LYS | A | 853 | 92.104 | 7.492  | 7.635  | 1.00 | 19.49 |
| ATOM | 1409 | CA   | LYS | A | 853 | 91.801 | 7.954  | 8.987  | 1.00 | 18.15 |
| ATOM | 1410 | CB   | LYS | A | 853 | 93.086 | 8.056  | 9.807  | 1.00 | 17.35 |
| ATOM | 1411 | CG   | LYS | A | 853 | 93.684 | 6.698  | 10.103 | 1.00 | 17.93 |
| ATOM | 1412 | CD   | LYS | A | 853 | 95.047 | 6.796  | 10.757 | 1.00 | 17.24 |
| ATOM | 1413 | CE   | LYS | A | 853 | 95.266 | 5.581  | 11.634 | 1.00 | 17.11 |
| ATOM | 1414 | NZ   | LYS | A | 853 | 96.565 | 5.647  | 12.331 | 1.00 | 17.16 |
| ATOM | 1415 | C    | LYS | A | 853 | 90.973 | 9.249  | 9.084  | 1.00 | 17.70 |
| ATOM | 1416 | O    | LYS | A | 853 | 90.508 | 9.609  | 10.168 | 1.00 | 17.62 |
| ATOM | 1417 | N    | TRP | A | 854 | 90.795 | 9.944  | 7.961  | 1.00 | 18.68 |
| ATOM | 1418 | CA   | TRP | A | 854 | 89.968 | 11.160 | 7.909  | 1.00 | 16.06 |
| ATOM | 1419 | CB   | TRP | A | 854 | 90.723 | 12.294 | 7.210  | 1.00 | 13.90 |
| ATOM | 1420 | CG   | TRP | A | 854 | 91.805 | 12.894 | 8.073  | 1.00 | 15.39 |
| ATOM | 1421 | CD1  | TRP | A | 854 | 91.727 | 14.044 | 8.799  | 1.00 | 15.01 |
| ATOM | 1422 | NE1  | TRP | A | 854 | 92.904 | 14.262 | 9.475  | 1.00 | 16.20 |
| ATOM | 1423 | CE2  | TRP | A | 854 | 93.775 | 13.240 | 9.200  | 1.00 | 15.44 |
| ATOM | 1424 | CD2  | TRP | A | 854 | 93.110 | 12.347 | 8.330  | 1.00 | 15.02 |
| ATOM | 1425 | CE3  | TRP | A | 854 | 93.794 | 11.201 | 7.894  | 1.00 | 15.16 |
| ATOM | 1426 | CZ3  | TRP | A | 854 | 95.106 | 10.983 | 8.343  | 1.00 | 14.84 |
| ATOM | 1427 | CH2  | TRP | A | 854 | 95.733 | 11.894 | 9.213  | 1.00 | 14.64 |
| ATOM | 1428 | CZ2  | TRP | A | 854 | 95.086 | 13.022 | 9.652  | 1.00 | 14.42 |
| ATOM | 1429 | C    | TRP | A | 854 | 88.635 | 10.900 | 7.206  | 1.00 | 17.07 |
| ATOM | 1430 | O    | TRP | A | 854 | 87.768 | 11.776 | 7.156  | 1.00 | 17.54 |
| ATOM | 1431 | N    | MET | A | 855 | 88.476 | 9.690  | 6.676  | 1.00 | 15.63 |
| ATOM | 1432 | CA   | MET | A | 855 | 87.315 | 9.347  | 5.868  | 1.00 | 16.76 |
| ATOM | 1433 | CB   | MET | A | 855 | 87.662 | 8.221  | 4.887  | 1.00 | 20.03 |
| ATOM | 1434 | CG   | MET | A | 855 | 88.523 | 8.675  | 3.726  | 1.00 | 21.78 |
| ATOM | 1435 | SD   | MET | A | 855 | 89.064 | 7.342  | 2.675  | 1.00 | 26.79 |
| ATOM | 1436 | CE   | MET | A | 855 | 87.552 | 6.797  | 2.042  | 1.00 | 26.15 |
| ATOM | 1437 | C    | MET | A | 855 | 86.105 | 8.960  | 6.714  | 1.00 | 15.89 |
| ATOM | 1438 | O    | MET | A | 855 | 86.186 | 8.100  | 7.601  | 1.00 | 15.81 |
| ATOM | 1439 | N    | ALA | A | 856 | 84.990 | 9.622  | 6.435  | 1.00 | 15.35 |
| ATOM | 1440 | CA   | ALA | A | 856 | 83.701 | 9.248  | 6.981  | 1.00 | 16.19 |
| ATOM | 1441 | CB   | ALA | A | 856 | 82.649 | 10.220 | 6.512  | 1.00 | 14.56 |

FIGURE 3BC

| | A | B | C | D | E | F | G | H | I | J |
|---|---|---|---|---|---|---|---|---|---|---|
| ATOM | 1442 | C | ALA | A | 856 | 83.346 | 7.829 | 6.531 | 1.00 | 16.29 |
| ATOM | 1443 | O | ALA | A | 856 | 83.751 | 7.403 | 5.446 | 1.00 | 18.72 |
| ATOM | 1444 | N | PRO | A | 857 | 82.590 | 7.097 | 7.349 | 1.00 | 16.34 |
| ATOM | 1445 | CA | PRO | A | 857 | 82.194 | 5.726 | 7.005 | 1.00 | 13.89 |
| ATOM | 1446 | CB | PRO | A | 857 | 81.101 | 5.406 | 8.030 | 1.00 | 11.22 |
| ATOM | 1447 | CG | PRO | A | 857 | 81.472 | 6.190 | 9.210 | 1.00 | 14.74 |
| ATOM | 1448 | CD | PRO | A | 857 | 82.049 | 7.506 | 8.661 | 1.00 | 16.67 |
| ATOM | 1449 | C | PRO | A | 857 | 81.631 | 5.640 | 5.596 | 1.00 | 13.96 |
| ATOM | 1450 | O | PRO | A | 857 | 82.011 | 4.722 | 4.879 | 1.00 | 11.19 |
| ATOM | 1451 | N | GLU | A | 858 | 80.776 | 6.584 | 5.196 | 1.00 | 14.13 |
| ATOM | 1452 | CA | GLU | A | 858 | 80.125 | 6.490 | 3.891 | 1.00 | 15.00 |
| ATOM | 1453 | CB | GLU | A | 858 | 78.932 | 7.454 | 3.769 | 1.00 | 15.28 |
| ATOM | 1454 | CG | GLU | A | 858 | 79.289 | 8.934 | 3.669 | 1.00 | 18.19 |
| ATOM | 1455 | CD | GLU | A | 858 | 79.336 | 9.645 | 5.025 | 1.00 | 21.66 |
| ATOM | 1456 | OE1 | GLU | A | 858 | 79.377 | 8.979 | 6.089 | 1.00 | 21.87 |
| ATOM | 1457 | OE2 | GLU | A | 858 | 79.345 | 10.889 | 5.030 | 1.00 | 22.37 |
| ATOM | 1458 | C | GLU | A | 858 | 81.132 | 6.657 | 2.745 | 1.00 | 15.69 |
| ATOM | 1459 | O | GLU | A | 858 | 80.928 | 6.126 | 1.650 | 1.00 | 15.41 |
| ATOM | 1460 | N | SER | A | 859 | 82.205 | 7.399 | 3.001 | 1.00 | 14.75 |
| ATOM | 1461 | CA | SER | A | 859 | 83.299 | 7.514 | 2.037 | 1.00 | 18.36 |
| ATOM | 1462 | CB | SER | A | 859 | 84.251 | 8.665 | 2.404 | 1.00 | 16.29 |
| ATOM | 1463 | OG | SER | A | 859 | 83.556 | 9.894 | 2.550 | 1.00 | 17.64 |
| ATOM | 1464 | C | SER | A | 859 | 84.076 | 6.211 | 2.012 | 1.00 | 18.91 |
| ATOM | 1465 | O | SER | A | 859 | 84.351 | 5.650 | 0.948 | 1.00 | 20.06 |
| ATOM | 1466 | N | LEU | A | 860 | 84.409 | 5.747 | 3.211 | 1.00 | 18.37 |
| ATOM | 1467 | CA | LEU | A | 860 | 85.237 | 4.576 | 3.434 | 1.00 | 18.95 |
| ATOM | 1468 | CB | LEU | A | 860 | 85.523 | 4.475 | 4.936 | 1.00 | 20.97 |
| ATOM | 1469 | CG | LEU | A | 860 | 86.631 | 3.607 | 5.517 | 1.00 | 23.40 |
| ATOM | 1470 | CD1 | LEU | A | 860 | 88.006 | 4.031 | 5.027 | 1.00 | 22.93 |
| ATOM | 1471 | CD2 | LEU | A | 860 | 86.555 | 3.682 | 7.038 | 1.00 | 23.68 |
| ATOM | 1472 | C | LEU | A | 860 | 84.578 | 3.299 | 2.924 | 1.00 | 18.90 |
| ATOM | 1473 | O | LEU | A | 860 | 85.256 | 2.425 | 2.390 | 1.00 | 19.79 |
| ATOM | 1474 | N | PHE | A | 861 | 83.256 | 3.205 | 3.067 | 1.00 | 16.94 |
| ATOM | 1475 | CA | PHE | A | 861 | 82.539 | 1.969 | 2.780 | 1.00 | 15.10 |
| ATOM | 1476 | CB | PHE | A | 861 | 81.672 | 1.549 | 3.975 | 1.00 | 14.09 |
| ATOM | 1477 | CG | PHE | A | 861 | 82.449 | 1.316 | 5.243 | 1.00 | 14.47 |
| ATOM | 1478 | CD1 | PHE | A | 861 | 82.167 | 2.048 | 6.385 | 1.00 | 15.36 |
| ATOM | 1479 | CE1 | PHE | A | 861 | 82.884 | 1.842 | 7.559 | 1.00 | 15.16 |
| ATOM | 1480 | CZ | PHE | A | 861 | 83.891 | 0.883 | 7.595 | 1.00 | 15.36 |
| ATOM | 1481 | CE2 | PHE | A | 861 | 84.178 | 0.144 | 6.465 | 1.00 | 13.38 |
| ATOM | 1482 | CD2 | PHE | A | 861 | 83.455 | 0.353 | 5.299 | 1.00 | 14.13 |
| ATOM | 1483 | C | PHE | A | 861 | 81.683 | 2.043 | 1.534 | 1.00 | 16.54 |
| ATOM | 1484 | O | PHE | A | 861 | 81.483 | 1.029 | 0.866 | 1.00 | 17.50 |
| ATOM | 1485 | N | GLU | A | 862 | 81.157 | 3.226 | 1.228 | 1.00 | 17.37 |
| ATOM | 1486 | CA | GLU | A | 862 | 80.222 | 3.377 | 0.109 | 1.00 | 18.25 |
| ATOM | 1487 | CB | GLU | A | 862 | 78.850 | 3.870 | 0.597 | 1.00 | 17.58 |
| ATOM | 1488 | CG | GLU | A | 862 | 78.197 | 3.038 | 1.692 | 1.00 | 18.73 |
| ATOM | 1489 | CD | GLU | A | 862 | 76.913 | 3.668 | 2.229 | 1.00 | 20.63 |
| ATOM | 1490 | OE1 | GLU | A | 862 | 76.948 | 4.228 | 3.354 | 1.00 | 19.20 |
| ATOM | 1491 | OE2 | GLU | A | 862 | 75.863 | 3.595 | 1.534 | 1.00 | 20.28 |
| ATOM | 1492 | C | GLU | A | 862 | 80.760 | 4.318 | -0.978 | 1.00 | 19.68 |
| ATOM | 1493 | O | GLU | A | 862 | 80.105 | 4.530 | -2.003 | 1.00 | 18.87 |

FIGURE 3BD

|   | A | B | C | D | E | F | G | H | I | J |
|---|---|---|---|---|---|---|---|---|---|---|
| ATOM | 1494 | N | GLY | A | 863 | 81.953 | 4.870 | -0.757 | 1.00 | 20.87 |
| ATOM | 1495 | CA | GLY | A | 863 | 82.524 | 5.847 | -1.673 | 1.00 | 21.93 |
| ATOM | 1496 | C | GLY | A | 863 | 81.659 | 7.088 | -1.873 | 1.00 | 23.09 |
| ATOM | 1497 | O | GLY | A | 863 | 81.656 | 7.681 | -2.954 | 1.00 | 23.52 |
| ATOM | 1498 | N | ILE | A | 864 | 80.927 | 7.478 | -0.831 | 1.00 | 21.77 |
| ATOM | 1499 | CA | ILE | A | 864 | 80.085 | 8.673 | -0.879 | 1.00 | 19.64 |
| ATOM | 1500 | CB | ILE | A | 864 | 78.706 | 8.400 | -0.224 | 1.00 | 17.56 |
| ATOM | 1501 | CG1 | ILE | A | 864 | 77.898 | 7.419 | -1.079 | 1.00 | 17.42 |
| ATOM | 1502 | CD1 | ILE | A | 864 | 76.708 | 6.798 | -0.358 | 1.00 | 15.38 |
| ATOM | 1503 | CG2 | ILE | A | 864 | 77.929 | 9.715 | 0.017 | 1.00 | 15.09 |
| ATOM | 1504 | C | ILE | A | 864 | 80.791 | 9.847 | -0.191 | 1.00 | 18.56 |
| ATOM | 1505 | O | ILE | A | 864 | 81.310 | 9.721 | 0.915 | 1.00 | 16.22 |
| ATOM | 1506 | N | TYR | A | 865 | 80.802 | 10.985 | -0.867 | 1.00 | 19.09 |
| ATOM | 1507 | CA | TYR | A | 865 | 81.389 | 12.195 | -0.323 | 1.00 | 22.74 |
| ATOM | 1508 | CB | TYR | A | 865 | 82.644 | 12.568 | -1.110 | 1.00 | 24.66 |
| ATOM | 1509 | CG | TYR | A | 865 | 83.869 | 11.752 | -0.779 | 1.00 | 28.77 |
| ATOM | 1510 | CD1 | TYR | A | 865 | 84.139 | 10.552 | -1.445 | 1.00 | 31.28 |
| ATOM | 1511 | CE1 | TYR | A | 865 | 85.275 | 9.804 | -1.149 | 1.00 | 31.12 |
| ATOM | 1512 | CZ | TYR | A | 865 | 86.149 | 10.264 | -0.182 | 1.00 | 34.16 |
| ATOM | 1513 | OH | TYR | A | 865 | 87.282 | 9.549 | 0.128 | 1.00 | 38.53 |
| ATOM | 1514 | CE2 | TYR | A | 865 | 85.904 | 11.454 | 0.487 | 1.00 | 34.04 |
| ATOM | 1515 | CD2 | TYR | A | 865 | 84.772 | 12.189 | 0.183 | 1.00 | 31.56 |
| ATOM | 1516 | C | TYR | A | 865 | 80.373 | 13.323 | -0.427 | 1.00 | 20.35 |
| ATOM | 1517 | O | TYR | A | 865 | 80.119 | 13.823 | -1.518 | 1.00 | 22.52 |
| ATOM | 1518 | N | THR | A | 866 | 79.774 | 13.694 | 0.698 | 1.00 | 17.03 |
| ATOM | 1519 | CA | THR | A | 866 | 78.929 | 14.884 | 0.758 | 1.00 | 17.48 |
| ATOM | 1520 | CB | THR | A | 866 | 77.481 | 14.546 | 1.188 | 1.00 | 17.90 |
| ATOM | 1521 | OG1 | THR | A | 866 | 77.498 | 14.016 | 2.520 | 1.00 | 20.98 |
| ATOM | 1522 | CG2 | THR | A | 866 | 76.881 | 13.426 | 0.346 | 1.00 | 14.98 |
| ATOM | 1523 | C | THR | A | 866 | 79.527 | 15.845 | 1.767 | 1.00 | 17.25 |
| ATOM | 1524 | O | THR | A | 866 | 80.527 | 15.529 | 2.426 | 1.00 | 17.32 |
| ATOM | 1525 | N | ILE | A | 867 | 78.903 | 17.009 | 1.909 | 1.00 | 16.65 |
| ATOM | 1526 | CA | ILE | A | 867 | 79.344 | 17.979 | 2.896 | 1.00 | 15.94 |
| ATOM | 1527 | CB | ILE | A | 867 | 78.582 | 19.336 | 2.746 | 1.00 | 16.72 |
| ATOM | 1528 | CG1 | ILE | A | 867 | 79.319 | 20.455 | 3.484 | 1.00 | 16.58 |
| ATOM | 1529 | CD1 | ILE | A | 867 | 80.576 | 20.910 | 2.781 | 1.00 | 16.17 |
| ATOM | 1530 | CG2 | ILE | A | 867 | 77.144 | 19.235 | 3.226 | 1.00 | 18.20 |
| ATOM | 1531 | C | ILE | A | 867 | 79.266 | 17.399 | 4.309 | 1.00 | 16.08 |
| ATOM | 1532 | O | ILE | A | 867 | 80.060 | 17.756 | 5.184 | 1.00 | 18.44 |
| ATOM | 1533 | N | LYS | A | 868 | 78.343 | 16.469 | 4.514 | 1.00 | 16.48 |
| ATOM | 1534 | CA | LYS | A | 868 | 78.229 | 15.778 | 5.793 | 1.00 | 16.61 |
| ATOM | 1535 | CB | LYS | A | 868 | 76.847 | 15.122 | 5.931 | 1.00 | 19.16 |
| ATOM | 1536 | CG | LYS | A | 868 | 75.733 | 16.119 | 6.317 | 1.00 | 18.80 |
| ATOM | 1537 | CD | LYS | A | 868 | 75.903 | 16.571 | 7.773 | 1.00 | 19.43 |
| ATOM | 1538 | CE | LYS | A | 868 | 74.655 | 17.217 | 8.329 | 1.00 | 19.05 |
| ATOM | 1539 | NZ | LYS | A | 868 | 73.539 | 16.260 | 8.580 | 1.00 | 21.75 |
| ATOM | 1540 | C | LYS | A | 868 | 79.373 | 14.789 | 6.043 | 1.00 | 16.52 |
| ATOM | 1541 | O | LYS | A | 868 | 79.730 | 14.540 | 7.190 | 1.00 | 17.49 |
| ATOM | 1542 | N | SER | A | 869 | 79.962 | 14.241 | 4.980 | 1.00 | 17.09 |
| ATOM | 1543 | CA | SER | A | 869 | 81.206 | 13.470 | 5.115 | 1.00 | 15.33 |
| ATOM | 1544 | CB | SER | A | 869 | 81.678 | 12.890 | 3.777 | 1.00 | 14.72 |
| ATOM | 1545 | OG | SER | A | 869 | 80.634 | 12.243 | 3.071 | 1.00 | 17.01 |

FIGURE 3BE

| | A | B | C | D | E | F | G | H | I | J |
|---|---|---|---|---|---|---|---|---|---|---|
| ATOM | 1546 | C | SER | A | 869 | 82.303 | 14.353 | 5.692 | 1.00 | 17.40 |
| ATOM | 1547 | O | SER | A | 869 | 83.097 | 13.903 | 6.528 | 1.00 | 18.62 |
| ATOM | 1548 | N | ASP | A | 870 | 82.337 | 15.613 | 5.250 | 1.00 | 16.42 |
| ATOM | 1549 | CA | ASP | A | 870 | 83.313 | 16.582 | 5.741 | 1.00 | 17.35 |
| ATOM | 1550 | CB | ASP | A | 870 | 83.278 | 17.862 | 4.913 | 1.00 | 16.86 |
| ATOM | 1551 | CG | ASP | A | 870 | 83.995 | 17.713 | 3.625 | 1.00 | 17.52 |
| ATOM | 1552 | OD1 | ASP | A | 870 | 83.522 | 18.252 | 2.608 | 1.00 | 17.62 |
| ATOM | 1553 | OD2 | ASP | A | 870 | 85.047 | 17.052 | 3.533 | 1.00 | 20.52 |
| ATOM | 1554 | C | ASP | A | 870 | 83.121 | 16.933 | 7.209 | 1.00 | 17.93 |
| ATOM | 1555 | O | ASP | A | 870 | 84.061 | 17.393 | 7.858 | 1.00 | 19.20 |
| ATOM | 1556 | N | VAL | A | 871 | 81.913 | 16.732 | 7.730 | 1.00 | 16.27 |
| ATOM | 1557 | CA | VAL | A | 871 | 81.685 | 16.963 | 9.150 | 1.00 | 17.02 |
| ATOM | 1558 | CB | VAL | A | 871 | 80.183 | 16.978 | 9.520 | 1.00 | 15.54 |
| ATOM | 1559 | CG1 | VAL | A | 871 | 79.998 | 17.080 | 11.025 | 1.00 | 12.16 |
| ATOM | 1560 | CG2 | VAL | A | 871 | 79.466 | 18.152 | 8.815 | 1.00 | 14.35 |
| ATOM | 1561 | C | VAL | A | 871 | 82.475 | 15.923 | 9.952 | 1.00 | 17.68 |
| ATOM | 1562 | O | VAL | A | 871 | 83.091 | 16.251 | 10.956 | 1.00 | 16.78 |
| ATOM | 1563 | N | TRP | A | 872 | 82.478 | 14.680 | 9.480 | 1.00 | 17.27 |
| ATOM | 1564 | CA | TRP | A | 872 | 83.279 | 13.633 | 10.108 | 1.00 | 17.66 |
| ATOM | 1565 | CB | TRP | A | 872 | 83.015 | 12.271 | 9.455 | 1.00 | 13.45 |
| ATOM | 1566 | CG | TRP | A | 872 | 83.858 | 11.160 | 10.017 | 1.00 | 13.09 |
| ATOM | 1567 | CD1 | TRP | A | 872 | 85.208 | 10.990 | 9.860 | 1.00 | 12.41 |
| ATOM | 1568 | NE1 | TRP | A | 872 | 85.623 | 9.855 | 10.510 | 1.00 | 12.57 |
| ATOM | 1569 | CE2 | TRP | A | 872 | 84.541 | 9.252 | 11.094 | 1.00 | 11.69 |
| ATOM | 1570 | CD2 | TRP | A | 872 | 83.408 | 10.047 | 10.801 | 1.00 | 13.32 |
| ATOM | 1571 | CE3 | TRP | A | 872 | 82.155 | 9.634 | 11.288 | 1.00 | 12.54 |
| ATOM | 1572 | CZ3 | TRP | A | 872 | 82.077 | 8.458 | 12.032 | 1.00 | 12.57 |
| ATOM | 1573 | CH2 | TRP | A | 872 | 83.226 | 7.697 | 12.306 | 1.00 | 13.70 |
| ATOM | 1574 | CZ2 | TRP | A | 872 | 84.465 | 8.079 | 11.847 | 1.00 | 12.18 |
| ATOM | 1575 | C | TRP | A | 872 | 84.775 | 13.985 | 10.070 | 1.00 | 17.28 |
| ATOM | 1576 | O | TRP | A | 872 | 85.441 | 13.965 | 11.104 | 1.00 | 16.71 |
| ATOM | 1577 | N | SER | A | 873 | 85.276 | 14.299 | 8.874 | 1.00 | 16.30 |
| ATOM | 1578 | CA | SER | A | 873 | 86.660 | 14.722 | 8.654 | 1.00 | 17.42 |
| ATOM | 1579 | CB | SER | A | 873 | 86.872 | 15.119 | 7.191 | 1.00 | 18.43 |
| ATOM | 1580 | OG | SER | A | 873 | 86.603 | 14.034 | 6.330 | 1.00 | 25.43 |
| ATOM | 1581 | C | SER | A | 873 | 87.009 | 15.910 | 9.524 | 1.00 | 16.70 |
| ATOM | 1582 | O | SER | A | 873 | 88.100 | 15.979 | 10.070 | 1.00 | 17.62 |
| ATOM | 1583 | N | TYR | A | 874 | 86.076 | 16.855 | 9.620 | 1.00 | 17.22 |
| ATOM | 1584 | CA | TYR | A | 874 | 86.229 | 18.018 | 10.473 | 1.00 | 16.43 |
| ATOM | 1585 | CB | TYR | A | 874 | 85.004 | 18.918 | 10.345 | 1.00 | 15.04 |
| ATOM | 1586 | CG | TYR | A | 874 | 85.001 | 20.080 | 11.302 | 1.00 | 13.98 |
| ATOM | 1587 | CD1 | TYR | A | 874 | 85.783 | 21.214 | 11.056 | 1.00 | 12.67 |
| ATOM | 1588 | CE1 | TYR | A | 874 | 85.781 | 22.287 | 11.945 | 1.00 | 14.07 |
| ATOM | 1589 | CZ | TYR | A | 874 | 84.985 | 22.225 | 13.085 | 1.00 | 13.86 |
| ATOM | 1590 | OH | TYR | A | 874 | 84.982 | 23.267 | 13.974 | 1.00 | 14.03 |
| ATOM | 1591 | CE2 | TYR | A | 874 | 84.209 | 21.109 | 13.348 | 1.00 | 13.81 |
| ATOM | 1592 | CD2 | TYR | A | 874 | 84.219 | 20.045 | 12.456 | 1.00 | 12.75 |
| ATOM | 1593 | C | TYR | A | 874 | 86.449 | 17.603 | 11.929 | 1.00 | 16.04 |
| ATOM | 1594 | O | TYR | A | 874 | 87.268 | 18.195 | 12.637 | 1.00 | 17.15 |
| ATOM | 1595 | N | GLY | A | 875 | 85.719 | 16.578 | 12.355 | 1.00 | 14.12 |
| ATOM | 1596 | CA | GLY | A | 875 | 85.853 | 16.025 | 13.686 | 1.00 | 16.74 |
| ATOM | 1597 | C | GLY | A | 875 | 87.235 | 15.444 | 13.905 | 1.00 | 16.58 |

FIGURE 3BF

| | A | B | C | D | E | F | G | H | I | J |
|---|---|---|---|---|---|---|---|---|---|---|
| ATOM | 1598 | O | GLY | A | 875 | 87.810 | 15.590 | 14.986 | 1.00 | 16.44 |
| ATOM | 1599 | N | ILE | A | 876 | 87.769 | 14.783 | 12.882 | 1.00 | 16.25 |
| ATOM | 1600 | CA | ILE | A | 876 | 89.118 | 14.236 | 12.973 | 1.00 | 17.91 |
| ATOM | 1601 | CB | ILE | A | 876 | 89.423 | 13.301 | 11.791 | 1.00 | 17.12 |
| ATOM | 1602 | CG1 | ILE | A | 876 | 88.368 | 12.173 | 11.697 | 1.00 | 16.18 |
| ATOM | 1603 | CD1 | ILE | A | 876 | 88.373 | 11.166 | 12.858 | 1.00 | 13.16 |
| ATOM | 1604 | CG2 | ILE | A | 876 | 90.843 | 12.743 | 11.913 | 1.00 | 15.38 |
| ATOM | 1605 | C | ILE | A | 876 | 90.130 | 15.382 | 13.058 | 1.00 | 19.06 |
| ATOM | 1606 | O | ILE | A | 876 | 91.070 | 15.340 | 13.872 | 1.00 | 18.29 |
| ATOM | 1607 | N | LEU | A | 877 | 89.907 | 16.407 | 12.234 | 1.00 | 15.55 |
| ATOM | 1608 | CA | LEU | A | 877 | 90.711 | 17.614 | 12.259 | 1.00 | 17.32 |
| ATOM | 1609 | CB | LEU | A | 877 | 90.264 | 18.586 | 11.154 | 1.00 | 19.15 |
| ATOM | 1610 | CG | LEU | A | 877 | 91.200 | 19.748 | 10.788 | 1.00 | 20.67 |
| ATOM | 1611 | CD1 | LEU | A | 877 | 90.975 | 20.155 | 9.350 | 1.00 | 21.66 |
| ATOM | 1612 | CD2 | LEU | A | 877 | 90.950 | 20.938 | 11.676 | 1.00 | 21.93 |
| ATOM | 1613 | C | LEU | A | 877 | 90.656 | 18.282 | 13.638 | 1.00 | 17.52 |
| ATOM | 1614 | O | LEU | A | 877 | 91.671 | 18.788 | 14.114 | 1.00 | 18.98 |
| ATOM | 1615 | N | LEU | A | 878 | 89.486 | 18.275 | 14.280 | 1.00 | 16.65 |
| ATOM | 1616 | CA | LEU | A | 878 | 89.357 | 18.851 | 15.619 | 1.00 | 16.94 |
| ATOM | 1617 | CB | LEU | A | 878 | 87.911 | 18.807 | 16.120 | 1.00 | 17.52 |
| ATOM | 1618 | CG | LEU | A | 878 | 86.904 | 19.867 | 15.635 | 1.00 | 20.28 |
| ATOM | 1619 | CD1 | LEU | A | 878 | 85.690 | 19.889 | 16.539 | 1.00 | 21.06 |
| ATOM | 1620 | CD2 | LEU | A | 878 | 87.493 | 21.258 | 15.556 | 1.00 | 20.42 |
| ATOM | 1621 | C | LEU | A | 878 | 90.259 | 18.094 | 16.574 | 1.00 | 17.71 |
| ATOM | 1622 | O | LEU | A | 878 | 90.976 | 18.687 | 17.382 | 1.00 | 18.27 |
| ATOM | 1623 | N | TRP | A | 879 | 90.236 | 16.771 | 16.459 | 1.00 | 18.05 |
| ATOM | 1624 | CA | TRP | A | 879 | 91.110 | 15.932 | 17.249 | 1.00 | 16.30 |
| ATOM | 1625 | CB | TRP | A | 879 | 90.862 | 14.466 | 16.927 | 1.00 | 15.64 |
| ATOM | 1626 | CG | TRP | A | 879 | 91.413 | 13.592 | 17.963 | 1.00 | 15.07 |
| ATOM | 1627 | CD1 | TRP | A | 879 | 90.789 | 13.175 | 19.108 | 1.00 | 15.29 |
| ATOM | 1628 | NE1 | TRP | A | 879 | 91.640 | 12.391 | 19.848 | 1.00 | 15.00 |
| ATOM | 1629 | CE2 | TRP | A | 879 | 92.835 | 12.288 | 19.184 | 1.00 | 14.15 |
| ATOM | 1630 | CD2 | TRP | A | 879 | 92.725 | 13.047 | 17.995 | 1.00 | 13.84 |
| ATOM | 1631 | CE3 | TRP | A | 879 | 93.824 | 13.105 | 17.131 | 1.00 | 13.47 |
| ATOM | 1632 | CZ3 | TRP | A | 879 | 94.978 | 12.428 | 17.475 | 1.00 | 14.57 |
| ATOM | 1633 | CH2 | TRP | A | 879 | 95.056 | 11.682 | 18.666 | 1.00 | 15.98 |
| ATOM | 1634 | CZ2 | TRP | A | 879 | 93.994 | 11.596 | 19.528 | 1.00 | 14.57 |
| ATOM | 1635 | C | TRP | A | 879 | 92.586 | 16.305 | 17.048 | 1.00 | 15.77 |
| ATOM | 1636 | O | TRP | A | 879 | 93.340 | 16.405 | 18.018 | 1.00 | 16.64 |
| ATOM | 1637 | N | GLU | A | 880 | 92.983 | 16.522 | 15.795 | 1.00 | 13.96 |
| ATOM | 1638 | CA | GLU | A | 880 | 94.337 | 16.965 | 15.476 | 1.00 | 13.46 |
| ATOM | 1639 | CB | GLU | A | 880 | 94.522 | 17.134 | 13.970 | 1.00 | 14.20 |
| ATOM | 1640 | CG | GLU | A | 880 | 94.466 | 15.851 | 13.167 | 1.00 | 15.21 |
| ATOM | 1641 | CD | GLU | A | 880 | 94.738 | 16.099 | 11.698 | 1.00 | 16.83 |
| ATOM | 1642 | OE1 | GLU | A | 880 | 95.922 | 16.008 | 11.293 | 1.00 | 14.24 |
| ATOM | 1643 | OE2 | GLU | A | 880 | 93.771 | 16.403 | 10.955 | 1.00 | 16.40 |
| ATOM | 1644 | C | GLU | A | 880 | 94.659 | 18.291 | 16.165 | 1.00 | 13.31 |
| ATOM | 1645 | O | GLU | A | 880 | 95.738 | 18.451 | 16.724 | 1.00 | 14.67 |
| ATOM | 1646 | N | ILE | A | 881 | 93.718 | 19.231 | 16.121 | 1.00 | 11.51 |
| ATOM | 1647 | CA | ILE | A | 881 | 93.895 | 20.524 | 16.763 | 1.00 | 10.88 |
| ATOM | 1648 | CB | ILE | A | 881 | 92.703 | 21.478 | 16.443 | 1.00 | 10.16 |
| ATOM | 1649 | CG1 | ILE | A | 881 | 92.711 | 21.870 | 14.956 | 1.00 | 10.14 |

FIGURE 3BG

| | A | B | C | D | E | F | G | H | I | J |
|---|---|---|---|---|---|---|---|---|---|---|
| ATOM | 1650 | CD1 | ILE | A | 881 | 91.512 | 22.760 | 14.520 | 1.00 | 9.59 |
| ATOM | 1651 | CG2 | ILE | A | 881 | 92.772 | 22.733 | 17.306 | 1.00 | 9.33 |
| ATOM | 1652 | C | ILE | A | 881 | 94.086 | 20.353 | 18.267 | 1.00 | 11.66 |
| ATOM | 1653 | O | ILE | A | 881 | 95.038 | 20.875 | 18.840 | 1.00 | 11.32 |
| ATOM | 1654 | N | PHE | A | 882 | 93.204 | 19.576 | 18.895 | 1.00 | 13.10 |
| ATOM | 1655 | CA | PHE | A | 882 | 93.177 | 19.501 | 20.351 | 1.00 | 11.57 |
| ATOM | 1656 | CB | PHE | A | 882 | 91.734 | 19.434 | 20.870 | 1.00 | 11.18 |
| ATOM | 1657 | CG | PHE | A | 882 | 90.959 | 20.704 | 20.628 | 1.00 | 10.23 |
| ATOM | 1658 | CD1 | PHE | A | 882 | 90.214 | 20.873 | 19.456 | 1.00 | 11.20 |
| ATOM | 1659 | CE1 | PHE | A | 882 | 89.510 | 22.055 | 19.216 | 1.00 | 8.89 |
| ATOM | 1660 | CZ | PHE | A | 882 | 89.564 | 23.081 | 20.146 | 1.00 | 8.17 |
| ATOM | 1661 | CE2 | PHE | A | 882 | 90.313 | 22.927 | 21.315 | 1.00 | 7.77 |
| ATOM | 1662 | CD2 | PHE | A | 882 | 91.010 | 21.749 | 21.543 | 1.00 | 8.12 |
| ATOM | 1663 | C | PHE | A | 882 | 94.096 | 18.447 | 20.950 | 1.00 | 12.33 |
| ATOM | 1664 | O | PHE | A | 882 | 94.133 | 18.263 | 22.174 | 1.00 | 14.53 |
| ATOM | 1665 | N | SER | A | 883 | 94.843 | 17.765 | 20.083 | 1.00 | 12.56 |
| ATOM | 1666 | CA | SER | A | 883 | 95.964 | 16.932 | 20.513 | 1.00 | 12.91 |
| ATOM | 1667 | CB | SER | A | 883 | 95.901 | 15.550 | 19.871 | 1.00 | 13.82 |
| ATOM | 1668 | OG | SER | A | 883 | 96.027 | 15.631 | 18.463 | 1.00 | 12.77 |
| ATOM | 1669 | C | SER | A | 883 | 97.280 | 17.614 | 20.146 | 1.00 | 15.04 |
| ATOM | 1670 | O | SER | A | 883 | 98.357 | 17.069 | 20.408 | 1.00 | 15.89 |
| ATOM | 1671 | N | LEU | A | 884 | 97.176 | 18.808 | 19.554 | 1.00 | 12.51 |
| ATOM | 1672 | CA | LEU | A | 884 | 98.326 | 19.545 | 19.029 | 1.00 | 13.46 |
| ATOM | 1673 | CB | LEU | A | 884 | 99.253 | 20.060 | 20.153 | 1.00 | 9.78 |
| ATOM | 1674 | CG | LEU | A | 884 | 98.684 | 21.072 | 21.162 | 1.00 | 8.76 |
| ATOM | 1675 | CD1 | LEU | A | 884 | 99.776 | 21.542 | 22.094 | 1.00 | 5.81 |
| ATOM | 1676 | CD2 | LEU | A | 884 | 97.976 | 22.269 | 20.507 | 1.00 | 6.33 |
| ATOM | 1677 | C | LEU | A | 884 | 99.103 | 18.736 | 17.983 | 1.00 | 13.84 |
| ATOM | 1678 | O | LEU | A | 884 | 100.341 | 18.692 | 17.993 | 1.00 | 14.66 |
| ATOM | 1679 | N | GLY | A | 885 | 98.355 | 18.088 | 17.097 | 1.00 | 13.53 |
| ATOM | 1680 | CA | GLY | A | 885 | 98.913 | 17.486 | 15.902 | 1.00 | 13.69 |
| ATOM | 1681 | C | GLY | A | 885 | 99.364 | 16.046 | 16.031 | 1.00 | 13.86 |
| ATOM | 1682 | O | GLY | A | 885 | 100.315 | 15.635 | 15.367 | 1.00 | 13.62 |
| ATOM | 1683 | N | VAL | A | 886 | 98.691 | 15.278 | 16.879 | 1.00 | 13.91 |
| ATOM | 1684 | CA | VAL | A | 886 | 98.954 | 13.848 | 16.954 | 1.00 | 14.24 |
| ATOM | 1685 | CB | VAL | A | 886 | 98.543 | 13.238 | 18.342 | 1.00 | 13.92 |
| ATOM | 1686 | CG1 | VAL | A | 886 | 98.766 | 11.729 | 18.397 | 1.00 | 13.51 |
| ATOM | 1687 | CG2 | VAL | A | 886 | 99.319 | 13.901 | 19.480 | 1.00 | 10.20 |
| ATOM | 1688 | C | VAL | A | 886 | 98.225 | 13.186 | 15.778 | 1.00 | 16.11 |
| ATOM | 1689 | O | VAL | A | 886 | 97.134 | 13.607 | 15.374 | 1.00 | 17.48 |
| ATOM | 1690 | N | ASN | A | 887 | 98.863 | 12.180 | 15.201 | 1.00 | 17.09 |
| ATOM | 1691 | CA | ASN | A | 887 | 98.241 | 11.351 | 14.187 | 1.00 | 17.38 |
| ATOM | 1692 | CB | ASN | A | 887 | 99.248 | 10.291 | 13.716 | 1.00 | 19.14 |
| ATOM | 1693 | CG | ASN | A | 887 | 98.770 | 9.511 | 12.498 | 1.00 | 22.15 |
| ATOM | 1694 | OD1 | ASN | A | 887 | 98.867 | 8.282 | 12.470 | 1.00 | 24.81 |
| ATOM | 1695 | ND2 | ASN | A | 887 | 98.276 | 10.214 | 11.481 | 1.00 | 20.31 |
| ATOM | 1696 | C | ASN | A | 887 | 96.981 | 10.701 | 14.766 | 1.00 | 15.73 |
| ATOM | 1697 | O | ASN | A | 887 | 97.027 | 10.122 | 15.848 | 1.00 | 17.72 |
| ATOM | 1698 | N | PRO | A | 888 | 95.852 | 10.816 | 14.067 | 1.00 | 14.82 |
| ATOM | 1699 | CA | PRO | A | 888 | 94.599 | 10.201 | 14.517 | 1.00 | 13.38 |
| ATOM | 1700 | CB | PRO | A | 888 | 93.626 | 10.527 | 13.386 | 1.00 | 11.87 |
| ATOM | 1701 | CG | PRO | A | 888 | 94.192 | 11.682 | 12.734 | 1.00 | 13.69 |

FIGURE 3BH

|  | A | B | C | D | E | F | G | H | I | J |
|---|---|---|---|---|---|---|---|---|---|---|
| ATOM | 1702 | CD | PRO | A | 888 | 95.677 | 11.536 | 12.795 | 1.00 | 13.59 |
| ATOM | 1703 | C | PRO | A | 888 | 94.731 | 8.684 | 14.672 | 1.00 | 15.12 |
| ATOM | 1704 | O | PRO | A | 888 | 95.536 | 8.052 | 13.976 | 1.00 | 14.52 |
| ATOM | 1705 | N | TYR | A | 889 | 93.930 | 8.116 | 15.573 | 1.00 | 16.95 |
| ATOM | 1706 | CA | TYR | A | 889 | 94.050 | 6.710 | 15.967 | 1.00 | 16.94 |
| ATOM | 1707 | CB | TYR | A | 889 | 93.363 | 5.792 | 14.943 | 1.00 | 15.28 |
| ATOM | 1708 | CG | TYR | A | 889 | 91.993 | 6.288 | 14.528 | 1.00 | 15.81 |
| ATOM | 1709 | CD1 | TYR | A | 889 | 91.841 | 7.133 | 13.430 | 1.00 | 15.40 |
| ATOM | 1710 | CE1 | TYR | A | 889 | 90.577 | 7.613 | 13.053 | 1.00 | 16.55 |
| ATOM | 1711 | CZ | TYR | A | 889 | 89.453 | 7.240 | 13.783 | 1.00 | 16.73 |
| ATOM | 1712 | OH | TYR | A | 889 | 88.215 | 7.709 | 13.405 | 1.00 | 16.23 |
| ATOM | 1713 | CE2 | TYR | A | 889 | 89.578 | 6.404 | 14.892 | 1.00 | 15.64 |
| ATOM | 1714 | CD2 | TYR | A | 889 | 90.846 | 5.936 | 15.258 | 1.00 | 15.81 |
| ATOM | 1715 | C | TYR | A | 889 | 95.525 | 6.359 | 16.158 | 1.00 | 16.65 |
| ATOM | 1716 | O | TYR | A | 889 | 96.043 | 5.461 | 15.484 | 1.00 | 18.09 |
| ATOM | 1717 | N | PRO | A | 890 | 96.203 | 7.071 | 17.068 | 1.00 | 17.06 |
| ATOM | 1718 | CA | PRO | A | 890 | 97.657 | 6.915 | 17.235 | 1.00 | 16.65 |
| ATOM | 1719 | CB | PRO | A | 890 | 97.980 | 7.813 | 18.444 | 1.00 | 14.79 |
| ATOM | 1720 | CG | PRO | A | 890 | 96.669 | 7.995 | 19.142 | 1.00 | 15.88 |
| ATOM | 1721 | CD | PRO | A | 890 | 95.649 | 8.046 | 18.031 | 1.00 | 15.32 |
| ATOM | 1722 | C | PRO | A | 890 | 98.018 | 5.459 | 17.531 | 1.00 | 16.40 |
| ATOM | 1723 | O | PRO | A | 890 | 97.379 | 4.837 | 18.395 | 1.00 | 15.50 |
| ATOM | 1724 | N | GLY | A | 891 | 99.001 | 4.925 | 16.805 | 1.00 | 13.78 |
| ATOM | 1725 | CA | GLY | A | 891 | 99.430 | 3.546 | 16.983 | 1.00 | 14.32 |
| ATOM | 1726 | C | GLY | A | 891 | 98.482 | 2.496 | 16.419 | 1.00 | 16.48 |
| ATOM | 1727 | O | GLY | A | 891 | 98.683 | 1.298 | 16.624 | 1.00 | 18.74 |
| ATOM | 1728 | N | ILE | A | 892 | 97.436 | 2.934 | 15.721 | 1.00 | 16.51 |
| ATOM | 1729 | CA | ILE | A | 892 | 96.536 | 2.001 | 15.066 | 1.00 | 17.00 |
| ATOM | 1730 | CB | ILE | A | 892 | 95.064 | 2.320 | 15.392 | 1.00 | 17.71 |
| ATOM | 1731 | CG1 | ILE | A | 892 | 94.806 | 2.114 | 16.890 | 1.00 | 17.56 |
| ATOM | 1732 | CD1 | ILE | A | 892 | 93.456 | 2.666 | 17.359 | 1.00 | 20.71 |
| ATOM | 1733 | CG2 | ILE | A | 892 | 94.124 | 1.472 | 14.530 | 1.00 | 15.58 |
| ATOM | 1734 | C | ILE | A | 892 | 96.806 | 2.018 | 13.562 | 1.00 | 15.84 |
| ATOM | 1735 | O | ILE | A | 892 | 96.569 | 3.022 | 12.902 | 1.00 | 16.22 |
| ATOM | 1736 | N | PRO | A | 893 | 97.313 | 0.907 | 13.032 | 1.00 | 14.21 |
| ATOM | 1737 | CA | PRO | A | 893 | 97.658 | 0.828 | 11.612 | 1.00 | 14.31 |
| ATOM | 1738 | CB | PRO | A | 893 | 98.425 | -0.498 | 11.508 | 1.00 | 13.98 |
| ATOM | 1739 | CG | PRO | A | 893 | 97.898 | -1.329 | 12.631 | 1.00 | 14.32 |
| ATOM | 1740 | CD | PRO | A | 893 | 97.567 | -0.363 | 13.739 | 1.00 | 13.77 |
| ATOM | 1741 | C | PRO | A | 893 | 96.404 | 0.781 | 10.749 | 1.00 | 15.10 |
| ATOM | 1742 | O | PRO | A | 893 | 95.310 | 0.462 | 11.233 | 1.00 | 14.74 |
| ATOM | 1743 | N | VAL | A | 894 | 96.572 | 1.113 | 9.477 | 1.00 | 14.14 |
| ATOM | 1744 | CA | VAL | A | 894 | 95.491 | 1.022 | 8.527 | 1.00 | 14.44 |
| ATOM | 1745 | CB | VAL | A | 894 | 95.619 | 2.079 | 7.434 | 1.00 | 14.68 |
| ATOM | 1746 | CG1 | VAL | A | 894 | 94.488 | 1.931 | 6.420 | 1.00 | 16.61 |
| ATOM | 1747 | CG2 | VAL | A | 894 | 95.606 | 3.463 | 8.054 | 1.00 | 14.58 |
| ATOM | 1748 | C | VAL | A | 894 | 95.502 | -0.384 | 7.945 | 1.00 | 15.14 |
| ATOM | 1749 | O | VAL | A | 894 | 96.414 | -0.760 | 7.204 | 1.00 | 18.06 |
| ATOM | 1750 | N | ASP | A | 895 | 94.497 | -1.164 | 8.328 | 1.00 | 13.74 |
| ATOM | 1751 | CA | ASP | A | 895 | 94.333 | -2.540 | 7.869 | 1.00 | 12.77 |
| ATOM | 1752 | CB | ASP | A | 895 | 95.305 | -3.497 | 8.587 | 1.00 | 12.81 |
| ATOM | 1753 | CG | ASP | A | 895 | 95.172 | -3.463 | 10.111 | 1.00 | 14.67 |

FIGURE 3BI

| | A | B | C | D | E | F | G | H | I | J |
|---|---|---|---|---|---|---|---|---|---|---|
| ATOM | 1754 | OD1 | ASP | A | 895 | 96.020 | -4.098 | 10.797 | 1.00 | 15.05 |
| ATOM | 1755 | OD2 | ASP | A | 895 | 94.263 | -2.849 | 10.712 | 1.00 | 13.61 |
| ATOM | 1756 | C | ASP | A | 895 | 92.875 | -2.957 | 8.063 | 1.00 | 10.47 |
| ATOM | 1757 | O | ASP | A | 895 | 92.041 | -2.136 | 8.444 | 1.00 | 10.30 |
| ATOM | 1758 | N | ALA | A | 896 | 92.563 | -4.219 | 7.797 | 1.00 | 9.40 |
| ATOM | 1759 | CA | ALA | A | 896 | 91.205 | -4.719 | 8.004 | 1.00 | 9.66 |
| ATOM | 1760 | CB | ALA | A | 896 | 91.152 | -6.227 | 7.822 | 1.00 | 7.47 |
| ATOM | 1761 | C | ALA | A | 896 | 90.626 | -4.306 | 9.369 | 1.00 | 9.58 |
| ATOM | 1762 | O | ALA | A | 896 | 89.466 | -3.902 | 9.454 | 1.00 | 11.45 |
| ATOM | 1763 | N | ASN | A | 897 | 91.441 | -4.374 | 10.419 | 1.00 | 9.19 |
| ATOM | 1764 | CA | ASN | A | 897 | 90.975 | -4.070 | 11.773 | 1.00 | 11.34 |
| ATOM | 1765 | CB | ASN | A | 897 | 91.984 | -4.531 | 12.823 | 1.00 | 9.99 |
| ATOM | 1766 | CG | ASN | A | 897 | 92.094 | -6.031 | 12.883 | 1.00 | 11.46 |
| ATOM | 1767 | OD1 | ASN | A | 897 | 91.119 | -6.745 | 12.630 | 1.00 | 13.26 |
| ATOM | 1768 | ND2 | ASN | A | 897 | 93.281 | -6.527 | 13.209 | 1.00 | 10.24 |
| ATOM | 1769 | C | ASN | A | 897 | 90.596 | -2.618 | 11.996 | 1.00 | 13.90 |
| ATOM | 1770 | O | ASN | A | 897 | 89.726 | -2.329 | 12.822 | 1.00 | 15.52 |
| ATOM | 1771 | N | PHE | A | 898 | 91.229 | -1.707 | 11.259 | 1.00 | 13.65 |
| ATOM | 1772 | CA | PHE | A | 898 | 90.804 | -0.314 | 11.301 | 1.00 | 14.39 |
| ATOM | 1773 | CB | PHE | A | 898 | 91.774 | 0.629 | 10.582 | 1.00 | 13.65 |
| ATOM | 1774 | CG | PHE | A | 898 | 91.319 | 2.060 | 10.613 | 1.00 | 15.37 |
| ATOM | 1775 | CD1 | PHE | A | 898 | 90.649 | 2.617 | 9.529 | 1.00 | 14.71 |
| ATOM | 1776 | CE1 | PHE | A | 898 | 90.205 | 3.919 | 9.569 | 1.00 | 14.70 |
| ATOM | 1777 | CZ | PHE | A | 898 | 90.414 | 4.682 | 10.710 | 1.00 | 16.39 |
| ATOM | 1778 | CE2 | PHE | A | 898 | 91.054 | 4.128 | 11.812 | 1.00 | 13.82 |
| ATOM | 1779 | CD2 | PHE | A | 898 | 91.499 | 2.831 | 11.760 | 1.00 | 15.11 |
| ATOM | 1780 | C | PHE | A | 898 | 89.412 | -0.134 | 10.716 | 1.00 | 14.79 |
| ATOM | 1781 | O | PHE | A | 898 | 88.587 | 0.589 | 11.282 | 1.00 | 18.67 |
| ATOM | 1782 | N | TYR | A | 899 | 89.162 | -0.750 | 9.565 | 1.00 | 13.41 |
| ATOM | 1783 | CA | TYR | A | 899 | 87.829 | -0.697 | 8.960 | 1.00 | 13.70 |
| ATOM | 1784 | CB | TYR | A | 899 | 87.777 | -1.521 | 7.671 | 1.00 | 13.03 |
| ATOM | 1785 | CG | TYR | A | 899 | 88.435 | -0.863 | 6.488 | 1.00 | 13.49 |
| ATOM | 1786 | CD1 | TYR | A | 899 | 89.814 | -0.917 | 6.314 | 1.00 | 15.55 |
| ATOM | 1787 | CE1 | TYR | A | 899 | 90.422 | -0.312 | 5.226 | 1.00 | 16.12 |
| ATOM | 1788 | CZ | TYR | A | 899 | 89.650 | 0.341 | 4.294 | 1.00 | 15.60 |
| ATOM | 1789 | OH | TYR | A | 899 | 90.244 | 0.932 | 3.209 | 1.00 | 17.11 |
| ATOM | 1790 | CE2 | TYR | A | 899 | 88.280 | 0.407 | 4.443 | 1.00 | 16.28 |
| ATOM | 1791 | CD2 | TYR | A | 899 | 87.682 | -0.195 | 5.537 | 1.00 | 15.48 |
| ATOM | 1792 | C | TYR | A | 899 | 86.809 | -1.236 | 9.958 | 1.00 | 11.87 |
| ATOM | 1793 | O | TYR | A | 899 | 85.774 | -0.621 | 10.186 | 1.00 | 9.90 |
| ATOM | 1794 | N | LYS | A | 900 | 87.146 | -2.380 | 10.551 | 1.00 | 11.15 |
| ATOM | 1795 | CA | LYS | A | 900 | 86.368 | -3.005 | 11.611 | 1.00 | 12.91 |
| ATOM | 1796 | CB | LYS | A | 900 | 87.040 | -4.293 | 12.064 | 1.00 | 12.38 |
| ATOM | 1797 | CG | LYS | A | 900 | 86.107 | -5.241 | 12.771 | 1.00 | 14.25 |
| ATOM | 1798 | CD | LYS | A | 900 | 86.523 | -6.684 | 12.536 | 1.00 | 17.06 |
| ATOM | 1799 | CE | LYS | A | 900 | 87.708 | -7.081 | 13.400 | 1.00 | 16.30 |
| ATOM | 1800 | NZ | LYS | A | 900 | 87.900 | -8.555 | 13.308 | 1.00 | 19.71 |
| ATOM | 1801 | C | LYS | A | 900 | 86.103 | -2.100 | 12.811 | 1.00 | 13.59 |
| ATOM | 1802 | O | LYS | A | 900 | 84.969 | -2.050 | 13.299 | 1.00 | 14.49 |
| ATOM | 1803 | N | LEU | A | 901 | 87.124 | -1.375 | 13.274 | 1.00 | 13.49 |
| ATOM | 1804 | CA | LEU | A | 901 | 86.939 | -0.435 | 14.385 | 1.00 | 13.01 |
| ATOM | 1805 | CB | LEU | A | 901 | 88.241 | 0.272 | 14.761 | 1.00 | 15.44 |

FIGURE 3BJ

| | A | B | C | D | E | F | G | H | I | J |
|---|---|---|---|---|---|---|---|---|---|---|
| ATOM | 1806 | CG | LEU | A | 901 | 89.261 | -0.480 | 15.624 | 1.00 | 20.34 |
| ATOM | 1807 | CD1 | LEU | A | 901 | 90.468 | 0.422 | 15.877 | 1.00 | 22.56 |
| ATOM | 1808 | CD2 | LEU | A | 901 | 88.674 | -0.986 | 16.952 | 1.00 | 20.90 |
| ATOM | 1809 | C | LEU | A | 901 | 85.861 | 0.591 | 14.050 | 1.00 | 12.94 |
| ATOM | 1810 | O | LEU | A | 901 | 84.913 | 0.766 | 14.821 | 1.00 | 12.29 |
| ATOM | 1811 | N | ILE | A | 902 | 85.992 | 1.237 | 12.889 | 1.00 | 12.38 |
| ATOM | 1812 | CA | ILE | A | 902 | 85.029 | 2.253 | 12.460 | 1.00 | 15.61 |
| ATOM | 1813 | CB | ILE | A | 902 | 85.497 | 2.970 | 11.159 | 1.00 | 14.94 |
| ATOM | 1814 | CG1 | ILE | A | 902 | 86.860 | 3.654 | 11.374 | 1.00 | 15.48 |
| ATOM | 1815 | CD1 | ILE | A | 902 | 86.914 | 4.632 | 12.576 | 1.00 | 14.13 |
| ATOM | 1816 | CG2 | ILE | A | 902 | 84.446 | 3.990 | 10.679 | 1.00 | 14.12 |
| ATOM | 1817 | C | ILE | A | 902 | 83.619 | 1.680 | 12.302 | 1.00 | 17.49 |
| ATOM | 1818 | O | ILE | A | 902 | 82.640 | 2.285 | 12.761 | 1.00 | 18.46 |
| ATOM | 1819 | N | GLN | A | 903 | 83.527 | 0.506 | 11.675 | 1.00 | 17.43 |
| ATOM | 1820 | CA | GLN | A | 903 | 82.247 | -0.177 | 11.481 | 1.00 | 18.10 |
| ATOM | 1821 | CB | GLN | A | 903 | 82.454 | -1.486 | 10.693 | 1.00 | 17.79 |
| ATOM | 1822 | CG | BGLN | A | 903 | 81.379 | -2.569 | 10.915 | 0.35 | 18.21 |
| ATOM | 1823 | CG | AGLN | A | 903 | 81.169 | -2.216 | 10.312 | 0.65 | 17.87 |
| ATOM | 1824 | CD | BGLN | A | 903 | 81.803 | -3.667 | 11.887 | 0.35 | 18.57 |
| ATOM | 1825 | CD | AGLN | A | 903 | 80.395 | -1.539 | 9.186 | 0.65 | 15.89 |
| ATOM | 1826 | OE1 | BGLN | A | 903 | 80.990 | -4.513 | 12.265 | 0.35 | 19.66 |
| ATOM | 1827 | OE1 | AGLN | A | 903 | 80.961 | -1.179 | 8.157 | 0.65 | 12.66 |
| ATOM | 1828 | NE2 | BGLN | A | 903 | 83.067 | -3.660 | 12.289 | 0.35 | 18.28 |
| ATOM | 1829 | NE2 | AGLN | A | 903 | 79.091 | -1.376 | 9.386 | 0.65 | 17.86 |
| ATOM | 1830 | C | GLN | A | 903 | 81.568 | -0.433 | 12.829 | 1.00 | 17.60 |
| ATOM | 1831 | O | GLN | A | 903 | 80.349 | -0.337 | 12.938 | 1.00 | 18.78 |
| ATOM | 1832 | N | ASN | A | 904 | 82.366 | -0.749 | 13.845 | 1.00 | 17.68 |
| ATOM | 1833 | CA | ASN | A | 904 | 81.837 | -1.035 | 15.173 | 1.00 | 19.48 |
| ATOM | 1834 | CB | ASN | A | 904 | 82.738 | -2.035 | 15.921 | 1.00 | 21.80 |
| ATOM | 1835 | CG | ASN | A | 904 | 82.570 | -3.469 | 15.420 | 1.00 | 24.77 |
| ATOM | 1836 | OD1 | ASN | A | 904 | 81.473 | -3.885 | 15.033 | 1.00 | 25.70 |
| ATOM | 1837 | ND2 | ASN | A | 904 | 83.664 | -4.232 | 15.425 | 1.00 | 26.66 |
| ATOM | 1838 | C | ASN | A | 904 | 81.557 | 0.210 | 16.024 | 1.00 | 18.79 |
| ATOM | 1839 | O | ASN | A | 904 | 81.233 | 0.103 | 17.204 | 1.00 | 18.48 |
| ATOM | 1840 | N | GLY | A | 905 | 81.663 | 1.386 | 15.412 | 1.00 | 19.78 |
| ATOM | 1841 | CA | GLY | A | 905 | 81.328 | 2.631 | 16.079 | 1.00 | 19.49 |
| ATOM | 1842 | C | GLY | A | 905 | 82.388 | 3.098 | 17.061 | 1.00 | 20.35 |
| ATOM | 1843 | O | GLY | A | 905 | 82.086 | 3.862 | 17.969 | 1.00 | 22.63 |
| ATOM | 1844 | N | PHE | A | 906 | 83.620 | 2.624 | 16.892 | 1.00 | 20.09 |
| ATOM | 1845 | CA | PHE | A | 906 | 84.764 | 3.168 | 17.612 | 1.00 | 21.08 |
| ATOM | 1846 | CB | PHE | A | 906 | 86.051 | 2.437 | 17.225 | 1.00 | 22.46 |
| ATOM | 1847 | CG | PHE | A | 906 | 87.275 | 2.917 | 17.965 | 1.00 | 25.19 |
| ATOM | 1848 | CD1 | PHE | A | 906 | 88.058 | 3.958 | 17.455 | 1.00 | 24.85 |
| ATOM | 1849 | CE1 | PHE | A | 906 | 89.196 | 4.401 | 18.135 | 1.00 | 24.79 |
| ATOM | 1850 | CZ | PHE | A | 906 | 89.560 | 3.808 | 19.342 | 1.00 | 24.94 |
| ATOM | 1851 | CE2 | PHE | A | 906 | 88.797 | 2.766 | 19.860 | 1.00 | 25.89 |
| ATOM | 1852 | CD2 | PHE | A | 906 | 87.655 | 2.325 | 19.170 | 1.00 | 26.39 |
| ATOM | 1853 | C | PHE | A | 906 | 84.927 | 4.661 | 17.326 | 1.00 | 21.51 |
| ATOM | 1854 | O | PHE | A | 906 | 84.777 | 5.116 | 16.188 | 1.00 | 21.00 |
| ATOM | 1855 | N | LYS | A | 907 | 85.228 | 5.411 | 18.377 | 1.00 | 21.20 |
| ATOM | 1856 | CA | LYS | A | 907 | 85.581 | 6.821 | 18.264 | 1.00 | 21.68 |
| ATOM | 1857 | CB | LYS | A | 907 | 84.439 | 7.710 | 18.768 | 1.00 | 22.65 |

FIGURE 3BK

|      | A    | B    | C   | D | E   | F      | G      | H      | I    | J     |
|------|------|------|-----|---|-----|--------|--------|--------|------|-------|
| ATOM | 1858 | CG   | LYS | A | 907 | 83.075 | 7.451  | 18.126 | 1.00 | 23.82 |
| ATOM | 1859 | CD   | LYS | A | 907 | 82.016 | 8.386  | 18.695 | 1.00 | 22.87 |
| ATOM | 1860 | CE   | LYS | A | 907 | 80.692 | 8.186  | 18.001 | 1.00 | 24.09 |
| ATOM | 1861 | NZ   | LYS | A | 907 | 79.777 | 9.345  | 18.196 | 1.00 | 24.40 |
| ATOM | 1862 | C    | LYS | A | 907 | 86.813 | 7.037  | 19.126 | 1.00 | 19.99 |
| ATOM | 1863 | O    | LYS | A | 907 | 86.989 | 6.356  | 20.137 | 1.00 | 18.90 |
| ATOM | 1864 | N    | MET | A | 908 | 87.665 | 7.980  | 18.742 | 1.00 | 18.90 |
| ATOM | 1865 | CA   | MET | A | 908 | 88.850 | 8.283  | 19.545 | 1.00 | 17.97 |
| ATOM | 1866 | CB   | MET | A | 908 | 89.749 | 9.281  | 18.828 | 1.00 | 18.21 |
| ATOM | 1867 | CG   | MET | A | 908 | 90.534 | 8.699  | 17.700 | 1.00 | 18.07 |
| ATOM | 1868 | SD   | MET | A | 908 | 91.673 | 9.926  | 17.080 | 1.00 | 19.54 |
| ATOM | 1869 | CE   | MET | A | 908 | 90.623 | 10.721 | 15.854 | 1.00 | 12.92 |
| ATOM | 1870 | C    | MET | A | 908 | 88.472 | 8.859  | 20.904 | 1.00 | 17.14 |
| ATOM | 1871 | O    | MET | A | 908 | 87.392 | 9.430  | 21.080 | 1.00 | 14.24 |
| ATOM | 1872 | N    | ASP | A | 909 | 89.385 | 8.712  | 21.857 | 1.00 | 19.42 |
| ATOM | 1873 | CA   | ASP | A | 909 | 89.240 | 9.311  | 23.177 | 1.00 | 19.74 |
| ATOM | 1874 | CB   | ASP | A | 909 | 90.232 | 8.664  | 24.153 | 1.00 | 22.62 |
| ATOM | 1875 | CG   | ASP | A | 909 | 89.992 | 7.165  | 24.342 | 1.00 | 26.90 |
| ATOM | 1876 | OD1  | ASP | A | 909 | 88.844 | 6.694  | 24.165 | 1.00 | 27.57 |
| ATOM | 1877 | OD2  | ASP | A | 909 | 90.905 | 6.376  | 24.676 | 1.00 | 30.07 |
| ATOM | 1878 | C    | ASP | A | 909 | 89.476 | 10.823 | 23.102 | 1.00 | 17.29 |
| ATOM | 1879 | O    | ASP | A | 909 | 90.008 | 11.334 | 22.112 | 1.00 | 14.58 |
| ATOM | 1880 | N    | GLN | A | 910 | 89.076 | 11.524 | 24.156 | 1.00 | 17.10 |
| ATOM | 1881 | CA   | GLN | A | 910 | 89.307 | 12.957 | 24.287 | 1.00 | 15.98 |
| ATOM | 1882 | CB   | GLN | A | 910 | 88.768 | 13.448 | 25.638 | 1.00 | 14.99 |
| ATOM | 1883 | CG   | GLN | A | 910 | 88.630 | 14.964 | 25.741 | 1.00 | 16.74 |
| ATOM | 1884 | CD   | GLN | A | 910 | 87.939 | 15.411 | 27.007 | 1.00 | 17.37 |
| ATOM | 1885 | OE1  | GLN | A | 910 | 87.002 | 14.766 | 27.460 | 1.00 | 22.13 |
| ATOM | 1886 | NE2  | GLN | A | 910 | 88.397 | 16.518 | 27.583 | 1.00 | 16.56 |
| ATOM | 1887 | C    | GLN | A | 910 | 90.798 | 13.284 | 24.170 | 1.00 | 15.06 |
| ATOM | 1888 | O    | GLN | A | 910 | 91.611 | 12.695 | 24.876 | 1.00 | 17.65 |
| ATOM | 1889 | N    | PRO | A | 911 | 91.171 | 14.203 | 23.280 | 1.00 | 14.32 |
| ATOM | 1890 | CA   | PRO | A | 911 | 92.568 | 14.657 | 23.226 | 1.00 | 13.88 |
| ATOM | 1891 | CB   | PRO | A | 911 | 92.640 | 15.485 | 21.943 | 1.00 | 14.17 |
| ATOM | 1892 | CG   | PRO | A | 911 | 91.211 | 15.842 | 21.589 | 1.00 | 14.28 |
| ATOM | 1893 | CD   | PRO | A | 911 | 90.317 | 14.857 | 22.270 | 1.00 | 13.95 |
| ATOM | 1894 | C    | PRO | A | 911 | 92.901 | 15.499 | 24.464 | 1.00 | 14.60 |
| ATOM | 1895 | O    | PRO | A | 911 | 91.988 | 16.029 | 25.110 | 1.00 | 13.44 |
| ATOM | 1896 | N    | PHE | A | 912 | 94.187 | 15.602 | 24.791 | 1.00 | 12.38 |
| ATOM | 1897 | CA   | PHE | A | 912 | 94.632 | 16.238 | 26.027 | 1.00 | 11.26 |
| ATOM | 1898 | CB   | PHE | A | 912 | 96.162 | 16.154 | 26.147 | 1.00 | 11.27 |
| ATOM | 1899 | CG   | PHE | A | 912 | 96.701 | 16.660 | 27.457 | 1.00 | 11.03 |
| ATOM | 1900 | CD1  | PHE | A | 912 | 96.758 | 15.830 | 28.568 | 1.00 | 10.63 |
| ATOM | 1901 | CE1  | PHE | A | 912 | 97.255 | 16.294 | 29.775 | 1.00 | 10.72 |
| ATOM | 1902 | CZ   | PHE | A | 912 | 97.700 | 17.607 | 29.884 | 1.00 | 10.64 |
| ATOM | 1903 | CE2  | PHE | A | 912 | 97.653 | 18.449 | 28.782 | 1.00 | 9.52  |
| ATOM | 1904 | CD2  | PHE | A | 912 | 97.159 | 17.972 | 27.576 | 1.00 | 11.42 |
| ATOM | 1905 | C    | PHE | A | 912 | 94.148 | 17.679 | 26.204 | 1.00 | 11.21 |
| ATOM | 1906 | O    | PHE | A | 912 | 93.879 | 18.109 | 27.325 | 1.00 | 12.27 |
| ATOM | 1907 | N    | TYR | A | 913 | 94.013 | 18.416 | 25.105 | 1.00 | 11.35 |
| ATOM | 1908 | CA   | TYR | A | 913 | 93.723 | 19.851 | 25.185 | 1.00 | 10.70 |
| ATOM | 1909 | CB   | TYR | A | 913 | 94.644 | 20.645 | 24.247 | 1.00 | 10.03 |

FIGURE 3BL

|   | A | B | C | D | E | F | G | H | I | J |
|---|---|---|---|---|---|---|---|---|---|---|
| ATOM | 1910 | CG  | TYR | A | 913 | 96.106  | 20.403 | 24.506 | 1.00 | 9.64 |
| ATOM | 1911 | CD1 | TYR | A | 913 | 96.794  | 19.386 | 23.837 | 1.00 | 10.68 |
| ATOM | 1912 | CE1 | TYR | A | 913 | 98.150  | 19.141 | 24.099 | 1.00 | 10.90 |
| ATOM | 1913 | CZ  | TYR | A | 913 | 98.818  | 19.931 | 25.020 | 1.00 | 10.32 |
| ATOM | 1914 | OH  | TYR | A | 913 | 100.152 | 19.705 | 25.273 | 1.00 | 12.46 |
| ATOM | 1915 | CE2 | TYR | A | 913 | 98.149  | 20.941 | 25.698 | 1.00 | 9.27 |
| ATOM | 1916 | CD2 | TYR | A | 913 | 96.803  | 21.168 | 25.441 | 1.00 | 9.46 |
| ATOM | 1917 | C   | TYR | A | 913 | 92.264  | 20.209 | 24.928 | 1.00 | 11.06 |
| ATOM | 1918 | O   | TYR | A | 913 | 91.891  | 21.371 | 25.015 | 1.00 | 13.12 |
| ATOM | 1919 | N   | ALA | A | 914 | 91.445  | 19.212 | 24.608 | 1.00 | 11.46 |
| ATOM | 1920 | CA  | ALA | A | 914 | 90.013  | 19.411 | 24.435 | 1.00 | 9.35 |
| ATOM | 1921 | CB  | ALA | A | 914 | 89.415  | 18.265 | 23.642 | 1.00 | 8.47 |
| ATOM | 1922 | C   | ALA | A | 914 | 89.311  | 19.528 | 25.777 | 1.00 | 10.99 |
| ATOM | 1923 | O   | ALA | A | 914 | 89.647  | 18.813 | 26.733 | 1.00 | 10.70 |
| ATOM | 1924 | N   | THR | A | 915 | 88.330  | 20.423 | 25.854 | 1.00 | 10.81 |
| ATOM | 1925 | CA  | THR | A | 915 | 87.407  | 20.414 | 26.988 | 1.00 | 11.78 |
| ATOM | 1926 | CB  | THR | A | 915 | 86.729  | 21.782 | 27.163 | 1.00 | 11.44 |
| ATOM | 1927 | OG1 | THR | A | 915 | 86.283  | 22.267 | 25.885 | 1.00 | 11.26 |
| ATOM | 1928 | CG2 | THR | A | 915 | 87.731  | 22.831 | 27.663 | 1.00 | 6.97 |
| ATOM | 1929 | C   | THR | A | 915 | 86.345  | 19.343 | 26.718 | 1.00 | 15.51 |
| ATOM | 1930 | O   | THR | A | 915 | 86.304  | 18.753 | 25.621 | 1.00 | 14.46 |
| ATOM | 1931 | N   | GLU | A | 916 | 85.490  | 19.092 | 27.705 | 1.00 | 17.99 |
| ATOM | 1932 | CA  | GLU | A | 916 | 84.338  | 18.210 | 27.507 | 1.00 | 22.55 |
| ATOM | 1933 | CB  | GLU | A | 916 | 83.511  | 18.101 | 28.793 | 1.00 | 27.01 |
| ATOM | 1934 | CG  | GLU | A | 916 | 82.976  | 16.708 | 29.147 | 1.00 | 35.31 |
| ATOM | 1935 | CD  | GLU | A | 916 | 83.532  | 15.570 | 28.294 | 1.00 | 39.76 |
| ATOM | 1936 | OE1 | GLU | A | 916 | 83.053  | 15.393 | 27.147 | 1.00 | 41.16 |
| ATOM | 1937 | OE2 | GLU | A | 916 | 84.433  | 14.838 | 28.780 | 1.00 | 41.31 |
| ATOM | 1938 | C   | GLU | A | 916 | 83.466  | 18.713 | 26.356 | 1.00 | 20.97 |
| ATOM | 1939 | O   | GLU | A | 916 | 83.117  | 17.946 | 25.464 | 1.00 | 19.54 |
| ATOM | 1940 | N   | GLU | A | 917 | 83.149  | 20.008 | 26.384 | 1.00 | 21.22 |
| ATOM | 1941 | CA  | GLU | A | 917 | 82.329  | 20.669 | 25.378 | 1.00 | 23.09 |
| ATOM | 1942 | CB  | GLU | A | 917 | 82.220  | 22.172 | 25.696 | 1.00 | 27.78 |
| ATOM | 1943 | CG  | GLU | A | 917 | 81.464  | 23.008 | 24.671 | 1.00 | 33.64 |
| ATOM | 1944 | CD  | GLU | A | 917 | 81.748  | 24.504 | 24.784 | 1.00 | 37.14 |
| ATOM | 1945 | OE1 | GLU | A | 917 | 81.314  | 25.114 | 25.789 | 1.00 | 37.95 |
| ATOM | 1946 | OE2 | GLU | A | 917 | 82.393  | 25.076 | 23.864 | 1.00 | 38.85 |
| ATOM | 1947 | C   | GLU | A | 917 | 82.870  | 20.434 | 23.969 | 1.00 | 21.89 |
| ATOM | 1948 | O   | GLU | A | 917 | 82.126  | 20.057 | 23.073 | 1.00 | 22.62 |
| ATOM | 1949 | N   | ILE | A | 918 | 84.170  | 20.634 | 23.780 | 1.00 | 20.77 |
| ATOM | 1950 | CA  | ILE | A | 918 | 84.790  | 20.424 | 22.474 | 1.00 | 18.91 |
| ATOM | 1951 | CB  | ILE | A | 918 | 86.229  | 21.020 | 22.448 | 1.00 | 19.98 |
| ATOM | 1952 | CG1 | ILE | A | 918 | 86.168  | 22.552 | 22.370 | 1.00 | 22.24 |
| ATOM | 1953 | CD1 | ILE | A | 918 | 85.653  | 23.101 | 21.029 | 1.00 | 24.77 |
| ATOM | 1954 | CG2 | ILE | A | 918 | 87.074  | 20.449 | 21.303 | 1.00 | 16.24 |
| ATOM | 1955 | C   | ILE | A | 918 | 84.766  | 18.942 | 22.086 | 1.00 | 18.15 |
| ATOM | 1956 | O   | ILE | A | 918 | 84.570  | 18.602 | 20.914 | 1.00 | 19.06 |
| ATOM | 1957 | N   | TYR | A | 919 | 84.952  | 18.064 | 23.066 | 1.00 | 15.78 |
| ATOM | 1958 | CA  | TYR | A | 919 | 84.897  | 16.633 | 22.799 | 1.00 | 16.86 |
| ATOM | 1959 | CB  | TYR | A | 919 | 85.487  | 15.829 | 23.959 | 1.00 | 16.71 |
| ATOM | 1960 | CG  | TYR | A | 919 | 85.579  | 14.345 | 23.668 | 1.00 | 16.88 |
| ATOM | 1961 | CD1 | TYR | A | 919 | 86.202  | 13.880 | 22.506 | 1.00 | 15.09 |

FIGURE 3BM

| | A | B | C | D | E | F | G | H | I | J |
|---|---|---|---|---|---|---|---|---|---|---|
| ATOM | 1962 | CE1 | TYR | A | 919 | 86.276 | 12.524 | 22.229 | 1.00 | 13.76 |
| ATOM | 1963 | CZ  | TYR | A | 919 | 85.729 | 11.619 | 23.120 | 1.00 | 13.51 |
| ATOM | 1964 | OH  | TYR | A | 919 | 85.804 | 10.287 | 22.847 | 1.00 | 15.21 |
| ATOM | 1965 | CE2 | TYR | A | 919 | 85.109 | 12.044 | 24.280 | 1.00 | 14.73 |
| ATOM | 1966 | CD2 | TYR | A | 919 | 85.027 | 13.407 | 24.546 | 1.00 | 16.65 |
| ATOM | 1967 | C   | TYR | A | 919 | 83.477 | 16.138 | 22.433 | 1.00 | 17.48 |
| ATOM | 1968 | O   | TYR | A | 919 | 83.327 | 15.261 | 21.582 | 1.00 | 16.73 |
| ATOM | 1969 | N   | ILE | A | 920 | 82.450 | 16.708 | 23.061 | 1.00 | 16.85 |
| ATOM | 1970 | CA  | ILE | A | 920 | 81.070 | 16.394 | 22.708 | 1.00 | 17.35 |
| ATOM | 1971 | CB  | ILE | A | 920 | 80.082 | 17.094 | 23.666 | 1.00 | 18.16 |
| ATOM | 1972 | CG1 | ILE | A | 920 | 80.105 | 16.412 | 25.039 | 1.00 | 17.91 |
| ATOM | 1973 | CD1 | ILE | A | 920 | 79.399 | 17.193 | 26.140 | 1.00 | 17.33 |
| ATOM | 1974 | CG2 | ILE | A | 920 | 78.649 | 17.087 | 23.093 | 1.00 | 17.40 |
| ATOM | 1975 | C   | ILE | A | 920 | 80.786 | 16.743 | 21.243 | 1.00 | 19.27 |
| ATOM | 1976 | O   | ILE | A | 920 | 80.154 | 15.961 | 20.524 | 1.00 | 19.04 |
| ATOM | 1977 | N   | ILE | A | 921 | 81.266 | 17.907 | 20.806 | 1.00 | 21.43 |
| ATOM | 1978 | CA  | ILE | A | 921 | 81.176 | 18.312 | 19.400 | 1.00 | 20.93 |
| ATOM | 1979 | CB  | ILE | A | 921 | 81.737 | 19.739 | 19.206 | 1.00 | 21.33 |
| ATOM | 1980 | CG1 | ILE | A | 921 | 80.704 | 20.768 | 19.657 | 1.00 | 21.70 |
| ATOM | 1981 | CD1 | ILE | A | 921 | 81.306 | 21.960 | 20.350 | 1.00 | 24.33 |
| ATOM | 1982 | CG2 | ILE | A | 921 | 82.120 | 19.999 | 17.750 | 1.00 | 21.22 |
| ATOM | 1983 | C   | ILE | A | 921 | 81.865 | 17.296 | 18.485 | 1.00 | 21.38 |
| ATOM | 1984 | O   | ILE | A | 921 | 81.274 | 16.847 | 17.497 | 1.00 | 23.83 |
| ATOM | 1985 | N   | MET | A | 922 | 83.098 | 16.924 | 18.829 | 1.00 | 20.57 |
| ATOM | 1986 | CA  | MET | A | 922 | 83.840 | 15.890 | 18.099 | 1.00 | 19.88 |
| ATOM | 1987 | CB  | MET | A | 922 | 85.121 | 15.537 | 18.837 | 1.00 | 19.41 |
| ATOM | 1988 | CG  | MET | A | 922 | 86.337 | 16.267 | 18.372 | 1.00 | 20.68 |
| ATOM | 1989 | SD  | MET | A | 922 | 87.739 | 15.866 | 19.429 | 1.00 | 19.89 |
| ATOM | 1990 | CE  | MET | A | 922 | 88.161 | 17.461 | 19.989 | 1.00 | 17.33 |
| ATOM | 1991 | C   | MET | A | 922 | 83.034 | 14.606 | 17.933 | 1.00 | 19.21 |
| ATOM | 1992 | O   | MET | A | 922 | 82.914 | 14.081 | 16.828 | 1.00 | 19.08 |
| ATOM | 1993 | N   | GLN | A | 923 | 82.509 | 14.103 | 19.047 | 1.00 | 17.15 |
| ATOM | 1994 | CA  | GLN | A | 923 | 81.734 | 12.868 | 19.058 | 1.00 | 19.97 |
| ATOM | 1995 | CB  | GLN | A | 923 | 81.279 | 12.514 | 20.478 | 1.00 | 21.34 |
| ATOM | 1996 | CG  | GLN | A | 923 | 82.394 | 11.986 | 21.356 | 1.00 | 25.53 |
| ATOM | 1997 | CD  | GLN | A | 923 | 81.958 | 11.822 | 22.790 | 1.00 | 29.23 |
| ATOM | 1998 | OE1 | GLN | A | 923 | 81.834 | 12.805 | 23.522 | 1.00 | 32.58 |
| ATOM | 1999 | NE2 | GLN | A | 923 | 81.716 | 10.585 | 23.199 | 1.00 | 29.60 |
| ATOM | 2000 | C   | GLN | A | 923 | 80.530 | 12.940 | 18.136 | 1.00 | 18.36 |
| ATOM | 2001 | O   | GLN | A | 923 | 80.256 | 11.990 | 17.408 | 1.00 | 16.38 |
| ATOM | 2002 | N   | SER | A | 924 | 79.820 | 14.068 | 18.167 | 1.00 | 17.57 |
| ATOM | 2003 | CA  | SER | A | 924 | 78.640 | 14.234 | 17.330 | 1.00 | 17.88 |
| ATOM | 2004 | CB  | SER | A | 924 | 77.867 | 15.501 | 17.704 | 1.00 | 18.40 |
| ATOM | 2005 | OG  | SER | A | 924 | 78.575 | 16.656 | 17.285 | 1.00 | 25.74 |
| ATOM | 2006 | C   | SER | A | 924 | 79.052 | 14.237 | 15.855 | 1.00 | 16.71 |
| ATOM | 2007 | O   | SER | A | 924 | 78.333 | 13.708 | 15.012 | 1.00 | 17.80 |
| ATOM | 2008 | N   | CYS | A | 925 | 80.215 | 14.814 | 15.558 | 1.00 | 14.94 |
| ATOM | 2009 | CA  | CYS | A | 925 | 80.763 | 14.815 | 14.199 | 1.00 | 14.58 |
| ATOM | 2010 | CB  | CYS | A | 925 | 82.050 | 15.648 | 14.124 | 1.00 | 13.19 |
| ATOM | 2011 | SG  | CYS | A | 925 | 81.831 | 17.443 | 14.302 | 1.00 | 14.20 |
| ATOM | 2012 | C   | CYS | A | 925 | 81.042 | 13.389 | 13.730 | 1.00 | 16.70 |
| ATOM | 2013 | O   | CYS | A | 925 | 81.065 | 13.115 | 12.532 | 1.00 | 17.24 |

FIGURE 3BN

| | A | B | C | D | E | F | G | H | I | J |
|---|---|---|---|---|---|---|---|---|---|---|
| ATOM | 2014 | N | TRP | A | 926 | 81.246 | 12.483 | 14.684 | 1.00 | 17.46 |
| ATOM | 2015 | CA | TRP | A | 926 | 81.567 | 11.098 | 14.371 | 1.00 | 16.98 |
| ATOM | 2016 | CB | TRP | A | 926 | 82.709 | 10.599 | 15.258 | 1.00 | 15.17 |
| ATOM | 2017 | CG | TRP | A | 926 | 83.989 | 11.374 | 15.091 | 1.00 | 15.81 |
| ATOM | 2018 | CD1 | TRP | A | 926 | 84.425 | 12.016 | 13.964 | 1.00 | 14.20 |
| ATOM | 2019 | NE1 | TRP | A | 926 | 85.643 | 12.608 | 14.199 | 1.00 | 13.90 |
| ATOM | 2020 | CE2 | TRP | A | 926 | 86.022 | 12.357 | 15.492 | 1.00 | 13.63 |
| ATOM | 2021 | CD2 | TRP | A | 926 | 85.005 | 11.581 | 16.086 | 1.00 | 13.86 |
| ATOM | 2022 | CE3 | TRP | A | 926 | 85.156 | 11.188 | 17.424 | 1.00 | 13.48 |
| ATOM | 2023 | CZ3 | TRP | A | 926 | 86.300 | 11.577 | 18.114 | 1.00 | 13.23 |
| ATOM | 2024 | CH2 | TRP | A | 926 | 87.294 | 12.341 | 17.487 | 1.00 | 15.80 |
| ATOM | 2025 | CZ2 | TRP | A | 926 | 87.171 | 12.742 | 16.181 | 1.00 | 14.06 |
| ATOM | 2026 | C | TRP | A | 926 | 80.357 | 10.167 | 14.485 | 1.00 | 16.19 |
| ATOM | 2027 | O | TRP | A | 926 | 80.508 | 8.961 | 14.718 | 1.00 | 15.72 |
| ATOM | 2028 | N | ALA | A | 927 | 79.159 | 10.722 | 14.336 | 1.00 | 13.82 |
| ATOM | 2029 | CA | ALA | A | 927 | 77.974 | 9.882 | 14.221 | 1.00 | 15.68 |
| ATOM | 2030 | CB | ALA | A | 927 | 76.709 | 10.725 | 14.156 | 1.00 | 11.83 |
| ATOM | 2031 | C | ALA | A | 927 | 78.142 | 9.035 | 12.952 | 1.00 | 17.56 |
| ATOM | 2032 | O | ALA | A | 927 | 78.485 | 9.556 | 11.879 | 1.00 | 18.50 |
| ATOM | 2033 | N | PHE | A | 928 | 77.934 | 7.730 | 13.082 | 1.00 | 17.68 |
| ATOM | 2034 | CA | PHE | A | 928 | 78.098 | 6.827 | 11.946 | 1.00 | 17.64 |
| ATOM | 2035 | CB | PHE | A | 928 | 77.829 | 5.376 | 12.349 | 1.00 | 14.71 |
| ATOM | 2036 | CG | PHE | A | 928 | 78.348 | 4.376 | 11.364 | 1.00 | 12.81 |
| ATOM | 2037 | CD1 | PHE | A | 928 | 79.677 | 3.955 | 11.416 | 1.00 | 11.41 |
| ATOM | 2038 | CE1 | PHE | A | 928 | 80.172 | 3.019 | 10.496 | 1.00 | 10.56 |
| ATOM | 2039 | CZ | PHE | A | 928 | 79.324 | 2.507 | 9.513 | 1.00 | 9.14 |
| ATOM | 2040 | CE2 | PHE | A | 928 | 77.993 | 2.930 | 9.460 | 1.00 | 9.55 |
| ATOM | 2041 | CD2 | PHE | A | 928 | 77.512 | 3.850 | 10.384 | 1.00 | 9.50 |
| ATOM | 2042 | C | PHE | A | 928 | 77.194 | 7.234 | 10.787 | 1.00 | 15.76 |
| ATOM | 2043 | O | PHE | A | 928 | 77.638 | 7.299 | 9.644 | 1.00 | 16.45 |
| ATOM | 2044 | N | ASP | A | 929 | 75.932 | 7.503 | 11.107 | 1.00 | 16.47 |
| ATOM | 2045 | CA | ASP | A | 929 | 74.944 | 8.003 | 10.159 | 1.00 | 15.74 |
| ATOM | 2046 | CB | ASP | A | 929 | 73.531 | 7.777 | 10.730 | 1.00 | 14.36 |
| ATOM | 2047 | CG | ASP | A | 929 | 72.416 | 8.052 | 9.722 | 1.00 | 16.33 |
| ATOM | 2048 | OD1 | ASP | A | 929 | 72.617 | 8.784 | 8.721 | 1.00 | 16.46 |
| ATOM | 2049 | OD2 | ASP | A | 929 | 71.277 | 7.560 | 9.859 | 1.00 | 17.29 |
| ATOM | 2050 | C | ASP | A | 929 | 75.204 | 9.492 | 9.910 | 1.00 | 15.15 |
| ATOM | 2051 | O | ASP | A | 929 | 75.002 | 10.330 | 10.802 | 1.00 | 14.51 |
| ATOM | 2052 | N | SER | A | 930 | 75.642 | 9.813 | 8.694 | 1.00 | 15.04 |
| ATOM | 2053 | CA | SER | A | 930 | 75.942 | 11.191 | 8.313 | 1.00 | 15.70 |
| ATOM | 2054 | CB | SER | A | 930 | 76.440 | 11.259 | 6.865 | 1.00 | 16.25 |
| ATOM | 2055 | OG | SER | A | 930 | 75.370 | 11.124 | 5.952 | 1.00 | 18.86 |
| ATOM | 2056 | C | SER | A | 930 | 74.767 | 12.156 | 8.522 | 1.00 | 16.29 |
| ATOM | 2057 | O | SER | A | 930 | 74.968 | 13.350 | 8.787 | 1.00 | 16.26 |
| ATOM | 2058 | N | ARG | A | 931 | 73.546 | 11.638 | 8.418 | 1.00 | 15.02 |
| ATOM | 2059 | CA | ARG | A | 931 | 72.356 | 12.464 | 8.606 | 1.00 | 15.01 |
| ATOM | 2060 | CB | ARG | A | 931 | 71.103 | 11.717 | 8.167 | 1.00 | 11.21 |
| ATOM | 2061 | CG | ARG | A | 931 | 71.122 | 11.296 | 6.712 | 1.00 | 11.64 |
| ATOM | 2062 | CD | ARG | A | 931 | 70.052 | 10.265 | 6.359 | 1.00 | 10.94 |
| ATOM | 2063 | NE | ARG | A | 931 | 70.167 | 9.088 | 7.205 | 1.00 | 9.07 |
| ATOM | 2064 | CZ | ARG | A | 931 | 69.324 | 8.077 | 7.190 | 1.00 | 7.93 |
| ATOM | 2065 | NH1 | ARG | A | 931 | 69.518 | 7.060 | 8.007 | 1.00 | 4.58 |

FIGURE 3BO

| | A | B | C | D | E | F | G | H | I | J |
|---|---|---|---|---|---|---|---|---|---|---|
| ATOM | 2066 | NH2 | ARG | A | 931 | 68.288 | 8.084 | 6.361 | 1.00 | 7.40 |
| ATOM | 2067 | C | ARG | A | 931 | 72.213 | 12.924 | 10.050 | 1.00 | 17.14 |
| ATOM | 2068 | O | ARG | A | 931 | 71.531 | 13.913 | 10.332 | 1.00 | 20.08 |
| ATOM | 2069 | N | LYS | A | 932 | 72.860 | 12.208 | 10.964 | 1.00 | 17.44 |
| ATOM | 2070 | CA | LYS | A | 932 | 72.758 | 12.533 | 12.378 | 1.00 | 18.18 |
| ATOM | 2071 | CB | LYS | A | 932 | 72.674 | 11.247 | 13.199 | 1.00 | 20.48 |
| ATOM | 2072 | CG | LYS | A | 932 | 71.369 | 10.488 | 12.936 | 1.00 | 24.13 |
| ATOM | 2073 | CD | LYS | A | 932 | 71.221 | 9.260 | 13.813 | 1.00 | 28.17 |
| ATOM | 2074 | CE | LYS | A | 932 | 69.743 | 8.924 | 13.992 | 1.00 | 32.95 |
| ATOM | 2075 | NZ | LYS | A | 932 | 69.457 | 7.452 | 13.949 | 1.00 | 34.31 |
| ATOM | 2076 | C | LYS | A | 932 | 73.882 | 13.460 | 12.858 | 1.00 | 17.55 |
| ATOM | 2077 | O | LYS | A | 932 | 73.910 | 13.865 | 14.012 | 1.00 | 19.05 |
| ATOM | 2078 | N | ARG | A | 933 | 74.794 | 13.805 | 11.956 | 1.00 | 16.56 |
| ATOM | 2079 | CA | ARG | A | 933 | 75.884 | 14.717 | 12.273 | 1.00 | 18.15 |
| ATOM | 2080 | CB | ARG | A | 933 | 77.018 | 14.566 | 11.250 | 1.00 | 16.90 |
| ATOM | 2081 | CG | ARG | A | 933 | 77.868 | 13.330 | 11.433 | 1.00 | 15.79 |
| ATOM | 2082 | CD | ARG | A | 933 | 78.837 | 13.062 | 10.283 | 1.00 | 13.69 |
| ATOM | 2083 | NE | ARG | A | 933 | 78.982 | 11.623 | 10.065 | 1.00 | 15.49 |
| ATOM | 2084 | CZ | ARG | A | 933 | 79.288 | 11.053 | 8.905 | 1.00 | 13.27 |
| ATOM | 2085 | NH1 | ARG | A | 933 | 79.521 | 11.789 | 7.819 | 1.00 | 11.23 |
| ATOM | 2086 | NH2 | ARG | A | 933 | 79.364 | 9.735 | 8.837 | 1.00 | 12.86 |
| ATOM | 2087 | C | ARG | A | 933 | 75.376 | 16.157 | 12.256 | 1.00 | 17.54 |
| ATOM | 2088 | O | ARG | A | 933 | 74.469 | 16.480 | 11.498 | 1.00 | 19.62 |
| ATOM | 2089 | N | PRO | A | 934 | 75.964 | 17.031 | 13.066 | 1.00 | 17.74 |
| ATOM | 2090 | CA | PRO | A | 934 | 75.639 | 18.460 | 12.989 | 1.00 | 15.95 |
| ATOM | 2091 | CB | PRO | A | 934 | 76.514 | 19.068 | 14.083 | 1.00 | 16.29 |
| ATOM | 2092 | CG | PRO | A | 934 | 77.642 | 18.095 | 14.233 | 1.00 | 17.21 |
| ATOM | 2093 | CD | PRO | A | 934 | 76.989 | 16.751 | 14.091 | 1.00 | 17.72 |
| ATOM | 2094 | C | PRO | A | 934 | 76.051 | 19.007 | 11.625 | 1.00 | 14.11 |
| ATOM | 2095 | O | PRO | A | 934 | 76.967 | 18.475 | 11.012 | 1.00 | 15.16 |
| ATOM | 2096 | N | SER | A | 935 | 75.378 | 20.040 | 11.141 | 1.00 | 13.57 |
| ATOM | 2097 | CA | SER | A | 935 | 75.831 | 20.702 | 9.920 | 1.00 | 13.71 |
| ATOM | 2098 | CB | SER | A | 935 | 74.662 | 21.391 | 9.229 | 1.00 | 10.93 |
| ATOM | 2099 | OG | SER | A | 935 | 74.111 | 22.373 | 10.087 | 1.00 | 12.20 |
| ATOM | 2100 | C | SER | A | 935 | 76.927 | 21.728 | 10.233 | 1.00 | 13.80 |
| ATOM | 2101 | O | SER | A | 935 | 77.180 | 22.046 | 11.401 | 1.00 | 13.73 |
| ATOM | 2102 | N | PHE | A | 936 | 77.569 | 22.255 | 9.193 | 1.00 | 13.76 |
| ATOM | 2103 | CA | PHE | A | 936 | 78.557 | 23.310 | 9.392 | 1.00 | 13.41 |
| ATOM | 2104 | CB | PHE | A | 936 | 79.419 | 23.520 | 8.148 | 1.00 | 11.53 |
| ATOM | 2105 | CG | PHE | A | 936 | 80.448 | 22.447 | 7.964 | 1.00 | 13.04 |
| ATOM | 2106 | CD1 | PHE | A | 936 | 81.480 | 22.287 | 8.887 | 1.00 | 12.67 |
| ATOM | 2107 | CE1 | PHE | A | 936 | 82.430 | 21.289 | 8.729 | 1.00 | 11.99 |
| ATOM | 2108 | CZ | PHE | A | 936 | 82.342 | 20.425 | 7.655 | 1.00 | 11.36 |
| ATOM | 2109 | CE2 | PHE | A | 936 | 81.316 | 20.567 | 6.738 | 1.00 | 12.32 |
| ATOM | 2110 | CD2 | PHE | A | 936 | 80.371 | 21.571 | 6.898 | 1.00 | 12.38 |
| ATOM | 2111 | C | PHE | A | 936 | 77.960 | 24.614 | 9.939 | 1.00 | 14.78 |
| ATOM | 2112 | O | PHE | A | 936 | 78.573 | 25.241 | 10.806 | 1.00 | 16.12 |
| ATOM | 2113 | N | PRO | A | 937 | 76.784 | 25.036 | 9.458 | 1.00 | 13.10 |
| ATOM | 2114 | CA | PRO | A | 937 | 76.064 | 26.134 | 10.118 | 1.00 | 11.09 |
| ATOM | 2115 | CB | PRO | A | 937 | 74.773 | 26.246 | 9.304 | 1.00 | 10.73 |
| ATOM | 2116 | CG | PRO | A | 937 | 75.175 | 25.764 | 7.941 | 1.00 | 10.73 |
| ATOM | 2117 | CD | PRO | A | 937 | 76.091 | 24.594 | 8.231 | 1.00 | 10.48 |

FIGURE 3BP

| | A | B | C | D | E | F | G | H | I | J |
|---|---|---|---|---|---|---|---|---|---|---|
| ATOM | 2118 | C | PRO | A | 937 | 75.780 | 25.877 | 11.605 | 1.00 | 10.85 |
| ATOM | 2119 | O | PRO | A | 937 | 75.808 | 26.832 | 12.368 | 1.00 | 13.02 |
| ATOM | 2120 | N | ASN | A | 938 | 75.520 | 24.635 | 12.011 | 1.00 | 12.17 |
| ATOM | 2121 | CA | ASN | A | 938 | 75.423 | 24.311 | 13.441 | 1.00 | 13.37 |
| ATOM | 2122 | CB | ASN | A | 938 | 75.069 | 22.836 | 13.667 | 1.00 | 15.06 |
| ATOM | 2123 | CG | ASN | A | 938 | 73.672 | 22.464 | 13.183 | 1.00 | 14.82 |
| ATOM | 2124 | OD1 | ASN | A | 938 | 73.354 | 21.280 | 13.084 | 1.00 | 15.94 |
| ATOM | 2125 | ND2 | ASN | A | 938 | 72.846 | 23.455 | 12.875 | 1.00 | 11.23 |
| ATOM | 2126 | C | ASN | A | 938 | 76.752 | 24.592 | 14.133 | 1.00 | 13.69 |
| ATOM | 2127 | O | ASN | A | 938 | 76.801 | 25.234 | 15.181 | 1.00 | 15.28 |
| ATOM | 2128 | N | LEU | A | 939 | 77.826 | 24.107 | 13.515 | 1.00 | 14.66 |
| ATOM | 2129 | CA | LEU | A | 939 | 79.178 | 24.230 | 14.040 | 1.00 | 14.38 |
| ATOM | 2130 | CB | LEU | A | 939 | 80.159 | 23.393 | 13.211 | 1.00 | 12.88 |
| ATOM | 2131 | CG | LEU | A | 939 | 79.906 | 21.886 | 13.370 | 1.00 | 14.36 |
| ATOM | 2132 | CD1 | LEU | A | 939 | 80.689 | 21.085 | 12.353 | 1.00 | 14.04 |
| ATOM | 2133 | CD2 | LEU | A | 939 | 80.184 | 21.403 | 14.793 | 1.00 | 14.35 |
| ATOM | 2134 | C | LEU | A | 939 | 79.647 | 25.667 | 14.164 | 1.00 | 15.24 |
| ATOM | 2135 | O | LEU | A | 939 | 80.253 | 26.014 | 15.172 | 1.00 | 18.11 |
| ATOM | 2136 | N | THR | A | 940 | 79.353 | 26.508 | 13.170 | 1.00 | 15.26 |
| ATOM | 2137 | CA | THR | A | 940 | 79.722 | 27.923 | 13.266 | 1.00 | 16.51 |
| ATOM | 2138 | CB | THR | A | 940 | 79.728 | 28.649 | 11.897 | 1.00 | 15.74 |
| ATOM | 2139 | OG1 | THR | A | 940 | 78.405 | 28.676 | 11.341 | 1.00 | 16.24 |
| ATOM | 2140 | CG2 | THR | A | 940 | 80.581 | 27.901 | 10.870 | 1.00 | 14.54 |
| ATOM | 2141 | C | THR | A | 940 | 78.856 | 28.682 | 14.263 | 1.00 | 17.94 |
| ATOM | 2142 | O | THR | A | 940 | 79.217 | 29.779 | 14.677 | 1.00 | 20.33 |
| ATOM | 2143 | N | SER | A | 941 | 77.720 | 28.105 | 14.649 | 1.00 | 19.32 |
| ATOM | 2144 | CA | SER | A | 941 | 76.914 | 28.682 | 15.722 | 1.00 | 21.72 |
| ATOM | 2145 | CB | SER | A | 941 | 75.432 | 28.359 | 15.543 | 1.00 | 22.52 |
| ATOM | 2146 | OG | SER | A | 941 | 74.955 | 28.881 | 14.317 | 1.00 | 24.79 |
| ATOM | 2147 | C | SER | A | 941 | 77.411 | 28.247 | 17.106 | 1.00 | 22.95 |
| ATOM | 2148 | O | SER | A | 941 | 77.436 | 29.052 | 18.021 | 1.00 | 23.72 |
| ATOM | 2149 | N | PHE | A | 942 | 77.808 | 26.983 | 17.252 | 1.00 | 25.33 |
| ATOM | 2150 | CA | PHE | A | 942 | 78.371 | 26.496 | 18.512 | 1.00 | 27.34 |
| ATOM | 2151 | CB | PHE | A | 942 | 78.676 | 24.985 | 18.460 | 1.00 | 30.40 |
| ATOM | 2152 | CG | PHE | A | 942 | 77.460 | 24.093 | 18.309 | 1.00 | 35.94 |
| ATOM | 2153 | CD1 | PHE | A | 942 | 76.230 | 24.428 | 18.880 | 1.00 | 39.21 |
| ATOM | 2154 | CE1 | PHE | A | 942 | 75.111 | 23.577 | 18.735 | 1.00 | 39.52 |
| ATOM | 2155 | CZ | PHE | A | 942 | 75.228 | 22.377 | 18.023 | 1.00 | 38.70 |
| ATOM | 2156 | CE2 | PHE | A | 942 | 76.449 | 22.031 | 17.457 | 1.00 | 37.60 |
| ATOM | 2157 | CD2 | PHE | A | 942 | 77.557 | 22.885 | 17.606 | 1.00 | 37.70 |
| ATOM | 2158 | C | PHE | A | 942 | 79.664 | 27.260 | 18.814 | 1.00 | 25.46 |
| ATOM | 2159 | O | PHE | A | 942 | 79.809 | 27.852 | 19.883 | 1.00 | 24.88 |
| ATOM | 2160 | N | LEU | A | 943 | 80.580 | 27.249 | 17.845 | 1.00 | 22.62 |
| ATOM | 2161 | CA | LEU | A | 943 | 81.944 | 27.756 | 18.003 | 1.00 | 20.46 |
| ATOM | 2162 | CB | LEU | A | 943 | 82.867 | 27.027 | 17.024 | 1.00 | 14.67 |
| ATOM | 2163 | CG | LEU | A | 943 | 82.887 | 25.510 | 17.205 | 1.00 | 12.29 |
| ATOM | 2164 | CD1 | LEU | A | 943 | 83.594 | 24.838 | 16.061 | 1.00 | 10.90 |
| ATOM | 2165 | CD2 | LEU | A | 943 | 83.532 | 25.132 | 18.515 | 1.00 | 10.50 |
| ATOM | 2166 | C | LEU | A | 943 | 82.074 | 29.269 | 17.831 | 1.00 | 21.84 |
| ATOM | 2167 | O | LEU | A | 943 | 81.102 | 29.943 | 17.491 | 1.00 | 23.70 |
| ATOM | 2168 | N | GLY | A | 944 | 83.273 | 29.799 | 18.067 | 1.00 | 25.70 |
| ATOM | 2169 | CA | GLY | A | 944 | 83.528 | 31.223 | 17.888 | 1.00 | 30.87 |

FIGURE 3BQ

| | A | B | C | D | E | F | G | H | I | J |
|---|---|---|---|---|---|---|---|---|---|---|
| ATOM | 2170 | C | GLY | A | 944 | 84.908 | 31.714 | 18.291 | 1.00 | 34.13 |
| ATOM | 2171 | O | GLY | A | 944 | 85.749 | 30.932 | 18.728 | 1.00 | 34.73 |
| ATOM | 2172 | N | CYS | A | 945 | 85.132 | 33.019 | 18.130 | 1.00 | 38.27 |
| ATOM | 2173 | CA | CYS | A | 945 | 86.365 | 33.686 | 18.559 | 1.00 | 41.55 |
| ATOM | 2174 | CB | CYS | A | 945 | 87.014 | 34.413 | 17.382 | 1.00 | 43.72 |
| ATOM | 2175 | SG | CYS | A | 945 | 87.617 | 33.299 | 16.095 | 1.00 | 48.99 |
| ATOM | 2176 | C | CYS | A | 945 | 86.094 | 34.673 | 19.694 | 1.00 | 42.73 |
| ATOM | 2177 | O | CYS | A | 945 | 87.013 | 35.312 | 20.221 | 1.00 | 45.21 |
| TER | 2177 | | CYS | A | 945 | | | | | |
| ATOM | 2178 | O24 | STA | A | 1 | 101.016 | 29.181 | 1.484 | 1.00 | 14.08 |
| ATOM | 2179 | C23 | STA | A | 1 | 100.429 | 28.371 | 0.775 | 1.00 | 13.67 |
| ATOM | 2180 | N22 | STA | A | 1 | 99.392 | 28.642 | -0.029 | 1.00 | 13.96 |
| ATOM | 2181 | C21 | STA | A | 1 | 98.905 | 27.471 | -0.753 | 1.00 | 14.38 |
| ATOM | 2182 | C20 | STA | A | 1 | 99.839 | 26.404 | -0.242 | 1.00 | 11.85 |
| ATOM | 2183 | C25 | STA | A | 1 | 100.738 | 26.967 | 0.667 | 1.00 | 11.83 |
| ATOM | 2184 | C26 | STA | A | 1 | 101.752 | 26.143 | 1.303 | 1.00 | 10.73 |
| ATOM | 2185 | C27 | STA | A | 1 | 102.797 | 26.404 | 2.256 | 1.00 | 9.17 |
| ATOM | 2186 | C28 | STA | A | 1 | 103.132 | 27.620 | 2.865 | 1.00 | 7.85 |
| ATOM | 2187 | C29 | STA | A | 1 | 104.229 | 27.476 | 3.749 | 1.00 | 7.67 |
| ATOM | 2188 | C30 | STA | A | 1 | 104.901 | 26.254 | 3.992 | 1.00 | 7.60 |
| ATOM | 2189 | C32 | STA | A | 1 | 103.467 | 25.197 | 2.507 | 1.00 | 8.75 |
| ATOM | 2190 | C31 | STA | A | 1 | 104.554 | 25.030 | 3.384 | 1.00 | 8.29 |
| ATOM | 2191 | C34 | STA | A | 1 | 101.823 | 24.752 | 1.000 | 1.00 | 10.18 |
| ATOM | 2192 | C35 | STA | A | 1 | 100.899 | 24.182 | 0.063 | 1.00 | 10.79 |
| ATOM | 2193 | N33 | STA | A | 1 | 102.863 | 24.176 | 1.734 | 1.00 | 10.23 |
| ATOM | 2194 | C5 | STA | A | 1 | 103.258 | 22.745 | 1.673 | 1.00 | 12.32 |
| ATOM | 2195 | C4 | STA | A | 1 | 102.685 | 21.971 | 2.869 | 1.00 | 12.67 |
| ATOM | 2196 | C3 | STA | A | 1 | 101.880 | 20.744 | 2.437 | 1.00 | 13.67 |
| ATOM | 2197 | N2 | STA | A | 1 | 101.225 | 20.061 | 3.544 | 1.00 | 14.52 |
| ATOM | 2198 | C1 | STA | A | 1 | 101.968 | 19.055 | 4.283 | 1.00 | 13.60 |
| ATOM | 2199 | C9 | STA | A | 1 | 100.843 | 21.168 | 1.418 | 1.00 | 13.52 |
| ATOM | 2200 | O10 | STA | A | 1 | 100.026 | 22.179 | 2.019 | 1.00 | 15.58 |
| ATOM | 2201 | C11 | STA | A | 1 | 98.628 | 21.916 | 1.974 | 1.00 | 16.37 |
| ATOM | 2202 | O6 | STA | A | 1 | 102.887 | 22.192 | 0.406 | 1.00 | 12.64 |
| ATOM | 2203 | C7 | STA | A | 1 | 101.539 | 21.717 | 0.162 | 1.00 | 12.33 |
| ATOM | 2204 | C8 | STA | A | 1 | 101.732 | 20.592 | -0.855 | 1.00 | 12.32 |
| ATOM | 2205 | N12 | STA | A | 1 | 100.771 | 22.872 | -0.404 | 1.00 | 10.17 |
| ATOM | 2206 | C13 | STA | A | 1 | 99.686 | 22.827 | -1.316 | 1.00 | 9.22 |
| ATOM | 2207 | C14 | STA | A | 1 | 99.155 | 21.760 | -2.050 | 1.00 | 7.19 |
| ATOM | 2208 | C15 | STA | A | 1 | 98.066 | 22.049 | -2.890 | 1.00 | 8.37 |
| ATOM | 2209 | C16 | STA | A | 1 | 97.543 | 23.360 | -2.996 | 1.00 | 7.20 |
| ATOM | 2210 | C17 | STA | A | 1 | 98.080 | 24.425 | -2.262 | 1.00 | 7.00 |
| ATOM | 2211 | C18 | STA | A | 1 | 99.160 | 24.125 | -1.417 | 1.00 | 8.60 |
| ATOM | 2212 | C19 | STA | A | 1 | 99.905 | 24.997 | -0.557 | 1.00 | 10.76 |

FIGURE 3BR

LEGEND

Column headings from left to right are (A)'Atom Number', (B)'Atom Type', (C)'Amino Acid', (D)'Chain Identifier', (E)'Amino Acid Number', (F)'X Coordinate', (G)'Y Coordinate', (H)'Z Coordinate', (I)'Occupancy' (OCC) and (J)'B factor'

FLT3 Coordinates corresponding to [SEQ. ID No. 3]
Molecule B

|      | A    | B   | C   | D | E   | F      | G      | H      | I    | J     |
|------|------|-----|-----|---|-----|--------|--------|--------|------|-------|
| ATOM | 2213 | C   | GLU | B | 596 | 67.615 | 33.439 | 27.176 | 1.00 | 33.65 |
| ATOM | 2214 | N   | GLU | B | 596 | 67.525 | 32.445 | 29.426 | 1.00 | 33.93 |
| ATOM | 2215 | O   | GLU | B | 596 | 68.325 | 34.439 | 26.975 | 1.00 | 33.36 |
| ATOM | 2216 | CA  | GLU | B | 596 | 68.101 | 32.321 | 28.093 | 1.00 | 34.00 |
| ATOM | 2217 | CB  | GLU | B | 596 | 67.761 | 30.958 | 27.486 | 1.00 | 33.80 |
| ATOM | 2218 | CD  | GLU | B | 596 | 70.147 | 30.382 | 26.893 | 1.00 | 33.52 |
| ATOM | 2219 | OE1 | GLU | B | 596 | 70.946 | 31.309 | 26.648 | 1.00 | 33.07 |
| ATOM | 2220 | OE2 | GLU | B | 596 | 70.466 | 29.355 | 27.529 | 1.00 | 33.14 |
| ATOM | 2221 | CG  | GLU | B | 596 | 68.720 | 30.507 | 26.396 | 1.00 | 33.98 |
| ATOM | 2222 | N   | TYR | B | 597 | 66.416 | 33.290 | 26.609 | 1.00 | 33.23 |
| ATOM | 2223 | CA  | TYR | B | 597 | 65.874 | 34.244 | 25.647 | 1.00 | 32.71 |
| ATOM | 2224 | CB  | TYR | B | 597 | 64.602 | 33.697 | 24.993 | 1.00 | 32.91 |
| ATOM | 2225 | CG  | TYR | B | 597 | 63.951 | 34.671 | 24.032 | 1.00 | 33.00 |
| ATOM | 2226 | CD1 | TYR | B | 597 | 62.787 | 35.361 | 24.385 | 1.00 | 33.37 |
| ATOM | 2227 | CE1 | TYR | B | 597 | 62.187 | 36.263 | 23.501 | 1.00 | 33.80 |
| ATOM | 2228 | CZ  | TYR | B | 597 | 62.759 | 36.484 | 22.252 | 1.00 | 33.66 |
| ATOM | 2229 | OH  | TYR | B | 597 | 62.183 | 37.372 | 21.369 | 1.00 | 33.25 |
| ATOM | 2230 | CE2 | TYR | B | 597 | 63.916 | 35.815 | 21.885 | 1.00 | 33.40 |
| ATOM | 2231 | CD2 | TYR | B | 597 | 64.506 | 34.914 | 22.775 | 1.00 | 33.00 |
| ATOM | 2232 | C   | TYR | B | 597 | 65.595 | 35.614 | 26.262 | 1.00 | 32.50 |
| ATOM | 2233 | O   | TYR | B | 597 | 64.917 | 35.725 | 27.288 | 1.00 | 31.85 |
| ATOM | 2234 | N   | GLU | B | 598 | 66.127 | 36.649 | 25.617 | 1.00 | 32.31 |
| ATOM | 2235 | CA  | GLU | B | 598 | 65.867 | 38.030 | 26.002 | 1.00 | 32.92 |
| ATOM | 2236 | CB  | GLU | B | 598 | 67.182 | 38.764 | 26.297 | 1.00 | 33.60 |
| ATOM | 2237 | CG  | GLU | B | 598 | 67.030 | 40.247 | 26.606 | 1.00 | 34.34 |
| ATOM | 2238 | CD  | GLU | B | 598 | 66.696 | 40.510 | 28.062 | 1.00 | 35.15 |
| ATOM | 2239 | OE1 | GLU | B | 598 | 67.614 | 40.440 | 28.911 | 1.00 | 34.94 |
| ATOM | 2240 | OE2 | GLU | B | 598 | 65.512 | 40.789 | 28.355 | 1.00 | 35.07 |
| ATOM | 2241 | C   | GLU | B | 598 | 65.107 | 38.717 | 24.874 | 1.00 | 32.61 |
| ATOM | 2242 | O   | GLU | B | 598 | 65.674 | 38.986 | 23.811 | 1.00 | 32.22 |
| ATOM | 2243 | N   | TYR | B | 599 | 63.823 | 38.982 | 25.102 | 1.00 | 32.40 |
| ATOM | 2244 | CA  | TYR | B | 599 | 62.996 | 39.658 | 24.106 | 1.00 | 32.19 |
| ATOM | 2245 | CB  | TYR | B | 599 | 61.512 | 39.615 | 24.487 | 1.00 | 32.40 |
| ATOM | 2246 | CG  | TYR | B | 599 | 60.626 | 40.419 | 23.560 | 1.00 | 32.64 |
| ATOM | 2247 | CD1 | TYR | B | 599 | 60.045 | 41.617 | 23.983 | 1.00 | 32.53 |
| ATOM | 2248 | CE1 | TYR | B | 599 | 59.235 | 42.363 | 23.128 | 1.00 | 32.75 |
| ATOM | 2249 | CZ  | TYR | B | 599 | 59.001 | 41.910 | 21.836 | 1.00 | 32.36 |
| ATOM | 2250 | OH  | TYR | B | 599 | 58.201 | 42.638 | 20.986 | 1.00 | 32.51 |
| ATOM | 2251 | CE2 | TYR | B | 599 | 59.570 | 40.727 | 21.394 | 1.00 | 32.65 |
| ATOM | 2252 | CD2 | TYR | B | 599 | 60.377 | 39.989 | 22.256 | 1.00 | 32.62 |
| ATOM | 2253 | C   | TYR | B | 599 | 63.464 | 41.096 | 23.921 | 1.00 | 31.68 |
| ATOM | 2254 | O   | TYR | B | 599 | 63.392 | 41.906 | 24.846 | 1.00 | 33.29 |

FIGURE 3BS

|      | A    | B   | C   | D | E   | F      | G      | H      | I    | J     |
|------|------|-----|-----|---|-----|--------|--------|--------|------|-------|
| ATOM | 2255 | N   | ASP | B | 600 | 63.959 | 41.394 | 22.724 | 1.00 | 30.35 |
| ATOM | 2256 | CA  | ASP | B | 600 | 64.442 | 42.727 | 22.396 | 1.00 | 29.26 |
| ATOM | 2257 | CB  | ASP | B | 600 | 65.298 | 42.685 | 21.127 | 1.00 | 30.60 |
| ATOM | 2258 | CG  | ASP | B | 600 | 66.332 | 43.794 | 21.078 | 1.00 | 31.82 |
| ATOM | 2259 | OD1 | ASP | B | 600 | 66.037 | 44.922 | 21.534 | 1.00 | 32.61 |
| ATOM | 2260 | OD2 | ASP | B | 600 | 67.468 | 43.631 | 20.587 | 1.00 | 33.03 |
| ATOM | 2261 | C   | ASP | B | 600 | 63.265 | 43.676 | 22.214 | 1.00 | 27.77 |
| ATOM | 2262 | O   | ASP | B | 600 | 62.359 | 43.408 | 21.420 | 1.00 | 28.31 |
| ATOM | 2263 | N   | LEU | B | 601 | 63.286 | 44.785 | 22.948 | 1.00 | 25.49 |
| ATOM | 2264 | CA  | LEU | B | 601 | 62.184 | 45.745 | 22.929 | 1.00 | 25.47 |
| ATOM | 2265 | CB  | LEU | B | 601 | 62.320 | 46.762 | 24.069 | 1.00 | 25.31 |
| ATOM | 2266 | CG  | LEU | B | 601 | 61.626 | 46.432 | 25.396 | 1.00 | 25.35 |
| ATOM | 2267 | CD1 | LEU | B | 601 | 61.920 | 47.515 | 26.436 | 1.00 | 24.89 |
| ATOM | 2268 | CD2 | LEU | B | 601 | 60.118 | 46.241 | 25.214 | 1.00 | 24.77 |
| ATOM | 2269 | C   | LEU | B | 601 | 62.035 | 46.469 | 21.592 | 1.00 | 24.70 |
| ATOM | 2270 | O   | LEU | B | 601 | 60.948 | 46.948 | 21.268 | 1.00 | 24.32 |
| ATOM | 2271 | N   | LYS | B | 602 | 63.123 | 46.540 | 20.825 | 1.00 | 24.34 |
| ATOM | 2272 | CA  | LYS | B | 602 | 63.113 | 47.158 | 19.495 | 1.00 | 24.31 |
| ATOM | 2273 | CB  | LYS | B | 602 | 64.517 | 47.138 | 18.869 | 1.00 | 25.12 |
| ATOM | 2274 | CG  | LYS | B | 602 | 65.053 | 45.740 | 18.543 | 1.00 | 26.32 |
| ATOM | 2275 | CD  | LYS | B | 602 | 65.876 | 45.718 | 17.263 | 1.00 | 26.85 |
| ATOM | 2276 | CE  | LYS | B | 602 | 66.176 | 44.287 | 16.836 | 1.00 | 26.87 |
| ATOM | 2277 | NZ  | LYS | B | 602 | 67.588 | 44.112 | 16.398 | 1.00 | 26.73 |
| ATOM | 2278 | C   | LYS | B | 602 | 62.083 | 46.523 | 18.546 | 1.00 | 23.56 |
| ATOM | 2279 | O   | LYS | B | 602 | 61.690 | 47.133 | 17.550 | 1.00 | 22.98 |
| ATOM | 2280 | N   | TRP | B | 603 | 61.650 | 45.305 | 18.871 | 1.00 | 22.96 |
| ATOM | 2281 | CA  | TRP | B | 603 | 60.641 | 44.592 | 18.090 | 1.00 | 22.45 |
| ATOM | 2282 | CB  | TRP | B | 603 | 60.721 | 43.083 | 18.343 | 1.00 | 21.57 |
| ATOM | 2283 | CG  | TRP | B | 603 | 61.872 | 42.415 | 17.654 | 1.00 | 20.88 |
| ATOM | 2284 | CD1 | TRP | B | 603 | 63.000 | 41.922 | 18.241 | 1.00 | 21.39 |
| ATOM | 2285 | NE1 | TRP | B | 603 | 63.834 | 41.383 | 17.291 | 1.00 | 21.71 |
| ATOM | 2286 | CE2 | TRP | B | 603 | 63.251 | 41.515 | 16.059 | 1.00 | 21.14 |
| ATOM | 2287 | CD2 | TRP | B | 603 | 62.012 | 42.167 | 16.250 | 1.00 | 21.10 |
| ATOM | 2288 | CE3 | TRP | B | 603 | 61.211 | 42.426 | 15.126 | 1.00 | 21.00 |
| ATOM | 2289 | CZ3 | TRP | B | 603 | 61.669 | 42.033 | 13.871 | 1.00 | 20.36 |
| ATOM | 2290 | CH2 | TRP | B | 603 | 62.906 | 41.393 | 13.718 | 1.00 | 21.08 |
| ATOM | 2291 | CZ2 | TRP | B | 603 | 63.711 | 41.123 | 14.798 | 1.00 | 20.89 |
| ATOM | 2292 | C   | TRP | B | 603 | 59.227 | 45.073 | 18.386 | 1.00 | 23.63 |
| ATOM | 2293 | O   | TRP | B | 603 | 58.341 | 44.967 | 17.532 | 1.00 | 24.30 |
| ATOM | 2294 | N   | GLU | B | 604 | 59.018 | 45.596 | 19.593 | 1.00 | 24.27 |
| ATOM | 2295 | CA  | GLU | B | 604 | 57.680 | 45.943 | 20.054 | 1.00 | 25.40 |
| ATOM | 2296 | CB  | GLU | B | 604 | 57.671 | 46.274 | 21.551 | 1.00 | 26.39 |
| ATOM | 2297 | CG  | GLU | B | 604 | 56.268 | 46.310 | 22.159 | 1.00 | 27.79 |
| ATOM | 2298 | CD  | GLU | B | 604 | 55.632 | 44.890 | 22.350 | 1.00 | 28.61 |
| ATOM | 2299 | OE1 | GLU | B | 604 | 54.408 | 44.796 | 22.652 | 1.00 | 28.64 |
| ATOM | 2300 | OE2 | GLU | B | 604 | 56.353 | 43.870 | 22.221 | 1.00 | 28.99 |
| ATOM | 2301 | C   | GLU | B | 604 | 57.054 | 47.083 | 19.256 | 1.00 | 26.94 |
| ATOM | 2302 | O   | GLU | B | 604 | 57.677 | 48.122 | 19.028 | 1.00 | 26.83 |
| ATOM | 2303 | N   | PHE | B | 605 | 55.812 | 46.858 | 18.828 | 1.00 | 28.61 |
| ATOM | 2304 | CA  | PHE | B | 605 | 55.008 | 47.869 | 18.141 | 1.00 | 30.03 |
| ATOM | 2305 | CB  | PHE | B | 605 | 54.672 | 47.401 | 16.708 | 1.00 | 31.53 |
| ATOM | 2306 | CG  | PHE | B | 605 | 53.886 | 48.424 | 15.902 | 1.00 | 34.20 |

FIGURE 3BT

| | A | B | C | D | E | F | G | H | I | J |
|---|---|---|---|---|---|---|---|---|---|---|
| ATOM | 2307 | CD1 | PHE | B | 605 | 52.479 | 48.372 | 15.828 | 1.00 | 35.23 |
| ATOM | 2308 | CE1 | PHE | B | 605 | 51.740 | 49.317 | 15.075 | 1.00 | 36.15 |
| ATOM | 2309 | CZ | PHE | B | 605 | 52.417 | 50.329 | 14.392 | 1.00 | 36.37 |
| ATOM | 2310 | CE2 | PHE | B | 605 | 53.826 | 50.389 | 14.462 | 1.00 | 36.17 |
| ATOM | 2311 | CD2 | PHE | B | 605 | 54.548 | 49.439 | 15.215 | 1.00 | 35.12 |
| ATOM | 2312 | C | PHE | B | 605 | 53.730 | 48.094 | 18.951 | 1.00 | 29.57 |
| ATOM | 2313 | O | PHE | B | 605 | 53.154 | 47.129 | 19.470 | 1.00 | 30.21 |
| ATOM | 2314 | N | PRO | B | 606 | 53.299 | 49.355 | 19.076 | 1.00 | 28.41 |
| ATOM | 2315 | CA | PRO | B | 606 | 52.040 | 49.682 | 19.768 | 1.00 | 28.31 |
| ATOM | 2316 | CB | PRO | B | 606 | 52.061 | 51.214 | 19.824 | 1.00 | 28.58 |
| ATOM | 2317 | CG | PRO | B | 606 | 52.906 | 51.628 | 18.658 | 1.00 | 28.82 |
| ATOM | 2318 | CD | PRO | B | 606 | 53.996 | 50.568 | 18.577 | 1.00 | 28.31 |
| ATOM | 2319 | C | PRO | B | 606 | 50.790 | 49.185 | 19.035 | 1.00 | 27.95 |
| ATOM | 2320 | O | PRO | B | 606 | 50.585 | 49.536 | 17.859 | 1.00 | 29.90 |
| ATOM | 2321 | N | ARG | B | 607 | 49.966 | 48.384 | 19.717 | 1.00 | 27.14 |
| ATOM | 2322 | CA | ARG | B | 607 | 48.812 | 47.722 | 19.085 | 1.00 | 26.85 |
| ATOM | 2323 | CB | ARG | B | 607 | 48.240 | 46.623 | 19.991 | 1.00 | 26.20 |
| ATOM | 2324 | CG | ARG | B | 607 | 47.783 | 47.107 | 21.349 | 1.00 | 27.39 |
| ATOM | 2325 | CD | ARG | B | 607 | 47.213 | 46.018 | 22.236 | 1.00 | 28.12 |
| ATOM | 2326 | NE | ARG | B | 607 | 48.247 | 45.087 | 22.679 | 1.00 | 28.14 |
| ATOM | 2327 | CZ | ARG | B | 607 | 48.305 | 43.808 | 22.326 | 1.00 | 28.56 |
| ATOM | 2328 | NH1 | ARG | B | 607 | 49.289 | 43.044 | 22.780 | 1.00 | 29.27 |
| ATOM | 2329 | NH2 | ARG | B | 607 | 47.382 | 43.286 | 21.525 | 1.00 | 27.73 |
| ATOM | 2330 | C | ARG | B | 607 | 47.696 | 48.680 | 18.639 | 1.00 | 27.45 |
| ATOM | 2331 | O | ARG | B | 607 | 46.872 | 48.334 | 17.784 | 1.00 | 28.08 |
| ATOM | 2332 | N | GLU | B | 608 | 47.680 | 49.878 | 19.218 | 1.00 | 26.54 |
| ATOM | 2333 | CA | GLU | B | 608 | 46.731 | 50.918 | 18.828 | 1.00 | 26.71 |
| ATOM | 2334 | CB | GLU | B | 608 | 46.657 | 52.015 | 19.903 | 1.00 | 26.29 |
| ATOM | 2335 | CG | GLU | B | 608 | 47.921 | 52.859 | 20.053 | 1.00 | 26.46 |
| ATOM | 2336 | CD | GLU | B | 608 | 48.749 | 52.488 | 21.275 | 1.00 | 26.61 |
| ATOM | 2337 | OE1 | GLU | B | 608 | 49.020 | 53.386 | 22.100 | 1.00 | 26.17 |
| ATOM | 2338 | OE2 | GLU | B | 608 | 49.142 | 51.304 | 21.408 | 1.00 | 27.30 |
| ATOM | 2339 | C | GLU | B | 608 | 47.048 | 51.518 | 17.449 | 1.00 | 27.01 |
| ATOM | 2340 | O | GLU | B | 608 | 46.288 | 52.349 | 16.938 | 1.00 | 27.90 |
| ATOM | 2341 | N | ASN | B | 609 | 48.168 | 51.092 | 16.861 | 1.00 | 26.23 |
| ATOM | 2342 | CA | ASN | B | 609 | 48.596 | 51.569 | 15.547 | 1.00 | 26.16 |
| ATOM | 2343 | CB | ASN | B | 609 | 50.096 | 51.905 | 15.561 | 1.00 | 26.42 |
| ATOM | 2344 | CG | ASN | B | 609 | 50.389 | 53.264 | 16.196 | 1.00 | 28.13 |
| ATOM | 2345 | OD1 | ASN | B | 609 | 50.060 | 53.505 | 17.363 | 1.00 | 28.16 |
| ATOM | 2346 | ND2 | ASN | B | 609 | 51.012 | 54.160 | 15.427 | 1.00 | 28.51 |
| ATOM | 2347 | C | ASN | B | 609 | 48.258 | 50.594 | 14.401 | 1.00 | 25.67 |
| ATOM | 2348 | O | ASN | B | 609 | 48.541 | 50.891 | 13.141 | 1.00 | 26.30 |
| ATOM | 2349 | N | LEU | B | 610 | 47.652 | 49.436 | 14.848 | 1.00 | 25.16 |
| ATOM | 2350 | CA | LEU | B | 610 | 47.320 | 48.335 | 13.945 | 1.00 | 25.23 |
| ATOM | 2351 | CB | LEU | B | 610 | 47.635 | 46.977 | 14.587 | 1.00 | 23.94 |
| ATOM | 2352 | CG | LEU | B | 610 | 49.071 | 46.464 | 14.622 | 1.00 | 23.41 |
| ATOM | 2353 | CD1 | LEU | B | 610 | 49.107 | 45.148 | 15.392 | 1.00 | 23.83 |
| ATOM | 2354 | CD2 | LEU | B | 610 | 49.643 | 46.284 | 13.220 | 1.00 | 23.29 |
| ATOM | 2355 | C | LEU | B | 610 | 45.857 | 48.362 | 13.532 | 1.00 | 25.42 |
| ATOM | 2356 | O | LEU | B | 610 | 44.988 | 47.857 | 14.249 | 1.00 | 26.14 |
| ATOM | 2357 | N | GLU | B | 611 | 45.599 | 48.957 | 12.370 | 1.00 | 24.81 |
| ATOM | 2358 | CA | GLU | B | 611 | 44.286 | 48.886 | 11.719 | 1.00 | 22.88 |

FIGURE 3BU

| | A | B | C | D | E | F | G | H | I | J |
|---|---|---|---|---|---|---|---|---|---|---|
| ATOM | 2359 | CB | GLU | B | 611 | 44.130 | 50.027 | 10.701 | 1.00 | 21.65 |
| ATOM | 2360 | CG | GLU | B | 611 | 42.702 | 50.484 | 10.462 | 1.00 | 21.62 |
| ATOM | 2361 | CD | GLU | B | 611 | 42.606 | 51.545 | 9.363 | 1.00 | 21.71 |
| ATOM | 2362 | OE1 | GLU | B | 611 | 43.396 | 51.477 | 8.394 | 1.00 | 22.27 |
| ATOM | 2363 | OE2 | GLU | B | 611 | 41.742 | 52.443 | 9.462 | 1.00 | 22.74 |
| ATOM | 2364 | C | GLU | B | 611 | 44.160 | 47.484 | 11.046 | 1.00 | 22.55 |
| ATOM | 2365 | O | GLU | B | 611 | 44.836 | 47.156 | 10.018 | 1.00 | 22.53 |
| ATOM | 2366 | N | PHE | B | 612 | 43.311 | 46.652 | 11.652 | 1.00 | 21.48 |
| ATOM | 2367 | CA | PHE | B | 612 | 43.055 | 45.297 | 11.165 | 1.00 | 19.73 |
| ATOM | 2368 | CB | PHE | B | 612 | 42.339 | 44.478 | 12.236 | 1.00 | 18.34 |
| ATOM | 2369 | CG | PHE | B | 612 | 43.256 | 43.908 | 13.258 | 1.00 | 18.23 |
| ATOM | 2370 | CD1 | PHE | B | 612 | 43.108 | 44.229 | 14.606 | 1.00 | 17.87 |
| ATOM | 2371 | CE1 | PHE | B | 612 | 43.967 | 43.704 | 15.563 | 1.00 | 17.12 |
| ATOM | 2372 | CZ | PHE | B | 612 | 44.998 | 42.847 | 15.170 | 1.00 | 19.16 |
| ATOM | 2373 | CE2 | PHE | B | 612 | 45.160 | 42.517 | 13.815 | 1.00 | 18.37 |
| ATOM | 2374 | CD2 | PHE | B | 612 | 44.289 | 43.050 | 12.874 | 1.00 | 19.27 |
| ATOM | 2375 | C | PHE | B | 612 | 42.235 | 45.237 | 9.880 | 1.00 | 21.30 |
| ATOM | 2376 | O | PHE | B | 612 | 41.328 | 46.044 | 9.652 | 1.00 | 18.55 |
| ATOM | 2377 | N | GLY | B | 613 | 42.574 | 44.253 | 9.051 | 1.00 | 23.46 |
| ATOM | 2378 | CA | GLY | B | 613 | 41.823 | 43.943 | 7.853 | 1.00 | 25.92 |
| ATOM | 2379 | C | GLY | B | 613 | 40.998 | 42.686 | 8.077 | 1.00 | 27.11 |
| ATOM | 2380 | O | GLY | B | 613 | 40.373 | 42.519 | 9.147 | 1.00 | 28.87 |
| ATOM | 2381 | N | LYS | B | 614 | 40.992 | 41.800 | 7.053 | 1.00 | 26.51 |
| ATOM | 2382 | CA | LYS | B | 614 | 40.204 | 40.575 | 7.122 | 1.00 | 28.09 |
| ATOM | 2383 | CB | LYS | B | 614 | 39.482 | 40.326 | 5.788 | 1.00 | 30.60 |
| ATOM | 2384 | CG | LYS | B | 614 | 37.992 | 40.703 | 5.806 | 1.00 | 33.41 |
| ATOM | 2385 | CD | LYS | B | 614 | 37.663 | 41.865 | 4.868 | 1.00 | 34.76 |
| ATOM | 2386 | CE | LYS | B | 614 | 36.777 | 41.413 | 3.709 | 1.00 | 35.33 |
| ATOM | 2387 | NZ | LYS | B | 614 | 37.558 | 40.714 | 2.641 | 1.00 | 34.77 |
| ATOM | 2388 | C | LYS | B | 614 | 41.053 | 39.364 | 7.542 | 1.00 | 27.46 |
| ATOM | 2389 | O | LYS | B | 614 | 42.300 | 39.419 | 7.540 | 1.00 | 25.01 |
| ATOM | 2390 | N | VAL | B | 615 | 40.358 | 38.287 | 7.926 | 1.00 | 26.66 |
| ATOM | 2391 | CA | VAL | B | 615 | 40.989 | 37.030 | 8.315 | 1.00 | 25.28 |
| ATOM | 2392 | CB | VAL | B | 615 | 39.981 | 36.065 | 8.995 | 1.00 | 24.75 |
| ATOM | 2393 | CG1 | VAL | B | 615 | 40.605 | 34.690 | 9.213 | 1.00 | 25.10 |
| ATOM | 2394 | CG2 | VAL | B | 615 | 39.495 | 36.641 | 10.316 | 1.00 | 24.91 |
| ATOM | 2395 | C | VAL | B | 615 | 41.613 | 36.369 | 7.087 | 1.00 | 24.98 |
| ATOM | 2396 | O | VAL | B | 615 | 40.913 | 35.959 | 6.156 | 1.00 | 25.50 |
| ATOM | 2397 | N | LEU | B | 616 | 42.937 | 36.282 | 7.093 | 1.00 | 23.71 |
| ATOM | 2398 | CA | LEU | B | 616 | 43.670 | 35.723 | 5.972 | 1.00 | 22.76 |
| ATOM | 2399 | CB | LEU | B | 616 | 45.097 | 36.273 | 5.946 | 1.00 | 22.21 |
| ATOM | 2400 | CG | LEU | B | 616 | 45.273 | 37.770 | 5.676 | 1.00 | 20.87 |
| ATOM | 2401 | CD1 | LEU | B | 616 | 46.740 | 38.138 | 5.810 | 1.00 | 20.18 |
| ATOM | 2402 | CD2 | LEU | B | 616 | 44.734 | 38.167 | 4.295 | 1.00 | 21.05 |
| ATOM | 2403 | C | LEU | B | 616 | 43.674 | 34.197 | 6.029 | 1.00 | 23.50 |
| ATOM | 2404 | O | LEU | B | 616 | 43.482 | 33.531 | 5.007 | 1.00 | 24.22 |
| ATOM | 2405 | N | GLY | B | 617 | 43.884 | 33.652 | 7.225 | 1.00 | 22.56 |
| ATOM | 2406 | CA | GLY | B | 617 | 43.857 | 32.216 | 7.432 | 1.00 | 22.54 |
| ATOM | 2407 | C | GLY | B | 617 | 43.496 | 31.831 | 8.850 | 1.00 | 23.55 |
| ATOM | 2408 | O | GLY | B | 617 | 43.624 | 32.635 | 9.773 | 1.00 | 24.54 |
| ATOM | 2409 | N | SER | B | 618 | 43.036 | 30.595 | 9.019 | 1.00 | 24.94 |
| ATOM | 2410 | CA | SER | B | 618 | 42.687 | 30.065 | 10.332 | 1.00 | 26.49 |

FIGURE 3BV

|      | A    | B    | C   | D | E   | F      | G      | H      | I    | J     |
|------|------|------|-----|---|-----|--------|--------|--------|------|-------|
| ATOM | 2411 | CB   | SER | B | 618 | 41.246 | 30.436 | 10.698 | 1.00 | 26.61 |
| ATOM | 2412 | OG   | SER | B | 618 | 40.344 | 29.407 | 10.331 | 1.00 | 26.94 |
| ATOM | 2413 | C    | SER | B | 618 | 42.876 | 28.553 | 10.384 | 1.00 | 28.35 |
| ATOM | 2414 | O    | SER | B | 618 | 43.009 | 27.893 |  9.350 | 1.00 | 29.98 |
| ATOM | 2415 | N    | GLY | B | 619 | 42.880 | 28.016 | 11.599 | 1.00 | 29.62 |
| ATOM | 2416 | CA   | GLY | B | 619 | 43.058 | 26.595 | 11.831 | 1.00 | 31.39 |
| ATOM | 2417 | C    | GLY | B | 619 | 43.360 | 26.352 | 13.295 | 1.00 | 33.09 |
| ATOM | 2418 | O    | GLY | B | 619 | 43.150 | 27.236 | 14.130 | 1.00 | 34.27 |
| ATOM | 2419 | N    | ALA | B | 620 | 43.853 | 25.156 | 13.608 | 1.00 | 33.77 |
| ATOM | 2420 | CA   | ALA | B | 620 | 44.209 | 24.800 | 14.981 | 1.00 | 33.86 |
| ATOM | 2421 | CB   | ALA | B | 620 | 44.572 | 23.321 | 15.072 | 1.00 | 34.10 |
| ATOM | 2422 | C    | ALA | B | 620 | 45.351 | 25.676 | 15.509 | 1.00 | 33.83 |
| ATOM | 2423 | O    | ALA | B | 620 | 45.352 | 26.070 | 16.679 | 1.00 | 34.37 |
| ATOM | 2424 | N    | PHE | B | 621 | 46.303 | 25.986 | 14.627 | 1.00 | 32.95 |
| ATOM | 2425 | CA   | PHE | B | 621 | 47.459 | 26.828 | 14.939 | 1.00 | 31.59 |
| ATOM | 2426 | CB   | PHE | B | 621 | 48.346 | 26.973 | 13.696 | 1.00 | 32.20 |
| ATOM | 2427 | CG   | PHE | B | 621 | 47.721 | 27.796 | 12.596 | 1.00 | 32.92 |
| ATOM | 2428 | CD1  | PHE | B | 621 | 46.900 | 27.197 | 11.640 | 1.00 | 33.20 |
| ATOM | 2429 | CE1  | PHE | B | 621 | 46.315 | 27.955 | 10.621 | 1.00 | 33.16 |
| ATOM | 2430 | CZ   | PHE | B | 621 | 46.546 | 29.328 | 10.556 | 1.00 | 32.96 |
| ATOM | 2431 | CE2  | PHE | B | 621 | 47.363 | 29.938 | 11.506 | 1.00 | 32.77 |
| ATOM | 2432 | CD2  | PHE | B | 621 | 47.947 | 29.171 | 12.518 | 1.00 | 32.86 |
| ATOM | 2433 | C    | PHE | B | 621 | 47.092 | 28.222 | 15.468 | 1.00 | 30.07 |
| ATOM | 2434 | O    | PHE | B | 621 | 47.883 | 28.847 | 16.176 | 1.00 | 31.61 |
| ATOM | 2435 | N    | GLY | B | 622 | 45.904 | 28.704 | 15.111 | 1.00 | 26.84 |
| ATOM | 2436 | CA   | GLY | B | 622 | 45.493 | 30.063 | 15.423 | 1.00 | 23.62 |
| ATOM | 2437 | C    | GLY | B | 622 | 44.924 | 30.762 | 14.202 | 1.00 | 21.16 |
| ATOM | 2438 | O    | GLY | B | 622 | 44.264 | 30.132 | 13.376 | 1.00 | 20.80 |
| ATOM | 2439 | N    | LYS | B | 623 | 45.171 | 32.064 | 14.086 | 1.00 | 19.04 |
| ATOM | 2440 | CA   | LYS | B | 623 | 44.698 | 32.824 | 12.930 | 1.00 | 18.33 |
| ATOM | 2441 | CB   | LYS | B | 623 | 43.270 | 33.370 | 13.137 | 1.00 | 19.02 |
| ATOM | 2442 | CG   | LYS | B | 623 | 43.059 | 34.260 | 14.361 | 1.00 | 18.63 |
| ATOM | 2443 | CD   | LYS | B | 623 | 41.602 | 34.715 | 14.481 | 1.00 | 19.38 |
| ATOM | 2444 | CE   | LYS | B | 623 | 40.826 | 33.881 | 15.501 | 1.00 | 19.48 |
| ATOM | 2445 | NZ   | LYS | B | 623 | 39.689 | 34.625 | 16.150 | 1.00 | 19.15 |
| ATOM | 2446 | C    | LYS | B | 623 | 45.653 | 33.928 | 12.503 | 1.00 | 17.85 |
| ATOM | 2447 | O    | LYS | B | 623 | 46.456 | 34.427 | 13.301 | 1.00 | 17.53 |
| ATOM | 2448 | N    | VAL | B | 624 | 45.562 | 34.291 | 11.227 | 1.00 | 16.85 |
| ATOM | 2449 | CA   | VAL | B | 624 | 46.361 | 35.372 | 10.663 | 1.00 | 17.40 |
| ATOM | 2450 | CB   | VAL | B | 624 | 47.330 | 34.868 |  9.568 | 1.00 | 15.45 |
| ATOM | 2451 | CG1  | VAL | B | 624 | 48.295 | 35.963 |  9.149 | 1.00 | 16.11 |
| ATOM | 2452 | CG2  | VAL | B | 624 | 48.115 | 33.660 | 10.064 | 1.00 | 16.89 |
| ATOM | 2453 | C    | VAL | B | 624 | 45.431 | 36.461 | 10.124 | 1.00 | 18.45 |
| ATOM | 2454 | O    | VAL | B | 624 | 44.455 | 36.174 |  9.424 | 1.00 | 19.68 |
| ATOM | 2455 | N    | MET | B | 625 | 45.726 | 37.708 | 10.469 | 1.00 | 18.61 |
| ATOM | 2456 | CA   | MET | B | 625 | 44.889 | 38.820 | 10.053 | 1.00 | 21.84 |
| ATOM | 2457 | CB   | MET | B | 625 | 44.264 | 39.520 | 11.267 | 1.00 | 24.03 |
| ATOM | 2458 | CG   | MET | B | 625 | 43.636 | 38.583 | 12.291 | 1.00 | 26.58 |
| ATOM | 2459 | SD   | MET | B | 625 | 41.857 | 38.733 | 12.348 | 1.00 | 29.83 |
| ATOM | 2460 | CE   | MET | B | 625 | 41.656 | 39.981 | 13.646 | 1.00 | 30.56 |
| ATOM | 2461 | C    | MET | B | 625 | 45.691 | 39.815 |  9.231 | 1.00 | 21.82 |
| ATOM | 2462 | O    | MET | B | 625 | 46.853 | 40.111 |  9.546 | 1.00 | 20.90 |

FIGURE 3BW

|       | A    | B   | C   | D | E   | F      | G      | H      | I    | J     |
|-------|------|-----|-----|---|-----|--------|--------|--------|------|-------|
| ATOM  | 2463 | N   | ASN | B | 626 | 45.075 | 40.318 | 8.164  | 1.00 | 21.30 |
| ATOM  | 2464 | CA  | ASN | B | 626 | 45.631 | 41.458 | 7.457  | 1.00 | 19.29 |
| ATOM  | 2465 | CB  | ASN | B | 626 | 44.850 | 41.723 | 6.146  | 1.00 | 17.47 |
| ATOM  | 2466 | CG  | ASN | B | 626 | 45.209 | 43.066 | 5.531  | 1.00 | 17.14 |
| ATOM  | 2467 | OD1 | ASN | B | 626 | 44.405 | 43.998 | 5.545  | 1.00 | 18.47 |
| ATOM  | 2468 | ND2 | ASN | B | 626 | 46.420 | 43.173 | 4.993  | 1.00 | 16.32 |
| ATOM  | 2469 | C   | ASN | B | 626 | 45.561 | 42.669 | 8.420  | 1.00 | 18.54 |
| ATOM  | 2470 | O   | ASN | B | 626 | 44.639 | 42.769 | 9.248  | 1.00 | 18.61 |
| ATOM  | 2471 | N   | ALA | B | 627 | 46.549 | 43.557 | 8.347  | 1.00 | 17.46 |
| ATOM  | 2472 | CA  | ALA | B | 627 | 46.503 | 44.809 | 9.094  | 1.00 | 19.16 |
| ATOM  | 2473 | CB  | ALA | B | 627 | 47.026 | 44.605 | 10.521 | 1.00 | 19.21 |
| ATOM  | 2474 | C   | ALA | B | 627 | 47.271 | 45.927 | 8.384  | 1.00 | 19.39 |
| ATOM  | 2475 | O   | ALA | B | 627 | 48.193 | 45.657 | 7.614  | 1.00 | 20.21 |
| ATOM  | 2476 | N   | THR | B | 628 | 46.854 | 47.181 | 8.612  | 1.00 | 19.27 |
| ATOM  | 2477 | CA  | THR | B | 628 | 47.694 | 48.320 | 8.263  | 1.00 | 19.43 |
| ATOM  | 2478 | CB  | THR | B | 628 | 46.871 | 49.462 | 7.583  | 1.00 | 19.29 |
| ATOM  | 2479 | OG1 | THR | B | 628 | 46.364 | 49.007 | 6.286  | 1.00 | 19.19 |
| ATOM  | 2480 | CG2 | THR | B | 628 | 47.793 | 50.605 | 7.177  | 1.00 | 19.02 |
| ATOM  | 2481 | C   | THR | B | 628 | 48.390 | 48.798 | 9.560  | 1.00 | 19.73 |
| ATOM  | 2482 | O   | THR | B | 628 | 47.732 | 49.129 | 10.575 | 1.00 | 17.03 |
| ATOM  | 2483 | N   | ALA | B | 629 | 49.725 | 48.782 | 9.520  | 1.00 | 20.82 |
| ATOM  | 2484 | CA  | ALA | B | 629 | 50.538 | 49.245 | 10.645 | 1.00 | 21.66 |
| ATOM  | 2485 | CB  | ALA | B | 629 | 51.676 | 48.258 | 10.941 | 1.00 | 21.49 |
| ATOM  | 2486 | C   | ALA | B | 629 | 51.085 | 50.627 | 10.322 | 1.00 | 22.67 |
| ATOM  | 2487 | O   | ALA | B | 629 | 51.838 | 50.803 | 9.358  | 1.00 | 22.96 |
| ATOM  | 2488 | N   | TYR | B | 630 | 50.695 | 51.606 | 11.132 | 1.00 | 24.19 |
| ATOM  | 2489 | CA  | TYR | B | 630 | 51.073 | 52.995 | 10.864 | 1.00 | 26.38 |
| ATOM  | 2490 | CB  | TYR | B | 630 | 49.944 | 53.944 | 11.295 | 1.00 | 27.28 |
| ATOM  | 2491 | CG  | TYR | B | 630 | 48.747 | 53.891 | 10.348 | 1.00 | 28.22 |
| ATOM  | 2492 | CD1 | TYR | B | 630 | 48.669 | 54.733 | 9.233  | 1.00 | 29.44 |
| ATOM  | 2493 | CE1 | TYR | B | 630 | 47.573 | 54.691 | 8.352  | 1.00 | 31.16 |
| ATOM  | 2494 | CZ  | TYR | B | 630 | 46.538 | 53.788 | 8.578  | 1.00 | 31.48 |
| ATOM  | 2495 | OH  | TYR | B | 630 | 45.446 | 53.758 | 7.708  | 1.00 | 32.14 |
| ATOM  | 2496 | CE2 | TYR | B | 630 | 46.598 | 52.930 | 9.680  | 1.00 | 30.00 |
| ATOM  | 2497 | CD2 | TYR | B | 630 | 47.700 | 52.986 | 10.555 | 1.00 | 28.50 |
| ATOM  | 2498 | C   | TYR | B | 630 | 52.417 | 53.382 | 11.527 | 1.00 | 27.54 |
| ATOM  | 2499 | O   | TYR | B | 630 | 52.538 | 53.536 | 12.811 | 1.00 | 27.97 |
| ATOM  | 2500 | N   | GLY | B | 631 | 53.422 | 53.520 | 10.636 | 1.00 | 28.99 |
| ATOM  | 2501 | CA  | GLY | B | 631 | 54.757 | 53.943 | 11.028 | 1.00 | 30.64 |
| ATOM  | 2502 | C   | GLY | B | 631 | 55.675 | 52.829 | 11.506 | 1.00 | 32.01 |
| ATOM  | 2503 | O   | GLY | B | 631 | 56.539 | 53.060 | 12.353 | 1.00 | 31.48 |
| ATOM  | 2504 | N   | ILE | B | 632 | 55.507 | 51.626 | 10.965 | 1.00 | 33.20 |
| ATOM  | 2505 | CA  | ILE | B | 632 | 56.349 | 50.502 | 11.376 | 1.00 | 34.43 |
| ATOM  | 2506 | CB  | ILE | B | 632 | 55.612 | 49.150 | 11.192 | 1.00 | 32.66 |
| ATOM  | 2507 | CG1 | ILE | B | 632 | 56.219 | 48.083 | 12.120 | 1.00 | 32.70 |
| ATOM  | 2508 | CD1 | ILE | B | 632 | 55.312 | 46.902 | 12.441 | 1.00 | 33.02 |
| ATOM  | 2509 | CG2 | ILE | B | 632 | 55.604 | 48.728 | 9.725  | 1.00 | 32.66 |
| ATOM  | 2510 | C   | ILE | B | 632 | 57.734 | 50.519 | 10.702 | 1.00 | 36.44 |
| ATOM  | 2511 | O   | ILE | B | 632 | 58.686 | 49.915 | 11.210 | 1.00 | 36.45 |
| ATOM  | 2512 | N   | SER | B | 633 | 57.842 | 51.232 | 9.580  | 1.00 | 39.26 |
| ATOM  | 2513 | CA  | SER | B | 633 | 59.114 | 51.385 | 8.869  | 1.00 | 41.71 |
| ATOM  | 2514 | CB  | SER | B | 633 | 58.956 | 51.060 | 7.379  | 1.00 | 42.45 |

FIGURE 3BX

| | A | B | C | D | E | F | G | H | I | J |
|---|---|---|---|---|---|---|---|---|---|---|
| ATOM | 2515 | OG | SER | B | 633 | 59.467 | 49.766 | 7.083 | 1.00 | 43.34 |
| ATOM | 2516 | C | SER | B | 633 | 59.738 | 52.773 | 9.067 | 1.00 | 42.89 |
| ATOM | 2517 | O | SER | B | 633 | 60.857 | 52.883 | 9.573 | 1.00 | 43.49 |
| ATOM | 2518 | N | LYS | B | 634 | 59.019 | 53.824 | 8.674 | 1.00 | 43.90 |
| ATOM | 2519 | CA | LYS | B | 634 | 59.507 | 55.194 | 8.848 | 1.00 | 44.83 |
| ATOM | 2520 | CB | LYS | B | 634 | 59.352 | 56.006 | 7.551 | 1.00 | 45.69 |
| ATOM | 2521 | CG | LYS | B | 634 | 60.347 | 57.167 | 7.414 | 1.00 | 46.43 |
| ATOM | 2522 | CD | LYS | B | 634 | 60.041 | 58.038 | 6.197 | 1.00 | 46.45 |
| ATOM | 2523 | CE | LYS | B | 634 | 61.071 | 57.836 | 5.089 | 1.00 | 46.51 |
| ATOM | 2524 | NZ | LYS | B | 634 | 60.969 | 56.483 | 4.455 | 1.00 | 46.33 |
| ATOM | 2525 | C | LYS | B | 634 | 58.837 | 55.892 | 10.045 | 1.00 | 45.03 |
| ATOM | 2526 | O | LYS | B | 634 | 59.089 | 55.527 | 11.197 | 1.00 | 45.47 |
| ATOM | 2527 | N | THR | B | 635 | 58.004 | 56.895 | 9.771 | 1.00 | 44.48 |
| ATOM | 2528 | CA | THR | B | 635 | 57.263 | 57.621 | 10.802 | 1.00 | 44.05 |
| ATOM | 2529 | CB | THR | B | 635 | 58.119 | 58.784 | 11.380 | 1.00 | 45.00 |
| ATOM | 2530 | OG1 | THR | B | 635 | 59.329 | 58.258 | 11.941 | 1.00 | 45.45 |
| ATOM | 2531 | CG2 | THR | B | 635 | 57.430 | 59.444 | 12.582 | 1.00 | 44.76 |
| ATOM | 2532 | C | THR | B | 635 | 55.943 | 58.135 | 10.219 | 1.00 | 43.39 |
| ATOM | 2533 | O | THR | B | 635 | 55.916 | 59.140 | 9.501 | 1.00 | 43.75 |
| ATOM | 2534 | N | GLY | B | 636 | 54.855 | 57.430 | 10.525 | 1.00 | 42.27 |
| ATOM | 2535 | CA | GLY | B | 636 | 53.542 | 57.757 | 9.990 | 1.00 | 40.96 |
| ATOM | 2536 | C | GLY | B | 636 | 53.360 | 57.352 | 8.535 | 1.00 | 39.99 |
| ATOM | 2537 | O | GLY | B | 636 | 52.444 | 57.835 | 7.861 | 1.00 | 40.00 |
| ATOM | 2538 | N | VAL | B | 637 | 54.236 | 56.468 | 8.055 | 1.00 | 38.22 |
| ATOM | 2539 | CA | VAL | B | 637 | 54.175 | 55.959 | 6.688 | 1.00 | 36.65 |
| ATOM | 2540 | CB | VAL | B | 637 | 55.550 | 56.042 | 5.961 | 1.00 | 37.09 |
| ATOM | 2541 | CG1 | VAL | B | 637 | 55.419 | 55.632 | 4.495 | 1.00 | 37.69 |
| ATOM | 2542 | CG2 | VAL | B | 637 | 56.131 | 57.446 | 6.058 | 1.00 | 37.86 |
| ATOM | 2543 | C | VAL | B | 637 | 53.650 | 54.525 | 6.723 | 1.00 | 35.03 |
| ATOM | 2544 | O | VAL | B | 637 | 54.403 | 53.571 | 6.959 | 1.00 | 36.07 |
| ATOM | 2545 | N | SER | B | 638 | 52.348 | 54.396 | 6.487 | 1.00 | 32.54 |
| ATOM | 2546 | CA | SER | B | 638 | 51.638 | 53.128 | 6.611 | 1.00 | 30.02 |
| ATOM | 2547 | CB | SER | B | 638 | 50.133 | 53.362 | 6.515 | 1.00 | 30.48 |
| ATOM | 2548 | OG | SER | B | 638 | 49.773 | 53.792 | 5.210 | 1.00 | 31.31 |
| ATOM | 2549 | C | SER | B | 638 | 52.046 | 52.088 | 5.574 | 1.00 | 28.40 |
| ATOM | 2550 | O | SER | B | 638 | 52.223 | 52.397 | 4.394 | 1.00 | 28.13 |
| ATOM | 2551 | N | ILE | B | 639 | 52.202 | 50.853 | 6.035 | 1.00 | 26.24 |
| ATOM | 2552 | CA | ILE | B | 639 | 52.338 | 49.707 | 5.146 | 1.00 | 24.94 |
| ATOM | 2553 | CB | ILE | B | 639 | 53.813 | 49.165 | 5.090 | 1.00 | 25.51 |
| ATOM | 2554 | CG1 | ILE | B | 639 | 54.219 | 48.503 | 6.410 | 1.00 | 24.42 |
| ATOM | 2555 | CD1 | ILE | B | 639 | 54.984 | 47.220 | 6.225 | 1.00 | 24.21 |
| ATOM | 2556 | CG2 | ILE | B | 639 | 54.808 | 50.268 | 4.684 | 1.00 | 26.14 |
| ATOM | 2557 | C | ILE | B | 639 | 51.341 | 48.612 | 5.540 | 1.00 | 22.79 |
| ATOM | 2558 | O | ILE | B | 639 | 50.802 | 48.609 | 6.655 | 1.00 | 21.48 |
| ATOM | 2559 | N | GLN | B | 640 | 51.097 | 47.696 | 4.608 | 1.00 | 21.56 |
| ATOM | 2560 | CA | GLN | B | 640 | 50.256 | 46.535 | 4.854 | 1.00 | 20.29 |
| ATOM | 2561 | CB | GLN | B | 640 | 49.764 | 45.974 | 3.522 | 1.00 | 20.47 |
| ATOM | 2562 | CG | GLN | B | 640 | 48.640 | 46.774 | 2.908 | 1.00 | 20.90 |
| ATOM | 2563 | CD | GLN | B | 640 | 47.402 | 46.746 | 3.769 | 1.00 | 21.62 |
| ATOM | 2564 | OE1 | GLN | B | 640 | 46.730 | 45.718 | 3.861 | 1.00 | 23.50 |
| ATOM | 2565 | NE2 | GLN | B | 640 | 47.101 | 47.867 | 4.416 | 1.00 | 21.49 |
| ATOM | 2566 | C | GLN | B | 640 | 51.018 | 45.460 | 5.623 | 1.00 | 19.17 |

FIGURE 3BY

| | A | B | C | D | E | F | G | H | I | J |
|---|---|---|---|---|---|---|---|---|---|---|
| ATOM | 2567 | O | GLN | B | 640 | 52.197 | 45.218 | 5.348 | 1.00 | 19.28 |
| ATOM | 2568 | N | VAL | B | 641 | 50.347 | 44.817 | 6.579 | 1.00 | 17.92 |
| ATOM | 2569 | CA | VAL | B | 641 | 50.956 | 43.720 | 7.349 | 1.00 | 17.86 |
| ATOM | 2570 | CB | VAL | B | 641 | 51.491 | 44.181 | 8.740 | 1.00 | 16.26 |
| ATOM | 2571 | CG1 | VAL | B | 641 | 52.600 | 45.213 | 8.587 | 1.00 | 15.99 |
| ATOM | 2572 | CG2 | VAL | B | 641 | 50.368 | 44.710 | 9.633 | 1.00 | 17.18 |
| ATOM | 2573 | C | VAL | B | 641 | 50.042 | 42.504 | 7.543 | 1.00 | 18.19 |
| ATOM | 2574 | O | VAL | B | 641 | 48.836 | 42.567 | 7.294 | 1.00 | 19.10 |
| ATOM | 2575 | N | ALA | B | 642 | 50.645 | 41.406 | 7.990 | 1.00 | 18.69 |
| ATOM | 2576 | CA | ALA | B | 642 | 49.942 | 40.174 | 8.326 | 1.00 | 19.28 |
| ATOM | 2577 | CB | ALA | B | 642 | 50.354 | 39.056 | 7.398 | 1.00 | 20.04 |
| ATOM | 2578 | C | ALA | B | 642 | 50.278 | 39.811 | 9.758 | 1.00 | 19.99 |
| ATOM | 2579 | O | ALA | B | 642 | 51.449 | 39.641 | 10.107 | 1.00 | 20.39 |
| ATOM | 2580 | N | VAL | B | 643 | 49.239 | 39.685 | 10.577 | 1.00 | 20.01 |
| ATOM | 2581 | CA | VAL | B | 643 | 49.391 | 39.551 | 12.020 | 1.00 | 18.81 |
| ATOM | 2582 | CB | VAL | B | 643 | 48.589 | 40.636 | 12.791 | 1.00 | 18.50 |
| ATOM | 2583 | CG1 | VAL | B | 643 | 48.985 | 40.654 | 14.258 | 1.00 | 18.74 |
| ATOM | 2584 | CG2 | VAL | B | 643 | 48.789 | 42.019 | 12.171 | 1.00 | 18.60 |
| ATOM | 2585 | C | VAL | B | 643 | 48.958 | 38.168 | 12.484 | 1.00 | 18.55 |
| ATOM | 2586 | O | VAL | B | 643 | 47.812 | 37.767 | 12.290 | 1.00 | 18.60 |
| ATOM | 2587 | N | LYS | B | 644 | 49.888 | 37.449 | 13.102 | 1.00 | 17.61 |
| ATOM | 2588 | CA | LYS | B | 644 | 49.601 | 36.137 | 13.654 | 1.00 | 16.89 |
| ATOM | 2589 | CB | LYS | B | 644 | 50.784 | 35.201 | 13.453 | 1.00 | 16.96 |
| ATOM | 2590 | CG | LYS | B | 644 | 50.384 | 33.751 | 13.370 | 1.00 | 18.18 |
| ATOM | 2591 | CD | LYS | B | 644 | 51.500 | 32.910 | 12.781 | 1.00 | 18.43 |
| ATOM | 2592 | CE | LYS | B | 644 | 51.133 | 31.438 | 12.790 | 1.00 | 18.02 |
| ATOM | 2593 | NZ | LYS | B | 644 | 50.977 | 30.885 | 14.156 | 1.00 | 17.15 |
| ATOM | 2594 | C | LYS | B | 644 | 49.255 | 36.237 | 15.130 | 1.00 | 16.52 |
| ATOM | 2595 | O | LYS | B | 644 | 49.834 | 37.035 | 15.864 | 1.00 | 15.60 |
| ATOM | 2596 | N | MET | B | 645 | 48.309 | 35.406 | 15.552 | 1.00 | 17.11 |
| ATOM | 2597 | CA | MET | B | 645 | 47.773 | 35.435 | 16.907 | 1.00 | 16.17 |
| ATOM | 2598 | CB | MET | B | 645 | 46.776 | 36.590 | 17.057 | 1.00 | 16.85 |
| ATOM | 2599 | CG | MET | B | 645 | 45.621 | 36.572 | 16.053 | 1.00 | 18.45 |
| ATOM | 2600 | SD | MET | B | 645 | 44.518 | 38.000 | 16.204 | 1.00 | 20.93 |
| ATOM | 2601 | CE | MET | B | 645 | 45.509 | 39.255 | 15.375 | 1.00 | 21.63 |
| ATOM | 2602 | C | MET | B | 645 | 47.086 | 34.111 | 17.217 | 1.00 | 16.34 |
| ATOM | 2603 | O | MET | B | 645 | 46.851 | 33.299 | 16.321 | 1.00 | 16.80 |
| ATOM | 2604 | N | LEU | B | 646 | 46.758 | 33.908 | 18.487 | 1.00 | 18.20 |
| ATOM | 2605 | CA | LEU | B | 646 | 46.013 | 32.736 | 18.927 | 1.00 | 19.87 |
| ATOM | 2606 | CB | LEU | B | 646 | 46.172 | 32.541 | 20.437 | 1.00 | 19.89 |
| ATOM | 2607 | CG | LEU | B | 646 | 47.574 | 32.390 | 21.026 | 1.00 | 20.00 |
| ATOM | 2608 | CD1 | LEU | B | 646 | 47.612 | 32.936 | 22.451 | 1.00 | 19.82 |
| ATOM | 2609 | CD2 | LEU | B | 646 | 48.021 | 30.939 | 20.991 | 1.00 | 19.89 |
| ATOM | 2610 | C | LEU | B | 646 | 44.533 | 32.888 | 18.592 | 1.00 | 21.60 |
| ATOM | 2611 | O | LEU | B | 646 | 44.070 | 33.983 | 18.252 | 1.00 | 21.21 |
| ATOM | 2612 | N | LYS | B | 647 | 43.792 | 31.788 | 18.704 | 1.00 | 23.54 |
| ATOM | 2613 | CA | LYS | B | 647 | 42.350 | 31.803 | 18.482 | 1.00 | 25.59 |
| ATOM | 2614 | CB | LYS | B | 647 | 41.828 | 30.378 | 18.250 | 1.00 | 26.75 |
| ATOM | 2615 | CG | LYS | B | 647 | 42.017 | 29.841 | 16.827 | 1.00 | 28.44 |
| ATOM | 2616 | CD | LYS | B | 647 | 40.785 | 30.073 | 15.946 | 1.00 | 29.43 |
| ATOM | 2617 | CE | LYS | B | 647 | 39.864 | 28.850 | 15.909 | 1.00 | 30.12 |
| ATOM | 2618 | NZ | LYS | B | 647 | 40.324 | 27.811 | 14.942 | 1.00 | 29.80 |

FIGURE 3BZ

|      | A    | B    | C   | D | E   | F      | G      | H      | I    | J     |
|------|------|------|-----|---|-----|--------|--------|--------|------|-------|
| ATOM | 2619 | C    | LYS | B | 647 | 41.630 | 32.483 | 19.657 | 1.00 | 26.71 |
| ATOM | 2620 | O    | LYS | B | 647 | 42.277 | 33.090 | 20.516 | 1.00 | 26.91 |
| ATOM | 2621 | N    | GLU | B | 648 | 40.298 | 32.392 | 19.678 | 1.00 | 27.06 |
| ATOM | 2622 | CA   | GLU | B | 648 | 39.477 | 32.985 | 20.735 | 1.00 | 27.13 |
| ATOM | 2623 | CB   | GLU | B | 648 | 37.992 | 32.699 | 20.485 | 1.00 | 28.17 |
| ATOM | 2624 | CG   | GLU | B | 648 | 37.051 | 33.812 | 20.927 | 1.00 | 28.42 |
| ATOM | 2625 | CD   | GLU | B | 648 | 36.640 | 33.701 | 22.387 | 1.00 | 29.26 |
| ATOM | 2626 | OE1  | GLU | B | 648 | 36.730 | 32.594 | 22.962 | 1.00 | 29.75 |
| ATOM | 2627 | OE2  | GLU | B | 648 | 36.221 | 34.728 | 22.965 | 1.00 | 29.59 |
| ATOM | 2628 | C    | GLU | B | 648 | 39.890 | 32.497 | 22.126 | 1.00 | 26.94 |
| ATOM | 2629 | O    | GLU | B | 648 | 40.157 | 33.306 | 23.017 | 1.00 | 27.44 |
| ATOM | 2630 | N    | LYS | B | 649 | 39.939 | 31.178 | 22.302 | 1.00 | 26.34 |
| ATOM | 2631 | CA   | LYS | B | 649 | 40.443 | 30.570 | 23.535 | 1.00 | 25.46 |
| ATOM | 2632 | CB   | LYS | B | 649 | 39.839 | 29.177 | 23.748 | 1.00 | 24.80 |
| ATOM | 2633 | CG   | LYS | B | 649 | 38.320 | 29.153 | 23.842 | 1.00 | 24.37 |
| ATOM | 2634 | CD   | LYS | B | 649 | 37.819 | 27.884 | 24.512 | 1.00 | 23.43 |
| ATOM | 2635 | CE   | LYS | B | 649 | 36.301 | 27.875 | 24.592 | 1.00 | 22.98 |
| ATOM | 2636 | NZ   | LYS | B | 649 | 35.793 | 26.744 | 25.413 | 1.00 | 22.72 |
| ATOM | 2637 | C    | LYS | B | 649 | 41.963 | 30.478 | 23.458 | 1.00 | 24.93 |
| ATOM | 2638 | O    | LYS | B | 649 | 42.514 | 30.089 | 22.424 | 1.00 | 25.07 |
| ATOM | 2639 | N    | ALA | B | 650 | 42.636 | 30.844 | 24.546 | 1.00 | 24.24 |
| ATOM | 2640 | CA   | ALA | B | 650 | 44.096 | 30.822 | 24.596 | 1.00 | 23.85 |
| ATOM | 2641 | CB   | ALA | B | 650 | 44.621 | 31.657 | 25.773 | 1.00 | 22.87 |
| ATOM | 2642 | C    | ALA | B | 650 | 44.651 | 29.396 | 24.639 | 1.00 | 23.58 |
| ATOM | 2643 | O    | ALA | B | 650 | 45.134 | 28.892 | 23.621 | 1.00 | 24.20 |
| ATOM | 2644 | N    | ASP | B | 651 | 44.554 | 28.756 | 25.806 | 1.00 | 22.67 |
| ATOM | 2645 | CA   | ASP | B | 651 | 45.146 | 27.438 | 26.078 | 1.00 | 22.39 |
| ATOM | 2646 | CB   | ASP | B | 651 | 44.679 | 26.378 | 25.067 | 1.00 | 21.93 |
| ATOM | 2647 | CG   | ASP | B | 651 | 45.189 | 24.988 | 25.397 | 1.00 | 22.02 |
| ATOM | 2648 | OD1  | ASP | B | 651 | 44.497 | 24.259 | 26.137 | 1.00 | 22.34 |
| ATOM | 2649 | OD2  | ASP | B | 651 | 46.271 | 24.540 | 24.963 | 1.00 | 22.21 |
| ATOM | 2650 | C    | ASP | B | 651 | 46.679 | 27.499 | 26.176 | 1.00 | 22.42 |
| ATOM | 2651 | O    | ASP | B | 651 | 47.364 | 27.856 | 25.216 | 1.00 | 21.69 |
| ATOM | 2652 | N    | SER | B | 652 | 47.196 | 27.143 | 27.351 | 1.00 | 23.07 |
| ATOM | 2653 | CA   | SER | B | 652 | 48.623 | 27.254 | 27.676 | 1.00 | 22.96 |
| ATOM | 2654 | CB   | SER | B | 652 | 48.871 | 26.763 | 29.103 | 1.00 | 22.18 |
| ATOM | 2655 | OG   | SER | B | 652 | 49.174 | 25.378 | 29.126 | 1.00 | 21.93 |
| ATOM | 2656 | C    | SER | B | 652 | 49.561 | 26.526 | 26.703 | 1.00 | 22.85 |
| ATOM | 2657 | O    | SER | B | 652 | 50.590 | 27.072 | 26.294 | 1.00 | 22.31 |
| ATOM | 2658 | N    | SER | B | 653 | 49.194 | 25.297 | 26.343 | 1.00 | 22.73 |
| ATOM | 2659 | CA   | SER | B | 653 | 50.000 | 24.452 | 25.463 | 1.00 | 21.88 |
| ATOM | 2660 | CB   | SER | B | 653 | 49.405 | 23.036 | 25.408 | 1.00 | 22.13 |
| ATOM | 2661 | OG   | SER | B | 653 | 49.610 | 22.424 | 24.139 | 1.00 | 21.69 |
| ATOM | 2662 | C    | SER | B | 653 | 50.151 | 25.044 | 24.058 | 1.00 | 21.78 |
| ATOM | 2663 | O    | SER | B | 653 | 50.954 | 24.560 | 23.257 | 1.00 | 22.56 |
| ATOM | 2664 | N    | GLU | B | 654 | 49.387 | 26.098 | 23.777 | 1.00 | 20.92 |
| ATOM | 2665 | CA   | GLU | B | 654 | 49.392 | 26.751 | 22.471 | 1.00 | 19.28 |
| ATOM | 2666 | CB   | GLU | B | 654 | 47.994 | 26.706 | 21.848 | 1.00 | 19.34 |
| ATOM | 2667 | CG   | GLU | B | 654 | 47.522 | 25.297 | 21.509 | 1.00 | 19.75 |
| ATOM | 2668 | CD   | GLU | B | 654 | 46.036 | 25.223 | 21.222 | 1.00 | 19.86 |
| ATOM | 2669 | OE1  | GLU | B | 654 | 45.628 | 25.593 | 20.100 | 1.00 | 19.97 |
| ATOM | 2670 | OE2  | GLU | B | 654 | 45.275 | 24.788 | 22.115 | 1.00 | 20.19 |

FIGURE 3CA

|      | A    | B    | C   | D   | E   | F      | G      | H      | I    | J     |
|------|------|------|-----|-----|-----|--------|--------|--------|------|-------|
| ATOM | 2671 | C    | GLU | B   | 654 | 49.901 | 28.188 | 22.551 | 1.00 | 18.88 |
| ATOM | 2672 | O    | GLU | B   | 654 | 50.384 | 28.737 | 21.560 | 1.00 | 19.17 |
| ATOM | 2673 | N    | ARG | B   | 655 | 49.792 | 28.792 | 23.732 | 1.00 | 18.49 |
| ATOM | 2674 | CA   | ARG | B   | 655 | 50.348 | 30.122 | 23.979 | 1.00 | 17.71 |
| ATOM | 2675 | CB   | ARG | B   | 655 | 49.756 | 30.733 | 25.252 | 1.00 | 18.78 |
| ATOM | 2676 | CG   | ARG | B   | 655 | 49.959 | 32.240 | 25.388 | 1.00 | 19.44 |
| ATOM | 2677 | CD   | ARG | B   | 655 | 49.155 | 32.879 | 26.513 | 1.00 | 20.16 |
| ATOM | 2678 | NE   | ARG | B   | 655 | 49.668 | 32.500 | 27.830 | 1.00 | 21.85 |
| ATOM | 2679 | CZ   | ARG | B   | 655 | 48.985 | 31.815 | 28.747 | 1.00 | 21.59 |
| ATOM | 2680 | NH1  | ARG | B   | 655 | 47.741 | 31.413 | 28.509 | 1.00 | 21.64 |
| ATOM | 2681 | NH2  | ARG | B   | 655 | 49.556 | 31.524 | 29.908 | 1.00 | 20.53 |
| ATOM | 2682 | C    | ARG | B   | 655 | 51.865 | 30.032 | 24.096 | 1.00 | 16.48 |
| ATOM | 2683 | O    | ARG | B   | 655 | 52.575 | 31.001 | 23.817 | 1.00 | 15.61 |
| ATOM | 2684 | N    | GLU | B   | 656 | 52.343 | 28.863 | 24.520 | 1.00 | 15.63 |
| ATOM | 2685 | CA   | GLU | B   | 656 | 53.770 | 28.564 | 24.568 | 1.00 | 16.60 |
| ATOM | 2686 | CB   | GLU | B   | 656 | 53.999 | 27.187 | 25.204 | 1.00 | 19.02 |
| ATOM | 2687 | CG   | GLU | B   | 656 | 55.435 | 26.899 | 25.617 | 1.00 | 21.60 |
| ATOM | 2688 | CD   | GLU | B   | 656 | 55.826 | 27.604 | 26.902 | 1.00 | 23.80 |
| ATOM | 2689 | OE1  | GLU | B   | 656 | 56.161 | 28.808 | 26.831 | 1.00 | 25.11 |
| ATOM | 2690 | OE2  | GLU | B   | 656 | 55.798 | 26.959 | 27.979 | 1.00 | 23.80 |
| ATOM | 2691 | C    | GLU | B   | 656 | 54.345 | 28.597 | 23.155 | 1.00 | 15.22 |
| ATOM | 2692 | O    | GLU | B   | 656 | 55.303 | 29.324 | 22.878 | 1.00 | 13.89 |
| ATOM | 2693 | N    | ALA | B   | 657 | 53.721 | 27.818 | 22.272 | 1.00 | 13.46 |
| ATOM | 2694 | CA   | ALA | B   | 657 | 54.110 | 27.705 | 20.875 | 1.00 | 11.46 |
| ATOM | 2695 | CB   | ALA | B   | 657 | 53.137 | 26.798 | 20.133 | 1.00 | 11.09 |
| ATOM | 2696 | C    | ALA | B   | 657 | 54.228 | 29.061 | 20.178 | 1.00 | 10.98 |
| ATOM | 2697 | O    | ALA | B   | 657 | 55.155 | 29.277 | 19.394 | 1.00 | 10.39 |
| ATOM | 2698 | N    | LEU | B   | 658 | 53.302 | 29.973 | 20.467 | 1.00 | 10.50 |
| ATOM | 2699 | CA   | LEU | B   | 658 | 53.338 | 31.306 | 19.867 | 1.00 | 11.51 |
| ATOM | 2700 | CB   | LEU | B   | 658 | 52.035 | 32.069 | 20.130 | 1.00 | 11.56 |
| ATOM | 2701 | CG   | LEU | B   | 658 | 51.817 | 33.409 | 19.411 | 1.00 | 12.50 |
| ATOM | 2702 | CD1  | LEU | B   | 658 | 51.897 | 33.275 | 17.887 | 1.00 | 11.81 |
| ATOM | 2703 | CD2  | LEU | B   | 658 | 50.487 | 34.029 | 19.825 | 1.00 | 11.96 |
| ATOM | 2704 | C    | LEU | B   | 658 | 54.567 | 32.110 | 20.319 | 1.00 | 12.44 |
| ATOM | 2705 | O    | LEU | B   | 658 | 55.254 | 32.712 | 19.489 | 1.00 | 13.41 |
| ATOM | 2706 | N    | MET | B   | 659 | 54.843 | 32.109 | 21.623 | 1.00 | 13.08 |
| ATOM | 2707 | CA   | MET | B   | 659 | 56.053 | 32.738 | 22.162 | 1.00 | 14.51 |
| ATOM | 2708 | CB   | MET | B   | 659 | 56.075 | 32.676 | 23.698 | 1.00 | 17.26 |
| ATOM | 2709 | CG   | MET | B   | 659 | 55.193 | 33.708 | 24.402 | 1.00 | 21.08 |
| ATOM | 2710 | SD   | MET | B   | 659 | 55.361 | 35.422 | 23.808 | 1.00 | 24.82 |
| ATOM | 2711 | CE   | MET | B   | 659 | 56.027 | 36.228 | 25.297 | 1.00 | 24.72 |
| ATOM | 2712 | C    | MET | B   | 659 | 57.310 | 32.078 | 21.594 | 1.00 | 12.49 |
| ATOM | 2713 | O    | MET | B   | 659 | 58.268 | 32.760 | 21.232 | 1.00 | 10.88 |
| ATOM | 2714 | N    | SER | B   | 660 | 57.283 | 30.748 | 21.520 | 1.00 | 11.77 |
| ATOM | 2715 | CA   | SER | B   | 660 | 58.327 | 29.954 | 20.873 | 1.00 | 13.27 |
| ATOM | 2716 | CB   | SER | B   | 660 | 57.972 | 28.470 | 20.966 | 1.00 | 13.61 |
| ATOM | 2717 | OG   | SER | B   | 660 | 59.084 | 27.661 | 20.653 | 1.00 | 16.03 |
| ATOM | 2718 | C    | SER | B   | 660 | 58.568 | 30.355 | 19.404 | 1.00 | 13.11 |
| ATOM | 2719 | O    | SER | B   | 660 | 59.717 | 30.449 | 18.959 | 1.00 | 12.04 |
| ATOM | 2720 | N    | GLU | B   | 661 | 57.480 | 30.600 | 18.672 | 1.00 | 12.12 |
| ATOM | 2721 | CA   | GLU | B   | 661 | 57.547 | 31.075 | 17.292 | 1.00 | 13.75 |
| ATOM | 2722 | CB   | GLU | B   | 661 | 56.158 | 31.011 | 16.632 | 1.00 | 15.08 |

FIGURE 3CB

|      | A    | B   | C   | D | E   | F      | G      | H      | I    | J     |
|------|------|-----|-----|---|-----|--------|--------|--------|------|-------|
| ATOM | 2723 | CG  | GLU | B | 661 | 56.101 | 31.496 | 15.188 | 1.00 | 17.53 |
| ATOM | 2724 | CD  | GLU | B | 661 | 54.683 | 31.711 | 14.661 | 1.00 | 19.46 |
| ATOM | 2725 | OE1 | GLU | B | 661 | 54.546 | 32.250 | 13.543 | 1.00 | 19.13 |
| ATOM | 2726 | OE2 | GLU | B | 661 | 53.702 | 31.346 | 15.349 | 1.00 | 20.99 |
| ATOM | 2727 | C   | GLU | B | 661 | 58.121 | 32.493 | 17.236 | 1.00 | 13.51 |
| ATOM | 2728 | O   | GLU | B | 661 | 58.861 | 32.836 | 16.306 | 1.00 | 13.39 |
| ATOM | 2729 | N   | LEU | B | 662 | 57.782 | 33.308 | 18.236 | 1.00 | 12.90 |
| ATOM | 2730 | CA  | LEU | B | 662 | 58.293 | 34.675 | 18.321 | 1.00 | 13.41 |
| ATOM | 2731 | CB  | LEU | B | 662 | 57.599 | 35.460 | 19.436 | 1.00 | 13.58 |
| ATOM | 2732 | CG  | LEU | B | 662 | 58.100 | 36.878 | 19.744 | 1.00 | 13.74 |
| ATOM | 2733 | CD1 | LEU | B | 662 | 57.970 | 37.803 | 18.535 | 1.00 | 12.53 |
| ATOM | 2734 | CD2 | LEU | B | 662 | 57.360 | 37.454 | 20.943 | 1.00 | 13.22 |
| ATOM | 2735 | C   | LEU | B | 662 | 59.802 | 34.684 | 18.527 | 1.00 | 13.97 |
| ATOM | 2736 | O   | LEU | B | 662 | 60.514 | 35.451 | 17.882 | 1.00 | 14.81 |
| ATOM | 2737 | N   | LYS | B | 663 | 60.278 | 33.821 | 19.419 | 1.00 | 13.51 |
| ATOM | 2738 | CA  | LYS | B | 663 | 61.702 | 33.697 | 19.682 | 1.00 | 15.91 |
| ATOM | 2739 | CB  | LYS | B | 663 | 61.967 | 32.637 | 20.759 | 1.00 | 16.97 |
| ATOM | 2740 | CG  | LYS | B | 663 | 61.386 | 32.991 | 22.118 | 1.00 | 18.33 |
| ATOM | 2741 | CD  | LYS | B | 663 | 61.601 | 31.887 | 23.143 | 1.00 | 19.26 |
| ATOM | 2742 | CE  | LYS | B | 663 | 60.737 | 32.119 | 24.377 | 1.00 | 19.06 |
| ATOM | 2743 | NZ  | LYS | B | 663 | 60.974 | 31.076 | 25.409 | 1.00 | 19.34 |
| ATOM | 2744 | C   | LYS | B | 663 | 62.444 | 33.359 | 18.391 | 1.00 | 16.54 |
| ATOM | 2745 | O   | LYS | B | 663 | 63.406 | 34.036 | 18.024 | 1.00 | 17.07 |
| ATOM | 2746 | N   | MET | B | 664 | 61.972 | 32.328 | 17.696 | 1.00 | 16.00 |
| ATOM | 2747 | CA  | MET | B | 664 | 62.574 | 31.914 | 16.436 | 1.00 | 16.63 |
| ATOM | 2748 | CB  | MET | B | 664 | 61.838 | 30.708 | 15.865 | 1.00 | 17.35 |
| ATOM | 2749 | CG  | MET | B | 664 | 62.545 | 30.068 | 14.679 | 1.00 | 19.29 |
| ATOM | 2750 | SD  | MET | B | 664 | 61.602 | 28.717 | 14.005 | 1.00 | 20.14 |
| ATOM | 2751 | CE  | MET | B | 664 | 61.811 | 27.512 | 15.321 | 1.00 | 21.65 |
| ATOM | 2752 | C   | MET | B | 664 | 62.602 | 33.037 | 15.403 | 1.00 | 16.73 |
| ATOM | 2753 | O   | MET | B | 664 | 63.633 | 33.289 | 14.787 | 1.00 | 17.31 |
| ATOM | 2754 | N   | MET | B | 665 | 61.473 | 33.714 | 15.225 | 1.00 | 17.30 |
| ATOM | 2755 | CA  | MET | B | 665 | 61.364 | 34.730 | 14.184 | 1.00 | 18.07 |
| ATOM | 2756 | CB  | MET | B | 665 | 59.902 | 34.983 | 13.825 | 1.00 | 17.91 |
| ATOM | 2757 | CG  | MET | B | 665 | 59.221 | 33.813 | 13.114 | 1.00 | 18.45 |
| ATOM | 2758 | SD  | MET | B | 665 | 60.266 | 32.895 | 11.931 | 1.00 | 19.67 |
| ATOM | 2759 | CE  | MET | B | 665 | 60.325 | 34.030 | 10.563 | 1.00 | 15.60 |
| ATOM | 2760 | C   | MET | B | 665 | 62.103 | 36.033 | 14.499 | 1.00 | 19.59 |
| ATOM | 2761 | O   | MET | B | 665 | 62.534 | 36.730 | 13.579 | 1.00 | 20.49 |
| ATOM | 2762 | N   | THR | B | 666 | 62.260 | 36.357 | 15.785 | 1.00 | 19.09 |
| ATOM | 2763 | CA  | THR | B | 666 | 63.057 | 37.522 | 16.187 | 1.00 | 19.77 |
| ATOM | 2764 | CB  | THR | B | 666 | 62.828 | 37.892 | 17.669 | 1.00 | 19.88 |
| ATOM | 2765 | OG1 | THR | B | 666 | 62.681 | 36.701 | 18.453 | 1.00 | 20.16 |
| ATOM | 2766 | CG2 | THR | B | 666 | 61.508 | 38.643 | 17.856 | 1.00 | 18.52 |
| ATOM | 2767 | C   | THR | B | 666 | 64.546 | 37.294 | 15.983 | 1.00 | 20.67 |
| ATOM | 2768 | O   | THR | B | 666 | 65.311 | 38.249 | 15.833 | 1.00 | 21.74 |
| ATOM | 2769 | N   | GLN | B | 667 | 64.956 | 36.027 | 15.983 | 1.00 | 20.61 |
| ATOM | 2770 | CA  | GLN | B | 667 | 66.373 | 35.689 | 15.992 | 1.00 | 19.06 |
| ATOM | 2771 | CB  | GLN | B | 667 | 66.678 | 34.712 | 17.135 | 1.00 | 21.06 |
| ATOM | 2772 | CG  | GLN | B | 667 | 66.379 | 35.283 | 18.530 | 1.00 | 22.57 |
| ATOM | 2773 | CD  | GLN | B | 667 | 66.823 | 34.371 | 19.666 | 1.00 | 24.13 |
| ATOM | 2774 | OE1 | GLN | B | 667 | 67.506 | 34.816 | 20.587 | 1.00 | 24.72 |

FIGURE 3CC

|  | A | B | C | D | E | F | G | H | I | J |
|---|---|---|---|---|---|---|---|---|---|---|
| ATOM | 2775 | NE2 | GLN | B | 667 | 66.431 | 33.102 | 19.608 | 1.00 | 25.31 |
| ATOM | 2776 | C | GLN | B | 667 | 66.872 | 35.153 | 14.654 | 1.00 | 16.84 |
| ATOM | 2777 | O | GLN | B | 667 | 68.079 | 35.022 | 14.444 | 1.00 | 17.38 |
| ATOM | 2778 | N | LEU | B | 668 | 65.942 | 34.870 | 13.747 | 1.00 | 15.51 |
| ATOM | 2779 | CA | LEU | B | 668 | 66.268 | 34.260 | 12.455 | 1.00 | 14.39 |
| ATOM | 2780 | CB | LEU | B | 668 | 64.992 | 33.785 | 11.739 | 1.00 | 12.81 |
| ATOM | 2781 | CG | LEU | B | 668 | 65.145 | 32.893 | 10.495 | 1.00 | 12.23 |
| ATOM | 2782 | CD1 | LEU | B | 668 | 65.698 | 31.522 | 10.858 | 1.00 | 9.84 |
| ATOM | 2783 | CD2 | LEU | B | 668 | 63.821 | 32.756 | 9.765 | 1.00 | 9.66 |
| ATOM | 2784 | C | LEU | B | 668 | 67.059 | 35.192 | 11.542 | 1.00 | 13.83 |
| ATOM | 2785 | O | LEU | B | 668 | 67.941 | 34.754 | 10.802 | 1.00 | 14.22 |
| ATOM | 2786 | N | GLY | B | 669 | 66.734 | 36.477 | 11.598 | 1.00 | 13.89 |
| ATOM | 2787 | CA | GLY | B | 669 | 67.247 | 37.431 | 10.638 | 1.00 | 13.59 |
| ATOM | 2788 | C | GLY | B | 669 | 66.332 | 37.420 | 9.436 | 1.00 | 14.05 |
| ATOM | 2789 | O | GLY | B | 669 | 65.645 | 36.426 | 9.180 | 1.00 | 15.25 |
| ATOM | 2790 | N | SER | B | 670 | 66.328 | 38.518 | 8.692 | 1.00 | 12.56 |
| ATOM | 2791 | CA | SER | B | 670 | 65.440 | 38.657 | 7.550 | 1.00 | 12.93 |
| ATOM | 2792 | CB | SER | B | 670 | 65.039 | 40.122 | 7.375 | 1.00 | 12.96 |
| ATOM | 2793 | OG | SER | B | 670 | 66.040 | 40.805 | 6.647 | 1.00 | 15.47 |
| ATOM | 2794 | C | SER | B | 670 | 66.037 | 38.113 | 6.244 | 1.00 | 11.87 |
| ATOM | 2795 | O | SER | B | 670 | 67.257 | 38.086 | 6.059 | 1.00 | 11.72 |
| ATOM | 2796 | N | HIS | B | 671 | 65.161 | 37.687 | 5.338 | 1.00 | 10.62 |
| ATOM | 2797 | CA | HIS | B | 671 | 65.569 | 37.287 | 3.996 | 1.00 | 10.34 |
| ATOM | 2798 | CB | HIS | B | 671 | 65.909 | 35.794 | 3.959 | 1.00 | 8.08 |
| ATOM | 2799 | CG | HIS | B | 671 | 66.498 | 35.347 | 2.664 | 1.00 | 5.72 |
| ATOM | 2800 | ND1 | HIS | B | 671 | 65.725 | 34.890 | 1.619 | 1.00 | 6.41 |
| ATOM | 2801 | CE1 | HIS | B | 671 | 66.509 | 34.562 | 0.607 | 1.00 | 6.90 |
| ATOM | 2802 | NE2 | HIS | B | 671 | 67.762 | 34.795 | 0.956 | 1.00 | 6.65 |
| ATOM | 2803 | CD2 | HIS | B | 671 | 67.782 | 35.294 | 2.237 | 1.00 | 5.09 |
| ATOM | 2804 | C | HIS | B | 671 | 64.471 | 37.597 | 2.992 | 1.00 | 10.69 |
| ATOM | 2805 | O | HIS | B | 671 | 63.290 | 37.509 | 3.328 | 1.00 | 9.95 |
| ATOM | 2806 | N | GLU | B | 672 | 64.872 | 37.953 | 1.767 | 1.00 | 12.44 |
| ATOM | 2807 | CA | GLU | B | 672 | 63.944 | 38.262 | 0.671 | 1.00 | 14.71 |
| ATOM | 2808 | CB | GLU | B | 672 | 64.689 | 38.397 | -0.671 | 1.00 | 19.29 |
| ATOM | 2809 | CG | GLU | B | 672 | 65.900 | 39.322 | -0.674 | 1.00 | 26.54 |
| ATOM | 2810 | CD | GLU | B | 672 | 67.211 | 38.583 | -0.417 | 1.00 | 30.21 |
| ATOM | 2811 | OE1 | GLU | B | 672 | 67.675 | 38.562 | 0.753 | 1.00 | 30.26 |
| ATOM | 2812 | OE2 | GLU | B | 672 | 67.778 | 38.020 | -1.386 | 1.00 | 32.43 |
| ATOM | 2813 | C | GLU | B | 672 | 62.852 | 37.201 | 0.516 | 1.00 | 14.66 |
| ATOM | 2814 | O | GLU | B | 672 | 61.699 | 37.528 | 0.266 | 1.00 | 14.79 |
| ATOM | 2815 | N | ASN | B | 673 | 63.222 | 35.932 | 0.672 | 1.00 | 13.88 |
| ATOM | 2816 | CA | ASN | B | 673 | 62.316 | 34.826 | 0.369 | 1.00 | 13.74 |
| ATOM | 2817 | CB | ASN | B | 673 | 62.992 | 33.840 | -0.574 | 1.00 | 10.92 |
| ATOM | 2818 | CG | ASN | B | 673 | 63.368 | 34.476 | -1.878 | 1.00 | 11.37 |
| ATOM | 2819 | OD1 | ASN | B | 673 | 64.526 | 34.451 | -2.275 | 1.00 | 11.93 |
| ATOM | 2820 | ND2 | ASN | B | 673 | 62.385 | 35.069 | -2.557 | 1.00 | 11.65 |
| ATOM | 2821 | C | ASN | B | 673 | 61.748 | 34.106 | 1.579 | 1.00 | 12.90 |
| ATOM | 2822 | O | ASN | B | 673 | 61.352 | 32.942 | 1.489 | 1.00 | 13.75 |
| ATOM | 2823 | N | ILE | B | 674 | 61.713 | 34.813 | 2.702 | 1.00 | 11.22 |
| ATOM | 2824 | CA | ILE | B | 674 | 61.072 | 34.331 | 3.911 | 1.00 | 13.84 |
| ATOM | 2825 | CB | ILE | B | 674 | 62.115 | 34.150 | 5.057 | 1.00 | 13.68 |
| ATOM | 2826 | CG1 | ILE | B | 674 | 63.269 | 33.217 | 4.639 | 1.00 | 11.61 |

FIGURE 3CD

|   | A    | B    | C   | D   | E   | F      | G      | H      | I    | J     |
|---|------|------|-----|-----|-----|--------|--------|--------|------|-------|
| ATOM | 2827 | CD1 | ILE | B | 674 | 62.876 | 31.773 | 4.317  | 1.00 | 9.72  |
| ATOM | 2828 | CG2 | ILE | B | 674 | 61.433 | 33.701 | 6.365  | 1.00 | 14.02 |
| ATOM | 2829 | C   | ILE | B | 674 | 60.028 | 35.366 | 4.308  | 1.00 | 15.33 |
| ATOM | 2830 | O   | ILE | B | 674 | 60.246 | 36.569 | 4.130  | 1.00 | 17.51 |
| ATOM | 2831 | N   | VAL | B | 675 | 58.888 | 34.898 | 4.814  | 1.00 | 14.56 |
| ATOM | 2832 | CA  | VAL | B | 675 | 57.917 | 35.782 | 5.439  | 1.00 | 15.86 |
| ATOM | 2833 | CB  | VAL | B | 675 | 56.575 | 35.080 | 5.688  | 1.00 | 16.52 |
| ATOM | 2834 | CG1 | VAL | B | 675 | 55.560 | 36.055 | 6.306  | 1.00 | 15.74 |
| ATOM | 2835 | CG2 | VAL | B | 675 | 56.034 | 34.495 | 4.397  | 1.00 | 15.10 |
| ATOM | 2836 | C   | VAL | B | 675 | 58.524 | 36.288 | 6.750  | 1.00 | 16.47 |
| ATOM | 2837 | O   | VAL | B | 675 | 58.452 | 35.620 | 7.787  | 1.00 | 16.14 |
| ATOM | 2838 | N   | ASN | B | 676 | 59.154 | 37.459 | 6.673  | 1.00 | 16.25 |
| ATOM | 2839 | CA  | ASN | B | 676 | 59.921 | 38.008 | 7.784  | 1.00 | 17.32 |
| ATOM | 2840 | CB  | ASN | B | 676 | 60.944 | 39.032 | 7.283  | 1.00 | 16.16 |
| ATOM | 2841 | CG  | ASN | B | 676 | 61.864 | 38.471 | 6.211  | 1.00 | 16.08 |
| ATOM | 2842 | OD1 | ASN | B | 676 | 62.630 | 37.529 | 6.454  | 1.00 | 15.52 |
| ATOM | 2843 | ND2 | ASN | B | 676 | 61.801 | 39.054 | 5.016  | 1.00 | 14.26 |
| ATOM | 2844 | C   | ASN | B | 676 | 59.032 | 38.652 | 8.833  | 1.00 | 18.40 |
| ATOM | 2845 | O   | ASN | B | 676 | 57.947 | 39.147 | 8.526  | 1.00 | 17.81 |
| ATOM | 2846 | N   | LEU | B | 677 | 59.500 | 38.633 | 10.077 | 1.00 | 19.90 |
| ATOM | 2847 | CA  | LEU | B | 677 | 58.828 | 39.334 | 11.159 | 1.00 | 19.65 |
| ATOM | 2848 | CB  | LEU | B | 677 | 59.249 | 38.755 | 12.508 | 1.00 | 21.47 |
| ATOM | 2849 | CG  | LEU | B | 677 | 58.448 | 39.170 | 13.745 | 1.00 | 22.99 |
| ATOM | 2850 | CD1 | LEU | B | 677 | 57.172 | 38.339 | 13.892 | 1.00 | 23.28 |
| ATOM | 2851 | CD2 | LEU | B | 677 | 59.329 | 39.042 | 14.974 | 1.00 | 21.61 |
| ATOM | 2852 | C   | LEU | B | 677 | 59.180 | 40.810 | 11.072 | 1.00 | 19.58 |
| ATOM | 2853 | O   | LEU | B | 677 | 60.308 | 41.170 | 10.723 | 1.00 | 19.98 |
| ATOM | 2854 | N   | LEU | B | 678 | 58.204 | 41.656 | 11.378 | 1.00 | 19.76 |
| ATOM | 2855 | CA  | LEU | B | 678 | 58.361 | 43.105 | 11.280 | 1.00 | 19.20 |
| ATOM | 2856 | CB  | LEU | B | 678 | 57.327 | 43.697 | 10.317 | 1.00 | 18.54 |
| ATOM | 2857 | CG  | LEU | B | 678 | 57.453 | 43.446 | 8.812  | 1.00 | 19.39 |
| ATOM | 2858 | CD1 | LEU | B | 678 | 56.347 | 44.193 | 8.060  | 1.00 | 17.88 |
| ATOM | 2859 | CD2 | LEU | B | 678 | 58.838 | 43.834 | 8.283  | 1.00 | 19.18 |
| ATOM | 2860 | C   | LEU | B | 678 | 58.194 | 43.755 | 12.642 | 1.00 | 19.23 |
| ATOM | 2861 | O   | LEU | B | 678 | 58.813 | 44.781 | 12.931 | 1.00 | 18.32 |
| ATOM | 2862 | N   | GLY | B | 679 | 57.335 | 43.155 | 13.464 | 1.00 | 18.54 |
| ATOM | 2863 | CA  | GLY | B | 679 | 57.064 | 43.646 | 14.800 | 1.00 | 17.18 |
| ATOM | 2864 | C   | GLY | B | 679 | 56.277 | 42.642 | 15.615 | 1.00 | 17.07 |
| ATOM | 2865 | O   | GLY | B | 679 | 55.890 | 41.584 | 15.121 | 1.00 | 17.37 |
| ATOM | 2866 | N   | ALA | B | 680 | 56.060 | 42.975 | 16.883 | 1.00 | 17.96 |
| ATOM | 2867 | CA  | ALA | B | 680 | 55.240 | 42.162 | 17.770 | 1.00 | 18.25 |
| ATOM | 2868 | CB  | ALA | B | 680 | 56.096 | 41.110 | 18.481 | 1.00 | 17.80 |
| ATOM | 2869 | C   | ALA | B | 680 | 54.543 | 43.053 | 18.786 | 1.00 | 18.28 |
| ATOM | 2870 | O   | ALA | B | 680 | 55.034 | 44.135 | 19.111 | 1.00 | 18.85 |
| ATOM | 2871 | N   | CYS | B | 681 | 53.388 | 42.603 | 19.265 | 1.00 | 18.80 |
| ATOM | 2872 | CA  | CYS | B | 681 | 52.743 | 43.215 | 20.422 | 1.00 | 19.24 |
| ATOM | 2873 | CB  | CYS | B | 681 | 51.348 | 43.765 | 20.075 | 1.00 | 20.06 |
| ATOM | 2874 | SG  | CYS | B | 681 | 51.276 | 44.826 | 18.555 | 1.00 | 23.25 |
| ATOM | 2875 | C   | CYS | B | 681 | 52.652 | 42.147 | 21.507 | 1.00 | 19.40 |
| ATOM | 2876 | O   | CYS | B | 681 | 52.015 | 41.101 | 21.315 | 1.00 | 19.18 |
| ATOM | 2877 | N   | THR | B | 682 | 53.318 | 42.409 | 22.632 | 1.00 | 19.87 |
| ATOM | 2878 | CA  | THR | B | 682 | 53.402 | 41.450 | 23.732 | 1.00 | 21.02 |

FIGURE 3CE

|      | A    | B    | C   | D | E   | F      | G      | H      | I    | J     |
|------|------|------|-----|---|-----|--------|--------|--------|------|-------|
| ATOM | 2879 | CB   | THR | B | 682 | 54.831 | 40.868 | 23.838 | 1.00 | 21.37 |
| ATOM | 2880 | OG1  | THR | B | 682 | 55.764 | 41.921 | 24.111 | 1.00 | 21.73 |
| ATOM | 2881 | CG2  | THR | B | 682 | 55.309 | 40.314 | 22.494 | 1.00 | 20.92 |
| ATOM | 2882 | C    | THR | B | 682 | 53.007 | 42.102 | 25.054 | 1.00 | 21.97 |
| ATOM | 2883 | O    | THR | B | 682 | 52.766 | 41.415 | 26.054 | 1.00 | 22.55 |
| ATOM | 2884 | N    | LEU | B | 683 | 52.951 | 43.433 | 25.046 | 1.00 | 22.86 |
| ATOM | 2885 | CA   | LEU | B | 683 | 52.595 | 44.214 | 26.227 | 1.00 | 22.69 |
| ATOM | 2886 | CB   | LEU | B | 683 | 53.548 | 45.411 | 26.370 | 1.00 | 22.64 |
| ATOM | 2887 | CG   | LEU | B | 683 | 54.949 | 45.238 | 26.992 | 1.00 | 23.23 |
| ATOM | 2888 | CD1  | LEU | B | 683 | 54.954 | 44.345 | 28.247 | 1.00 | 23.50 |
| ATOM | 2889 | CD2  | LEU | B | 683 | 55.965 | 44.744 | 25.954 | 1.00 | 23.37 |
| ATOM | 2890 | C    | LEU | B | 683 | 51.149 | 44.702 | 26.152 | 1.00 | 22.89 |
| ATOM | 2891 | O    | LEU | B | 683 | 50.631 | 44.972 | 25.062 | 1.00 | 23.55 |
| ATOM | 2892 | N    | SER | B | 684 | 50.507 | 44.794 | 27.318 | 1.00 | 23.05 |
| ATOM | 2893 | CA   | SER | B | 684 | 49.162 | 45.370 | 27.482 | 1.00 | 23.05 |
| ATOM | 2894 | CB   | SER | B | 684 | 49.214 | 46.900 | 27.340 | 1.00 | 22.93 |
| ATOM | 2895 | OG   | SER | B | 684 | 50.009 | 47.479 | 28.363 | 1.00 | 22.63 |
| ATOM | 2896 | C    | SER | B | 684 | 48.058 | 44.777 | 26.579 | 1.00 | 23.60 |
| ATOM | 2897 | O    | SER | B | 684 | 47.108 | 45.511 | 26.142 | 1.00 | 23.53 |
| ATOM | 2898 | N    | GLY | B | 685 | 48.186 | 43.453 | 26.317 | 1.00 | 23.38 |
| ATOM | 2899 | CA   | GLY | B | 685 | 47.182 | 42.741 | 25.541 | 1.00 | 22.63 |
| ATOM | 2900 | C    | GLY | B | 685 | 47.623 | 41.362 | 25.068 | 1.00 | 22.57 |
| ATOM | 2901 | O    | GLY | B | 685 | 48.665 | 40.849 | 25.508 | 1.00 | 22.96 |
| ATOM | 2902 | N    | PRO | B | 686 | 46.830 | 40.754 | 24.180 | 1.00 | 22.61 |
| ATOM | 2903 | CA   | PRO | B | 686 | 47.177 | 39.453 | 23.587 | 1.00 | 21.65 |
| ATOM | 2904 | CB   | PRO | B | 686 | 45.962 | 39.134 | 22.705 | 1.00 | 21.73 |
| ATOM | 2905 | CG   | PRO | B | 686 | 45.320 | 40.457 | 22.434 | 1.00 | 21.83 |
| ATOM | 2906 | CD   | PRO | B | 686 | 45.531 | 41.255 | 23.686 | 1.00 | 21.96 |
| ATOM | 2907 | C    | PRO | B | 686 | 48.433 | 39.531 | 22.726 | 1.00 | 21.40 |
| ATOM | 2908 | O    | PRO | B | 686 | 48.730 | 40.599 | 22.178 | 1.00 | 21.56 |
| ATOM | 2909 | N    | ILE | B | 687 | 49.148 | 38.412 | 22.609 | 1.00 | 20.40 |
| ATOM | 2910 | CA   | ILE | B | 687 | 50.335 | 38.327 | 21.763 | 1.00 | 19.29 |
| ATOM | 2911 | CB   | ILE | B | 687 | 51.121 | 37.030 | 22.056 | 1.00 | 19.97 |
| ATOM | 2912 | CG1  | ILE | B | 687 | 51.510 | 36.957 | 23.533 | 1.00 | 21.12 |
| ATOM | 2913 | CD1  | ILE | B | 687 | 51.059 | 35.684 | 24.213 | 1.00 | 22.12 |
| ATOM | 2914 | CG2  | ILE | B | 687 | 52.366 | 36.938 | 21.182 | 1.00 | 19.94 |
| ATOM | 2915 | C    | ILE | B | 687 | 49.966 | 38.409 | 20.280 | 1.00 | 18.94 |
| ATOM | 2916 | O    | ILE | B | 687 | 49.105 | 37.659 | 19.796 | 1.00 | 17.35 |
| ATOM | 2917 | N    | TYR | B | 688 | 50.617 | 39.338 | 19.578 | 1.00 | 18.37 |
| ATOM | 2918 | CA   | TYR | B | 688 | 50.508 | 39.468 | 18.127 | 1.00 | 17.09 |
| ATOM | 2919 | CB   | TYR | B | 688 | 49.871 | 40.809 | 17.739 | 1.00 | 16.71 |
| ATOM | 2920 | CG   | TYR | B | 688 | 48.414 | 41.022 | 18.111 | 1.00 | 15.99 |
| ATOM | 2921 | CD1  | TYR | B | 688 | 47.865 | 42.304 | 18.095 | 1.00 | 15.15 |
| ATOM | 2922 | CE1  | TYR | B | 688 | 46.533 | 42.521 | 18.425 | 1.00 | 15.09 |
| ATOM | 2923 | CZ   | TYR | B | 688 | 45.727 | 41.449 | 18.777 | 1.00 | 15.41 |
| ATOM | 2924 | OH   | TYR | B | 688 | 44.405 | 41.667 | 19.110 | 1.00 | 15.05 |
| ATOM | 2925 | CE2  | TYR | B | 688 | 46.242 | 40.163 | 18.795 | 1.00 | 15.02 |
| ATOM | 2926 | CD2  | TYR | B | 688 | 47.579 | 39.955 | 18.457 | 1.00 | 15.98 |
| ATOM | 2927 | C    | TYR | B | 688 | 51.898 | 39.415 | 17.508 | 1.00 | 17.18 |
| ATOM | 2928 | O    | TYR | B | 688 | 52.831 | 40.059 | 17.998 | 1.00 | 18.79 |
| ATOM | 2929 | N    | LEU | B | 689 | 52.036 | 38.639 | 16.438 | 1.00 | 17.52 |
| ATOM | 2930 | CA   | LEU | B | 689 | 53.265 | 38.597 | 15.656 | 1.00 | 15.65 |

FIGURE 3CF

| | A | B | C | D | E | F | G | H | I | J |
|---|---|---|---|---|---|---|---|---|---|---|
| ATOM | 2931 | CB | LEU | B | 689 | 53.706 | 37.151 | 15.433 | 1.00 | 16.84 |
| ATOM | 2932 | CG | LEU | B | 689 | 54.772 | 36.563 | 16.363 | 1.00 | 17.16 |
| ATOM | 2933 | CD1 | LEU | B | 689 | 54.317 | 36.566 | 17.815 | 1.00 | 18.40 |
| ATOM | 2934 | CD2 | LEU | B | 689 | 55.119 | 35.155 | 15.926 | 1.00 | 16.32 |
| ATOM | 2935 | C | LEU | B | 689 | 52.988 | 39.269 | 14.326 | 1.00 | 15.05 |
| ATOM | 2936 | O | LEU | B | 689 | 52.093 | 38.853 | 13.594 | 1.00 | 13.42 |
| ATOM | 2937 | N | ILE | B | 690 | 53.736 | 40.324 | 14.025 | 1.00 | 15.47 |
| ATOM | 2938 | CA | ILE | B | 690 | 53.511 | 41.087 | 12.800 | 1.00 | 16.85 |
| ATOM | 2939 | CB | ILE | B | 690 | 53.560 | 42.630 | 13.063 | 1.00 | 17.04 |
| ATOM | 2940 | CG1 | ILE | B | 690 | 52.720 | 43.017 | 14.290 | 1.00 | 16.06 |
| ATOM | 2941 | CD1 | ILE | B | 690 | 52.984 | 44.448 | 14.827 | 1.00 | 14.33 |
| ATOM | 2942 | CG2 | ILE | B | 690 | 53.064 | 43.398 | 11.850 | 1.00 | 16.66 |
| ATOM | 2943 | C | ILE | B | 690 | 54.504 | 40.667 | 11.719 | 1.00 | 17.96 |
| ATOM | 2944 | O | ILE | B | 690 | 55.703 | 40.942 | 11.820 | 1.00 | 19.18 |
| ATOM | 2945 | N | PHE | B | 691 | 53.988 | 39.987 | 10.697 | 1.00 | 17.88 |
| ATOM | 2946 | CA | PHE | B | 691 | 54.784 | 39.531 | 9.559 | 1.00 | 17.82 |
| ATOM | 2947 | CB | PHE | B | 691 | 54.418 | 38.091 | 9.207 | 1.00 | 17.32 |
| ATOM | 2948 | CG | PHE | B | 691 | 54.830 | 37.092 | 10.234 | 1.00 | 18.59 |
| ATOM | 2949 | CD1 | PHE | B | 691 | 53.890 | 36.559 | 11.111 | 1.00 | 19.19 |
| ATOM | 2950 | CE1 | PHE | B | 691 | 54.265 | 35.614 | 12.071 | 1.00 | 20.87 |
| ATOM | 2951 | CZ | PHE | B | 691 | 55.600 | 35.198 | 12.157 | 1.00 | 19.77 |
| ATOM | 2952 | CE2 | PHE | B | 691 | 56.544 | 35.728 | 11.280 | 1.00 | 19.28 |
| ATOM | 2953 | CD2 | PHE | B | 691 | 56.157 | 36.670 | 10.325 | 1.00 | 18.01 |
| ATOM | 2954 | C | PHE | B | 691 | 54.555 | 40.394 | 8.325 | 1.00 | 18.34 |
| ATOM | 2955 | O | PHE | B | 691 | 53.559 | 41.122 | 8.234 | 1.00 | 16.81 |
| ATOM | 2956 | N | GLU | B | 692 | 55.476 | 40.295 | 7.370 | 1.00 | 18.19 |
| ATOM | 2957 | CA | GLU | B | 692 | 55.286 | 40.909 | 6.065 | 1.00 | 19.62 |
| ATOM | 2958 | CB | GLU | B | 692 | 56.431 | 40.546 | 5.128 | 1.00 | 20.51 |
| ATOM | 2959 | CG | GLU | B | 692 | 57.742 | 41.255 | 5.398 | 1.00 | 23.25 |
| ATOM | 2960 | CD | GLU | B | 692 | 58.917 | 40.536 | 4.764 | 1.00 | 25.24 |
| ATOM | 2961 | OE1 | GLU | B | 692 | 58.842 | 39.301 | 4.605 | 1.00 | 27.05 |
| ATOM | 2962 | OE2 | GLU | B | 692 | 59.920 | 41.201 | 4.426 | 1.00 | 26.58 |
| ATOM | 2963 | C | GLU | B | 692 | 53.977 | 40.397 | 5.473 | 1.00 | 19.63 |
| ATOM | 2964 | O | GLU | B | 692 | 53.585 | 39.252 | 5.706 | 1.00 | 21.54 |
| ATOM | 2965 | N | TYR | B | 693 | 53.300 | 41.258 | 4.725 | 1.00 | 18.97 |
| ATOM | 2966 | CA | TYR | B | 693 | 52.057 | 40.894 | 4.067 | 1.00 | 18.09 |
| ATOM | 2967 | CB | TYR | B | 693 | 51.068 | 42.062 | 4.113 | 1.00 | 17.89 |
| ATOM | 2968 | CG | TYR | B | 693 | 49.754 | 41.807 | 3.406 | 1.00 | 16.76 |
| ATOM | 2969 | CD1 | TYR | B | 693 | 49.382 | 42.570 | 2.302 | 1.00 | 16.90 |
| ATOM | 2970 | CE1 | TYR | B | 693 | 48.172 | 42.348 | 1.651 | 1.00 | 16.56 |
| ATOM | 2971 | CZ | TYR | B | 693 | 47.325 | 41.349 | 2.102 | 1.00 | 16.32 |
| ATOM | 2972 | OH | TYR | B | 693 | 46.131 | 41.130 | 1.454 | 1.00 | 17.95 |
| ATOM | 2973 | CE2 | TYR | B | 693 | 47.668 | 40.579 | 3.198 | 1.00 | 15.56 |
| ATOM | 2974 | CD2 | TYR | B | 693 | 48.879 | 40.812 | 3.846 | 1.00 | 16.51 |
| ATOM | 2975 | C | TYR | B | 693 | 52.367 | 40.511 | 2.635 | 1.00 | 17.19 |
| ATOM | 2976 | O | TYR | B | 693 | 53.101 | 41.214 | 1.937 | 1.00 | 16.83 |
| ATOM | 2977 | N | CYS | B | 694 | 51.827 | 39.374 | 2.216 | 1.00 | 17.52 |
| ATOM | 2978 | CA | CYS | B | 694 | 51.994 | 38.881 | 0.857 | 1.00 | 16.23 |
| ATOM | 2979 | CB | CYS | B | 694 | 52.638 | 37.499 | 0.877 | 1.00 | 17.50 |
| ATOM | 2980 | SG | CYS | B | 694 | 54.197 | 37.444 | 1.797 | 1.00 | 18.96 |
| ATOM | 2981 | C | CYS | B | 694 | 50.616 | 38.842 | 0.223 | 1.00 | 15.06 |
| ATOM | 2982 | O | CYS | B | 694 | 49.835 | 37.933 | 0.483 | 1.00 | 15.12 |

FIGURE 3CG

|   | A | B | C | D | E | F | G | H | I | J |
|---|---|---|---|---|---|---|---|---|---|---|
| ATOM | 2983 | N   | CYS | B | 695 | 50.318 | 39.850 | -0.593 | 1.00 | 13.66 |
| ATOM | 2984 | CA  | CYS | B | 695 | 48.941 | 40.121 | -1.022 | 1.00 | 13.66 |
| ATOM | 2985 | CB  | CYS | B | 695 | 48.834 | 41.490 | -1.704 | 1.00 | 13.29 |
| ATOM | 2986 | SG  | CYS | B | 695 | 49.909 | 41.704 | -3.133 | 1.00 | 16.20 |
| ATOM | 2987 | C   | CYS | B | 695 | 48.268 | 39.048 | -1.884 | 1.00 | 12.20 |
| ATOM | 2988 | O   | CYS | B | 695 | 47.039 | 38.997 | -1.939 | 1.00 | 10.41 |
| ATOM | 2989 | N   | TYR | B | 696 | 49.055 | 38.191 | -2.538 | 1.00 | 11.64 |
| ATOM | 2990 | CA  | TYR | B | 696 | 48.482 | 37.211 | -3.468 | 1.00 | 11.53 |
| ATOM | 2991 | CB  | TYR | B | 696 | 49.318 | 37.118 | -4.753 | 1.00 | 12.99 |
| ATOM | 2992 | CG  | TYR | B | 696 | 49.307 | 38.416 | -5.528 | 1.00 | 14.61 |
| ATOM | 2993 | CD1 | TYR | B | 696 | 48.129 | 38.903 | -6.082 | 1.00 | 16.79 |
| ATOM | 2994 | CE1 | TYR | B | 696 | 48.105 | 40.105 | -6.775 | 1.00 | 18.48 |
| ATOM | 2995 | CZ  | TYR | B | 696 | 49.270 | 40.840 | -6.913 | 1.00 | 18.34 |
| ATOM | 2996 | OH  | TYR | B | 696 | 49.236 | 42.037 | -7.597 | 1.00 | 19.32 |
| ATOM | 2997 | CE2 | TYR | B | 696 | 50.454 | 40.380 | -6.368 | 1.00 | 16.39 |
| ATOM | 2998 | CD2 | TYR | B | 696 | 50.465 | 39.177 | -5.673 | 1.00 | 15.40 |
| ATOM | 2999 | C   | TYR | B | 696 | 48.208 | 35.842 | -2.848 | 1.00 | 10.66 |
| ATOM | 3000 | O   | TYR | B | 696 | 47.829 | 34.893 | -3.551 | 1.00 | 10.87 |
| ATOM | 3001 | N   | GLY | B | 697 | 48.372 | 35.756 | -1.529 | 1.00 |  8.97 |
| ATOM | 3002 | CA  | GLY | B | 697 | 48.108 | 34.531 | -0.791 | 1.00 | 11.59 |
| ATOM | 3003 | C   | GLY | B | 697 | 49.126 | 33.430 | -1.034 | 1.00 | 13.58 |
| ATOM | 3004 | O   | GLY | B | 697 | 50.244 | 33.693 | -1.483 | 1.00 | 14.74 |
| ATOM | 3005 | N   | ASP | B | 698 | 48.730 | 32.191 | -0.751 | 1.00 | 15.09 |
| ATOM | 3006 | CA  | ASP | B | 698 | 49.643 | 31.057 | -0.852 | 1.00 | 16.82 |
| ATOM | 3007 | CB  | ASP | B | 698 | 49.205 | 29.900 |  0.054 | 1.00 | 19.84 |
| ATOM | 3008 | CG  | ASP | B | 698 | 47.929 | 29.234 | -0.414 | 1.00 | 22.22 |
| ATOM | 3009 | OD1 | ASP | B | 698 | 46.851 | 29.652 |  0.043 | 1.00 | 25.03 |
| ATOM | 3010 | OD2 | ASP | B | 698 | 47.903 | 28.287 | -1.228 | 1.00 | 23.76 |
| ATOM | 3011 | C   | ASP | B | 698 | 49.847 | 30.595 | -2.291 | 1.00 | 17.10 |
| ATOM | 3012 | O   | ASP | B | 698 | 48.947 | 30.701 | -3.132 | 1.00 | 17.77 |
| ATOM | 3013 | N   | LEU | B | 699 | 51.042 | 30.079 | -2.555 | 1.00 | 15.94 |
| ATOM | 3014 | CA  | LEU | B | 699 | 51.465 | 29.730 | -3.904 | 1.00 | 13.77 |
| ATOM | 3015 | CB  | LEU | B | 699 | 52.898 | 29.196 | -3.886 | 1.00 | 11.37 |
| ATOM | 3016 | CG  | LEU | B | 699 | 53.542 | 28.869 | -5.231 | 1.00 |  9.93 |
| ATOM | 3017 | CD1 | LEU | B | 699 | 53.554 | 30.081 | -6.166 | 1.00 |  9.03 |
| ATOM | 3018 | CD2 | LEU | B | 699 | 54.940 | 28.331 | -5.010 | 1.00 |  9.60 |
| ATOM | 3019 | C   | LEU | B | 699 | 50.538 | 28.732 | -4.578 | 1.00 | 14.81 |
| ATOM | 3020 | O   | LEU | B | 699 | 50.298 | 28.824 | -5.780 | 1.00 | 14.99 |
| ATOM | 3021 | N   | LEU | B | 700 | 50.025 | 27.778 | -3.806 | 1.00 | 14.60 |
| ATOM | 3022 | CA  | LEU | B | 700 | 49.147 | 26.759 | -4.353 | 1.00 | 15.57 |
| ATOM | 3023 | CB  | LEU | B | 700 | 48.744 | 25.732 | -3.284 | 1.00 | 15.23 |
| ATOM | 3024 | CG  | LEU | B | 700 | 47.793 | 24.616 | -3.742 | 1.00 | 13.43 |
| ATOM | 3025 | CD1 | LEU | B | 700 | 48.348 | 23.894 | -4.967 | 1.00 |  9.82 |
| ATOM | 3026 | CD2 | LEU | B | 700 | 47.504 | 23.644 | -2.603 | 1.00 | 11.40 |
| ATOM | 3027 | C   | LEU | B | 700 | 47.920 | 27.392 | -5.000 | 1.00 | 15.82 |
| ATOM | 3028 | O   | LEU | B | 700 | 47.641 | 27.157 | -6.185 | 1.00 | 16.59 |
| ATOM | 3029 | N   | ASN | B | 701 | 47.209 | 28.212 | -4.234 | 1.00 | 15.85 |
| ATOM | 3030 | CA  | ASN | B | 701 | 46.026 | 28.872 | -4.747 | 1.00 | 16.67 |
| ATOM | 3031 | CB  | ASN | B | 701 | 45.275 | 29.593 | -3.634 | 1.00 | 22.95 |
| ATOM | 3032 | CG  | ASN | B | 701 | 44.344 | 28.672 | -2.889 | 1.00 | 28.48 |
| ATOM | 3033 | OD1 | ASN | B | 701 | 43.514 | 27.979 | -3.498 | 1.00 | 30.07 |
| ATOM | 3034 | ND2 | ASN | B | 701 | 44.482 | 28.636 | -1.561 | 1.00 | 30.50 |

FIGURE 3CH

| | A | B | C | D | E | F | G | H | I | J |
|---|---|---|---|---|---|---|---|---|---|---|
| ATOM | 3035 | C | ASN | B | 701 | 46.355 | 29.820 | -5.878 | 1.00 | 15.81 |
| ATOM | 3036 | O | ASN | B | 701 | 45.564 | 29.969 | -6.816 | 1.00 | 17.21 |
| ATOM | 3037 | N | TYR | B | 702 | 47.519 | 30.457 | -5.787 | 1.00 | 12.35 |
| ATOM | 3038 | CA | TYR | B | 702 | 47.973 | 31.375 | -6.819 | 1.00 | 13.75 |
| ATOM | 3039 | CB | TYR | B | 702 | 49.271 | 32.064 | -6.397 | 1.00 | 13.85 |
| ATOM | 3040 | CG | TYR | B | 702 | 49.806 | 33.018 | -7.434 | 1.00 | 13.59 |
| ATOM | 3041 | CD1 | TYR | B | 702 | 50.753 | 32.600 | -8.373 | 1.00 | 12.57 |
| ATOM | 3042 | CE1 | TYR | B | 702 | 51.241 | 33.470 | -9.332 | 1.00 | 13.63 |
| ATOM | 3043 | CZ | TYR | B | 702 | 50.774 | 34.775 | -9.361 | 1.00 | 16.69 |
| ATOM | 3044 | OH | TYR | B | 702 | 51.248 | 35.652 | -10.308 | 1.00 | 19.99 |
| ATOM | 3045 | CE2 | TYR | B | 702 | 49.828 | 35.215 | -8.442 | 1.00 | 15.30 |
| ATOM | 3046 | CD2 | TYR | B | 702 | 49.352 | 34.333 | -7.487 | 1.00 | 13.71 |
| ATOM | 3047 | C | TYR | B | 702 | 48.167 | 30.645 | -8.150 | 1.00 | 14.12 |
| ATOM | 3048 | O | TYR | B | 702 | 47.686 | 31.102 | -9.197 | 1.00 | 13.75 |
| ATOM | 3049 | N | LEU | B | 703 | 48.872 | 29.518 | -8.097 | 1.00 | 12.74 |
| ATOM | 3050 | CA | LEU | B | 703 | 49.070 | 28.667 | -9.270 | 1.00 | 13.43 |
| ATOM | 3051 | CB | LEU | B | 703 | 49.919 | 27.440 | -8.924 | 1.00 | 11.12 |
| ATOM | 3052 | CG | LEU | B | 703 | 51.382 | 27.730 | -8.589 | 1.00 | 13.57 |
| ATOM | 3053 | CD1 | LEU | B | 703 | 51.989 | 26.586 | -7.782 | 1.00 | 14.06 |
| ATOM | 3054 | CD2 | LEU | B | 703 | 52.199 | 28.006 | -9.851 | 1.00 | 14.16 |
| ATOM | 3055 | C | LEU | B | 703 | 47.733 | 28.241 | -9.866 | 1.00 | 13.26 |
| ATOM | 3056 | O | LEU | B | 703 | 47.524 | 28.381 | -11.070 | 1.00 | 12.58 |
| ATOM | 3057 | N | ARG | B | 704 | 46.828 | 27.751 | -9.014 | 1.00 | 14.39 |
| ATOM | 3058 | CA | ARG | B | 704 | 45.486 | 27.333 | -9.445 | 1.00 | 15.00 |
| ATOM | 3059 | CB | ARG | B | 704 | 44.680 | 26.742 | -8.283 | 1.00 | 13.97 |
| ATOM | 3060 | CG | ARG | B | 704 | 45.233 | 25.402 | -7.820 | 1.00 | 15.04 |
| ATOM | 3061 | CD | ARG | B | 704 | 44.509 | 24.788 | -6.649 | 1.00 | 15.43 |
| ATOM | 3062 | NE | ARG | B | 704 | 45.130 | 23.520 | -6.295 | 1.00 | 16.27 |
| ATOM | 3063 | CZ | ARG | B | 704 | 44.683 | 22.682 | -5.364 | 1.00 | 17.50 |
| ATOM | 3064 | NH1 | ARG | B | 704 | 45.338 | 21.547 | -5.137 | 1.00 | 18.26 |
| ATOM | 3065 | NH2 | ARG | B | 704 | 43.595 | 22.964 | -4.662 | 1.00 | 15.01 |
| ATOM | 3066 | C | ARG | B | 704 | 44.713 | 28.460 | -10.108 | 1.00 | 14.54 |
| ATOM | 3067 | O | ARG | B | 704 | 44.093 | 28.254 | -11.149 | 1.00 | 16.97 |
| ATOM | 3068 | N | SER | B | 705 | 44.781 | 29.653 | -9.524 | 1.00 | 14.52 |
| ATOM | 3069 | CA | SER | B | 705 | 44.092 | 30.821 | -10.068 | 1.00 | 16.46 |
| ATOM | 3070 | CB | SER | B | 705 | 44.119 | 31.974 | -9.063 | 1.00 | 17.38 |
| ATOM | 3071 | OG | SER | B | 705 | 45.386 | 32.607 | -9.068 | 1.00 | 19.61 |
| ATOM | 3072 | C | SER | B | 705 | 44.671 | 31.290 | -11.405 | 1.00 | 16.67 |
| ATOM | 3073 | O | SER | B | 705 | 43.995 | 31.960 | -12.172 | 1.00 | 17.99 |
| ATOM | 3074 | N | LYS | B | 706 | 45.918 | 30.934 | -11.681 | 1.00 | 17.86 |
| ATOM | 3075 | CA | LYS | B | 706 | 46.595 | 31.435 | -12.868 | 1.00 | 18.49 |
| ATOM | 3076 | CB | LYS | B | 706 | 48.026 | 31.869 | -12.524 | 1.00 | 19.73 |
| ATOM | 3077 | CG | LYS | B | 706 | 48.110 | 33.218 | -11.795 | 1.00 | 21.52 |
| ATOM | 3078 | CD | LYS | B | 706 | 47.778 | 34.389 | -12.715 | 1.00 | 21.36 |
| ATOM | 3079 | CE | LYS | B | 706 | 47.981 | 35.725 | -12.019 | 1.00 | 22.61 |
| ATOM | 3080 | NZ | LYS | B | 706 | 46.705 | 36.470 | -11.840 | 1.00 | 23.95 |
| ATOM | 3081 | C | LYS | B | 706 | 46.584 | 30.438 | -14.022 | 1.00 | 19.24 |
| ATOM | 3082 | O | LYS | B | 706 | 47.074 | 30.746 | -15.108 | 1.00 | 17.04 |
| ATOM | 3083 | N | ARG | B | 707 | 45.999 | 29.262 | -13.775 | 1.00 | 21.58 |
| ATOM | 3084 | CA | ARG | B | 707 | 45.930 | 28.146 | -14.732 | 1.00 | 23.57 |
| ATOM | 3085 | CB | ARG | B | 707 | 44.999 | 27.058 | -14.187 | 1.00 | 22.33 |
| ATOM | 3086 | CG | ARG | B | 707 | 45.653 | 25.722 | -13.917 | 1.00 | 20.45 |

FIGURE 3CI

|  | A | B | C | D | E | F | G | H | I | J |
|---|---|---|---|---|---|---|---|---|---|---|
| ATOM | 3087 | CD | ARG | B | 707 | 44.769 | 24.764 | -13.143 | 1.00 | 20.60 |
| ATOM | 3088 | NE | ARG | B | 707 | 45.474 | 24.145 | -12.017 | 1.00 | 22.07 |
| ATOM | 3089 | CZ | ARG | B | 707 | 44.997 | 23.146 | -11.279 | 1.00 | 20.39 |
| ATOM | 3090 | NH1 | ARG | B | 707 | 45.721 | 22.656 | -10.280 | 1.00 | 17.97 |
| ATOM | 3091 | NH2 | ARG | B | 707 | 43.796 | 22.634 | -11.532 | 1.00 | 21.21 |
| ATOM | 3092 | C | ARG | B | 707 | 45.465 | 28.540 | -16.137 | 1.00 | 27.20 |
| ATOM | 3093 | O | ARG | B | 707 | 46.123 | 28.215 | -17.126 | 1.00 | 29.85 |
| ATOM | 3094 | N | GLU | B | 708 | 44.335 | 29.243 | -16.206 | 1.00 | 29.88 |
| ATOM | 3095 | CA | GLU | B | 708 | 43.699 | 29.642 | -17.463 | 1.00 | 31.83 |
| ATOM | 3096 | CB | GLU | B | 708 | 42.202 | 29.911 | -17.211 | 1.00 | 35.26 |
| ATOM | 3097 | CG | GLU | B | 708 | 41.268 | 28.706 | -17.356 | 1.00 | 39.88 |
| ATOM | 3098 | CD | GLU | B | 708 | 41.704 | 27.477 | -16.560 | 1.00 | 43.46 |
| ATOM | 3099 | OE1 | GLU | B | 708 | 41.792 | 27.551 | -15.308 | 1.00 | 45.04 |
| ATOM | 3100 | OE2 | GLU | B | 708 | 41.959 | 26.424 | -17.187 | 1.00 | 44.97 |
| ATOM | 3101 | C | GLU | B | 708 | 44.368 | 30.884 | -18.072 | 1.00 | 30.45 |
| ATOM | 3102 | O | GLU | B | 708 | 43.939 | 31.400 | -19.105 | 1.00 | 30.41 |
| ATOM | 3103 | N | LYS | B | 709 | 45.418 | 31.354 | -17.411 | 1.00 | 29.94 |
| ATOM | 3104 | CA | LYS | B | 709 | 46.132 | 32.569 | -17.788 | 1.00 | 29.81 |
| ATOM | 3105 | CB | LYS | B | 709 | 46.057 | 33.595 | -16.645 | 1.00 | 31.95 |
| ATOM | 3106 | CG | LYS | B | 709 | 44.953 | 34.636 | -16.772 | 1.00 | 35.24 |
| ATOM | 3107 | CD | LYS | B | 709 | 44.754 | 35.375 | -15.448 | 1.00 | 36.78 |
| ATOM | 3108 | CE | LYS | B | 709 | 43.269 | 35.591 | -15.146 | 1.00 | 38.74 |
| ATOM | 3109 | NZ | LYS | B | 709 | 42.943 | 37.007 | -14.789 | 1.00 | 38.41 |
| ATOM | 3110 | C | LYS | B | 709 | 47.594 | 32.227 | -18.042 | 1.00 | 27.53 |
| ATOM | 3111 | O | LYS | B | 709 | 48.432 | 33.120 | -18.209 | 1.00 | 28.09 |
| ATOM | 3112 | N | PHE | B | 710 | 47.904 | 30.931 | -18.030 | 1.00 | 23.62 |
| ATOM | 3113 | CA | PHE | B | 710 | 49.276 | 30.492 | -18.208 | 1.00 | 19.74 |
| ATOM | 3114 | CB | PHE | B | 710 | 49.519 | 29.095 | -17.642 | 1.00 | 16.93 |
| ATOM | 3115 | CG | PHE | B | 710 | 50.941 | 28.646 | -17.802 | 1.00 | 15.04 |
| ATOM | 3116 | CD1 | PHE | B | 710 | 51.356 | 28.010 | -18.973 | 1.00 | 13.47 |
| ATOM | 3117 | CE1 | PHE | B | 710 | 52.674 | 27.639 | -19.146 | 1.00 | 14.24 |
| ATOM | 3118 | CZ | PHE | B | 710 | 53.602 | 27.900 | -18.142 | 1.00 | 13.66 |
| ATOM | 3119 | CE2 | PHE | B | 710 | 53.204 | 28.550 | -16.987 | 1.00 | 13.64 |
| ATOM | 3120 | CD2 | PHE | B | 710 | 51.881 | 28.926 | -16.823 | 1.00 | 13.39 |
| ATOM | 3121 | C | PHE | B | 710 | 49.722 | 30.554 | -19.667 | 1.00 | 19.66 |
| ATOM | 3122 | O | PHE | B | 710 | 49.021 | 30.108 | -20.570 | 1.00 | 19.44 |
| ATOM | 3123 | N | HIS | B | 711 | 50.923 | 31.077 | -19.865 | 1.00 | 20.17 |
| ATOM | 3124 | CA | HIS | B | 711 | 51.445 | 31.390 | -21.181 | 1.00 | 23.73 |
| ATOM | 3125 | CB | HIS | B | 711 | 51.084 | 32.860 | -21.492 | 1.00 | 26.57 |
| ATOM | 3126 | CG | HIS | B | 711 | 52.042 | 33.599 | -22.379 | 1.00 | 29.80 |
| ATOM | 3127 | ND1 | HIS | B | 711 | 51.661 | 34.723 | -23.084 | 1.00 | 30.69 |
| ATOM | 3128 | CE1 | HIS | B | 711 | 52.694 | 35.185 | -23.766 | 1.00 | 31.30 |
| ATOM | 3129 | NE2 | HIS | B | 711 | 53.736 | 34.411 | -23.520 | 1.00 | 31.24 |
| ATOM | 3130 | CD2 | HIS | B | 711 | 53.355 | 33.413 | -22.653 | 1.00 | 30.78 |
| ATOM | 3131 | C | HIS | B | 711 | 52.934 | 31.088 | -21.079 | 1.00 | 24.38 |
| ATOM | 3132 | O | HIS | B | 711 | 53.627 | 31.642 | -20.238 | 1.00 | 25.77 |
| ATOM | 3133 | N | ARG | B | 712 | 53.399 | 30.158 | -21.906 | 1.00 | 24.74 |
| ATOM | 3134 | CA | ARG | B | 712 | 54.745 | 29.606 | -21.803 | 1.00 | 25.45 |
| ATOM | 3135 | CB | ARG | B | 712 | 54.913 | 28.462 | -22.808 | 1.00 | 27.47 |
| ATOM | 3136 | CG | ARG | B | 712 | 56.213 | 27.689 | -22.683 | 1.00 | 30.85 |
| ATOM | 3137 | CD | ARG | B | 712 | 57.294 | 28.157 | -23.640 | 1.00 | 33.32 |
| ATOM | 3138 | NE | ARG | B | 712 | 58.196 | 27.079 | -24.028 | 1.00 | 35.54 |

FIGURE 3CJ

|   | A | B | C | D | E | F | G | H | I | J |
|---|---|---|---|---|---|---|---|---|---|---|
| ATOM | 3139 | CZ | ARG | B | 712 | 58.515 | 26.794 | -25.280 | 1.00 | 36.25 |
| ATOM | 3140 | NH1 | ARG | B | 712 | 58.007 | 27.515 | -26.278 | 1.00 | 37.75 |
| ATOM | 3141 | NH2 | ARG | B | 712 | 59.342 | 25.790 | -25.541 | 1.00 | 34.36 |
| ATOM | 3142 | C | ARG | B | 712 | 55.833 | 30.648 | -22.023 | 1.00 | 25.80 |
| ATOM | 3143 | O | ARG | B | 712 | 56.726 | 30.813 | -21.190 | 1.00 | 23.07 |
| ATOM | 3144 | N | THR | B | 713 | 55.741 | 31.327 | -23.163 | 1.00 | 28.24 |
| ATOM | 3145 | CA | THR | B | 713 | 56.736 | 32.280 | -23.634 | 1.00 | 31.29 |
| ATOM | 3146 | CB | THR | B | 713 | 56.316 | 32.829 | -25.013 | 1.00 | 32.11 |
| ATOM | 3147 | OG1 | THR | B | 713 | 55.621 | 31.809 | -25.749 | 1.00 | 32.01 |
| ATOM | 3148 | CG2 | THR | B | 713 | 57.538 | 33.132 | -25.867 | 1.00 | 32.98 |
| ATOM | 3149 | C | THR | B | 713 | 56.924 | 33.435 | -22.660 | 1.00 | 34.30 |
| ATOM | 3150 | O | THR | B | 713 | 55.969 | 33.884 | -22.022 | 1.00 | 32.91 |
| ATOM | 3151 | N | ALA | B | 776 | 58.167 | 33.901 | -22.554 | 1.00 | 37.66 |
| ATOM | 3152 | CA | ALA | B | 776 | 58.522 | 35.017 | -21.687 | 1.00 | 39.32 |
| ATOM | 3153 | CB | ALA | B | 776 | 60.021 | 35.257 | -21.725 | 1.00 | 40.13 |
| ATOM | 3154 | C | ALA | B | 776 | 57.766 | 36.266 | -22.113 | 1.00 | 40.54 |
| ATOM | 3155 | O | ALA | B | 776 | 57.744 | 36.614 | -23.294 | 1.00 | 41.65 |
| ATOM | 3156 | N | SER | B | 777 | 57.134 | 36.923 | -21.145 | 1.00 | 41.48 |
| ATOM | 3157 | CA | SER | B | 777 | 56.293 | 38.078 | -21.426 | 1.00 | 42.92 |
| ATOM | 3158 | CB | SER | B | 777 | 54.820 | 37.663 | -21.492 | 1.00 | 42.85 |
| ATOM | 3159 | OG | SER | B | 777 | 53.992 | 38.769 | -21.809 | 1.00 | 42.80 |
| ATOM | 3160 | C | SER | B | 777 | 56.487 | 39.191 | -20.400 | 1.00 | 43.91 |
| ATOM | 3161 | O | SER | B | 777 | 56.826 | 38.934 | -19.237 | 1.00 | 44.04 |
| ATOM | 3162 | N | GLU | B | 778 | 56.268 | 40.424 | -20.853 | 1.00 | 44.02 |
| ATOM | 3163 | CA | GLU | B | 778 | 56.339 | 41.607 | -20.000 | 1.00 | 44.49 |
| ATOM | 3164 | CB | GLU | B | 778 | 56.638 | 42.852 | -20.843 | 1.00 | 45.94 |
| ATOM | 3165 | CG | GLU | B | 778 | 57.572 | 43.848 | -20.174 | 1.00 | 47.77 |
| ATOM | 3166 | CD | GLU | B | 778 | 59.036 | 43.563 | -20.459 | 1.00 | 48.76 |
| ATOM | 3167 | OE1 | GLU | B | 778 | 59.616 | 44.261 | -21.322 | 1.00 | 48.91 |
| ATOM | 3168 | OE2 | GLU | B | 778 | 59.605 | 42.645 | -19.820 | 1.00 | 48.00 |
| ATOM | 3169 | C | GLU | B | 778 | 55.051 | 41.808 | -19.191 | 1.00 | 43.14 |
| ATOM | 3170 | O | GLU | B | 778 | 55.048 | 42.542 | -18.199 | 1.00 | 43.16 |
| ATOM | 3171 | N | ASP | B | 779 | 53.969 | 41.157 | -19.627 | 1.00 | 41.00 |
| ATOM | 3172 | CA | ASP | B | 779 | 52.669 | 41.212 | -18.952 | 1.00 | 38.10 |
| ATOM | 3173 | CB | ASP | B | 779 | 51.668 | 40.272 | -19.633 | 1.00 | 38.35 |
| ATOM | 3174 | CG | ASP | B | 779 | 50.221 | 40.634 | -19.335 | 1.00 | 38.17 |
| ATOM | 3175 | OD1 | ASP | B | 779 | 49.833 | 40.657 | -18.147 | 1.00 | 37.18 |
| ATOM | 3176 | OD2 | ASP | B | 779 | 49.393 | 40.901 | -20.232 | 1.00 | 38.77 |
| ATOM | 3177 | C | ASP | B | 779 | 52.777 | 40.859 | -17.473 | 1.00 | 36.02 |
| ATOM | 3178 | O | ASP | B | 779 | 53.452 | 39.889 | -17.100 | 1.00 | 35.84 |
| ATOM | 3179 | N | LEU | B | 780 | 52.106 | 41.654 | -16.640 | 1.00 | 32.52 |
| ATOM | 3180 | CA | LEU | B | 780 | 52.150 | 41.469 | -15.192 | 1.00 | 29.04 |
| ATOM | 3181 | CB | LEU | B | 780 | 51.938 | 42.802 | -14.460 | 1.00 | 28.63 |
| ATOM | 3182 | CG | LEU | B | 780 | 52.990 | 43.914 | -14.572 | 1.00 | 28.30 |
| ATOM | 3183 | CD1 | LEU | B | 780 | 52.506 | 45.172 | -13.863 | 1.00 | 27.25 |
| ATOM | 3184 | CD2 | LEU | B | 780 | 54.343 | 43.480 | -14.016 | 1.00 | 27.96 |
| ATOM | 3185 | C | LEU | B | 780 | 51.135 | 40.435 | -14.713 | 1.00 | 26.91 |
| ATOM | 3186 | O | LEU | B | 780 | 51.304 | 39.843 | -13.648 | 1.00 | 28.04 |
| ATOM | 3187 | N | ASN | B | 781 | 50.095 | 40.210 | -15.511 | 1.00 | 24.33 |
| ATOM | 3188 | CA | ASN | B | 781 | 48.981 | 39.356 | -15.106 | 1.00 | 24.28 |
| ATOM | 3189 | CB | ASN | B | 781 | 47.653 | 40.076 | -15.366 | 1.00 | 23.96 |
| ATOM | 3190 | CG | ASN | B | 781 | 47.585 | 41.434 | -14.659 | 1.00 | 25.16 |

FIGURE 3CK

| | A | B | C | D | E | F | G | H | I | J |
|---|---|---|---|---|---|---|---|---|---|---|
| ATOM | 3191 | OD1 | ASN | B | 781 | 47.734 | 41.519 | -13.432 | 1.00 | 24.03 |
| ATOM | 3192 | ND2 | ASN | B | 781 | 47.391 | 42.499 | -15.433 | 1.00 | 23.93 |
| ATOM | 3193 | C | ASN | B | 781 | 49.006 | 37.941 | -15.704 | 1.00 | 24.00 |
| ATOM | 3194 | O | ASN | B | 781 | 48.279 | 37.044 | -15.263 | 1.00 | 25.11 |
| ATOM | 3195 | N | VAL | B | 782 | 49.866 | 37.746 | -16.693 | 1.00 | 20.93 |
| ATOM | 3196 | CA | VAL | B | 782 | 50.099 | 36.438 | -17.269 | 1.00 | 17.51 |
| ATOM | 3197 | CB | VAL | B | 782 | 50.505 | 36.590 | -18.746 | 1.00 | 17.49 |
| ATOM | 3198 | CG1 | VAL | B | 782 | 51.466 | 35.508 | -19.180 | 1.00 | 19.03 |
| ATOM | 3199 | CG2 | VAL | B | 782 | 49.263 | 36.615 | -19.636 | 1.00 | 16.25 |
| ATOM | 3200 | C | VAL | B | 782 | 51.186 | 35.746 | -16.450 | 1.00 | 16.35 |
| ATOM | 3201 | O | VAL | B | 782 | 52.165 | 36.384 | -16.056 | 1.00 | 17.87 |
| ATOM | 3202 | N | LEU | B | 783 | 50.982 | 34.463 | -16.160 | 1.00 | 13.13 |
| ATOM | 3203 | CA | LEU | B | 783 | 52.002 | 33.619 | -15.545 | 1.00 | 12.54 |
| ATOM | 3204 | CB | LEU | B | 783 | 51.367 | 32.614 | -14.571 | 1.00 | 11.46 |
| ATOM | 3205 | CG | LEU | B | 783 | 52.323 | 31.824 | -13.667 | 1.00 | 12.95 |
| ATOM | 3206 | CD1 | LEU | B | 783 | 53.026 | 32.721 | -12.672 | 1.00 | 13.58 |
| ATOM | 3207 | CD2 | LEU | B | 783 | 51.606 | 30.706 | -12.928 | 1.00 | 14.98 |
| ATOM | 3208 | C | LEU | B | 783 | 52.760 | 32.874 | -16.640 | 1.00 | 13.19 |
| ATOM | 3209 | O | LEU | B | 783 | 52.141 | 32.257 | -17.514 | 1.00 | 13.94 |
| ATOM | 3210 | N | THR | B | 784 | 54.090 | 32.933 | -16.598 | 1.00 | 12.55 |
| ATOM | 3211 | CA | THR | B | 784 | 54.917 | 32.286 | -17.626 | 1.00 | 11.32 |
| ATOM | 3212 | CB | THR | B | 784 | 55.833 | 33.295 | -18.314 | 1.00 | 9.85 |
| ATOM | 3213 | OG1 | THR | B | 784 | 56.791 | 33.769 | -17.362 | 1.00 | 10.11 |
| ATOM | 3214 | CG2 | THR | B | 784 | 55.061 | 34.539 | -18.755 | 1.00 | 7.79 |
| ATOM | 3215 | C | THR | B | 784 | 55.779 | 31.153 | -17.090 | 1.00 | 13.04 |
| ATOM | 3216 | O | THR | B | 784 | 55.855 | 30.933 | -15.878 | 1.00 | 12.99 |
| ATOM | 3217 | N | PHE | B | 785 | 56.439 | 30.443 | -18.006 | 1.00 | 13.63 |
| ATOM | 3218 | CA | PHE | B | 785 | 57.410 | 29.422 | -17.626 | 1.00 | 13.00 |
| ATOM | 3219 | CB | PHE | B | 785 | 57.936 | 28.648 | -18.839 | 1.00 | 12.48 |
| ATOM | 3220 | CG | PHE | B | 785 | 58.916 | 27.579 | -18.472 | 1.00 | 11.99 |
| ATOM | 3221 | CD1 | PHE | B | 785 | 58.472 | 26.356 | -17.966 | 1.00 | 10.41 |
| ATOM | 3222 | CE1 | PHE | B | 785 | 59.383 | 25.362 | -17.598 | 1.00 | 11.30 |
| ATOM | 3223 | CZ | PHE | B | 785 | 60.751 | 25.600 | -17.717 | 1.00 | 11.26 |
| ATOM | 3224 | CE2 | PHE | B | 785 | 61.203 | 26.831 | -18.215 | 1.00 | 11.49 |
| ATOM | 3225 | CD2 | PHE | B | 785 | 60.287 | 27.808 | -18.587 | 1.00 | 10.89 |
| ATOM | 3226 | C | PHE | B | 785 | 58.573 | 30.022 | -16.832 | 1.00 | 13.81 |
| ATOM | 3227 | O | PHE | B | 785 | 58.984 | 29.454 | -15.815 | 1.00 | 12.87 |
| ATOM | 3228 | N | GLU | B | 786 | 59.093 | 31.159 | -17.302 | 1.00 | 14.70 |
| ATOM | 3229 | CA | GLU | B | 786 | 60.118 | 31.909 | -16.571 | 1.00 | 16.97 |
| ATOM | 3230 | CB | GLU | B | 786 | 60.445 | 33.230 | -17.278 | 1.00 | 21.67 |
| ATOM | 3231 | CG | GLU | B | 786 | 61.921 | 33.608 | -17.237 | 1.00 | 30.49 |
| ATOM | 3232 | CD | GLU | B | 786 | 62.234 | 34.969 | -17.876 | 1.00 | 36.36 |
| ATOM | 3233 | OE1 | GLU | B | 786 | 63.209 | 35.626 | -17.425 | 1.00 | 38.99 |
| ATOM | 3234 | OE2 | GLU | B | 786 | 61.531 | 35.392 | -18.833 | 1.00 | 37.71 |
| ATOM | 3235 | C | GLU | B | 786 | 59.699 | 32.168 | -15.115 | 1.00 | 14.41 |
| ATOM | 3236 | O | GLU | B | 786 | 60.514 | 32.044 | -14.200 | 1.00 | 11.23 |
| ATOM | 3237 | N | ASP | B | 787 | 58.423 | 32.500 | -14.911 | 1.00 | 13.41 |
| ATOM | 3238 | CA | ASP | B | 787 | 57.882 | 32.760 | -13.573 | 1.00 | 12.85 |
| ATOM | 3239 | CB | ASP | B | 787 | 56.459 | 33.296 | -13.665 | 1.00 | 12.90 |
| ATOM | 3240 | CG | ASP | B | 787 | 56.404 | 34.649 | -14.309 | 1.00 | 15.76 |
| ATOM | 3241 | OD1 | ASP | B | 787 | 55.361 | 34.981 | -14.925 | 1.00 | 16.42 |
| ATOM | 3242 | OD2 | ASP | B | 787 | 57.373 | 35.442 | -14.258 | 1.00 | 15.32 |

FIGURE 3CL

|  | A | B | C | D | E | F | G | H | I | J |
|---|---|---|---|---|---|---|---|---|---|---|
| ATOM | 3243 | C | ASP | B | 787 | 57.909 | 31.535 | -12.685 | 1.00 | 13.45 |
| ATOM | 3244 | O | ASP | B | 787 | 58.181 | 31.638 | -11.491 | 1.00 | 14.57 |
| ATOM | 3245 | N | LEU | B | 788 | 57.626 | 30.377 | -13.278 | 1.00 | 13.05 |
| ATOM | 3246 | CA | LEU | B | 788 | 57.692 | 29.114 | -12.567 | 1.00 | 12.89 |
| ATOM | 3247 | CB | LEU | B | 788 | 57.089 | 27.982 | -13.401 | 1.00 | 11.56 |
| ATOM | 3248 | CG | LEU | B | 788 | 55.646 | 28.105 | -13.905 | 1.00 | 10.90 |
| ATOM | 3249 | CD1 | LEU | B | 788 | 55.211 | 26.794 | -14.561 | 1.00 | 7.95 |
| ATOM | 3250 | CD2 | LEU | B | 788 | 54.666 | 28.522 | -12.783 | 1.00 | 9.05 |
| ATOM | 3251 | C | LEU | B | 788 | 59.131 | 28.800 | -12.179 | 1.00 | 14.25 |
| ATOM | 3252 | O | LEU | B | 788 | 59.388 | 28.417 | -11.041 | 1.00 | 14.41 |
| ATOM | 3253 | N | LEU | B | 789 | 60.065 | 28.979 | -13.117 | 1.00 | 14.72 |
| ATOM | 3254 | CA | LEU | B | 789 | 61.493 | 28.813 | -12.825 | 1.00 | 18.27 |
| ATOM | 3255 | CB | LEU | B | 789 | 62.345 | 29.188 | -14.041 | 1.00 | 17.31 |
| ATOM | 3256 | CG | LEU | B | 789 | 62.618 | 28.179 | -15.153 | 1.00 | 20.44 |
| ATOM | 3257 | CD1 | LEU | B | 789 | 63.621 | 28.773 | -16.141 | 1.00 | 21.59 |
| ATOM | 3258 | CD2 | LEU | B | 789 | 63.127 | 26.857 | -14.620 | 1.00 | 21.42 |
| ATOM | 3259 | C | LEU | B | 789 | 61.903 | 29.705 | -11.649 | 1.00 | 18.11 |
| ATOM | 3260 | O | LEU | B | 789 | 62.591 | 29.277 | -10.725 | 1.00 | 17.08 |
| ATOM | 3261 | N | CYS | B | 790 | 61.459 | 30.953 | -11.722 | 1.00 | 18.80 |
| ATOM | 3262 | CA | CYS | B | 790 | 61.734 | 31.969 | -10.730 | 1.00 | 18.44 |
| ATOM | 3263 | CB | CYS | B | 790 | 61.207 | 33.308 | -11.233 | 1.00 | 20.76 |
| ATOM | 3264 | SG | CYS | B | 790 | 61.768 | 34.716 | -10.267 | 1.00 | 25.11 |
| ATOM | 3265 | C | CYS | B | 790 | 61.136 | 31.626 | -9.367 | 1.00 | 17.55 |
| ATOM | 3266 | O | CYS | B | 790 | 61.780 | 31.844 | -8.346 | 1.00 | 16.56 |
| ATOM | 3267 | N | PHE | B | 791 | 59.920 | 31.081 | -9.350 | 1.00 | 16.72 |
| ATOM | 3268 | CA | PHE | B | 791 | 59.337 | 30.565 | -8.115 | 1.00 | 15.89 |
| ATOM | 3269 | CB | PHE | B | 791 | 57.951 | 29.970 | -8.366 | 1.00 | 16.61 |
| ATOM | 3270 | CG | PHE | B | 791 | 56.869 | 30.989 | -8.636 | 1.00 | 17.06 |
| ATOM | 3271 | CD1 | PHE | B | 791 | 55.692 | 30.604 | -9.279 | 1.00 | 15.97 |
| ATOM | 3272 | CE1 | PHE | B | 791 | 54.673 | 31.532 | -9.527 | 1.00 | 17.19 |
| ATOM | 3273 | CZ | PHE | B | 791 | 54.826 | 32.846 | -9.136 | 1.00 | 15.38 |
| ATOM | 3274 | CE2 | PHE | B | 791 | 55.998 | 33.241 | -8.491 | 1.00 | 17.24 |
| ATOM | 3275 | CD2 | PHE | B | 791 | 57.010 | 32.315 | -8.246 | 1.00 | 16.06 |
| ATOM | 3276 | C | PHE | B | 791 | 60.251 | 29.478 | -7.543 | 1.00 | 16.96 |
| ATOM | 3277 | O | PHE | B | 791 | 60.599 | 29.498 | -6.363 | 1.00 | 18.92 |
| ATOM | 3278 | N | ALA | B | 792 | 60.644 | 28.538 | -8.395 | 1.00 | 15.70 |
| ATOM | 3279 | CA | ALA | B | 792 | 61.509 | 27.439 | -7.997 | 1.00 | 15.70 |
| ATOM | 3280 | CB | ALA | B | 792 | 61.808 | 26.535 | -9.198 | 1.00 | 13.08 |
| ATOM | 3281 | C | ALA | B | 792 | 62.804 | 27.987 | -7.400 | 1.00 | 16.01 |
| ATOM | 3282 | O | ALA | B | 792 | 63.225 | 27.568 | -6.315 | 1.00 | 16.21 |
| ATOM | 3283 | N | TYR | B | 793 | 63.414 | 28.940 | -8.104 | 1.00 | 14.39 |
| ATOM | 3284 | CA | TYR | B | 793 | 64.663 | 29.542 | -7.661 | 1.00 | 14.50 |
| ATOM | 3285 | CB | TYR | B | 793 | 65.172 | 30.561 | -8.673 | 1.00 | 14.17 |
| ATOM | 3286 | CG | TYR | B | 793 | 66.394 | 31.305 | -8.195 | 1.00 | 16.09 |
| ATOM | 3287 | CD1 | TYR | B | 793 | 66.333 | 32.667 | -7.913 | 1.00 | 17.04 |
| ATOM | 3288 | CE1 | TYR | B | 793 | 67.454 | 33.355 | -7.468 | 1.00 | 18.77 |
| ATOM | 3289 | CZ | TYR | B | 793 | 68.653 | 32.672 | -7.295 | 1.00 | 18.58 |
| ATOM | 3290 | OH | TYR | B | 793 | 69.768 | 33.352 | -6.852 | 1.00 | 21.15 |
| ATOM | 3291 | CE2 | TYR | B | 793 | 68.734 | 31.320 | -7.562 | 1.00 | 15.87 |
| ATOM | 3292 | CD2 | TYR | B | 793 | 67.611 | 30.643 | -8.006 | 1.00 | 15.49 |
| ATOM | 3293 | C | TYR | B | 793 | 64.511 | 30.205 | -6.297 | 1.00 | 15.45 |
| ATOM | 3294 | O | TYR | B | 793 | 65.316 | 29.962 | -5.393 | 1.00 | 16.76 |

FIGURE 3CM

| | A | B | C | D | E | F | G | H | I | J |
|---|---|---|---|---|---|---|---|---|---|---|
| ATOM | 3295 | N | GLN | B | 794 | 63.469 | 31.023 | -6.158 | 1.00 | 13.12 |
| ATOM | 3296 | CA | GLN | B | 794 | 63.234 | 31.793 | -4.942 | 1.00 | 12.88 |
| ATOM | 3297 | CB | GLN | B | 794 | 62.064 | 32.744 | -5.132 | 1.00 | 12.49 |
| ATOM | 3298 | CG | GLN | B | 794 | 62.359 | 33.947 | -5.988 | 1.00 | 12.76 |
| ATOM | 3299 | CD | GLN | B | 794 | 61.129 | 34.810 | -6.157 | 1.00 | 15.83 |
| ATOM | 3300 | OE1 | GLN | B | 794 | 60.817 | 35.609 | -5.277 | 1.00 | 18.54 |
| ATOM | 3301 | NE2 | GLN | B | 794 | 60.418 | 34.645 | -7.274 | 1.00 | 13.51 |
| ATOM | 3302 | C | GLN | B | 794 | 62.977 | 30.928 | -3.717 | 1.00 | 12.99 |
| ATOM | 3303 | O | GLN | B | 794 | 63.438 | 31.261 | -2.627 | 1.00 | 11.17 |
| ATOM | 3304 | N | VAL | B | 795 | 62.237 | 29.829 | -3.898 | 1.00 | 11.04 |
| ATOM | 3305 | CA | VAL | B | 795 | 61.975 | 28.908 | -2.805 | 1.00 | 11.30 |
| ATOM | 3306 | CB | VAL | B | 795 | 60.881 | 27.852 | -3.153 | 1.00 | 11.23 |
| ATOM | 3307 | CG1 | VAL | B | 795 | 60.784 | 26.790 | -2.062 | 1.00 | 10.96 |
| ATOM | 3308 | CG2 | VAL | B | 795 | 59.524 | 28.509 | -3.341 | 1.00 | 10.26 |
| ATOM | 3309 | C | VAL | B | 795 | 63.299 | 28.237 | -2.401 | 1.00 | 14.09 |
| ATOM | 3310 | O | VAL | B | 795 | 63.588 | 28.100 | -1.211 | 1.00 | 15.76 |
| ATOM | 3311 | N | ALA | B | 796 | 64.106 | 27.851 | -3.390 | 1.00 | 13.08 |
| ATOM | 3312 | CA | ALA | B | 796 | 65.424 | 27.279 | -3.117 | 1.00 | 14.98 |
| ATOM | 3313 | CB | ALA | B | 796 | 66.108 | 26.805 | -4.413 | 1.00 | 12.06 |
| ATOM | 3314 | C | ALA | B | 796 | 66.310 | 28.273 | -2.359 | 1.00 | 15.28 |
| ATOM | 3315 | O | ALA | B | 796 | 67.048 | 27.887 | -1.446 | 1.00 | 15.79 |
| ATOM | 3316 | N | LYS | B | 797 | 66.221 | 29.547 | -2.723 | 1.00 | 14.58 |
| ATOM | 3317 | CA | LYS | B | 797 | 66.974 | 30.587 | -2.029 | 1.00 | 18.13 |
| ATOM | 3318 | CB | LYS | B | 797 | 66.856 | 31.928 | -2.755 | 1.00 | 22.00 |
| ATOM | 3319 | CG | LYS | B | 797 | 67.871 | 32.098 | -3.868 | 1.00 | 26.98 |
| ATOM | 3320 | CD | LYS | B | 797 | 68.683 | 33.371 | -3.694 | 1.00 | 32.46 |
| ATOM | 3321 | CE | LYS | B | 797 | 70.009 | 33.079 | -2.987 | 1.00 | 35.90 |
| ATOM | 3322 | NZ | LYS | B | 797 | 71.181 | 33.416 | -3.843 | 1.00 | 37.73 |
| ATOM | 3323 | C | LYS | B | 797 | 66.549 | 30.722 | -0.570 | 1.00 | 15.08 |
| ATOM | 3324 | O | LYS | B | 797 | 67.394 | 30.828 | 0.314 | 1.00 | 14.35 |
| ATOM | 3325 | N | GLY | B | 798 | 65.242 | 30.691 | -0.329 | 1.00 | 13.69 |
| ATOM | 3326 | CA | GLY | B | 798 | 64.706 | 30.726 | 1.019 | 1.00 | 14.16 |
| ATOM | 3327 | C | GLY | B | 798 | 65.140 | 29.537 | 1.855 | 1.00 | 13.55 |
| ATOM | 3328 | O | GLY | B | 798 | 65.513 | 29.688 | 3.017 | 1.00 | 14.72 |
| ATOM | 3329 | N | MET | B | 799 | 65.098 | 28.352 | 1.264 | 1.00 | 13.00 |
| ATOM | 3330 | CA | MET | B | 799 | 65.536 | 27.154 | 1.965 | 1.00 | 13.46 |
| ATOM | 3331 | CB | MET | B | 799 | 65.192 | 25.899 | 1.173 | 1.00 | 12.76 |
| ATOM | 3332 | CG | MET | B | 799 | 63.721 | 25.528 | 1.197 | 1.00 | 13.77 |
| ATOM | 3333 | SD | MET | B | 799 | 62.983 | 25.424 | 2.851 | 1.00 | 17.81 |
| ATOM | 3334 | CE | MET | B | 799 | 64.099 | 24.271 | 3.715 | 1.00 | 13.65 |
| ATOM | 3335 | C | MET | B | 799 | 67.033 | 27.208 | 2.265 | 1.00 | 14.51 |
| ATOM | 3336 | O | MET | B | 799 | 67.466 | 26.802 | 3.341 | 1.00 | 17.71 |
| ATOM | 3337 | N | GLU | B | 800 | 67.807 | 27.736 | 1.323 | 1.00 | 12.75 |
| ATOM | 3338 | CA | GLU | B | 800 | 69.246 | 27.882 | 1.483 | 1.00 | 12.98 |
| ATOM | 3339 | CB | GLU | B | 800 | 69.846 | 28.473 | 0.213 | 1.00 | 13.91 |
| ATOM | 3340 | CG | GLU | B | 800 | 71.353 | 28.602 | 0.217 | 1.00 | 17.10 |
| ATOM | 3341 | CD | GLU | B | 800 | 71.881 | 29.245 | -1.050 | 1.00 | 19.72 |
| ATOM | 3342 | OE1 | GLU | B | 800 | 72.569 | 28.557 | -1.823 | 1.00 | 20.71 |
| ATOM | 3343 | OE2 | GLU | B | 800 | 71.610 | 30.443 | -1.274 | 1.00 | 24.28 |
| ATOM | 3344 | C | GLU | B | 800 | 69.547 | 28.785 | 2.671 | 1.00 | 14.79 |
| ATOM | 3345 | O | GLU | B | 800 | 70.453 | 28.508 | 3.476 | 1.00 | 15.23 |
| ATOM | 3346 | N | PHE | B | 801 | 68.786 | 29.874 | 2.767 | 1.00 | 12.66 |

FIGURE 3CN

|  | A | B | C | D | E | F | G | H | I | J |
|---|---|---|---|---|---|---|---|---|---|---|
| ATOM | 3347 | CA | PHE | B | 801 | 68.884 | 30.785 | 3.893 | 1.00 | 9.98 |
| ATOM | 3348 | CB | PHE | B | 801 | 67.904 | 31.945 | 3.718 | 1.00 | 8.75 |
| ATOM | 3349 | CG | PHE | B | 801 | 67.793 | 32.837 | 4.916 | 1.00 | 7.24 |
| ATOM | 3350 | CD1 | PHE | B | 801 | 66.706 | 32.728 | 5.777 | 1.00 | 7.19 |
| ATOM | 3351 | CE1 | PHE | B | 801 | 66.591 | 33.558 | 6.884 | 1.00 | 7.51 |
| ATOM | 3352 | CZ | PHE | B | 801 | 67.570 | 34.514 | 7.137 | 1.00 | 8.03 |
| ATOM | 3353 | CE2 | PHE | B | 801 | 68.658 | 34.640 | 6.277 | 1.00 | 7.09 |
| ATOM | 3354 | CD2 | PHE | B | 801 | 68.762 | 33.802 | 5.174 | 1.00 | 6.24 |
| ATOM | 3355 | C | PHE | B | 801 | 68.608 | 30.017 | 5.183 | 1.00 | 10.78 |
| ATOM | 3356 | O | PHE | B | 801 | 69.371 | 30.124 | 6.142 | 1.00 | 11.90 |
| ATOM | 3357 | N | LEU | B | 802 | 67.542 | 29.217 | 5.191 | 1.00 | 11.68 |
| ATOM | 3358 | CA | LEU | B | 802 | 67.197 | 28.422 | 6.372 | 1.00 | 12.82 |
| ATOM | 3359 | CB | LEU | B | 802 | 65.845 | 27.733 | 6.202 | 1.00 | 11.28 |
| ATOM | 3360 | CG | LEU | B | 802 | 64.671 | 28.712 | 6.144 | 1.00 | 9.78 |
| ATOM | 3361 | CD1 | LEU | B | 802 | 63.379 | 27.948 | 5.932 | 1.00 | 11.35 |
| ATOM | 3362 | CD2 | LEU | B | 802 | 64.600 | 29.608 | 7.387 | 1.00 | 7.83 |
| ATOM | 3363 | C | LEU | B | 802 | 68.281 | 27.412 | 6.742 | 1.00 | 12.84 |
| ATOM | 3364 | O | LEU | B | 802 | 68.594 | 27.246 | 7.919 | 1.00 | 13.15 |
| ATOM | 3365 | N | GLU | B | 803 | 68.854 | 26.761 | 5.733 | 1.00 | 11.86 |
| ATOM | 3366 | CA | GLU | B | 803 | 70.001 | 25.881 | 5.921 | 1.00 | 14.45 |
| ATOM | 3367 | CB | GLU | B | 803 | 70.519 | 25.421 | 4.558 | 1.00 | 16.42 |
| ATOM | 3368 | CG | GLU | B | 803 | 71.771 | 24.559 | 4.580 | 1.00 | 19.28 |
| ATOM | 3369 | CD | GLU | B | 803 | 72.124 | 24.026 | 3.196 | 1.00 | 21.84 |
| ATOM | 3370 | OE1 | GLU | B | 803 | 71.235 | 24.001 | 2.319 | 1.00 | 22.07 |
| ATOM | 3371 | OE2 | GLU | B | 803 | 73.286 | 23.631 | 2.975 | 1.00 | 20.85 |
| ATOM | 3372 | C | GLU | B | 803 | 71.110 | 26.591 | 6.716 | 1.00 | 13.26 |
| ATOM | 3373 | O | GLU | B | 803 | 71.612 | 26.066 | 7.709 | 1.00 | 10.24 |
| ATOM | 3374 | N | PHE | B | 804 | 71.447 | 27.804 | 6.294 | 1.00 | 10.46 |
| ATOM | 3375 | CA | PHE | B | 804 | 72.547 | 28.551 | 6.886 | 1.00 | 9.68 |
| ATOM | 3376 | CB | BPHE | B | 804 | 73.200 | 29.494 | 5.871 | 0.35 | 9.81 |
| ATOM | 3377 | CB | APHE | B | 804 | 72.963 | 29.641 | 5.864 | 0.65 | 9.44 |
| ATOM | 3378 | CG | BPHE | B | 804 | 74.002 | 28.755 | 4.835 | 0.35 | 9.92 |
| ATOM | 3379 | CG | APHE | B | 804 | 73.639 | 30.867 | 6.451 | 0.65 | 9.57 |
| ATOM | 3380 | CD1 | BPHE | B | 804 | 75.333 | 28.430 | 5.070 | 0.35 | 9.63 |
| ATOM | 3381 | CD1 | APHE | B | 804 | 72.917 | 32.046 | 6.665 | 0.65 | 8.76 |
| ATOM | 3382 | CE1 | BPHE | B | 804 | 76.070 | 27.715 | 4.131 | 0.35 | 9.72 |
| ATOM | 3383 | CE1 | APHE | B | 804 | 73.544 | 33.189 | 7.186 | 0.65 | 7.22 |
| ATOM | 3384 | CZ | BPHE | B | 804 | 75.469 | 27.295 | 2.952 | 0.35 | 9.89 |
| ATOM | 3385 | CZ | APHE | B | 804 | 74.910 | 33.171 | 7.470 | 0.65 | 6.90 |
| ATOM | 3386 | CE2 | BPHE | B | 804 | 74.135 | 27.598 | 2.710 | 0.35 | 10.34 |
| ATOM | 3387 | CE2 | APHE | B | 804 | 75.648 | 32.016 | 7.237 | 0.65 | 7.68 |
| ATOM | 3388 | CD2 | BPHE | B | 804 | 73.407 | 28.316 | 3.656 | 0.35 | 10.64 |
| ATOM | 3389 | CD2 | APHE | B | 804 | 75.010 | 30.869 | 6.725 | 0.65 | 9.89 |
| ATOM | 3390 | C | PHE | B | 804 | 72.167 | 29.163 | 8.234 | 1.00 | 9.01 |
| ATOM | 3391 | O | PHE | B | 804 | 73.030 | 29.521 | 9.036 | 1.00 | 7.53 |
| ATOM | 3392 | N | LYS | B | 805 | 70.863 | 29.201 | 8.498 | 1.00 | 10.13 |
| ATOM | 3393 | CA | LYS | B | 805 | 70.350 | 29.632 | 9.792 | 1.00 | 12.64 |
| ATOM | 3394 | CB | LYS | B | 805 | 69.130 | 30.552 | 9.621 | 1.00 | 10.64 |
| ATOM | 3395 | CG | LYS | B | 805 | 69.459 | 31.912 | 9.025 | 1.00 | 11.18 |
| ATOM | 3396 | CD | LYS | B | 805 | 70.322 | 32.745 | 9.983 | 1.00 | 11.67 |
| ATOM | 3397 | CE | LYS | B | 805 | 70.811 | 34.027 | 9.337 | 1.00 | 10.86 |
| ATOM | 3398 | NZ | LYS | B | 805 | 71.213 | 35.032 | 10.375 | 1.00 | 15.26 |

FIGURE 3CO

| | A | B | C | D | E | F | G | H | I | J |
|---|---|---|---|---|---|---|---|---|---|---|
| ATOM | 3399 | C | LYS | B | 805 | 70.027 | 28.440 | 10.703 | 1.00 | 13.80 |
| ATOM | 3400 | O | LYS | B | 805 | 69.384 | 28.605 | 11.743 | 1.00 | 17.15 |
| ATOM | 3401 | N | SER | B | 806 | 70.498 | 27.254 | 10.314 | 1.00 | 12.51 |
| ATOM | 3402 | CA | SER | B | 806 | 70.377 | 26.033 | 11.117 | 1.00 | 12.87 |
| ATOM | 3403 | CB | SER | B | 806 | 71.140 | 26.150 | 12.440 | 1.00 | 13.04 |
| ATOM | 3404 | OG | SER | B | 806 | 72.540 | 26.166 | 12.239 | 1.00 | 15.58 |
| ATOM | 3405 | C | SER | B | 806 | 68.913 | 25.703 | 11.377 | 1.00 | 13.83 |
| ATOM | 3406 | O | SER | B | 806 | 68.496 | 25.505 | 12.514 | 1.00 | 10.94 |
| ATOM | 3407 | N | CYS | B | 807 | 68.139 | 25.661 | 10.301 | 1.00 | 13.74 |
| ATOM | 3408 | CA | CYS | B | 807 | 66.732 | 25.356 | 10.390 | 1.00 | 14.46 |
| ATOM | 3409 | CB | CYS | B | 807 | 65.902 | 26.592 | 10.045 | 1.00 | 14.65 |
| ATOM | 3410 | SG | CYS | B | 807 | 65.972 | 27.842 | 11.321 | 1.00 | 15.45 |
| ATOM | 3411 | C | CYS | B | 807 | 66.401 | 24.240 | 9.434 | 1.00 | 15.18 |
| ATOM | 3412 | O | CYS | B | 807 | 67.140 | 23.974 | 8.494 | 1.00 | 16.93 |
| ATOM | 3413 | N | VAL | B | 808 | 65.288 | 23.577 | 9.709 | 1.00 | 16.40 |
| ATOM | 3414 | CA | VAL | B | 808 | 64.686 | 22.622 | 8.801 | 1.00 | 16.99 |
| ATOM | 3415 | CB | VAL | B | 808 | 64.807 | 21.176 | 9.347 | 1.00 | 17.11 |
| ATOM | 3416 | CG1 | VAL | B | 808 | 63.918 | 20.209 | 8.582 | 1.00 | 19.85 |
| ATOM | 3417 | CG2 | VAL | B | 808 | 66.250 | 20.700 | 9.260 | 1.00 | 16.89 |
| ATOM | 3418 | C | VAL | B | 808 | 63.242 | 23.074 | 8.718 | 1.00 | 18.62 |
| ATOM | 3419 | O | VAL | B | 808 | 62.713 | 23.666 | 9.663 | 1.00 | 22.21 |
| ATOM | 3420 | N | HIS | B | 809 | 62.612 | 22.863 | 7.578 | 1.00 | 19.49 |
| ATOM | 3421 | CA | HIS | B | 809 | 61.213 | 23.196 | 7.466 | 1.00 | 20.03 |
| ATOM | 3422 | CB | HIS | B | 809 | 60.960 | 24.023 | 6.209 | 1.00 | 19.92 |
| ATOM | 3423 | CG | HIS | B | 809 | 59.738 | 24.876 | 6.306 | 1.00 | 19.35 |
| ATOM | 3424 | ND1 | HIS | B | 809 | 58.468 | 24.344 | 6.380 | 1.00 | 18.21 |
| ATOM | 3425 | CE1 | HIS | B | 809 | 57.590 | 25.325 | 6.483 | 1.00 | 20.37 |
| ATOM | 3426 | NE2 | HIS | B | 809 | 58.245 | 26.472 | 6.492 | 1.00 | 21.03 |
| ATOM | 3427 | CD2 | HIS | B | 809 | 59.591 | 26.218 | 6.390 | 1.00 | 19.68 |
| ATOM | 3428 | C | HIS | B | 809 | 60.420 | 21.905 | 7.449 | 1.00 | 20.92 |
| ATOM | 3429 | O | HIS | B | 809 | 60.535 | 21.138 | 6.508 | 1.00 | 21.05 |
| ATOM | 3430 | N | ARG | B | 810 | 59.629 | 21.652 | 8.491 | 1.00 | 22.73 |
| ATOM | 3431 | CA | ARG | B | 810 | 58.878 | 20.390 | 8.574 | 1.00 | 24.84 |
| ATOM | 3432 | CB | ARG | B | 810 | 58.499 | 20.024 | 10.019 | 1.00 | 26.58 |
| ATOM | 3433 | CG | ARG | B | 810 | 59.621 | 20.086 | 11.042 | 1.00 | 30.29 |
| ATOM | 3434 | CD | ARG | B | 810 | 60.578 | 18.921 | 10.989 | 1.00 | 32.08 |
| ATOM | 3435 | NE | ARG | B | 810 | 60.584 | 18.122 | 12.216 | 1.00 | 34.30 |
| ATOM | 3436 | CZ | ARG | B | 810 | 61.639 | 17.974 | 13.016 | 1.00 | 36.80 |
| ATOM | 3437 | NH1 | ARG | B | 810 | 62.792 | 18.588 | 12.751 | 1.00 | 37.46 |
| ATOM | 3438 | NH2 | ARG | B | 810 | 61.546 | 17.208 | 14.092 | 1.00 | 37.92 |
| ATOM | 3439 | C | ARG | B | 810 | 57.623 | 20.393 | 7.706 | 1.00 | 23.84 |
| ATOM | 3440 | O | ARG | B | 810 | 56.859 | 19.427 | 7.714 | 1.00 | 25.58 |
| ATOM | 3441 | N | ASP | B | 811 | 57.405 | 21.472 | 6.963 | 1.00 | 23.12 |
| ATOM | 3442 | CA | ASP | B | 811 | 56.177 | 21.606 | 6.192 | 1.00 | 22.59 |
| ATOM | 3443 | CB | ASP | B | 811 | 55.052 | 22.164 | 7.069 | 1.00 | 21.73 |
| ATOM | 3444 | CG | ASP | B | 811 | 53.684 | 21.770 | 6.565 | 1.00 | 23.46 |
| ATOM | 3445 | OD1 | ASP | B | 811 | 52.694 | 22.045 | 7.276 | 1.00 | 26.48 |
| ATOM | 3446 | OD2 | ASP | B | 811 | 53.498 | 21.196 | 5.464 | 1.00 | 21.43 |
| ATOM | 3447 | C | ASP | B | 811 | 56.339 | 22.430 | 4.917 | 1.00 | 21.66 |
| ATOM | 3448 | O | ASP | B | 811 | 55.569 | 23.366 | 4.655 | 1.00 | 22.70 |
| ATOM | 3449 | N | LEU | B | 812 | 57.343 | 22.075 | 4.126 | 1.00 | 20.69 |
| ATOM | 3450 | CA | LEU | B | 812 | 57.591 | 22.745 | 2.867 | 1.00 | 19.74 |

FIGURE 3CP

|      | A    | B    | C   | D | E   | F      | G      | H      | I    | J     |
|------|------|------|-----|---|-----|--------|--------|--------|------|-------|
| ATOM | 3451 | CB   | LEU | B | 812 | 59.036 | 22.525 | 2.409  | 1.00 | 18.47 |
| ATOM | 3452 | CG   | LEU | B | 812 | 59.515 | 23.271 | 1.157  | 1.00 | 20.70 |
| ATOM | 3453 | CD1  | LEU | B | 812 | 59.318 | 24.809 | 1.274  | 1.00 | 18.67 |
| ATOM | 3454 | CD2  | LEU | B | 812 | 60.963 | 22.917 | 0.828  | 1.00 | 18.30 |
| ATOM | 3455 | C    | LEU | B | 812 | 56.591 | 22.240 | 1.837  | 1.00 | 21.43 |
| ATOM | 3456 | O    | LEU | B | 812 | 56.602 | 21.069 | 1.466  | 1.00 | 24.40 |
| ATOM | 3457 | N    | ALA | B | 813 | 55.710 | 23.133 | 1.404  | 1.00 | 19.70 |
| ATOM | 3458 | CA   | ALA | B | 813 | 54.707 | 22.838 | 0.385  | 1.00 | 19.11 |
| ATOM | 3459 | CB   | ALA | B | 813 | 53.539 | 22.083 | 0.990  | 1.00 | 16.44 |
| ATOM | 3460 | C    | ALA | B | 813 | 54.244 | 24.166 | -0.210 | 1.00 | 20.40 |
| ATOM | 3461 | O    | ALA | B | 813 | 54.468 | 25.232 | 0.384  | 1.00 | 18.75 |
| ATOM | 3462 | N    | ALA | B | 814 | 53.612 | 24.108 | -1.381 | 1.00 | 20.44 |
| ATOM | 3463 | CA   | ALA | B | 814 | 53.098 | 25.316 | -2.035 | 1.00 | 18.57 |
| ATOM | 3464 | CB   | ALA | B | 814 | 52.455 | 24.978 | -3.376 | 1.00 | 19.18 |
| ATOM | 3465 | C    | ALA | B | 814 | 52.128 | 26.089 | -1.142 | 1.00 | 16.60 |
| ATOM | 3466 | O    | ALA | B | 814 | 52.156 | 27.316 | -1.117 | 1.00 | 17.71 |
| ATOM | 3467 | N    | ARG | B | 815 | 51.299 | 25.373 | -0.383 | 1.00 | 16.66 |
| ATOM | 3468 | CA   | ARG | B | 815 | 50.341 | 26.009 | 0.543  | 1.00 | 16.35 |
| ATOM | 3469 | CB   | ARG | B | 815 | 49.399 | 24.968 | 1.152  | 1.00 | 14.54 |
| ATOM | 3470 | CG   | ARG | B | 815 | 50.059 | 24.082 | 2.192  | 1.00 | 15.92 |
| ATOM | 3471 | CD   | ARG | B | 815 | 49.197 | 22.944 | 2.745  | 1.00 | 17.54 |
| ATOM | 3472 | NE   | ARG | B | 815 | 50.055 | 22.038 | 3.508  | 1.00 | 22.41 |
| ATOM | 3473 | CZ   | ARG | B | 815 | 50.672 | 20.958 | 3.017  | 1.00 | 22.03 |
| ATOM | 3474 | NH1  | ARG | B | 815 | 51.451 | 20.238 | 3.812  | 1.00 | 19.28 |
| ATOM | 3475 | NH2  | ARG | B | 815 | 50.499 | 20.584 | 1.748  | 1.00 | 21.13 |
| ATOM | 3476 | C    | ARG | B | 815 | 51.011 | 26.848 | 1.652  | 1.00 | 17.45 |
| ATOM | 3477 | O    | ARG | B | 815 | 50.371 | 27.712 | 2.263  | 1.00 | 16.74 |
| ATOM | 3478 | N    | ASN | B | 816 | 52.295 | 26.598 | 1.906  | 1.00 | 17.96 |
| ATOM | 3479 | CA   | ASN | B | 816 | 53.027 | 27.344 | 2.930  | 1.00 | 17.44 |
| ATOM | 3480 | CB   | ASN | B | 816 | 53.665 | 26.395 | 3.935  | 1.00 | 17.47 |
| ATOM | 3481 | CG   | ASN | B | 816 | 52.636 | 25.641 | 4.744  | 1.00 | 19.54 |
| ATOM | 3482 | OD1  | ASN | B | 816 | 52.815 | 24.457 | 5.057  | 1.00 | 21.03 |
| ATOM | 3483 | ND2  | ASN | B | 816 | 51.548 | 26.322 | 5.095  | 1.00 | 17.35 |
| ATOM | 3484 | C    | ASN | B | 816 | 54.050 | 28.317 | 2.360  | 1.00 | 16.62 |
| ATOM | 3485 | O    | ASN | B | 816 | 54.870 | 28.890 | 3.092  | 1.00 | 16.63 |
| ATOM | 3486 | N    | VAL | B | 817 | 53.981 | 28.512 | 1.050  | 1.00 | 13.74 |
| ATOM | 3487 | CA   | VAL | B | 817 | 54.758 | 29.547 | 0.393  | 1.00 | 14.10 |
| ATOM | 3488 | CB   | VAL | B | 817 | 55.543 | 28.979 | -0.812 | 1.00 | 14.07 |
| ATOM | 3489 | CG1  | VAL | B | 817 | 56.210 | 30.098 | -1.620 | 1.00 | 12.21 |
| ATOM | 3490 | CG2  | VAL | B | 817 | 56.589 | 27.958 | -0.324 | 1.00 | 12.53 |
| ATOM | 3491 | C    | VAL | B | 817 | 53.767 | 30.629 | -0.022 | 1.00 | 15.09 |
| ATOM | 3492 | O    | VAL | B | 817 | 52.637 | 30.326 | -0.402 | 1.00 | 16.32 |
| ATOM | 3493 | N    | LEU | B | 818 | 54.181 | 31.886 | 0.071  | 1.00 | 13.83 |
| ATOM | 3494 | CA   | LEU | B | 818 | 53.282 | 32.998 | -0.184 | 1.00 | 15.91 |
| ATOM | 3495 | CB   | LEU | B | 818 | 53.125 | 33.838 | 1.083  | 1.00 | 17.68 |
| ATOM | 3496 | CG   | LEU | B | 818 | 52.527 | 33.148 | 2.307  | 1.00 | 17.73 |
| ATOM | 3497 | CD1  | LEU | B | 818 | 52.638 | 34.088 | 3.456  | 1.00 | 18.67 |
| ATOM | 3498 | CD2  | LEU | B | 818 | 51.065 | 32.778 | 2.083  | 1.00 | 19.55 |
| ATOM | 3499 | C    | LEU | B | 818 | 53.760 | 33.872 | -1.333 | 1.00 | 16.91 |
| ATOM | 3500 | O    | LEU | B | 818 | 54.963 | 33.984 | -1.577 | 1.00 | 17.68 |
| ATOM | 3501 | N    | VAL | B | 819 | 52.812 | 34.498 | -2.030 | 1.00 | 16.48 |
| ATOM | 3502 | CA   | VAL | B | 819 | 53.133 | 35.311 | -3.197 | 1.00 | 16.32 |

FIGURE 3CQ

|      | A    | B    | C   | D   | E | F      | G      | H       | I    | J     |
|------|------|------|-----|-----|---|--------|--------|---------|------|-------|
| ATOM | 3503 | CB   | VAL | B | 819 | 52.367 | 34.848 | -4.469  | 1.00 | 17.71 |
| ATOM | 3504 | CG1  | VAL | B | 819 | 52.942 | 35.496 | -5.722  | 1.00 | 17.84 |
| ATOM | 3505 | CG2  | VAL | B | 819 | 52.411 | 33.330 | -4.616  | 1.00 | 17.68 |
| ATOM | 3506 | C    | VAL | B | 819 | 52.858 | 36.776 | -2.916  | 1.00 | 16.62 |
| ATOM | 3507 | O    | VAL | B | 819 | 51.837 | 37.132 | -2.325  | 1.00 | 18.28 |
| ATOM | 3508 | N    | THR | B | 820 | 53.790 | 37.623 | -3.329  | 1.00 | 16.80 |
| ATOM | 3509 | CA   | THR | B | 820 | 53.621 | 39.062 | -3.210  | 1.00 | 16.48 |
| ATOM | 3510 | CB   | THR | B | 820 | 54.463 | 39.631 | -2.025  | 1.00 | 15.94 |
| ATOM | 3511 | OG1  | THR | B | 820 | 54.285 | 41.049 | -1.937  | 1.00 | 18.76 |
| ATOM | 3512 | CG2  | THR | B | 820 | 55.959 | 39.473 | -2.257  | 1.00 | 16.10 |
| ATOM | 3513 | C    | THR | B | 820 | 53.909 | 39.737 | -4.556  | 1.00 | 17.36 |
| ATOM | 3514 | O    | THR | B | 820 | 53.976 | 39.064 | -5.592  | 1.00 | 17.36 |
| ATOM | 3515 | N    | HIS | B | 821 | 54.048 | 41.060 | -4.541  | 1.00 | 18.70 |
| ATOM | 3516 | CA   | HIS | B | 821 | 54.274 | 41.840 | -5.753  | 1.00 | 19.39 |
| ATOM | 3517 | CB   | HIS | B | 821 | 54.331 | 43.327 | -5.418  | 1.00 | 18.95 |
| ATOM | 3518 | CG   | HIS | B | 821 | 53.033 | 43.879 | -4.919  | 1.00 | 20.34 |
| ATOM | 3519 | ND1  | HIS | B | 821 | 52.822 | 44.198 | -3.595  | 1.00 | 21.21 |
| ATOM | 3520 | CE1  | HIS | B | 821 | 51.595 | 44.668 | -3.450  | 1.00 | 22.78 |
| ATOM | 3521 | NE2  | HIS | B | 821 | 51.000 | 44.657 | -4.631  | 1.00 | 22.57 |
| ATOM | 3522 | CD2  | HIS | B | 821 | 51.878 | 44.169 | -5.567  | 1.00 | 20.03 |
| ATOM | 3523 | C    | HIS | B | 821 | 55.535 | 41.421 | -6.505  | 1.00 | 20.10 |
| ATOM | 3524 | O    | HIS | B | 821 | 56.531 | 41.022 | -5.896  | 1.00 | 21.62 |
| ATOM | 3525 | N    | GLY | B | 822 | 55.465 | 41.501 | -7.833  | 1.00 | 19.52 |
| ATOM | 3526 | CA   | GLY | B | 822 | 56.604 | 41.254 | -8.698  | 1.00 | 18.44 |
| ATOM | 3527 | C    | GLY | B | 822 | 56.950 | 39.788 | -8.827  | 1.00 | 19.11 |
| ATOM | 3528 | O    | GLY | B | 822 | 58.098 | 39.451 | -9.110  | 1.00 | 20.35 |
| ATOM | 3529 | N    | LYS | B | 823 | 55.953 | 38.926 | -8.630  | 1.00 | 18.80 |
| ATOM | 3530 | CA   | LYS | B | 823 | 56.129 | 37.470 | -8.669  | 1.00 | 19.82 |
| ATOM | 3531 | CB   | LYS | B | 823 | 56.449 | 36.978 | -10.091 | 1.00 | 21.36 |
| ATOM | 3532 | CG   | LYS | B | 823 | 55.491 | 37.477 | -11.186 | 1.00 | 22.04 |
| ATOM | 3533 | CD   | LYS | B | 823 | 54.457 | 36.427 | -11.548 | 1.00 | 22.09 |
| ATOM | 3534 | CE   | LYS | B | 823 | 53.405 | 36.971 | -12.506 | 1.00 | 24.27 |
| ATOM | 3535 | NZ   | LYS | B | 823 | 53.925 | 37.199 | -13.884 | 1.00 | 25.31 |
| ATOM | 3536 | C    | LYS | B | 823 | 57.179 | 36.983 | -7.654  | 1.00 | 18.84 |
| ATOM | 3537 | O    | LYS | B | 823 | 57.861 | 35.984 | -7.870  | 1.00 | 18.97 |
| ATOM | 3538 | N    | VAL | B | 824 | 57.286 | 37.700 | -6.540  | 1.00 | 17.25 |
| ATOM | 3539 | CA   | VAL | B | 824 | 58.189 | 37.326 | -5.460  | 1.00 | 16.75 |
| ATOM | 3540 | CB   | VAL | B | 824 | 58.669 | 38.573 | -4.655  | 1.00 | 15.38 |
| ATOM | 3541 | CG1  | VAL | B | 824 | 59.462 | 38.166 | -3.426  | 1.00 | 14.86 |
| ATOM | 3542 | CG2  | VAL | B | 824 | 59.496 | 39.500 | -5.536  | 1.00 | 13.51 |
| ATOM | 3543 | C    | VAL | B | 824 | 57.472 | 36.337 | -4.546  | 1.00 | 16.39 |
| ATOM | 3544 | O    | VAL | B | 824 | 56.291 | 36.521 | -4.223  | 1.00 | 18.27 |
| ATOM | 3545 | N    | VAL | B | 825 | 58.171 | 35.280 | -4.151  | 1.00 | 15.21 |
| ATOM | 3546 | CA   | VAL | B | 825 | 57.611 | 34.343 | -3.187  | 1.00 | 15.82 |
| ATOM | 3547 | CB   | VAL | B | 825 | 57.354 | 32.920 | -3.770  | 1.00 | 16.31 |
| ATOM | 3548 | CG1  | VAL | B | 825 | 56.253 | 32.968 | -4.815  | 1.00 | 18.11 |
| ATOM | 3549 | CG2  | VAL | B | 825 | 58.620 | 32.292 | -4.336  | 1.00 | 15.31 |
| ATOM | 3550 | C    | VAL | B | 825 | 58.417 | 34.269 | -1.895  | 1.00 | 15.81 |
| ATOM | 3551 | O    | VAL | B | 825 | 59.643 | 34.450 | -1.886  | 1.00 | 15.05 |
| ATOM | 3552 | N    | LYS | B | 826 | 57.691 | 34.015 | -0.810  | 1.00 | 14.00 |
| ATOM | 3553 | CA   | LYS | B | 826 | 58.241 | 33.964 | 0.528   | 1.00 | 12.03 |
| ATOM | 3554 | CB   | LYS | B | 826 | 57.824 | 35.217 | 1.293   | 1.00 | 9.65  |

FIGURE 3CR

|  | A | B | C | D | E | F | G | H | I | J |
|---|---|---|---|---|---|---|---|---|---|---|
| ATOM | 3555 | CG | LYS | B | 826 | 58.653 | 36.431 | 0.963 | 1.00 | 7.12 |
| ATOM | 3556 | CD | LYS | B | 826 | 57.893 | 37.722 | 1.227 | 1.00 | 5.82 |
| ATOM | 3557 | CE | LYS | B | 826 | 58.796 | 38.933 | 1.095 | 1.00 | 3.98 |
| ATOM | 3558 | NZ | LYS | B | 826 | 59.993 | 38.849 | 1.995 | 1.00 | 5.65 |
| ATOM | 3559 | C | LYS | B | 826 | 57.731 | 32.710 | 1.239 | 1.00 | 13.61 |
| ATOM | 3560 | O | LYS | B | 826 | 56.532 | 32.410 | 1.203 | 1.00 | 13.68 |
| ATOM | 3561 | N | ILE | B | 827 | 58.647 | 31.973 | 1.863 | 1.00 | 12.90 |
| ATOM | 3562 | CA | ILE | B | 827 | 58.284 | 30.808 | 2.661 | 1.00 | 12.32 |
| ATOM | 3563 | CB | ILE | B | 827 | 59.484 | 29.849 | 2.810 | 1.00 | 12.42 |
| ATOM | 3564 | CG1 | ILE | B | 827 | 60.042 | 29.438 | 1.443 | 1.00 | 12.00 |
| ATOM | 3565 | CD1 | ILE | B | 827 | 61.431 | 28.787 | 1.531 | 1.00 | 12.29 |
| ATOM | 3566 | CG2 | ILE | B | 827 | 59.106 | 28.634 | 3.660 | 1.00 | 10.27 |
| ATOM | 3567 | C | ILE | B | 827 | 57.858 | 31.288 | 4.032 | 1.00 | 12.79 |
| ATOM | 3568 | O | ILE | B | 827 | 58.564 | 32.082 | 4.658 | 1.00 | 14.32 |
| ATOM | 3569 | N | CYS | B | 828 | 56.718 | 30.807 | 4.512 | 1.00 | 14.91 |
| ATOM | 3570 | CA | CYS | B | 828 | 56.301 | 31.143 | 5.872 | 1.00 | 17.84 |
| ATOM | 3571 | CB | CYS | B | 828 | 54.778 | 31.338 | 5.982 | 1.00 | 19.57 |
| ATOM | 3572 | SG | CYS | B | 828 | 53.811 | 29.814 | 6.052 | 1.00 | 24.52 |
| ATOM | 3573 | C | CYS | B | 828 | 56.838 | 30.127 | 6.883 | 1.00 | 17.60 |
| ATOM | 3574 | O | CYS | B | 828 | 57.360 | 29.079 | 6.506 | 1.00 | 18.57 |
| ATOM | 3575 | N | ASP | B | 829 | 56.706 | 30.452 | 8.163 | 1.00 | 18.36 |
| ATOM | 3576 | CA | ASP | B | 829 | 57.325 | 29.686 | 9.230 | 1.00 | 18.29 |
| ATOM | 3577 | CB | ASP | B | 829 | 57.740 | 30.630 | 10.362 | 1.00 | 18.33 |
| ATOM | 3578 | CG | ASP | B | 829 | 56.553 | 31.250 | 11.083 | 1.00 | 18.16 |
| ATOM | 3579 | OD1 | ASP | B | 829 | 55.388 | 30.962 | 10.735 | 1.00 | 17.35 |
| ATOM | 3580 | OD2 | ASP | B | 829 | 56.699 | 32.047 | 12.026 | 1.00 | 19.20 |
| ATOM | 3581 | C | ASP | B | 829 | 56.455 | 28.560 | 9.786 | 1.00 | 18.70 |
| ATOM | 3582 | O | ASP | B | 829 | 56.773 | 27.984 | 10.831 | 1.00 | 18.33 |
| ATOM | 3583 | N | PHE | B | 830 | 55.359 | 28.250 | 9.104 | 1.00 | 20.04 |
| ATOM | 3584 | CA | PHE | B | 830 | 54.480 | 27.186 | 9.567 | 1.00 | 21.59 |
| ATOM | 3585 | CB | PHE | B | 830 | 53.117 | 27.240 | 8.871 | 1.00 | 24.76 |
| ATOM | 3586 | CG | PHE | B | 830 | 52.128 | 26.253 | 9.419 | 1.00 | 28.46 |
| ATOM | 3587 | CD1 | PHE | B | 830 | 51.705 | 25.175 | 8.649 | 1.00 | 30.64 |
| ATOM | 3588 | CE1 | PHE | B | 830 | 50.800 | 24.247 | 9.158 | 1.00 | 31.89 |
| ATOM | 3589 | CZ | PHE | B | 830 | 50.319 | 24.391 | 10.457 | 1.00 | 31.55 |
| ATOM | 3590 | CE2 | PHE | B | 830 | 50.742 | 25.462 | 11.235 | 1.00 | 30.85 |
| ATOM | 3591 | CD2 | PHE | B | 830 | 51.640 | 26.384 | 10.715 | 1.00 | 29.53 |
| ATOM | 3592 | C | PHE | B | 830 | 55.154 | 25.839 | 9.360 | 1.00 | 21.33 |
| ATOM | 3593 | O | PHE | B | 830 | 55.190 | 25.322 | 8.243 | 1.00 | 24.87 |
| ATOM | 3594 | N | GLY | B | 831 | 55.702 | 25.288 | 10.439 | 1.00 | 19.06 |
| ATOM | 3595 | CA | GLY | B | 831 | 56.478 | 24.063 | 10.373 | 1.00 | 19.33 |
| ATOM | 3596 | C | GLY | B | 831 | 57.986 | 24.288 | 10.431 | 1.00 | 21.48 |
| ATOM | 3597 | O | GLY | B | 831 | 58.760 | 23.325 | 10.416 | 1.00 | 20.05 |
| ATOM | 3598 | N | LEU | B | 832 | 58.402 | 25.553 | 10.499 | 1.00 | 21.43 |
| ATOM | 3599 | CA | LEU | B | 832 | 59.813 | 25.902 | 10.632 | 1.00 | 21.82 |
| ATOM | 3600 | CB | LEU | B | 832 | 60.027 | 27.400 | 10.381 | 1.00 | 22.22 |
| ATOM | 3601 | CG | LEU | B | 832 | 61.460 | 27.939 | 10.429 | 1.00 | 22.44 |
| ATOM | 3602 | CD1 | LEU | B | 832 | 62.290 | 27.313 | 9.330 | 1.00 | 22.89 |
| ATOM | 3603 | CD2 | LEU | B | 832 | 61.479 | 29.459 | 10.317 | 1.00 | 23.88 |
| ATOM | 3604 | C | LEU | B | 832 | 60.359 | 25.513 | 12.006 | 1.00 | 22.06 |
| ATOM | 3605 | O | LEU | B | 832 | 59.765 | 25.830 | 13.034 | 1.00 | 21.35 |
| ATOM | 3606 | N | ALA | B | 833 | 61.495 | 24.821 | 12.010 | 1.00 | 22.80 |

FIGURE 3CS

| | A | B | C | D | E | F | G | H | I | J |
|---|---|---|---|---|---|---|---|---|---|---|
| ATOM | 3607 | CA | ALA | B | 833 | 62.125 | 24.371 | 13.246 | 1.00 | 24.13 |
| ATOM | 3608 | CB | ALA | B | 833 | 61.885 | 22.883 | 13.443 | 1.00 | 22.06 |
| ATOM | 3609 | C | ALA | B | 833 | 63.618 | 24.676 | 13.240 | 1.00 | 26.68 |
| ATOM | 3610 | O | ALA | B | 833 | 64.274 | 24.557 | 12.204 | 1.00 | 26.86 |
| ATOM | 3611 | N | ARG | B | 834 | 64.152 | 25.063 | 14.397 | 1.00 | 30.17 |
| ATOM | 3612 | CA | ARG | B | 834 | 65.590 | 25.295 | 14.531 | 1.00 | 33.72 |
| ATOM | 3613 | CB | ARG | B | 834 | 65.893 | 26.234 | 15.697 | 1.00 | 36.77 |
| ATOM | 3614 | CG | ARG | B | 834 | 65.770 | 27.708 | 15.321 | 1.00 | 40.58 |
| ATOM | 3615 | CD | ARG | B | 834 | 66.899 | 28.602 | 15.834 | 1.00 | 44.64 |
| ATOM | 3616 | NE | ARG | B | 834 | 67.829 | 28.997 | 14.769 | 1.00 | 47.10 |
| ATOM | 3617 | CZ | ARG | B | 834 | 68.203 | 30.252 | 14.504 | 1.00 | 48.58 |
| ATOM | 3618 | NH1 | ARG | B | 834 | 69.058 | 30.491 | 13.517 | 1.00 | 48.29 |
| ATOM | 3619 | NH2 | ARG | B | 834 | 67.731 | 31.272 | 15.220 | 1.00 | 49.22 |
| ATOM | 3620 | C | ARG | B | 834 | 66.371 | 23.984 | 14.636 | 1.00 | 34.50 |
| ATOM | 3621 | O | ARG | B | 834 | 65.812 | 22.961 | 15.018 | 1.00 | 36.02 |
| ATOM | 3622 | N | ASP | B | 835 | 67.660 | 24.051 | 14.289 | 1.00 | 36.14 |
| ATOM | 3623 | CA | ASP | B | 835 | 68.588 | 22.912 | 14.074 | 1.00 | 35.88 |
| ATOM | 3624 | CB | ASP | B | 835 | 68.479 | 21.818 | 15.141 | 1.00 | 37.96 |
| ATOM | 3625 | CG | ASP | B | 835 | 68.561 | 22.362 | 16.541 | 1.00 | 40.17 |
| ATOM | 3626 | OD1 | ASP | B | 835 | 69.469 | 23.176 | 16.821 | 1.00 | 41.13 |
| ATOM | 3627 | OD2 | ASP | B | 835 | 67.746 | 22.035 | 17.427 | 1.00 | 42.88 |
| ATOM | 3628 | C | ASP | B | 835 | 68.503 | 22.316 | 12.666 | 1.00 | 33.99 |
| ATOM | 3629 | O | ASP | B | 835 | 69.501 | 22.297 | 11.944 | 1.00 | 30.51 |
| TER | 3629 | | ASP | B | 835 | | | | | |
| ATOM | 3630 | C | LEU | B | 850 | 50.978 | 15.314 | 7.451 | 1.00 | 27.17 |
| ATOM | 3631 | N | LEU | B | 850 | 49.890 | 15.600 | 9.640 | 1.00 | 29.37 |
| ATOM | 3632 | O | LEU | B | 850 | 50.107 | 14.783 | 6.750 | 1.00 | 27.04 |
| ATOM | 3633 | CA | LEU | B | 850 | 51.063 | 15.073 | 8.954 | 1.00 | 30.28 |
| ATOM | 3634 | CB | LEU | B | 850 | 51.225 | 13.579 | 9.239 | 1.00 | 32.27 |
| ATOM | 3635 | CD1 | LEU | B | 850 | 53.557 | 14.162 | 9.962 | 1.00 | 36.30 |
| ATOM | 3636 | CD2 | LEU | B | 850 | 52.705 | 11.883 | 10.347 | 1.00 | 36.63 |
| ATOM | 3637 | CG | LEU | B | 850 | 52.659 | 13.071 | 9.399 | 1.00 | 35.79 |
| ATOM | 3638 | N | PRO | B | 851 | 51.957 | 15.999 | 6.811 | 1.00 | 23.09 |
| ATOM | 3639 | CA | PRO | B | 851 | 51.958 | 16.228 | 5.358 | 1.00 | 19.44 |
| ATOM | 3640 | CB | PRO | B | 851 | 52.746 | 17.530 | 5.222 | 1.00 | 19.15 |
| ATOM | 3641 | CG | PRO | B | 851 | 53.673 | 17.547 | 6.399 | 1.00 | 18.79 |
| ATOM | 3642 | CD | PRO | B | 851 | 52.994 | 16.790 | 7.499 | 1.00 | 20.58 |
| ATOM | 3643 | C | PRO | B | 851 | 52.665 | 15.101 | 4.606 | 1.00 | 18.09 |
| ATOM | 3644 | O | PRO | B | 851 | 53.718 | 15.323 | 4.003 | 1.00 | 17.82 |
| ATOM | 3645 | N | VAL | B | 852 | 52.069 | 13.911 | 4.631 | 1.00 | 16.14 |
| ATOM | 3646 | CA | VAL | B | 852 | 52.745 | 12.681 | 4.222 | 1.00 | 16.42 |
| ATOM | 3647 | CB | VAL | B | 852 | 51.835 | 11.450 | 4.433 | 1.00 | 16.46 |
| ATOM | 3648 | CG1 | VAL | B | 852 | 52.389 | 10.227 | 3.715 | 1.00 | 16.34 |
| ATOM | 3649 | CG2 | VAL | B | 852 | 51.651 | 11.168 | 5.928 | 1.00 | 16.60 |
| ATOM | 3650 | C | VAL | B | 852 | 53.289 | 12.725 | 2.790 | 1.00 | 16.88 |
| ATOM | 3651 | O | VAL | B | 852 | 54.414 | 12.271 | 2.521 | 1.00 | 17.25 |
| ATOM | 3652 | N | LYS | B | 853 | 52.504 | 13.297 | 1.885 | 1.00 | 16.02 |
| ATOM | 3653 | CA | LYS | B | 853 | 52.869 | 13.342 | 0.473 | 1.00 | 16.79 |
| ATOM | 3654 | CB | LYS | B | 853 | 51.648 | 13.693 | -0.388 | 1.00 | 16.01 |
| ATOM | 3655 | CG | LYS | B | 853 | 50.755 | 12.486 | -0.653 | 1.00 | 15.76 |
| ATOM | 3656 | CD | LYS | B | 853 | 49.460 | 12.869 | -1.328 | 1.00 | 15.65 |
| ATOM | 3657 | CE | LYS | B | 853 | 48.708 | 11.641 | -1.783 | 1.00 | 14.13 |

FIGURE 3CT

| | A | B | C | D | E | F | G | H | I | J |
|---|---|---|---|---|---|---|---|---|---|---|
| ATOM | 3658 | NZ | LYS | B | 853 | 47.954 | 11.888 | -3.054 | 1.00 | 12.40 |
| ATOM | 3659 | C | LYS | B | 853 | 54.057 | 14.258 | 0.180 | 1.00 | 16.70 |
| ATOM | 3660 | O | LYS | B | 853 | 54.617 | 14.204 | -0.907 | 1.00 | 18.86 |
| ATOM | 3661 | N | TRP | B | 854 | 54.443 | 15.079 | 1.157 | 1.00 | 16.16 |
| ATOM | 3662 | CA | TRP | B | 854 | 55.593 | 15.977 | 1.025 | 1.00 | 16.36 |
| ATOM | 3663 | CB | TRP | B | 854 | 55.219 | 17.388 | 1.487 | 1.00 | 15.89 |
| ATOM | 3664 | CG | TRP | B | 854 | 54.363 | 18.122 | 0.510 | 1.00 | 16.05 |
| ATOM | 3665 | CD1 | TRP | B | 854 | 54.773 | 19.054 | -0.398 | 1.00 | 15.85 |
| ATOM | 3666 | NE1 | TRP | B | 854 | 53.704 | 19.496 | -1.140 | 1.00 | 13.97 |
| ATOM | 3667 | CE2 | TRP | B | 854 | 52.570 | 18.854 | -0.716 | 1.00 | 15.21 |
| ATOM | 3668 | CD2 | TRP | B | 854 | 52.950 | 17.973 | 0.322 | 1.00 | 14.80 |
| ATOM | 3669 | CE3 | TRP | B | 854 | 51.960 | 17.184 | 0.928 | 1.00 | 14.23 |
| ATOM | 3670 | CZ3 | TRP | B | 854 | 50.636 | 17.306 | 0.491 | 1.00 | 14.17 |
| ATOM | 3671 | CH2 | TRP | B | 854 | 50.291 | 18.192 | -0.545 | 1.00 | 14.51 |
| ATOM | 3672 | CZ2 | TRP | B | 854 | 51.239 | 18.977 | -1.157 | 1.00 | 15.89 |
| ATOM | 3673 | C | TRP | B | 854 | 56.827 | 15.498 | 1.808 | 1.00 | 18.33 |
| ATOM | 3674 | O | TRP | B | 854 | 57.883 | 16.129 | 1.764 | 1.00 | 16.83 |
| ATOM | 3675 | N | MET | B | 855 | 56.700 | 14.377 | 2.510 | 1.00 | 19.25 |
| ATOM | 3676 | CA | MET | B | 855 | 57.743 | 13.956 | 3.433 | 1.00 | 18.02 |
| ATOM | 3677 | CB | MET | B | 855 | 57.135 | 13.296 | 4.662 | 1.00 | 18.00 |
| ATOM | 3678 | CG | MET | B | 855 | 56.585 | 14.299 | 5.651 | 1.00 | 19.69 |
| ATOM | 3679 | SD | MET | B | 855 | 55.548 | 13.515 | 6.857 | 1.00 | 21.52 |
| ATOM | 3680 | CE | MET | B | 855 | 56.824 | 12.796 | 7.953 | 1.00 | 20.44 |
| ATOM | 3681 | C | MET | B | 855 | 58.770 | 13.043 | 2.802 | 1.00 | 17.22 |
| ATOM | 3682 | O | MET | B | 855 | 58.433 | 12.123 | 2.067 | 1.00 | 19.09 |
| ATOM | 3683 | N | ALA | B | 856 | 60.033 | 13.320 | 3.100 | 1.00 | 16.48 |
| ATOM | 3684 | CA | ALA | B | 856 | 61.131 | 12.466 | 2.695 | 1.00 | 15.46 |
| ATOM | 3685 | CB | ALA | B | 856 | 62.429 | 13.064 | 3.157 | 1.00 | 13.43 |
| ATOM | 3686 | C | ALA | B | 856 | 60.932 | 11.073 | 3.304 | 1.00 | 15.44 |
| ATOM | 3687 | O | ALA | B | 856 | 60.418 | 10.952 | 4.424 | 1.00 | 15.44 |
| ATOM | 3688 | N | PRO | B | 857 | 61.324 | 10.027 | 2.577 | 1.00 | 14.84 |
| ATOM | 3689 | CA | PRO | B | 857 | 61.240 | 8.659 | 3.101 | 1.00 | 15.59 |
| ATOM | 3690 | CB | PRO | B | 857 | 61.920 | 7.809 | 2.014 | 1.00 | 15.55 |
| ATOM | 3691 | CG | PRO | B | 857 | 62.631 | 8.777 | 1.128 | 1.00 | 14.85 |
| ATOM | 3692 | CD | PRO | B | 857 | 61.850 | 10.055 | 1.203 | 1.00 | 15.44 |
| ATOM | 3693 | C | PRO | B | 857 | 61.939 | 8.502 | 4.453 | 1.00 | 15.43 |
| ATOM | 3694 | O | PRO | B | 857 | 61.396 | 7.793 | 5.302 | 1.00 | 15.31 |
| ATOM | 3695 | N | GLU | B | 858 | 63.079 | 9.161 | 4.673 | 1.00 | 13.42 |
| ATOM | 3696 | CA | GLU | B | 858 | 63.757 | 9.027 | 5.970 | 1.00 | 14.75 |
| ATOM | 3697 | CB | GLU | B | 858 | 65.213 | 9.528 | 5.932 | 1.00 | 14.76 |
| ATOM | 3698 | CG | GLU | B | 858 | 65.386 | 11.036 | 5.865 | 1.00 | 15.50 |
| ATOM | 3699 | CD | GLU | B | 858 | 65.349 | 11.581 | 4.446 | 1.00 | 16.93 |
| ATOM | 3700 | OE1 | GLU | B | 858 | 64.975 | 10.832 | 3.512 | 1.00 | 13.94 |
| ATOM | 3701 | OE2 | GLU | B | 858 | 65.683 | 12.776 | 4.274 | 1.00 | 17.01 |
| ATOM | 3702 | C | GLU | B | 858 | 62.967 | 9.654 | 7.127 | 1.00 | 15.65 |
| ATOM | 3703 | O | GLU | B | 858 | 63.102 | 9.235 | 8.282 | 1.00 | 16.29 |
| ATOM | 3704 | N | SER | B | 859 | 62.134 | 10.644 | 6.816 | 1.00 | 13.68 |
| ATOM | 3705 | CA | SER | B | 859 | 61.281 | 11.242 | 7.828 | 1.00 | 15.12 |
| ATOM | 3706 | CB | SER | B | 859 | 60.717 | 12.585 | 7.347 | 1.00 | 16.17 |
| ATOM | 3707 | OG | SER | B | 859 | 61.765 | 13.479 | 6.971 | 1.00 | 16.85 |
| ATOM | 3708 | C | SER | B | 859 | 60.161 | 10.271 | 8.167 | 1.00 | 16.30 |
| ATOM | 3709 | O | SER | B | 859 | 59.877 | 10.017 | 9.337 | 1.00 | 15.06 |

FIGURE 3CU

| | A | B | C | D | E | F | G | H | I | J |
|---|---|---|---|---|---|---|---|---|---|---|
| ATOM | 3710 | N | LEU | B | 860 | 59.538 | 9.725 | 7.127 | 1.00 | 15.57 |
| ATOM | 3711 | CA | LEU | B | 860 | 58.459 | 8.775 | 7.285 | 1.00 | 14.13 |
| ATOM | 3712 | CB | LEU | B | 860 | 57.846 | 8.453 | 5.918 | 1.00 | 15.74 |
| ATOM | 3713 | CG | LEU | B | 860 | 56.983 | 9.513 | 5.228 | 1.00 | 14.72 |
| ATOM | 3714 | CD1 | LEU | B | 860 | 56.659 | 9.064 | 3.825 | 1.00 | 13.54 |
| ATOM | 3715 | CD2 | LEU | B | 860 | 55.711 | 9.765 | 6.006 | 1.00 | 14.97 |
| ATOM | 3716 | C | LEU | B | 860 | 58.916 | 7.483 | 7.945 | 1.00 | 15.26 |
| ATOM | 3717 | O | LEU | B | 860 | 58.221 | 6.947 | 8.816 | 1.00 | 15.13 |
| ATOM | 3718 | N | PHE | B | 861 | 60.078 | 6.978 | 7.526 | 1.00 | 13.87 |
| ATOM | 3719 | CA | PHE | B | 861 | 60.469 | 5.608 | 7.859 | 1.00 | 11.79 |
| ATOM | 3720 | CB | PHE | B | 861 | 60.910 | 4.846 | 6.601 | 1.00 | 11.54 |
| ATOM | 3721 | CG | PHE | B | 861 | 59.880 | 4.829 | 5.488 | 1.00 | 11.48 |
| ATOM | 3722 | CD1 | PHE | B | 861 | 60.228 | 5.217 | 4.198 | 1.00 | 11.60 |
| ATOM | 3723 | CE1 | PHE | B | 861 | 59.293 | 5.199 | 3.160 | 1.00 | 10.49 |
| ATOM | 3724 | CZ | PHE | B | 861 | 57.999 | 4.791 | 3.406 | 1.00 | 11.77 |
| ATOM | 3725 | CE2 | PHE | B | 861 | 57.634 | 4.387 | 4.695 | 1.00 | 12.59 |
| ATOM | 3726 | CD2 | PHE | B | 861 | 58.574 | 4.415 | 5.724 | 1.00 | 11.79 |
| ATOM | 3727 | C | PHE | B | 861 | 61.545 | 5.526 | 8.934 | 1.00 | 12.96 |
| ATOM | 3728 | O | PHE | B | 861 | 61.771 | 4.456 | 9.506 | 1.00 | 12.81 |
| ATOM | 3729 | N | GLU | B | 862 | 62.202 | 6.650 | 9.214 | 1.00 | 13.32 |
| ATOM | 3730 | CA | GLU | B | 862 | 63.301 | 6.674 | 10.178 | 1.00 | 12.89 |
| ATOM | 3731 | CB | GLU | B | 862 | 64.648 | 6.801 | 9.447 | 1.00 | 12.66 |
| ATOM | 3732 | CG | GLU | B | 862 | 64.939 | 5.623 | 8.528 | 1.00 | 14.02 |
| ATOM | 3733 | CD | GLU | B | 862 | 66.273 | 5.725 | 7.814 | 1.00 | 17.85 |
| ATOM | 3734 | OE1 | GLU | B | 862 | 66.280 | 6.117 | 6.625 | 1.00 | 17.50 |
| ATOM | 3735 | OE2 | GLU | B | 862 | 67.313 | 5.382 | 8.429 | 1.00 | 18.76 |
| ATOM | 3736 | C | GLU | B | 862 | 63.130 | 7.786 | 11.209 | 1.00 | 14.13 |
| ATOM | 3737 | O | GLU | B | 862 | 63.844 | 7.832 | 12.210 | 1.00 | 13.05 |
| ATOM | 3738 | N | GLY | B | 863 | 62.173 | 8.678 | 10.959 | 1.00 | 16.93 |
| ATOM | 3739 | CA | GLY | B | 863 | 61.950 | 9.840 | 11.804 | 1.00 | 16.25 |
| ATOM | 3740 | C | GLY | B | 863 | 63.110 | 10.814 | 11.771 | 1.00 | 18.11 |
| ATOM | 3741 | O | GLY | B | 863 | 63.405 | 11.450 | 12.779 | 1.00 | 19.93 |
| ATOM | 3742 | N | ILE | B | 864 | 63.771 | 10.913 | 10.616 | 1.00 | 18.51 |
| ATOM | 3743 | CA | ILE | B | 864 | 64.908 | 11.813 | 10.426 | 1.00 | 15.64 |
| ATOM | 3744 | CB | ILE | B | 864 | 66.073 | 11.094 | 9.719 | 1.00 | 14.93 |
| ATOM | 3745 | CG1 | ILE | B | 864 | 66.726 | 10.078 | 10.667 | 1.00 | 15.65 |
| ATOM | 3746 | CD1 | ILE | B | 864 | 67.646 | 9.074 | 9.993 | 1.00 | 13.72 |
| ATOM | 3747 | CG2 | ILE | B | 864 | 67.107 | 12.123 | 9.240 | 1.00 | 14.64 |
| ATOM | 3748 | C | ILE | B | 864 | 64.475 | 13.018 | 9.613 | 1.00 | 17.27 |
| ATOM | 3749 | O | ILE | B | 864 | 63.831 | 12.877 | 8.558 | 1.00 | 16.03 |
| ATOM | 3750 | N | TYR | B | 865 | 64.831 | 14.203 | 10.106 | 1.00 | 18.04 |
| ATOM | 3751 | CA | TYR | B | 865 | 64.477 | 15.452 | 9.440 | 1.00 | 17.70 |
| ATOM | 3752 | CB | TYR | B | 865 | 63.414 | 16.202 | 10.235 | 1.00 | 19.36 |
| ATOM | 3753 | CG | TYR | B | 865 | 62.084 | 15.516 | 10.372 | 1.00 | 22.37 |
| ATOM | 3754 | CD1 | TYR | B | 865 | 61.860 | 14.560 | 11.379 | 1.00 | 23.22 |
| ATOM | 3755 | CE1 | TYR | B | 865 | 60.613 | 13.940 | 11.517 | 1.00 | 23.20 |
| ATOM | 3756 | CZ | TYR | B | 865 | 59.580 | 14.291 | 10.651 | 1.00 | 24.34 |
| ATOM | 3757 | OH | TYR | B | 865 | 58.341 | 13.702 | 10.770 | 1.00 | 28.53 |
| ATOM | 3758 | CE2 | TYR | B | 865 | 59.774 | 15.243 | 9.662 | 1.00 | 23.90 |
| ATOM | 3759 | CD2 | TYR | B | 865 | 61.023 | 15.848 | 9.522 | 1.00 | 23.33 |
| ATOM | 3760 | C | TYR | B | 865 | 65.704 | 16.340 | 9.345 | 1.00 | 18.10 |
| ATOM | 3761 | O | TYR | B | 865 | 66.110 | 16.958 | 10.330 | 1.00 | 18.78 |

FIGURE 3CV

|      | A    | B   | C   | D | E   | F      | G      | H      | I    | J     |
|------|------|-----|-----|---|-----|--------|--------|--------|------|-------|
| ATOM | 3762 | N   | THR | B | 866 | 66.306 | 16.397 | 8.165  | 1.00 | 17.27 |
| ATOM | 3763 | CA  | THR | B | 866 | 67.443 | 17.282 | 7.953  | 1.00 | 15.83 |
| ATOM | 3764 | CB  | THR | B | 866 | 68.721 | 16.484 | 7.595  | 1.00 | 16.06 |
| ATOM | 3765 | OG1 | THR | B | 866 | 68.496 | 15.737 | 6.387  | 1.00 | 17.14 |
| ATOM | 3766 | CG2 | THR | B | 866 | 69.017 | 15.415 | 8.639  | 1.00 | 14.04 |
| ATOM | 3767 | C   | THR | B | 866 | 67.094 | 18.200 | 6.812  | 1.00 | 15.73 |
| ATOM | 3768 | O   | THR | B | 866 | 66.052 | 18.053 | 6.180  | 1.00 | 14.57 |
| ATOM | 3769 | N   | ILE | B | 867 | 67.984 | 19.139 | 6.533  | 1.00 | 15.12 |
| ATOM | 3770 | CA  | ILE | B | 867 | 67.825 | 19.989 | 5.379  | 1.00 | 14.89 |
| ATOM | 3771 | CB  | ILE | B | 867 | 68.973 | 21.034 | 5.310  | 1.00 | 15.14 |
| ATOM | 3772 | CG1 | ILE | B | 867 | 68.627 | 22.128 | 4.294  | 1.00 | 13.89 |
| ATOM | 3773 | CD1 | ILE | B | 867 | 67.531 | 23.058 | 4.779  | 1.00 | 11.41 |
| ATOM | 3774 | CG2 | ILE | B | 867 | 70.332 | 20.375 | 5.059  | 1.00 | 14.59 |
| ATOM | 3775 | C   | ILE | B | 867 | 67.683 | 19.168 | 4.088  | 1.00 | 15.96 |
| ATOM | 3776 | O   | ILE | B | 867 | 66.930 | 19.557 | 3.188  | 1.00 | 17.57 |
| ATOM | 3777 | N   | LYS | B | 868 | 68.358 | 18.019 | 4.017  | 1.00 | 15.23 |
| ATOM | 3778 | CA  | LYS | B | 868 | 68.228 | 17.125 | 2.858  | 1.00 | 14.87 |
| ATOM | 3779 | CB  | LYS | B | 868 | 69.326 | 16.056 | 2.848  | 1.00 | 16.43 |
| ATOM | 3780 | CG  | LYS | B | 868 | 70.687 | 16.580 | 2.415  | 1.00 | 16.90 |
| ATOM | 3781 | CD  | LYS | B | 868 | 70.601 | 17.211 | 1.045  | 1.00 | 19.62 |
| ATOM | 3782 | CE  | LYS | B | 868 | 71.887 | 17.068 | 0.268  | 1.00 | 22.63 |
| ATOM | 3783 | NZ  | LYS | B | 868 | 72.170 | 15.682 | -0.167 | 1.00 | 22.43 |
| ATOM | 3784 | C   | LYS | B | 868 | 66.838 | 16.492 | 2.732  | 1.00 | 16.14 |
| ATOM | 3785 | O   | LYS | B | 868 | 66.403 | 16.196 | 1.629  | 1.00 | 17.44 |
| ATOM | 3786 | N   | SER | B | 869 | 66.143 | 16.283 | 3.850  | 1.00 | 15.76 |
| ATOM | 3787 | CA  | SER | B | 869 | 64.729 | 15.886 | 3.800  | 1.00 | 17.28 |
| ATOM | 3788 | CB  | SER | B | 869 | 64.156 | 15.627 | 5.200  | 1.00 | 14.27 |
| ATOM | 3789 | OG  | SER | B | 869 | 65.067 | 14.887 | 5.985  | 1.00 | 19.49 |
| ATOM | 3790 | C   | SER | B | 869 | 63.903 | 16.971 | 3.109  | 1.00 | 18.66 |
| ATOM | 3791 | O   | SER | B | 869 | 62.960 | 16.671 | 2.381  | 1.00 | 21.16 |
| ATOM | 3792 | N   | ASP | B | 870 | 64.266 | 18.228 | 3.343  | 1.00 | 16.97 |
| ATOM | 3793 | CA  | ASP | B | 870 | 63.582 | 19.343 | 2.706  | 1.00 | 20.02 |
| ATOM | 3794 | CB  | ASP | B | 870 | 64.039 | 20.670 | 3.309  | 1.00 | 21.05 |
| ATOM | 3795 | CG  | ASP | B | 870 | 63.344 | 20.965 | 4.596  | 1.00 | 20.16 |
| ATOM | 3796 | OD1 | ASP | B | 870 | 63.946 | 21.579 | 5.498  | 1.00 | 19.45 |
| ATOM | 3797 | OD2 | ASP | B | 870 | 62.178 | 20.587 | 4.792  | 1.00 | 24.05 |
| ATOM | 3798 | C   | ASP | B | 870 | 63.756 | 19.377 | 1.203  | 1.00 | 18.50 |
| ATOM | 3799 | O   | ASP | B | 870 | 62.900 | 19.911 | 0.503  | 1.00 | 18.98 |
| ATOM | 3800 | N   | VAL | B | 871 | 64.861 | 18.816 | 0.713  | 1.00 | 17.07 |
| ATOM | 3801 | CA  | VAL | B | 871 | 65.125 | 18.779 | -0.719 | 1.00 | 16.69 |
| ATOM | 3802 | CB  | VAL | B | 871 | 66.569 | 18.298 | -1.030 | 1.00 | 17.82 |
| ATOM | 3803 | CG1 | VAL | B | 871 | 66.752 | 17.978 | -2.519 | 1.00 | 15.37 |
| ATOM | 3804 | CG2 | VAL | B | 871 | 67.590 | 19.345 | -0.570 | 1.00 | 16.46 |
| ATOM | 3805 | C   | VAL | B | 871 | 64.074 | 17.889 | -1.377 | 1.00 | 17.56 |
| ATOM | 3806 | O   | VAL | B | 871 | 63.594 | 18.193 | -2.465 | 1.00 | 18.53 |
| ATOM | 3807 | N   | TRP | B | 872 | 63.701 | 16.804 | -0.699 | 1.00 | 16.09 |
| ATOM | 3808 | CA  | TRP | B | 872 | 62.632 | 15.948 | -1.188 | 1.00 | 15.22 |
| ATOM | 3809 | CB  | TRP | B | 872 | 62.459 | 14.717 | -0.298 | 1.00 | 13.44 |
| ATOM | 3810 | CG  | TRP | B | 872 | 61.337 | 13.809 | -0.716 | 1.00 | 13.03 |
| ATOM | 3811 | CD1 | TRP | B | 872 | 59.983 | 14.041 | -0.588 | 1.00 | 11.21 |
| ATOM | 3812 | NE1 | TRP | B | 872 | 59.269 | 12.971 | -1.073 | 1.00 | 10.82 |
| ATOM | 3813 | CE2 | TRP | B | 872 | 60.148 | 12.017 | -1.520 | 1.00 | 13.09 |

FIGURE 3CW

| | A | B | C | D | E | F | G | H | I | J |
|---|---|---|---|---|---|---|---|---|---|---|
| ATOM | 3814 | CD2 | TRP | B | 872 | 61.461 | 12.513 | -1.307 | 1.00 | 12.61 |
| ATOM | 3815 | CE3 | TRP | B | 872 | 62.546 | 11.715 | -1.685 | 1.00 | 12.64 |
| ATOM | 3816 | CZ3 | TRP | B | 872 | 62.296 | 10.461 | -2.249 | 1.00 | 13.87 |
| ATOM | 3817 | CH2 | TRP | B | 872 | 60.983 | 10.005 | -2.449 | 1.00 | 14.46 |
| ATOM | 3818 | CZ2 | TRP | B | 872 | 59.900 | 10.765 | -2.088 | 1.00 | 13.57 |
| ATOM | 3819 | C | TRP | B | 872 | 61.338 | 16.758 | -1.272 | 1.00 | 14.12 |
| ATOM | 3820 | O | TRP | B | 872 | 60.694 | 16.790 | -2.324 | 1.00 | 14.99 |
| ATOM | 3821 | N | SER | B | 873 | 60.981 | 17.411 | -0.168 | 1.00 | 12.09 |
| ATOM | 3822 | CA | SER | B | 873 | 59.792 | 18.260 | -0.100 | 1.00 | 15.05 |
| ATOM | 3823 | CB | SER | B | 873 | 59.695 | 18.942 | 1.259 | 1.00 | 15.84 |
| ATOM | 3824 | OG | SER | B | 873 | 59.638 | 17.987 | 2.293 | 1.00 | 20.91 |
| ATOM | 3825 | C | SER | B | 873 | 59.848 | 19.320 | -1.185 | 1.00 | 15.12 |
| ATOM | 3826 | O | SER | B | 873 | 58.864 | 19.581 | -1.866 | 1.00 | 15.98 |
| ATOM | 3827 | N | TYR | B | 874 | 61.023 | 19.907 | -1.356 | 1.00 | 16.59 |
| ATOM | 3828 | CA | TYR | B | 874 | 61.233 | 20.877 | -2.405 | 1.00 | 17.37 |
| ATOM | 3829 | CB | TYR | B | 874 | 62.680 | 21.360 | -2.396 | 1.00 | 16.46 |
| ATOM | 3830 | CG | TYR | B | 874 | 62.986 | 22.333 | -3.498 | 1.00 | 17.08 |
| ATOM | 3831 | CD1 | TYR | B | 874 | 62.592 | 23.668 | -3.401 | 1.00 | 14.09 |
| ATOM | 3832 | CE1 | TYR | B | 874 | 62.881 | 24.579 | -4.414 | 1.00 | 14.45 |
| ATOM | 3833 | CZ | TYR | B | 874 | 63.563 | 24.153 | -5.534 | 1.00 | 15.82 |
| ATOM | 3834 | OH | TYR | B | 874 | 63.832 | 25.052 | -6.536 | 1.00 | 16.65 |
| ATOM | 3835 | CE2 | TYR | B | 874 | 63.962 | 22.823 | -5.664 | 1.00 | 16.47 |
| ATOM | 3836 | CD2 | TYR | B | 874 | 63.665 | 21.919 | -4.650 | 1.00 | 15.99 |
| ATOM | 3837 | C | TYR | B | 874 | 60.867 | 20.285 | -3.758 | 1.00 | 17.61 |
| ATOM | 3838 | O | TYR | B | 874 | 60.238 | 20.962 | -4.581 | 1.00 | 17.81 |
| ATOM | 3839 | N | GLY | B | 875 | 61.249 | 19.024 | -3.976 | 1.00 | 16.85 |
| ATOM | 3840 | CA | GLY | B | 875 | 60.960 | 18.333 | -5.224 | 1.00 | 17.32 |
| ATOM | 3841 | C | GLY | B | 875 | 59.464 | 18.197 | -5.462 | 1.00 | 18.69 |
| ATOM | 3842 | O | GLY | B | 875 | 58.983 | 18.361 | -6.584 | 1.00 | 17.54 |
| ATOM | 3843 | N | ILE | B | 876 | 58.730 | 17.908 | -4.391 | 1.00 | 17.98 |
| ATOM | 3844 | CA | ILE | B | 876 | 57.289 | 17.782 | -4.468 | 1.00 | 18.06 |
| ATOM | 3845 | CB | ILE | B | 876 | 56.728 | 17.204 | -3.147 | 1.00 | 17.57 |
| ATOM | 3846 | CG1 | ILE | B | 876 | 57.354 | 15.822 | -2.850 | 1.00 | 16.00 |
| ATOM | 3847 | CD1 | ILE | B | 876 | 56.854 | 14.659 | -3.737 | 1.00 | 13.95 |
| ATOM | 3848 | CG2 | ILE | B | 876 | 55.198 | 17.153 | -3.184 | 1.00 | 14.28 |
| ATOM | 3849 | C | ILE | B | 876 | 56.690 | 19.153 | -4.792 | 1.00 | 19.33 |
| ATOM | 3850 | O | ILE | B | 876 | 55.792 | 19.273 | -5.645 | 1.00 | 17.18 |
| ATOM | 3851 | N | LEU | B | 877 | 57.210 | 20.177 | -4.116 | 1.00 | 19.14 |
| ATOM | 3852 | CA | LEU | B | 877 | 56.810 | 21.556 | -4.352 | 1.00 | 19.77 |
| ATOM | 3853 | CB | LEU | B | 877 | 57.517 | 22.498 | -3.373 | 1.00 | 19.73 |
| ATOM | 3854 | CG | LEU | B | 877 | 56.880 | 23.877 | -3.121 | 1.00 | 22.61 |
| ATOM | 3855 | CD1 | LEU | B | 877 | 57.300 | 24.423 | -1.776 | 1.00 | 24.44 |
| ATOM | 3856 | CD2 | LEU | B | 877 | 57.294 | 24.856 | -4.169 | 1.00 | 23.29 |
| ATOM | 3857 | C | LEU | B | 877 | 57.094 | 21.955 | -5.815 | 1.00 | 19.99 |
| ATOM | 3858 | O | LEU | B | 877 | 56.304 | 22.678 | -6.423 | 1.00 | 20.58 |
| ATOM | 3859 | N | LEU | B | 878 | 58.205 | 21.478 | -6.378 | 1.00 | 16.88 |
| ATOM | 3860 | CA | LEU | B | 878 | 58.488 | 21.722 | -7.784 | 1.00 | 16.46 |
| ATOM | 3861 | CB | LEU | B | 878 | 59.850 | 21.150 | -8.204 | 1.00 | 17.52 |
| ATOM | 3862 | CG | LEU | B | 878 | 61.171 | 21.861 | -7.858 | 1.00 | 19.39 |
| ATOM | 3863 | CD1 | LEU | B | 878 | 62.344 | 21.133 | -8.496 | 1.00 | 19.16 |
| ATOM | 3864 | CD2 | LEU | B | 878 | 61.209 | 23.317 | -8.265 | 1.00 | 17.58 |
| ATOM | 3865 | C | LEU | B | 878 | 57.370 | 21.083 | -8.604 | 1.00 | 17.69 |

FIGURE 3CX

|      | A    | B    | C   | D | E   | F      | G      | H       | I    | J     |
|------|------|------|-----|---|-----|--------|--------|---------|------|-------|
| ATOM | 3866 | O    | LEU | B | 878 | 56.810 | 21.712 | -9.507  | 1.00 | 17.37 |
| ATOM | 3867 | N    | TRP | B | 879 | 57.035 | 19.836 | -8.279  | 1.00 | 16.91 |
| ATOM | 3868 | CA   | TRP | B | 879 | 55.948 | 19.164 | -8.970  | 1.00 | 16.55 |
| ATOM | 3869 | CB   | TRP | B | 879 | 55.702 | 17.765 | -8.413  | 1.00 | 14.68 |
| ATOM | 3870 | CG   | TRP | B | 879 | 54.909 | 16.958 | -9.370  | 1.00 | 15.57 |
| ATOM | 3871 | CD1  | TRP | B | 879 | 55.384 | 16.227 | -10.428 | 1.00 | 15.99 |
| ATOM | 3872 | NE1  | TRP | B | 879 | 54.339 | 15.643 | -11.107 | 1.00 | 17.10 |
| ATOM | 3873 | CE2  | TRP | B | 879 | 53.159 | 15.998 | -10.501 | 1.00 | 15.16 |
| ATOM | 3874 | CD2  | TRP | B | 879 | 53.484 | 16.833 | -9.403  | 1.00 | 14.45 |
| ATOM | 3875 | CE3  | TRP | B | 879 | 52.443 | 17.336 | -8.609  | 1.00 | 13.19 |
| ATOM | 3876 | CZ3  | TRP | B | 879 | 51.135 | 16.986 | -8.921  | 1.00 | 15.55 |
| ATOM | 3877 | CH2  | TRP | B | 879 | 50.848 | 16.139 | -10.017 | 1.00 | 14.64 |
| ATOM | 3878 | CZ2  | TRP | B | 879 | 51.842 | 15.648 | -10.819 | 1.00 | 13.87 |
| ATOM | 3879 | C    | TRP | B | 879 | 54.668 | 20.005 | -8.936  | 1.00 | 15.75 |
| ATOM | 3880 | O    | TRP | B | 879 | 54.012 | 20.178 | -9.969  | 1.00 | 13.69 |
| ATOM | 3881 | N    | GLU | B | 880 | 54.345 | 20.537 | -7.754  | 1.00 | 14.61 |
| ATOM | 3882 | CA   | GLU | B | 880 | 53.197 | 21.418 | -7.567  | 1.00 | 13.67 |
| ATOM | 3883 | CB   | GLU | B | 880 | 53.108 | 21.905 | -6.119  | 1.00 | 13.14 |
| ATOM | 3884 | CG   | GLU | B | 880 | 52.782 | 20.844 | -5.086  | 1.00 | 13.17 |
| ATOM | 3885 | CD   | GLU | B | 880 | 52.517 | 21.450 | -3.720  | 1.00 | 14.74 |
| ATOM | 3886 | OE1  | GLU | B | 880 | 51.339 | 21.699 | -3.400  | 1.00 | 15.99 |
| ATOM | 3887 | OE2  | GLU | B | 880 | 53.484 | 21.690 | -2.967  | 1.00 | 15.60 |
| ATOM | 3888 | C    | GLU | B | 880 | 53.276 | 22.631 | -8.479  | 1.00 | 15.43 |
| ATOM | 3889 | O    | GLU | B | 880 | 52.277 | 23.010 | -9.103  | 1.00 | 18.44 |
| ATOM | 3890 | N    | ILE | B | 881 | 54.454 | 23.254 | -8.539  | 1.00 | 14.29 |
| ATOM | 3891 | CA   | ILE | B | 881 | 54.635 | 24.435 | -9.369  | 1.00 | 13.62 |
| ATOM | 3892 | CB   | ILE | B | 881 | 56.028 | 25.058 | -9.175  | 1.00 | 13.61 |
| ATOM | 3893 | CG1  | ILE | B | 881 | 56.168 | 25.651 | -7.771  | 1.00 | 14.36 |
| ATOM | 3894 | CD1  | ILE | B | 881 | 57.608 | 25.991 | -7.385  | 1.00 | 14.49 |
| ATOM | 3895 | CG2  | ILE | B | 881 | 56.273 | 26.143 | -10.240 | 1.00 | 13.16 |
| ATOM | 3896 | C    | ILE | B | 881 | 54.403 | 24.108 | -10.841 | 1.00 | 14.07 |
| ATOM | 3897 | O    | ILE | B | 881 | 53.607 | 24.777 | -11.510 | 1.00 | 13.93 |
| ATOM | 3898 | N    | PHE | B | 882 | 55.088 | 23.076 | -11.335 | 1.00 | 12.55 |
| ATOM | 3899 | CA   | PHE | B | 882 | 55.082 | 22.778 | -12.766 | 1.00 | 12.00 |
| ATOM | 3900 | CB   | PHE | B | 882 | 56.427 | 22.185 | -13.207 | 1.00 | 11.47 |
| ATOM | 3901 | CG   | PHE | B | 882 | 57.564 | 23.171 | -13.117 | 1.00 | 11.03 |
| ATOM | 3902 | CD1  | PHE | B | 882 | 58.331 | 23.270 | -11.953 | 1.00 | 10.64 |
| ATOM | 3903 | CE1  | PHE | B | 882 | 59.373 | 24.205 | -11.844 | 1.00 | 10.43 |
| ATOM | 3904 | CZ   | PHE | B | 882 | 59.655 | 25.058 | -12.908 | 1.00 | 11.03 |
| ATOM | 3905 | CE2  | PHE | B | 882 | 58.882 | 24.983 | -14.082 | 1.00 | 12.87 |
| ATOM | 3906 | CD2  | PHE | B | 882 | 57.837 | 24.037 | -14.175 | 1.00 | 11.47 |
| ATOM | 3907 | C    | PHE | B | 882 | 53.876 | 21.956 | -13.212 | 1.00 | 12.57 |
| ATOM | 3908 | O    | PHE | B | 882 | 53.737 | 21.632 | -14.390 | 1.00 | 13.12 |
| ATOM | 3909 | N    | SER | B | 883 | 53.004 | 21.626 | -12.262 | 1.00 | 12.74 |
| ATOM | 3910 | CA   | SER | B | 883 | 51.697 | 21.067 | -12.584 | 1.00 | 13.95 |
| ATOM | 3911 | CB   | SER | B | 883 | 51.365 | 19.885 | -11.671 | 1.00 | 13.75 |
| ATOM | 3912 | OG   | SER | B | 883 | 51.209 | 20.326 | -10.333 | 1.00 | 14.42 |
| ATOM | 3913 | C    | SER | B | 883 | 50.649 | 22.153 | -12.423 | 1.00 | 15.28 |
| ATOM | 3914 | O    | SER | B | 883 | 49.472 | 21.920 | -12.669 | 1.00 | 17.77 |
| ATOM | 3915 | N    | LEU | B | 884 | 51.092 | 23.341 | -12.011 | 1.00 | 15.10 |
| ATOM | 3916 | CA   | LEU | B | 884 | 50.205 | 24.467 | -11.698 | 1.00 | 14.35 |
| ATOM | 3917 | CB   | LEU | B | 884 | 49.515 | 25.026 | -12.955 | 1.00 | 12.35 |

FIGURE 3CY

|  | A | B | C | D | E | F | G | H | I | J |
|---|---|---|---|---|---|---|---|---|---|---|
| ATOM | 3918 | CG | LEU | B | 884 | 50.379 | 25.644 | -14.065 | 1.00 | 11.37 |
| ATOM | 3919 | CD1 | LEU | B | 884 | 49.504 | 26.205 | -15.183 | 1.00 | 9.40 |
| ATOM | 3920 | CD2 | LEU | B | 884 | 51.316 | 26.712 | -13.535 | 1.00 | 9.98 |
| ATOM | 3921 | C | LEU | B | 884 | 49.185 | 24.110 | -10.615 | 1.00 | 14.50 |
| ATOM | 3922 | O | LEU | B | 884 | 47.982 | 24.368 | -10.762 | 1.00 | 13.85 |
| ATOM | 3923 | N | GLY | B | 885 | 49.681 | 23.492 | -9.542 | 1.00 | 13.23 |
| ATOM | 3924 | CA | GLY | B | 885 | 48.902 | 23.289 | -8.336 | 1.00 | 12.77 |
| ATOM | 3925 | C | GLY | B | 885 | 48.094 | 22.009 | -8.237 | 1.00 | 15.10 |
| ATOM | 3926 | O | GLY | B | 885 | 47.121 | 21.944 | -7.480 | 1.00 | 17.26 |
| ATOM | 3927 | N | VAL | B | 886 | 48.469 | 20.989 | -9.003 | 1.00 | 16.16 |
| ATOM | 3928 | CA | VAL | B | 886 | 47.826 | 19.692 | -8.846 | 1.00 | 15.32 |
| ATOM | 3929 | CB | VAL | B | 886 | 48.099 | 18.737 | -10.035 | 1.00 | 15.17 |
| ATOM | 3930 | CG1 | VAL | B | 886 | 47.499 | 17.344 | -9.771 | 1.00 | 13.87 |
| ATOM | 3931 | CG2 | VAL | B | 886 | 47.538 | 19.316 | -11.339 | 1.00 | 11.50 |
| ATOM | 3932 | C | VAL | B | 886 | 48.319 | 19.098 | -7.531 | 1.00 | 16.80 |
| ATOM | 3933 | O | VAL | B | 886 | 49.477 | 19.308 | -7.142 | 1.00 | 16.63 |
| ATOM | 3934 | N | ASN | B | 887 | 47.424 | 18.400 | -6.835 | 1.00 | 15.69 |
| ATOM | 3935 | CA | ASN | B | 887 | 47.768 | 17.694 | -5.612 | 1.00 | 16.74 |
| ATOM | 3936 | CB | ASN | B | 887 | 46.492 | 17.170 | -4.943 | 1.00 | 15.98 |
| ATOM | 3937 | CG | ASN | B | 887 | 46.748 | 16.554 | -3.568 | 1.00 | 17.87 |
| ATOM | 3938 | OD1 | ASN | B | 887 | 46.433 | 15.380 | -3.332 | 1.00 | 16.92 |
| ATOM | 3939 | ND2 | ASN | B | 887 | 47.303 | 17.345 | -2.653 | 1.00 | 16.26 |
| ATOM | 3940 | C | ASN | B | 887 | 48.742 | 16.547 | -5.931 | 1.00 | 18.29 |
| ATOM | 3941 | O | ASN | B | 887 | 48.489 | 15.762 | -6.845 | 1.00 | 19.76 |
| ATOM | 3942 | N | PRO | B | 888 | 49.858 | 16.464 | -5.205 | 1.00 | 18.08 |
| ATOM | 3943 | CA | PRO | B | 888 | 50.849 | 15.396 | -5.415 | 1.00 | 18.80 |
| ATOM | 3944 | CB | PRO | B | 888 | 51.786 | 15.541 | -4.211 | 1.00 | 17.87 |
| ATOM | 3945 | CG | PRO | B | 888 | 51.687 | 16.974 | -3.846 | 1.00 | 18.81 |
| ATOM | 3946 | CD | PRO | B | 888 | 50.271 | 17.390 | -4.136 | 1.00 | 19.01 |
| ATOM | 3947 | C | PRO | B | 888 | 50.226 | 14.005 | -5.421 | 1.00 | 18.20 |
| ATOM | 3948 | O | PRO | B | 888 | 49.201 | 13.779 | -4.755 | 1.00 | 19.21 |
| ATOM | 3949 | N | TYR | B | 889 | 50.843 | 13.096 | -6.175 | 1.00 | 15.97 |
| ATOM | 3950 | CA | TYR | B | 889 | 50.324 | 11.739 | -6.364 | 1.00 | 16.77 |
| ATOM | 3951 | CB | TYR | B | 889 | 50.708 | 10.836 | -5.178 | 1.00 | 14.51 |
| ATOM | 3952 | CG | TYR | B | 889 | 52.175 | 10.920 | -4.804 | 1.00 | 14.01 |
| ATOM | 3953 | CD1 | TYR | B | 889 | 52.607 | 11.784 | -3.797 | 1.00 | 14.68 |
| ATOM | 3954 | CE1 | TYR | B | 889 | 53.954 | 11.890 | -3.455 | 1.00 | 14.41 |
| ATOM | 3955 | CZ | TYR | B | 889 | 54.885 | 11.115 | -4.120 | 1.00 | 16.18 |
| ATOM | 3956 | OH | TYR | B | 889 | 56.215 | 11.211 | -3.776 | 1.00 | 18.75 |
| ATOM | 3957 | CE2 | TYR | B | 889 | 54.486 | 10.249 | -5.133 | 1.00 | 15.24 |
| ATOM | 3958 | CD2 | TYR | B | 889 | 53.129 | 10.160 | -5.471 | 1.00 | 13.68 |
| ATOM | 3959 | C | TYR | B | 889 | 48.809 | 11.765 | -6.574 | 1.00 | 17.73 |
| ATOM | 3960 | O | TYR | B | 889 | 48.071 | 11.166 | -5.794 | 1.00 | 19.27 |
| ATOM | 3961 | N | PRO | B | 890 | 48.344 | 12.469 | -7.612 | 1.00 | 18.15 |
| ATOM | 3962 | CA | PRO | B | 890 | 46.906 | 12.738 | -7.769 | 1.00 | 19.24 |
| ATOM | 3963 | CB | PRO | B | 890 | 46.833 | 13.542 | -9.074 | 1.00 | 17.31 |
| ATOM | 3964 | CG | PRO | B | 890 | 48.095 | 13.212 | -9.803 | 1.00 | 16.95 |
| ATOM | 3965 | CD | PRO | B | 890 | 49.128 | 13.035 | -8.725 | 1.00 | 17.04 |
| ATOM | 3966 | C | PRO | B | 890 | 46.124 | 11.437 | -7.897 | 1.00 | 20.32 |
| ATOM | 3967 | O | PRO | B | 890 | 46.533 | 10.554 | -8.659 | 1.00 | 19.91 |
| ATOM | 3968 | N | GLY | B | 891 | 45.042 | 11.311 | -7.130 | 1.00 | 20.19 |
| ATOM | 3969 | CA | GLY | B | 891 | 44.222 | 10.111 | -7.156 | 1.00 | 19.77 |

FIGURE 3CZ

|  | A | B | C | D | E | F | G | H | I | J |
|---|---|---|---|---|---|---|---|---|---|---|
| ATOM | 3970 | C | GLY | B | 891 | 44.760 | 8.940 | -6.351 | 1.00 | 19.98 |
| ATOM | 3971 | O | GLY | B | 891 | 44.072 | 7.927 | -6.207 | 1.00 | 20.48 |
| ATOM | 3972 | N | ILE | B | 892 | 45.984 | 9.066 | -5.838 | 1.00 | 18.83 |
| ATOM | 3973 | CA | ILE | B | 892 | 46.581 | 8.024 | -5.003 | 1.00 | 19.88 |
| ATOM | 3974 | CB | ILE | B | 892 | 48.073 | 7.786 | -5.357 | 1.00 | 18.65 |
| ATOM | 3975 | CG1 | ILE | B | 892 | 48.221 | 7.309 | -6.805 | 1.00 | 17.91 |
| ATOM | 3976 | CD1 | ILE | B | 892 | 49.657 | 7.368 | -7.327 | 1.00 | 17.38 |
| ATOM | 3977 | CG2 | ILE | B | 892 | 48.686 | 6.765 | -4.412 | 1.00 | 18.72 |
| ATOM | 3978 | C | ILE | B | 892 | 46.425 | 8.414 | -3.536 | 1.00 | 19.70 |
| ATOM | 3979 | O | ILE | B | 892 | 47.043 | 9.376 | -3.088 | 1.00 | 20.73 |
| ATOM | 3980 | N | PRO | B | 893 | 45.598 | 7.675 | -2.792 | 1.00 | 18.43 |
| ATOM | 3981 | CA | PRO | B | 893 | 45.325 | 8.008 | -1.389 | 1.00 | 17.94 |
| ATOM | 3982 | CB | PRO | B | 893 | 44.131 | 7.107 | -1.046 | 1.00 | 16.33 |
| ATOM | 3983 | CG | PRO | B | 893 | 44.269 | 5.939 | -1.951 | 1.00 | 16.53 |
| ATOM | 3984 | CD | PRO | B | 893 | 44.878 | 6.462 | -3.223 | 1.00 | 16.45 |
| ATOM | 3985 | C | PRO | B | 893 | 46.521 | 7.680 | -0.489 | 1.00 | 18.28 |
| ATOM | 3986 | O | PRO | B | 893 | 47.356 | 6.854 | -0.868 | 1.00 | 17.77 |
| ATOM | 3987 | N | VAL | B | 894 | 46.605 | 8.326 | 0.672 | 1.00 | 18.13 |
| ATOM | 3988 | CA | VAL | B | 894 | 47.626 | 7.981 | 1.662 | 1.00 | 18.58 |
| ATOM | 3989 | CB | VAL | B | 894 | 47.949 | 9.163 | 2.609 | 1.00 | 19.13 |
| ATOM | 3990 | CG1 | VAL | B | 894 | 48.920 | 8.732 | 3.706 | 1.00 | 20.03 |
| ATOM | 3991 | CG2 | VAL | B | 894 | 48.531 | 10.339 | 1.832 | 1.00 | 19.47 |
| ATOM | 3992 | C | VAL | B | 894 | 47.142 | 6.772 | 2.466 | 1.00 | 18.23 |
| ATOM | 3993 | O | VAL | B | 894 | 46.207 | 6.880 | 3.261 | 1.00 | 19.53 |
| ATOM | 3994 | N | ASP | B | 895 | 47.758 | 5.619 | 2.219 | 1.00 | 16.10 |
| ATOM | 3995 | CA | ASP | B | 895 | 47.420 | 4.377 | 2.915 | 1.00 | 16.19 |
| ATOM | 3996 | CB | ASP | B | 895 | 46.151 | 3.715 | 2.331 | 1.00 | 16.64 |
| ATOM | 3997 | CG | ASP | B | 895 | 46.289 | 3.327 | 0.855 | 1.00 | 17.73 |
| ATOM | 3998 | OD1 | ASP | B | 895 | 45.247 | 3.000 | 0.241 | 1.00 | 18.54 |
| ATOM | 3999 | OD2 | ASP | B | 895 | 47.369 | 3.305 | 0.221 | 1.00 | 16.84 |
| ATOM | 4000 | C | ASP | B | 895 | 48.611 | 3.429 | 2.897 | 1.00 | 15.29 |
| ATOM | 4001 | O | ASP | B | 895 | 49.702 | 3.826 | 2.493 | 1.00 | 16.67 |
| ATOM | 4002 | N | ALA | B | 896 | 48.403 | 2.187 | 3.335 | 1.00 | 14.94 |
| ATOM | 4003 | CA | ALA | B | 896 | 49.472 | 1.185 | 3.359 | 1.00 | 14.64 |
| ATOM | 4004 | CB | ALA | B | 896 | 48.920 | -0.192 | 3.690 | 1.00 | 11.18 |
| ATOM | 4005 | C | ALA | B | 896 | 50.253 | 1.148 | 2.046 | 1.00 | 14.56 |
| ATOM | 4006 | O | ALA | B | 896 | 51.480 | 1.106 | 2.054 | 1.00 | 13.64 |
| ATOM | 4007 | N | ASN | B | 897 | 49.533 | 1.205 | 0.931 | 1.00 | 15.58 |
| ATOM | 4008 | CA | ASN | B | 897 | 50.131 | 1.064 | -0.388 | 1.00 | 17.91 |
| ATOM | 4009 | CB | ASN | B | 897 | 49.061 | 0.783 | -1.436 | 1.00 | 22.15 |
| ATOM | 4010 | CG | ASN | B | 897 | 49.360 | -0.463 | -2.239 | 1.00 | 26.28 |
| ATOM | 4011 | OD1 | ASN | B | 897 | 50.291 | -0.482 | -3.054 | 1.00 | 27.83 |
| ATOM | 4012 | ND2 | ASN | B | 897 | 48.576 | -1.520 | -2.010 | 1.00 | 26.87 |
| ATOM | 4013 | C | ASN | B | 897 | 50.966 | 2.249 | -0.826 | 1.00 | 18.39 |
| ATOM | 4014 | O | ASN | B | 897 | 51.925 | 2.088 | -1.587 | 1.00 | 18.87 |
| ATOM | 4015 | N | PHE | B | 898 | 50.599 | 3.440 | -0.357 | 1.00 | 17.16 |
| ATOM | 4016 | CA | PHE | B | 898 | 51.375 | 4.624 | -0.671 | 1.00 | 17.54 |
| ATOM | 4017 | CB | PHE | B | 898 | 50.709 | 5.902 | -0.150 | 1.00 | 16.40 |
| ATOM | 4018 | CG | PHE | B | 898 | 51.554 | 7.138 | -0.358 | 1.00 | 15.32 |
| ATOM | 4019 | CD1 | PHE | B | 898 | 52.365 | 7.623 | 0.662 | 1.00 | 14.76 |
| ATOM | 4020 | CE1 | PHE | B | 898 | 53.161 | 8.747 | 0.465 | 1.00 | 16.20 |
| ATOM | 4021 | CZ | PHE | B | 898 | 53.158 | 9.394 | -0.767 | 1.00 | 14.74 |

FIGURE 3DA

| | A | B | C | D | E | F | G | H | I | J |
|---|---|---|---|---|---|---|---|---|---|---|
| ATOM | 4022 | CE2 | PHE | B | 898 | 52.366 | 8.908 | -1.797 | 1.00 | 15.69 |
| ATOM | 4023 | CD2 | PHE | B | 898 | 51.570 | 7.784 | -1.592 | 1.00 | 15.00 |
| ATOM | 4024 | C | PHE | B | 898 | 52.794 | 4.499 | -0.102 | 1.00 | 17.87 |
| ATOM | 4025 | O | PHE | B | 898 | 53.770 | 4.844 | -0.770 | 1.00 | 19.28 |
| ATOM | 4026 | N | TYR | B | 899 | 52.889 | 4.013 | 1.132 | 1.00 | 17.40 |
| ATOM | 4027 | CA | TYR | B | 899 | 54.174 | 3.807 | 1.786 | 1.00 | 18.03 |
| ATOM | 4028 | CB | TYR | B | 899 | 53.986 | 3.453 | 3.265 | 1.00 | 16.54 |
| ATOM | 4029 | CG | TYR | B | 899 | 53.250 | 4.536 | 4.013 | 1.00 | 16.27 |
| ATOM | 4030 | CD1 | TYR | B | 899 | 52.016 | 4.282 | 4.609 | 1.00 | 15.07 |
| ATOM | 4031 | CE1 | TYR | B | 899 | 51.328 | 5.279 | 5.274 | 1.00 | 15.73 |
| ATOM | 4032 | CZ | TYR | B | 899 | 51.872 | 6.553 | 5.346 | 1.00 | 17.90 |
| ATOM | 4033 | OH | TYR | B | 899 | 51.198 | 7.549 | 6.016 | 1.00 | 22.31 |
| ATOM | 4034 | CE2 | TYR | B | 899 | 53.093 | 6.837 | 4.759 | 1.00 | 16.59 |
| ATOM | 4035 | CD2 | TYR | B | 899 | 53.771 | 5.832 | 4.089 | 1.00 | 16.48 |
| ATOM | 4036 | C | TYR | B | 899 | 54.993 | 2.755 | 1.060 | 1.00 | 18.00 |
| ATOM | 4037 | O | TYR | B | 899 | 56.197 | 2.944 | 0.867 | 1.00 | 18.23 |
| ATOM | 4038 | N | LYS | B | 900 | 54.333 | 1.671 | 0.644 | 1.00 | 16.97 |
| ATOM | 4039 | CA | LYS | B | 900 | 54.966 | 0.634 | -0.175 | 1.00 | 18.39 |
| ATOM | 4040 | CB | LYS | B | 900 | 53.966 | -0.460 | -0.540 | 1.00 | 18.05 |
| ATOM | 4041 | CG | LYS | B | 900 | 53.898 | -1.589 | 0.465 | 1.00 | 20.92 |
| ATOM | 4042 | CD | LYS | B | 900 | 52.643 | -2.436 | 0.265 | 1.00 | 21.68 |
| ATOM | 4043 | CE | LYS | B | 900 | 52.145 | -3.011 | 1.578 | 1.00 | 21.84 |
| ATOM | 4044 | NZ | LYS | B | 900 | 51.002 | -3.944 | 1.374 | 1.00 | 23.08 |
| ATOM | 4045 | C | LYS | B | 900 | 55.577 | 1.217 | -1.450 | 1.00 | 19.30 |
| ATOM | 4046 | O | LYS | B | 900 | 56.731 | 0.921 | -1.781 | 1.00 | 19.19 |
| ATOM | 4047 | N | LEU | B | 901 | 54.803 | 2.055 | -2.145 | 1.00 | 17.13 |
| ATOM | 4048 | CA | LEU | B | 901 | 55.249 | 2.684 | -3.379 | 1.00 | 15.72 |
| ATOM | 4049 | CB | LEU | B | 901 | 54.135 | 3.549 | -3.983 | 1.00 | 15.22 |
| ATOM | 4050 | CG | LEU | B | 901 | 52.898 | 2.874 | -4.601 | 1.00 | 16.26 |
| ATOM | 4051 | CD1 | LEU | B | 901 | 51.882 | 3.924 | -5.024 | 1.00 | 15.96 |
| ATOM | 4052 | CD2 | LEU | B | 901 | 53.228 | 1.939 | -5.774 | 1.00 | 14.64 |
| ATOM | 4053 | C | LEU | B | 901 | 56.500 | 3.520 | -3.125 | 1.00 | 17.78 |
| ATOM | 4054 | O | LEU | B | 901 | 57.507 | 3.371 | -3.820 | 1.00 | 19.86 |
| ATOM | 4055 | N | ILE | B | 902 | 56.441 | 4.384 | -2.117 | 1.00 | 16.16 |
| ATOM | 4056 | CA | ILE | B | 902 | 57.561 | 5.269 | -1.803 | 1.00 | 16.93 |
| ATOM | 4057 | CB | ILE | B | 902 | 57.158 | 6.294 | -0.711 | 1.00 | 15.73 |
| ATOM | 4058 | CG1 | ILE | B | 902 | 56.071 | 7.256 | -1.233 | 1.00 | 14.96 |
| ATOM | 4059 | CD1 | ILE | B | 902 | 56.396 | 7.982 | -2.562 | 1.00 | 12.55 |
| ATOM | 4060 | CG2 | ILE | B | 902 | 58.378 | 7.032 | -0.173 | 1.00 | 13.26 |
| ATOM | 4061 | C | ILE | B | 902 | 58.800 | 4.478 | -1.394 | 1.00 | 18.10 |
| ATOM | 4062 | O | ILE | B | 902 | 59.907 | 4.772 | -1.841 | 1.00 | 18.66 |
| ATOM | 4063 | N | GLN | B | 903 | 58.593 | 3.466 | -0.556 | 1.00 | 18.69 |
| ATOM | 4064 | CA | GLN | B | 903 | 59.658 | 2.585 | -0.110 | 1.00 | 18.62 |
| ATOM | 4065 | CB | GLN | B | 903 | 59.100 | 1.560 | 0.891 | 1.00 | 17.27 |
| ATOM | 4066 | CG | GLN | B | 903 | 60.124 | 0.632 | 1.531 | 1.00 | 14.53 |
| ATOM | 4067 | CD | GLN | B | 903 | 61.298 | 1.363 | 2.158 | 1.00 | 15.73 |
| ATOM | 4068 | OE1 | GLN | B | 903 | 62.434 | 1.226 | 1.698 | 1.00 | 15.94 |
| ATOM | 4069 | NE2 | GLN | B | 903 | 61.033 | 2.130 | 3.214 | 1.00 | 14.37 |
| ATOM | 4070 | C | GLN | B | 903 | 60.339 | 1.894 | -1.296 | 1.00 | 19.40 |
| ATOM | 4071 | O | GLN | B | 903 | 61.552 | 1.689 | -1.287 | 1.00 | 20.86 |
| ATOM | 4072 | N | ASN | B | 904 | 59.561 | 1.562 | -2.320 | 1.00 | 20.41 |
| ATOM | 4073 | CA | ASN | B | 904 | 60.082 | 0.861 | -3.488 | 1.00 | 21.54 |

FIGURE 3DB

| | A | B | C | D | E | F | G | H | I | J |
|---|---|---|---|---|---|---|---|---|---|---|
| ATOM | 4074 | CB | ASN | B | 904 | 59.112 | -0.242 | -3.910 | 1.00 | 24.49 |
| ATOM | 4075 | CG | ASN | B | 904 | 59.058 | -1.377 | -2.896 | 1.00 | 27.56 |
| ATOM | 4076 | OD1 | ASN | B | 904 | 59.983 | -2.186 | -2.799 | 1.00 | 29.53 |
| ATOM | 4077 | ND2 | ASN | B | 904 | 57.986 | -1.423 | -2.118 | 1.00 | 27.99 |
| ATOM | 4078 | C | ASN | B | 904 | 60.446 | 1.768 | -4.669 | 1.00 | 21.85 |
| ATOM | 4079 | O | ASN | B | 904 | 60.528 | 1.314 | -5.812 | 1.00 | 21.25 |
| ATOM | 4080 | N | GLY | B | 905 | 60.653 | 3.051 | -4.389 | 1.00 | 21.06 |
| ATOM | 4081 | CA | GLY | B | 905 | 61.231 | 3.953 | -5.366 | 1.00 | 23.38 |
| ATOM | 4082 | C | GLY | B | 905 | 60.284 | 4.695 | -6.295 | 1.00 | 23.58 |
| ATOM | 4083 | O | GLY | B | 905 | 60.748 | 5.367 | -7.212 | 1.00 | 24.87 |
| ATOM | 4084 | N | PHE | B | 906 | 58.977 | 4.588 | -6.064 | 1.00 | 21.74 |
| ATOM | 4085 | CA | PHE | B | 906 | 57.987 | 5.296 | -6.875 | 1.00 | 20.18 |
| ATOM | 4086 | CB | PHE | B | 906 | 56.572 | 5.058 | -6.340 | 1.00 | 19.54 |
| ATOM | 4087 | CG | PHE | B | 906 | 55.488 | 5.618 | -7.210 | 1.00 | 20.30 |
| ATOM | 4088 | CD1 | PHE | B | 906 | 54.928 | 6.867 | -6.935 | 1.00 | 20.80 |
| ATOM | 4089 | CE1 | PHE | B | 906 | 53.914 | 7.394 | -7.747 | 1.00 | 20.79 |
| ATOM | 4090 | CZ | PHE | B | 906 | 53.450 | 6.668 | -8.835 | 1.00 | 20.55 |
| ATOM | 4091 | CE2 | PHE | B | 906 | 54.000 | 5.409 | -9.116 | 1.00 | 20.77 |
| ATOM | 4092 | CD2 | PHE | B | 906 | 55.011 | 4.895 | -8.302 | 1.00 | 20.85 |
| ATOM | 4093 | C | PHE | B | 906 | 58.274 | 6.793 | -6.909 | 1.00 | 19.53 |
| ATOM | 4094 | O | PHE | B | 906 | 58.591 | 7.397 | -5.883 | 1.00 | 18.95 |
| ATOM | 4095 | N | LYS | B | 907 | 58.163 | 7.375 | -8.099 | 1.00 | 17.56 |
| ATOM | 4096 | CA | LYS | B | 907 | 58.319 | 8.811 | -8.294 | 1.00 | 16.76 |
| ATOM | 4097 | CB | LYS | B | 907 | 59.683 | 9.142 | -8.923 | 1.00 | 16.59 |
| ATOM | 4098 | CG | LYS | B | 907 | 60.882 | 8.964 | -8.022 | 1.00 | 17.77 |
| ATOM | 4099 | CD | LYS | B | 907 | 62.175 | 9.224 | -8.794 | 1.00 | 19.83 |
| ATOM | 4100 | CE | LYS | B | 907 | 63.364 | 8.564 | -8.113 | 1.00 | 21.82 |
| ATOM | 4101 | NZ | LYS | B | 907 | 64.558 | 9.451 | -8.146 | 1.00 | 24.67 |
| ATOM | 4102 | C | LYS | B | 907 | 57.233 | 9.247 | -9.251 | 1.00 | 14.97 |
| ATOM | 4103 | O | LYS | B | 907 | 56.898 | 8.510 | -10.175 | 1.00 | 15.81 |
| ATOM | 4104 | N | MET | B | 908 | 56.707 | 10.452 | -9.059 | 1.00 | 14.80 |
| ATOM | 4105 | CA | MET | B | 908 | 55.683 | 10.987 | -9.957 | 1.00 | 14.45 |
| ATOM | 4106 | CB | MET | B | 908 | 55.152 | 12.307 | -9.424 | 1.00 | 14.18 |
| ATOM | 4107 | CG | MET | B | 908 | 54.178 | 12.176 | -8.284 | 1.00 | 15.02 |
| ATOM | 4108 | SD | MET | B | 908 | 53.491 | 13.794 | -7.838 | 1.00 | 16.46 |
| ATOM | 4109 | CE | MET | B | 908 | 54.775 | 14.400 | -6.799 | 1.00 | 12.15 |
| ATOM | 4110 | C | MET | B | 908 | 56.238 | 11.210 | -11.362 | 1.00 | 16.30 |
| ATOM | 4111 | O | MET | B | 908 | 57.442 | 11.447 | -11.543 | 1.00 | 16.02 |
| ATOM | 4112 | N | ASP | B | 909 | 55.353 | 11.132 | -12.350 | 1.00 | 15.64 |
| ATOM | 4113 | CA | ASP | B | 909 | 55.693 | 11.469 | -13.731 | 1.00 | 17.12 |
| ATOM | 4114 | CB | ASP | B | 909 | 54.587 | 10.999 | -14.694 | 1.00 | 18.69 |
| ATOM | 4115 | CG | ASP | B | 909 | 54.417 | 9.477 | -14.709 | 1.00 | 21.93 |
| ATOM | 4116 | OD1 | ASP | B | 909 | 53.327 | 9.003 | -15.100 | 1.00 | 23.00 |
| ATOM | 4117 | OD2 | ASP | B | 909 | 55.314 | 8.676 | -14.352 | 1.00 | 22.51 |
| ATOM | 4118 | C | ASP | B | 909 | 55.910 | 12.974 | -13.908 | 1.00 | 16.86 |
| ATOM | 4119 | O | ASP | B | 909 | 55.530 | 13.795 | -13.056 | 1.00 | 15.50 |
| ATOM | 4120 | N | GLN | B | 910 | 56.527 | 13.323 | -15.027 | 1.00 | 16.36 |
| ATOM | 4121 | CA | GLN | B | 910 | 56.694 | 14.707 | -15.428 | 1.00 | 17.29 |
| ATOM | 4122 | CB | GLN | B | 910 | 57.406 | 14.751 | -16.774 | 1.00 | 19.12 |
| ATOM | 4123 | CG | GLN | B | 910 | 58.180 | 16.023 | -17.018 | 1.00 | 20.45 |
| ATOM | 4124 | CD | GLN | B | 910 | 58.844 | 16.039 | -18.373 | 1.00 | 21.24 |
| ATOM | 4125 | OE1 | GLN | B | 910 | 58.893 | 17.077 | -19.027 | 1.00 | 24.13 |

FIGURE 3DC

|      | A    | B   | C   | D | E   | F      | G      | H       | I    | J     |
|------|------|-----|-----|---|-----|--------|--------|---------|------|-------|
| ATOM | 4126 | NE2 | GLN | B | 910 | 59.364 | 14.898 | -18.796 | 1.00 | 21.38 |
| ATOM | 4127 | C   | GLN | B | 910 | 55.352 | 15.435 | -15.526 | 1.00 | 15.44 |
| ATOM | 4128 | O   | GLN | B | 910 | 54.459 | 14.986 | -16.233 | 1.00 | 15.57 |
| ATOM | 4129 | N   | PRO | B | 911 | 55.206 | 16.552 | -14.814 | 1.00 | 14.96 |
| ATOM | 4130 | CA  | PRO | B | 911 | 54.010 | 17.391 | -14.963 | 1.00 | 13.25 |
| ATOM | 4131 | CB  | PRO | B | 911 | 54.122 | 18.405 | -13.825 | 1.00 | 12.87 |
| ATOM | 4132 | CG  | PRO | B | 911 | 55.552 | 18.356 | -13.352 | 1.00 | 13.35 |
| ATOM | 4133 | CD  | PRO | B | 911 | 56.165 | 17.089 | -13.830 | 1.00 | 13.13 |
| ATOM | 4134 | C   | PRO | B | 911 | 54.051 | 18.089 | -16.316 | 1.00 | 14.99 |
| ATOM | 4135 | O   | PRO | B | 911 | 55.129 | 18.193 | -16.904 | 1.00 | 14.64 |
| ATOM | 4136 | N   | PHE | B | 912 | 52.899 | 18.546 | -16.804 | 1.00 | 15.30 |
| ATOM | 4137 | CA  | PHE | B | 912 | 52.804 | 19.086 | -18.155 | 1.00 | 15.24 |
| ATOM | 4138 | CB  | PHE | B | 912 | 51.355 | 19.422 | -18.496 | 1.00 | 15.92 |
| ATOM | 4139 | CG  | PHE | B | 912 | 51.145 | 19.805 | -19.937 | 1.00 | 18.02 |
| ATOM | 4140 | CD1 | PHE | B | 912 | 50.896 | 18.829 | -20.900 | 1.00 | 18.18 |
| ATOM | 4141 | CE1 | PHE | B | 912 | 50.695 | 19.177 | -22.227 | 1.00 | 18.36 |
| ATOM | 4142 | CZ  | PHE | B | 912 | 50.750 | 20.513 | -22.607 | 1.00 | 18.71 |
| ATOM | 4143 | CE2 | PHE | B | 912 | 51.008 | 21.497 | -21.659 | 1.00 | 17.67 |
| ATOM | 4144 | CD2 | PHE | B | 912 | 51.199 | 21.141 | -20.334 | 1.00 | 17.95 |
| ATOM | 4145 | C   | PHE | B | 912 | 53.707 | 20.293 | -18.426 | 1.00 | 15.66 |
| ATOM | 4146 | O   | PHE | B | 912 | 54.240 | 20.429 | -19.525 | 1.00 | 17.32 |
| ATOM | 4147 | N   | TYR | B | 913 | 53.878 | 21.162 | -17.436 | 1.00 | 16.19 |
| ATOM | 4148 | CA  | TYR | B | 913 | 54.576 | 22.431 | -17.652 | 1.00 | 17.04 |
| ATOM | 4149 | CB  | TYR | B | 913 | 53.880 | 23.574 | -16.900 | 1.00 | 17.60 |
| ATOM | 4150 | CG  | TYR | B | 913 | 52.422 | 23.688 | -17.259 | 1.00 | 19.80 |
| ATOM | 4151 | CD1 | TYR | B | 913 | 51.443 | 23.076 | -16.475 | 1.00 | 21.96 |
| ATOM | 4152 | CE1 | TYR | B | 913 | 50.100 | 23.160 | -16.814 | 1.00 | 23.64 |
| ATOM | 4153 | CZ  | TYR | B | 913 | 49.731 | 23.863 | -17.948 | 1.00 | 23.95 |
| ATOM | 4154 | OH  | TYR | B | 913 | 48.401 | 23.953 | -18.298 | 1.00 | 26.27 |
| ATOM | 4155 | CE2 | TYR | B | 913 | 50.691 | 24.469 | -18.742 | 1.00 | 22.57 |
| ATOM | 4156 | CD2 | TYR | B | 913 | 52.023 | 24.370 | -18.400 | 1.00 | 19.58 |
| ATOM | 4157 | C   | TYR | B | 913 | 56.054 | 22.386 | -17.318 | 1.00 | 16.51 |
| ATOM | 4158 | O   | TYR | B | 913 | 56.729 | 23.410 | -17.350 | 1.00 | 19.25 |
| ATOM | 4159 | N   | ALA | B | 914 | 56.558 | 21.199 | -17.009 | 1.00 | 15.54 |
| ATOM | 4160 | CA  | ALA | B | 914 | 57.978 | 21.022 | -16.756 | 1.00 | 15.75 |
| ATOM | 4161 | CB  | ALA | B | 914 | 58.200 | 19.912 | -15.727 | 1.00 | 14.04 |
| ATOM | 4162 | C   | ALA | B | 914 | 58.718 | 20.702 | -18.053 | 1.00 | 17.34 |
| ATOM | 4163 | O   | ALA | B | 914 | 58.184 | 20.010 | -18.933 | 1.00 | 18.27 |
| ATOM | 4164 | N   | THR | B | 915 | 59.941 | 21.221 | -18.167 | 1.00 | 17.59 |
| ATOM | 4165 | CA  | THR | B | 915 | 60.881 | 20.781 | -19.192 | 1.00 | 17.41 |
| ATOM | 4166 | CB  | THR | B | 915 | 61.994 | 21.819 | -19.411 | 1.00 | 17.03 |
| ATOM | 4167 | OG1 | THR | B | 915 | 62.510 | 22.240 | -18.139 | 1.00 | 16.93 |
| ATOM | 4168 | CG2 | THR | B | 915 | 61.455 | 23.094 | -20.071 | 1.00 | 13.45 |
| ATOM | 4169 | C   | THR | B | 915 | 61.522 | 19.499 | -18.691 | 1.00 | 20.83 |
| ATOM | 4170 | O   | THR | B | 915 | 61.368 | 19.136 | -17.514 | 1.00 | 18.80 |
| ATOM | 4171 | N   | GLU | B | 916 | 62.253 | 18.826 | -19.577 | 1.00 | 23.65 |
| ATOM | 4172 | CA  | GLU | B | 916 | 63.030 | 17.653 | -19.200 | 1.00 | 27.87 |
| ATOM | 4173 | CB  | GLU | B | 916 | 63.766 | 17.080 | -20.413 | 1.00 | 32.70 |
| ATOM | 4174 | CG  | GLU | B | 916 | 64.142 | 15.603 | -20.297 | 1.00 | 40.69 |
| ATOM | 4175 | CD  | GLU | B | 916 | 63.081 | 14.762 | -19.589 | 1.00 | 44.71 |
| ATOM | 4176 | OE1 | GLU | B | 916 | 61.969 | 14.599 | -20.145 | 1.00 | 46.83 |
| ATOM | 4177 | OE2 | GLU | B | 916 | 63.356 | 14.263 | -18.474 | 1.00 | 46.37 |

FIGURE 3DD

| | A | B | C | D | E | F | G | H | I | J |
|---|---|---|---|---|---|---|---|---|---|---|
| ATOM | 4178 | C | GLU | B | 916 | 64.018 | 17.994 | -18.086 | 1.00 | 26.61 |
| ATOM | 4179 | O | GLU | B | 916 | 64.189 | 17.220 | -17.142 | 1.00 | 24.96 |
| ATOM | 4180 | N | GLU | B | 917 | 64.634 | 19.171 | -18.203 | 1.00 | 25.36 |
| ATOM | 4181 | CA | GLU | B | 917 | 65.663 | 19.637 | -17.281 | 1.00 | 26.20 |
| ATOM | 4182 | CB | GLU | B | 917 | 66.251 | 20.962 | -17.783 | 1.00 | 30.90 |
| ATOM | 4183 | CG | GLU | B | 917 | 67.730 | 21.161 | -17.490 | 1.00 | 37.89 |
| ATOM | 4184 | CD | GLU | B | 917 | 68.261 | 22.495 | -18.001 | 1.00 | 41.89 |
| ATOM | 4185 | OE1 | GLU | B | 917 | 67.902 | 23.550 | -17.416 | 1.00 | 43.85 |
| ATOM | 4186 | OE2 | GLU | B | 917 | 69.045 | 22.493 | -18.982 | 1.00 | 42.66 |
| ATOM | 4187 | C | GLU | B | 917 | 65.120 | 19.800 | -15.864 | 1.00 | 24.06 |
| ATOM | 4188 | O | GLU | B | 917 | 65.772 | 19.420 | -14.893 | 1.00 | 25.57 |
| ATOM | 4189 | N | ILE | B | 918 | 63.923 | 20.365 | -15.755 | 1.00 | 20.90 |
| ATOM | 4190 | CA | ILE | B | 918 | 63.297 | 20.619 | -14.463 | 1.00 | 19.55 |
| ATOM | 4191 | CB | ILE | B | 918 | 62.139 | 21.644 | -14.638 | 1.00 | 20.53 |
| ATOM | 4192 | CG1 | ILE | B | 918 | 62.695 | 23.075 | -14.624 | 1.00 | 22.17 |
| ATOM | 4193 | CD1 | ILE | B | 918 | 63.088 | 23.574 | -13.228 | 1.00 | 24.75 |
| ATOM | 4194 | CG2 | ILE | B | 918 | 61.048 | 21.459 | -13.596 | 1.00 | 15.74 |
| ATOM | 4195 | C | ILE | B | 918 | 62.826 | 19.301 | -13.838 | 1.00 | 17.65 |
| ATOM | 4196 | O | ILE | B | 918 | 62.911 | 19.102 | -12.628 | 1.00 | 18.24 |
| ATOM | 4197 | N | TYR | B | 919 | 62.342 | 18.397 | -14.676 | 1.00 | 16.46 |
| ATOM | 4198 | CA | TYR | B | 919 | 61.970 | 17.072 | -14.215 | 1.00 | 15.19 |
| ATOM | 4199 | CB | TYR | B | 919 | 61.201 | 16.318 | -15.288 | 1.00 | 13.22 |
| ATOM | 4200 | CG | TYR | B | 919 | 60.664 | 14.998 | -14.792 | 1.00 | 15.62 |
| ATOM | 4201 | CD1 | TYR | B | 919 | 59.857 | 14.933 | -13.646 | 1.00 | 13.53 |
| ATOM | 4202 | CE1 | TYR | B | 919 | 59.371 | 13.722 | -13.181 | 1.00 | 13.87 |
| ATOM | 4203 | CZ | TYR | B | 919 | 59.690 | 12.556 | -13.871 | 1.00 | 16.02 |
| ATOM | 4204 | OH | TYR | B | 919 | 59.214 | 11.346 | -13.430 | 1.00 | 17.01 |
| ATOM | 4205 | CE2 | TYR | B | 919 | 60.488 | 12.595 | -15.009 | 1.00 | 14.62 |
| ATOM | 4206 | CD2 | TYR | B | 919 | 60.973 | 13.805 | -15.460 | 1.00 | 14.01 |
| ATOM | 4207 | C | TYR | B | 919 | 63.183 | 16.262 | -13.733 | 1.00 | 14.84 |
| ATOM | 4208 | O | TYR | B | 919 | 63.100 | 15.566 | -12.718 | 1.00 | 13.49 |
| ATOM | 4209 | N | ILE | B | 920 | 64.309 | 16.367 | -14.438 | 1.00 | 14.39 |
| ATOM | 4210 | CA | ILE | B | 920 | 65.531 | 15.709 | -13.974 | 1.00 | 16.73 |
| ATOM | 4211 | CB | ILE | B | 920 | 66.718 | 15.934 | -14.956 | 1.00 | 17.81 |
| ATOM | 4212 | CG1 | ILE | B | 920 | 66.530 | 15.089 | -16.223 | 1.00 | 16.46 |
| ATOM | 4213 | CD1 | ILE | B | 920 | 67.408 | 15.521 | -17.390 | 1.00 | 17.45 |
| ATOM | 4214 | CG2 | ILE | B | 920 | 68.062 | 15.587 | -14.288 | 1.00 | 16.55 |
| ATOM | 4215 | C | ILE | B | 920 | 65.871 | 16.175 | -12.556 | 1.00 | 18.89 |
| ATOM | 4216 | O | ILE | B | 920 | 66.235 | 15.360 | -11.700 | 1.00 | 20.05 |
| ATOM | 4217 | N | ILE | B | 921 | 65.716 | 17.480 | -12.311 | 1.00 | 20.45 |
| ATOM | 4218 | CA | ILE | B | 921 | 65.965 | 18.071 | -10.997 | 1.00 | 19.51 |
| ATOM | 4219 | CB | ILE | B | 921 | 65.930 | 19.618 | -11.076 | 1.00 | 19.81 |
| ATOM | 4220 | CG1 | ILE | B | 921 | 67.175 | 20.147 | -11.796 | 1.00 | 19.81 |
| ATOM | 4221 | CD1 | ILE | B | 921 | 66.996 | 21.530 | -12.404 | 1.00 | 22.63 |
| ATOM | 4222 | CG2 | ILE | B | 921 | 65.821 | 20.242 | -9.691 | 1.00 | 18.07 |
| ATOM | 4223 | C | ILE | B | 921 | 64.988 | 17.532 | -9.952 | 1.00 | 20.75 |
| ATOM | 4224 | O | ILE | B | 921 | 65.387 | 17.204 | -8.827 | 1.00 | 22.57 |
| ATOM | 4225 | N | MET | B | 922 | 63.718 | 17.422 | -10.329 | 1.00 | 20.80 |
| ATOM | 4226 | CA | MET | B | 922 | 62.706 | 16.814 | -9.463 | 1.00 | 21.48 |
| ATOM | 4227 | CB | MET | B | 922 | 61.360 | 16.721 | -10.172 | 1.00 | 20.92 |
| ATOM | 4228 | CG | MET | B | 922 | 60.529 | 17.947 | -10.077 | 1.00 | 21.75 |
| ATOM | 4229 | SD | MET | B | 922 | 59.023 | 17.715 | -11.019 | 1.00 | 22.28 |

FIGURE 3DE

| | A | B | C | D | E | F | G | H | I | J |
|---|---|---|---|---|---|---|---|---|---|---|
| ATOM | 4230 | CE | MET | B | 922 | 58.937 | 19.274 | -11.783 | 1.00 | 19.01 |
| ATOM | 4231 | C | MET | B | 922 | 63.117 | 15.407 | -9.060 | 1.00 | 21.20 |
| ATOM | 4232 | O | MET | B | 922 | 63.077 | 15.061 | -7.877 | 1.00 | 22.43 |
| ATOM | 4233 | N | GLN | B | 923 | 63.505 | 14.606 | -10.052 | 1.00 | 18.40 |
| ATOM | 4234 | CA | GLN | B | 923 | 63.878 | 13.212 | -9.823 | 1.00 | 17.81 |
| ATOM | 4235 | CB | GLN | B | 923 | 64.182 | 12.504 | -11.140 | 1.00 | 17.44 |
| ATOM | 4236 | CG | GLN | B | 923 | 62.938 | 12.186 | -11.946 | 1.00 | 19.66 |
| ATOM | 4237 | CD | GLN | B | 923 | 63.264 | 11.540 | -13.277 | 1.00 | 22.21 |
| ATOM | 4238 | OE1 | GLN | B | 923 | 63.798 | 12.195 | -14.175 | 1.00 | 24.54 |
| ATOM | 4239 | NE2 | GLN | B | 923 | 62.936 | 10.261 | -13.415 | 1.00 | 20.24 |
| ATOM | 4240 | C | GLN | B | 923 | 65.053 | 13.099 | -8.876 | 1.00 | 16.48 |
| ATOM | 4241 | O | GLN | B | 923 | 65.066 | 12.230 | -8.007 | 1.00 | 17.18 |
| ATOM | 4242 | N | SER | B | 924 | 66.031 | 13.986 | -9.060 | 1.00 | 17.16 |
| ATOM | 4243 | CA | SER | B | 924 | 67.186 | 14.124 | -8.173 | 1.00 | 16.82 |
| ATOM | 4244 | CB | SER | B | 924 | 68.045 | 15.293 | -8.638 | 1.00 | 18.00 |
| ATOM | 4245 | OG | SER | B | 924 | 69.083 | 14.823 | -9.458 | 1.00 | 24.65 |
| ATOM | 4246 | C | SER | B | 924 | 66.770 | 14.396 | -6.736 | 1.00 | 15.99 |
| ATOM | 4247 | O | SER | B | 924 | 67.313 | 13.811 | -5.801 | 1.00 | 15.77 |
| ATOM | 4248 | N | CYS | B | 925 | 65.831 | 15.320 | -6.570 | 1.00 | 14.44 |
| ATOM | 4249 | CA | CYS | B | 925 | 65.312 | 15.668 | -5.256 | 1.00 | 15.35 |
| ATOM | 4250 | CB | CYS | B | 925 | 64.328 | 16.831 | -5.366 | 1.00 | 14.04 |
| ATOM | 4251 | SG | CYS | B | 925 | 65.110 | 18.383 | -5.858 | 1.00 | 15.15 |
| ATOM | 4252 | C | CYS | B | 925 | 64.627 | 14.466 | -4.621 | 1.00 | 17.10 |
| ATOM | 4253 | O | CYS | B | 925 | 64.515 | 14.395 | -3.399 | 1.00 | 17.19 |
| ATOM | 4254 | N | TRP | B | 926 | 64.188 | 13.525 | -5.460 | 1.00 | 15.66 |
| ATOM | 4255 | CA | TRP | B | 926 | 63.519 | 12.325 | -4.987 | 1.00 | 15.69 |
| ATOM | 4256 | CB | TRP | B | 926 | 62.272 | 12.022 | -5.830 | 1.00 | 14.35 |
| ATOM | 4257 | CG | TRP | B | 926 | 61.287 | 13.132 | -5.842 | 1.00 | 14.96 |
| ATOM | 4258 | CD1 | TRP | B | 926 | 61.065 | 14.046 | -4.848 | 1.00 | 14.46 |
| ATOM | 4259 | NE1 | TRP | B | 926 | 60.081 | 14.928 | -5.228 | 1.00 | 15.27 |
| ATOM | 4260 | CE2 | TRP | B | 926 | 59.643 | 14.599 | -6.485 | 1.00 | 14.17 |
| ATOM | 4261 | CD2 | TRP | B | 926 | 60.384 | 13.471 | -6.907 | 1.00 | 15.98 |
| ATOM | 4262 | CE3 | TRP | B | 926 | 60.131 | 12.938 | -8.187 | 1.00 | 14.90 |
| ATOM | 4263 | CZ3 | TRP | B | 926 | 59.158 | 13.534 | -8.982 | 1.00 | 14.36 |
| ATOM | 4264 | CH2 | TRP | B | 926 | 58.432 | 14.650 | -8.524 | 1.00 | 15.71 |
| ATOM | 4265 | CZ2 | TRP | B | 926 | 58.663 | 15.197 | -7.282 | 1.00 | 14.17 |
| ATOM | 4266 | C | TRP | B | 926 | 64.437 | 11.109 | -4.935 | 1.00 | 14.77 |
| ATOM | 4267 | O | TRP | B | 926 | 63.966 | 9.975 | -4.976 | 1.00 | 15.40 |
| ATOM | 4268 | N | ALA | B | 927 | 65.743 | 11.326 | -4.852 | 1.00 | 14.03 |
| ATOM | 4269 | CA | ALA | B | 927 | 66.634 | 10.204 | -4.557 | 1.00 | 15.96 |
| ATOM | 4270 | CB | ALA | B | 927 | 68.092 | 10.636 | -4.554 | 1.00 | 13.26 |
| ATOM | 4271 | C | ALA | B | 927 | 66.225 | 9.639 | -3.200 | 1.00 | 14.76 |
| ATOM | 4272 | O | ALA | B | 927 | 66.028 | 10.391 | -2.240 | 1.00 | 16.10 |
| ATOM | 4273 | N | PHE | B | 928 | 66.056 | 8.327 | -3.125 | 1.00 | 13.75 |
| ATOM | 4274 | CA | PHE | B | 928 | 65.604 | 7.718 | -1.882 | 1.00 | 14.61 |
| ATOM | 4275 | CB | PHE | B | 928 | 65.398 | 6.209 | -2.048 | 1.00 | 13.58 |
| ATOM | 4276 | CG | PHE | B | 928 | 64.648 | 5.584 | -0.917 | 1.00 | 12.37 |
| ATOM | 4277 | CD1 | PHE | B | 928 | 63.258 | 5.550 | -0.921 | 1.00 | 12.44 |
| ATOM | 4278 | CE1 | PHE | B | 928 | 62.555 | 4.973 | 0.137 | 1.00 | 13.67 |
| ATOM | 4279 | CZ | PHE | B | 928 | 63.245 | 4.443 | 1.220 | 1.00 | 12.22 |
| ATOM | 4280 | CE2 | PHE | B | 928 | 64.625 | 4.490 | 1.234 | 1.00 | 13.52 |
| ATOM | 4281 | CD2 | PHE | B | 928 | 65.323 | 5.060 | 0.166 | 1.00 | 11.43 |

FIGURE 3DF

| | A | B | C | D | E | F | G | H | I | J |
|---|---|---|---|---|---|---|---|---|---|---|
| ATOM | 4282 | C | PHE | B | 928 | 66.588 | 7.999 | -0.756 | 1.00 | 16.25 |
| ATOM | 4283 | O | PHE | B | 928 | 66.192 | 8.346 | 0.354 | 1.00 | 19.57 |
| ATOM | 4284 | N | ASP | B | 929 | 67.870 | 7.837 | -1.064 | 1.00 | 16.91 |
| ATOM | 4285 | CA | ASP | B | 929 | 68.970 | 8.126 | -0.166 | 1.00 | 15.68 |
| ATOM | 4286 | CB | ASP | B | 929 | 70.191 | 7.331 | -0.643 | 1.00 | 15.67 |
| ATOM | 4287 | CG | ASP | B | 929 | 71.435 | 7.564 | 0.200 | 1.00 | 16.96 |
| ATOM | 4288 | OD1 | ASP | B | 929 | 71.409 | 8.348 | 1.176 | 1.00 | 17.79 |
| ATOM | 4289 | OD2 | ASP | B | 929 | 72.510 | 6.993 | -0.065 | 1.00 | 17.88 |
| ATOM | 4290 | C | ASP | B | 929 | 69.241 | 9.632 | -0.209 | 1.00 | 18.33 |
| ATOM | 4291 | O | ASP | B | 929 | 69.695 | 10.168 | -1.232 | 1.00 | 20.08 |
| ATOM | 4292 | N | SER | B | 930 | 68.981 | 10.305 | 0.910 | 1.00 | 17.68 |
| ATOM | 4293 | CA | SER | B | 930 | 69.124 | 11.760 | 0.999 | 1.00 | 17.03 |
| ATOM | 4294 | CB | SER | B | 930 | 68.670 | 12.263 | 2.374 | 1.00 | 16.25 |
| ATOM | 4295 | OG | SER | B | 930 | 69.567 | 11.860 | 3.384 | 1.00 | 14.34 |
| ATOM | 4296 | C | SER | B | 930 | 70.530 | 12.271 | 0.667 | 1.00 | 17.09 |
| ATOM | 4297 | O | SER | B | 930 | 70.692 | 13.371 | 0.139 | 1.00 | 16.53 |
| ATOM | 4298 | N | ARG | B | 931 | 71.541 | 11.456 | 0.947 | 1.00 | 18.45 |
| ATOM | 4299 | CA | ARG | B | 931 | 72.918 | 11.797 | 0.595 | 1.00 | 18.93 |
| ATOM | 4300 | CB | ARG | B | 931 | 73.879 | 10.724 | 1.115 | 1.00 | 16.40 |
| ATOM | 4301 | CG | ARG | B | 931 | 73.753 | 10.468 | 2.617 | 1.00 | 13.13 |
| ATOM | 4302 | CD | ARG | B | 931 | 74.462 | 9.226 | 3.104 | 1.00 | 11.79 |
| ATOM | 4303 | NE | ARG | B | 931 | 74.026 | 8.037 | 2.379 | 1.00 | 12.05 |
| ATOM | 4304 | CZ | ARG | B | 931 | 74.566 | 6.834 | 2.520 | 1.00 | 10.29 |
| ATOM | 4305 | NH1 | ARG | B | 931 | 74.103 | 5.817 | 1.808 | 1.00 | 6.74 |
| ATOM | 4306 | NH2 | ARG | B | 931 | 75.574 | 6.651 | 3.365 | 1.00 | 9.10 |
| ATOM | 4307 | C | ARG | B | 931 | 73.098 | 11.995 | -0.914 | 1.00 | 20.93 |
| ATOM | 4308 | O | ARG | B | 931 | 74.022 | 12.691 | -1.350 | 1.00 | 23.18 |
| ATOM | 4309 | N | LYS | B | 932 | 72.209 | 11.388 | -1.704 | 1.00 | 20.63 |
| ATOM | 4310 | CA | LYS | B | 932 | 72.305 | 11.448 | -3.161 | 1.00 | 19.83 |
| ATOM | 4311 | CB | LYS | B | 932 | 71.838 | 10.132 | -3.798 | 1.00 | 22.75 |
| ATOM | 4312 | CG | LYS | B | 932 | 72.539 | 8.870 | -3.259 | 1.00 | 23.92 |
| ATOM | 4313 | CD | LYS | B | 932 | 73.832 | 8.592 | -3.984 | 1.00 | 28.12 |
| ATOM | 4314 | CE | LYS | B | 932 | 74.616 | 7.421 | -3.350 | 1.00 | 31.51 |
| ATOM | 4315 | NZ | LYS | B | 932 | 74.231 | 6.071 | -3.877 | 1.00 | 30.23 |
| ATOM | 4316 | C | LYS | B | 932 | 71.542 | 12.625 | -3.756 | 1.00 | 18.83 |
| ATOM | 4317 | O | LYS | B | 932 | 71.644 | 12.888 | -4.946 | 1.00 | 19.37 |
| ATOM | 4318 | N | ARG | B | 933 | 70.777 | 13.328 | -2.928 | 1.00 | 17.02 |
| ATOM | 4319 | CA | ARG | B | 933 | 70.007 | 14.479 | -3.382 | 1.00 | 13.98 |
| ATOM | 4320 | CB | ARG | B | 933 | 68.918 | 14.807 | -2.360 | 1.00 | 14.09 |
| ATOM | 4321 | CG | ARG | B | 933 | 67.823 | 13.758 | -2.281 | 1.00 | 13.34 |
| ATOM | 4322 | CD | ARG | B | 933 | 66.843 | 13.974 | -1.161 | 1.00 | 13.83 |
| ATOM | 4323 | NE | ARG | B | 933 | 66.266 | 12.705 | -0.750 | 1.00 | 16.33 |
| ATOM | 4324 | CZ | ARG | B | 933 | 65.788 | 12.453 | 0.457 | 1.00 | 18.40 |
| ATOM | 4325 | NH1 | ARG | B | 933 | 65.798 | 13.403 | 1.397 | 1.00 | 17.33 |
| ATOM | 4326 | NH2 | ARG | B | 933 | 65.305 | 11.243 | 0.724 | 1.00 | 14.82 |
| ATOM | 4327 | C | ARG | B | 933 | 70.915 | 15.696 | -3.598 | 1.00 | 15.36 |
| ATOM | 4328 | O | ARG | B | 933 | 71.960 | 15.820 | -2.949 | 1.00 | 14.34 |
| ATOM | 4329 | N | PRO | B | 934 | 70.543 | 16.586 | -4.518 | 1.00 | 15.58 |
| ATOM | 4330 | CA | PRO | B | 934 | 71.253 | 17.859 | -4.658 | 1.00 | 15.95 |
| ATOM | 4331 | CB | PRO | B | 934 | 70.552 | 18.519 | -5.847 | 1.00 | 16.20 |
| ATOM | 4332 | CG | PRO | B | 934 | 69.191 | 17.876 | -5.893 | 1.00 | 15.31 |
| ATOM | 4333 | CD | PRO | B | 934 | 69.443 | 16.465 | -5.492 | 1.00 | 15.78 |

FIGURE 3DG

|  | A | B | C | D | E | F | G | H | I | J |
|---|---|---|---|---|---|---|---|---|---|---|
| ATOM | 4334 | C | PRO | B | 934 | 71.048 | 18.685 | -3.387 | 1.00 | 15.17 |
| ATOM | 4335 | O | PRO | B | 934 | 70.047 | 18.500 | -2.690 | 1.00 | 14.47 |
| ATOM | 4336 | N | SER | B | 935 | 71.993 | 19.557 | -3.068 | 1.00 | 13.81 |
| ATOM | 4337 | CA | SER | B | 935 | 71.818 | 20.431 | -1.921 | 1.00 | 13.89 |
| ATOM | 4338 | CB | SER | B | 935 | 73.172 | 20.809 | -1.335 | 1.00 | 12.69 |
| ATOM | 4339 | OG | SER | B | 935 | 73.866 | 21.658 | -2.222 | 1.00 | 11.21 |
| ATOM | 4340 | C | SER | B | 935 | 71.077 | 21.674 | -2.375 | 1.00 | 15.50 |
| ATOM | 4341 | O | SER | B | 935 | 70.948 | 21.915 | -3.575 | 1.00 | 15.56 |
| ATOM | 4342 | N | PHE | B | 936 | 70.598 | 22.470 | -1.423 | 1.00 | 16.73 |
| ATOM | 4343 | CA | PHE | B | 936 | 69.951 | 23.732 | -1.763 | 1.00 | 15.69 |
| ATOM | 4344 | CB | PHE | B | 936 | 69.261 | 24.363 | -0.551 | 1.00 | 14.34 |
| ATOM | 4345 | CG | PHE | B | 936 | 67.949 | 23.721 | -0.230 | 1.00 | 15.00 |
| ATOM | 4346 | CD1 | PHE | B | 936 | 66.891 | 23.775 | -1.141 | 1.00 | 14.68 |
| ATOM | 4347 | CE1 | PHE | B | 936 | 65.686 | 23.164 | -0.864 | 1.00 | 14.65 |
| ATOM | 4348 | CZ | PHE | B | 936 | 65.521 | 22.478 | 0.329 | 1.00 | 15.16 |
| ATOM | 4349 | CE2 | PHE | B | 936 | 66.568 | 22.404 | 1.233 | 1.00 | 14.23 |
| ATOM | 4350 | CD2 | PHE | B | 936 | 67.778 | 23.020 | 0.948 | 1.00 | 13.17 |
| ATOM | 4351 | C | PHE | B | 936 | 70.874 | 24.705 | -2.493 | 1.00 | 17.04 |
| ATOM | 4352 | O | PHE | B | 936 | 70.430 | 25.370 | -3.437 | 1.00 | 20.07 |
| ATOM | 4353 | N | PRO | B | 937 | 72.137 | 24.811 | -2.078 | 1.00 | 15.50 |
| ATOM | 4354 | CA | PRO | B | 937 | 73.131 | 25.527 | -2.892 | 1.00 | 14.29 |
| ATOM | 4355 | CB | PRO | B | 937 | 74.429 | 25.369 | -2.089 | 1.00 | 14.21 |
| ATOM | 4356 | CG | PRO | B | 937 | 73.971 | 25.199 | -0.671 | 1.00 | 13.15 |
| ATOM | 4357 | CD | PRO | B | 937 | 72.709 | 24.361 | -0.793 | 1.00 | 13.80 |
| ATOM | 4358 | C | PRO | B | 937 | 73.281 | 24.966 | -4.314 | 1.00 | 14.84 |
| ATOM | 4359 | O | PRO | B | 937 | 73.466 | 25.763 | -5.227 | 1.00 | 15.53 |
| ATOM | 4360 | N | ASN | B | 938 | 73.191 | 23.649 | -4.514 | 1.00 | 15.23 |
| ATOM | 4361 | CA | ASN | B | 938 | 73.190 | 23.118 | -5.882 | 1.00 | 15.63 |
| ATOM | 4362 | CB | ASN | B | 938 | 73.092 | 21.589 | -5.922 | 1.00 | 14.60 |
| ATOM | 4363 | CG | ASN | B | 938 | 74.294 | 20.891 | -5.302 | 1.00 | 15.72 |
| ATOM | 4364 | OD1 | ASN | B | 938 | 74.195 | 19.732 | -4.883 | 1.00 | 15.91 |
| ATOM | 4365 | ND2 | ASN | B | 938 | 75.431 | 21.578 | -5.244 | 1.00 | 13.94 |
| ATOM | 4366 | C | ASN | B | 938 | 72.015 | 23.717 | -6.650 | 1.00 | 15.55 |
| ATOM | 4367 | O | ASN | B | 938 | 72.173 | 24.231 | -7.763 | 1.00 | 16.86 |
| ATOM | 4368 | N | LEU | B | 939 | 70.848 | 23.680 | -6.020 | 1.00 | 14.18 |
| ATOM | 4369 | CA | LEU | B | 939 | 69.616 | 24.173 | -6.628 | 1.00 | 16.54 |
| ATOM | 4370 | CB | LEU | B | 939 | 68.402 | 23.826 | -5.761 | 1.00 | 14.71 |
| ATOM | 4371 | CG | LEU | B | 939 | 68.212 | 22.310 | -5.622 | 1.00 | 17.33 |
| ATOM | 4372 | CD1 | LEU | B | 939 | 67.321 | 21.948 | -4.435 | 1.00 | 15.19 |
| ATOM | 4373 | CD2 | LEU | B | 939 | 67.684 | 21.710 | -6.918 | 1.00 | 16.10 |
| ATOM | 4374 | C | LEU | B | 939 | 69.639 | 25.663 | -6.978 | 1.00 | 17.07 |
| ATOM | 4375 | O | LEU | B | 939 | 69.165 | 26.045 | -8.047 | 1.00 | 19.15 |
| ATOM | 4376 | N | THR | B | 940 | 70.196 | 26.498 | -6.102 | 1.00 | 15.75 |
| ATOM | 4377 | CA | THR | B | 940 | 70.282 | 27.926 | -6.396 | 1.00 | 16.85 |
| ATOM | 4378 | CB | THR | B | 940 | 70.621 | 28.777 | -5.147 | 1.00 | 14.46 |
| ATOM | 4379 | OG1 | THR | B | 940 | 71.856 | 28.323 | -4.572 | 1.00 | 13.44 |
| ATOM | 4380 | CG2 | THR | B | 940 | 69.571 | 28.591 | -4.055 | 1.00 | 11.13 |
| ATOM | 4381 | C | THR | B | 940 | 71.282 | 28.206 | -7.505 | 1.00 | 17.95 |
| ATOM | 4382 | O | THR | B | 940 | 71.194 | 29.229 | -8.169 | 1.00 | 19.75 |
| ATOM | 4383 | N | SER | B | 941 | 72.239 | 27.303 | -7.689 | 1.00 | 19.49 |
| ATOM | 4384 | CA | SER | B | 941 | 73.143 | 27.375 | -8.831 | 1.00 | 21.17 |
| ATOM | 4385 | CB | SER | B | 941 | 74.426 | 26.606 | -8.554 | 1.00 | 19.83 |

FIGURE 3DH

| | A | B | C | D | E | F | G | H | I | J |
|---|---|---|---|---|---|---|---|---|---|---|
| ATOM | 4386 | OG | SER | B | 941 | 75.129 | 27.233 | -7.502 | 1.00 | 21.48 |
| ATOM | 4387 | C | SER | B | 941 | 72.477 | 26.888 | -10.124 | 1.00 | 22.96 |
| ATOM | 4388 | O | SER | B | 941 | 72.645 | 27.508 | -11.165 | 1.00 | 24.12 |
| ATOM | 4389 | N | PHE | B | 942 | 71.727 | 25.787 | -10.042 | 1.00 | 24.99 |
| ATOM | 4390 | CA | PHE | B | 942 | 71.028 | 25.213 | -11.190 | 1.00 | 26.56 |
| ATOM | 4391 | CB | PHE | B | 942 | 70.309 | 23.893 | -10.819 | 1.00 | 29.16 |
| ATOM | 4392 | CG | PHE | B | 942 | 71.227 | 22.691 | -10.597 | 1.00 | 32.61 |
| ATOM | 4393 | CD1 | PHE | B | 942 | 72.438 | 22.549 | -11.277 | 1.00 | 34.89 |
| ATOM | 4394 | CE1 | PHE | B | 942 | 73.264 | 21.418 | -11.058 | 1.00 | 35.26 |
| ATOM | 4395 | CZ | PHE | B | 942 | 72.864 | 20.418 | -10.159 | 1.00 | 33.21 |
| ATOM | 4396 | CE2 | PHE | B | 942 | 71.659 | 20.545 | -9.486 | 1.00 | 32.56 |
| ATOM | 4397 | CD2 | PHE | B | 942 | 70.845 | 21.672 | -9.711 | 1.00 | 33.80 |
| ATOM | 4398 | C | PHE | B | 942 | 69.992 | 26.213 | -11.701 | 1.00 | 26.65 |
| ATOM | 4399 | O | PHE | B | 942 | 69.909 | 26.463 | -12.901 | 1.00 | 28.72 |
| ATOM | 4400 | N | LEU | B | 943 | 69.219 | 26.789 | -10.781 | 1.00 | 23.87 |
| ATOM | 4401 | CA | LEU | B | 943 | 68.099 | 27.667 | -11.118 | 1.00 | 23.43 |
| ATOM | 4402 | CB | LEU | B | 943 | 66.913 | 27.381 | -10.192 | 1.00 | 22.42 |
| ATOM | 4403 | CG | LEU | B | 943 | 66.456 | 25.920 | -10.075 | 1.00 | 22.14 |
| ATOM | 4404 | CD1 | LEU | B | 943 | 65.575 | 25.755 | -8.866 | 1.00 | 20.82 |
| ATOM | 4405 | CD2 | LEU | B | 943 | 65.726 | 25.466 | -11.336 | 1.00 | 21.52 |
| ATOM | 4406 | C | LEU | B | 943 | 68.465 | 29.150 | -11.071 | 1.00 | 24.99 |
| ATOM | 4407 | O | LEU | B | 943 | 69.571 | 29.510 | -10.660 | 1.00 | 25.26 |
| ATOM | 4408 | N | GLY | B | 944 | 67.539 | 30.008 | -11.500 | 1.00 | 27.96 |
| ATOM | 4409 | CA | GLY | B | 944 | 67.776 | 31.448 | -11.523 | 1.00 | 30.70 |
| ATOM | 4410 | C | GLY | B | 944 | 66.621 | 32.306 | -12.022 | 1.00 | 32.46 |
| ATOM | 4411 | O | GLY | B | 944 | 65.470 | 31.879 | -12.009 | 1.00 | 31.41 |
| ATOM | 4412 | N | CYS | B | 945 | 66.942 | 33.528 | -12.447 | 1.00 | 36.73 |
| ATOM | 4413 | CA | CYS | B | 945 | 65.975 | 34.460 | -13.041 | 1.00 | 39.73 |
| ATOM | 4414 | CB | CYS | B | 945 | 65.495 | 35.479 | -12.004 | 1.00 | 41.65 |
| ATOM | 4415 | SG | CYS | B | 945 | 64.947 | 34.737 | -10.451 | 1.00 | 45.20 |
| ATOM | 4416 | C | CYS | B | 945 | 66.575 | 35.193 | -14.237 | 1.00 | 39.14 |
| ATOM | 4417 | O | CYS | B | 945 | 65.865 | 35.867 | -14.987 | 1.00 | 41.22 |
| TER | 4417 | | CYS | B | 945 | | | | | |
| ATOM | 4418 | O24 | STA | B | 1 | 50.453 | 37.722 | 3.942 | 1.00 | 16.94 |
| ATOM | 4419 | C23 | STA | B | 1 | 50.768 | 36.891 | 4.782 | 1.00 | 15.21 |
| ATOM | 4420 | N22 | STA | B | 1 | 51.825 | 36.970 | 5.603 | 1.00 | 14.95 |
| ATOM | 4421 | C21 | STA | B | 1 | 51.948 | 35.831 | 6.506 | 1.00 | 15.06 |
| ATOM | 4422 | C20 | STA | B | 1 | 50.744 | 35.021 | 6.085 | 1.00 | 15.30 |
| ATOM | 4423 | C25 | STA | B | 1 | 50.057 | 35.673 | 5.056 | 1.00 | 13.88 |
| ATOM | 4424 | C26 | STA | B | 1 | 48.868 | 35.082 | 4.475 | 1.00 | 13.30 |
| ATOM | 4425 | C27 | STA | B | 1 | 47.951 | 35.472 | 3.439 | 1.00 | 13.36 |
| ATOM | 4426 | C28 | STA | B | 1 | 47.973 | 36.627 | 2.647 | 1.00 | 12.97 |
| ATOM | 4427 | C29 | STA | B | 1 | 46.894 | 36.655 | 1.734 | 1.00 | 12.55 |
| ATOM | 4428 | C30 | STA | B | 1 | 45.909 | 35.648 | 1.629 | 1.00 | 12.13 |
| ATOM | 4429 | C32 | STA | B | 1 | 46.968 | 34.473 | 3.322 | 1.00 | 13.59 |
| ATOM | 4430 | C31 | STA | B | 1 | 45.889 | 34.482 | 2.420 | 1.00 | 12.97 |
| ATOM | 4431 | C34 | STA | B | 1 | 48.394 | 33.831 | 4.967 | 1.00 | 13.66 |
| ATOM | 4432 | C35 | STA | B | 1 | 49.104 | 33.170 | 6.022 | 1.00 | 13.63 |
| ATOM | 4433 | N33 | STA | B | 1 | 47.247 | 33.446 | 4.256 | 1.00 | 13.89 |
| ATOM | 4434 | C5 | STA | B | 1 | 46.383 | 32.280 | 4.576 | 1.00 | 15.50 |
| ATOM | 4435 | C4 | STA | B | 1 | 46.423 | 31.210 | 3.475 | 1.00 | 17.49 |
| ATOM | 4436 | C3 | STA | B | 1 | 47.488 | 30.129 | 3.665 | 1.00 | 18.61 |

FIGURE 3DI

| | A | B | C | D | E | F | G | H | I | J |
|---|---|---|---|---|---|---|---|---|---|---|
| ATOM | 4437 | N2 | STA | B | 1 | 46.908 | 28.821 | 3.899 | 1.00 | 21.04 |
| ATOM | 4438 | C1 | STA | B | 1 | 47.506 | 27.634 | 3.318 | 1.00 | 20.51 |
| ATOM | 4439 | C9 | STA | B | 1 | 48.448 | 30.513 | 4.773 | 1.00 | 17.20 |
| ATOM | 4440 | O10 | STA | B | 1 | 49.570 | 29.664 | 4.910 | 1.00 | 19.01 |
| ATOM | 4441 | C11 | STA | B | 1 | 50.762 | 30.314 | 4.484 | 1.00 | 19.90 |
| ATOM | 4442 | O6 | STA | B | 1 | 46.638 | 31.750 | 5.882 | 1.00 | 16.79 |
| ATOM | 4443 | C7 | STA | B | 1 | 47.849 | 30.996 | 6.097 | 1.00 | 16.52 |
| ATOM | 4444 | C8 | STA | B | 1 | 47.442 | 29.872 | 7.049 | 1.00 | 17.19 |
| ATOM | 4445 | N12 | STA | B | 1 | 48.838 | 31.964 | 6.669 | 1.00 | 14.47 |
| ATOM | 4446 | C13 | STA | B | 1 | 49.857 | 31.740 | 7.627 | 1.00 | 13.77 |
| ATOM | 4447 | C14 | STA | B | 1 | 50.065 | 30.696 | 8.536 | 1.00 | 13.68 |
| ATOM | 4448 | C15 | STA | B | 1 | 51.173 | 30.781 | 9.397 | 1.00 | 12.89 |
| ATOM | 4449 | C16 | STA | B | 1 | 52.047 | 31.886 | 9.352 | 1.00 | 13.04 |
| ATOM | 4450 | C17 | STA | B | 1 | 51.834 | 32.938 | 8.440 | 1.00 | 14.03 |
| ATOM | 4451 | C18 | STA | B | 1 | 50.725 | 32.837 | 7.583 | 1.00 | 13.94 |
| ATOM | 4452 | C19 | STA | B | 1 | 50.272 | 33.750 | 6.578 | 1.00 | 14.58 |
| TER | | | | | | | | | | |
| ATOM | 4453 | O | HOH | W | 936 | 80.623 | 6.256 | 14.610 | 1.00 | 22.36 |
| ATOM | 4454 | O | HOH | W | 937 | 85.093 | 24.786 | 25.407 | 1.00 | 38.88 |
| ATOM | 4455 | O | HOH | W | 938 | 95.993 | 13.778 | 22.831 | 1.00 | 16.85 |
| ATOM | 4456 | O | HOH | W | 941 | 100.367 | 6.637 | 14.523 | 1.00 | 31.34 |
| ATOM | 4457 | O | HOH | W | 942 | 88.118 | 8.428 | 10.865 | 1.00 | 17.68 |
| ATOM | 4458 | O | HOH | W | 945 | 65.190 | 1.984 | 3.073 | 1.00 | 33.37 |
| ATOM | 4459 | O | HOH | W | 946 | 95.077 | 7.413 | 6.872 | 1.00 | 20.79 |
| ATOM | 4460 | O | HOH | W | 947 | 95.539 | 5.471 | 4.379 | 1.00 | 24.84 |
| ATOM | 4461 | O | HOH | W | 949 | 98.446 | 14.198 | 8.238 | 1.00 | 27.28 |
| ATOM | 4462 | O | HOH | W | 950 | 71.037 | 21.514 | 1.190 | 1.00 | 21.45 |
| ATOM | 4463 | O | HOH | W | 951 | 81.074 | 30.560 | 6.219 | 1.00 | 27.63 |
| ATOM | 4464 | O | HOH | W | 952 | 87.907 | 6.542 | 8.918 | 1.00 | 24.61 |
| ATOM | 4465 | O | HOH | W | 953 | 106.538 | 34.319 | 14.218 | 1.00 | 65.16 |
| ATOM | 4466 | O | HOH | W | 954 | 100.838 | 34.810 | 5.757 | 1.00 | 26.51 |
| ATOM | 4467 | O | HOH | W | 955 | 98.676 | 36.414 | -0.313 | 1.00 | 40.04 |
| ATOM | 4468 | O | HOH | W | 956 | 87.219 | 32.730 | -7.150 | 1.00 | 46.89 |
| ATOM | 4469 | O | HOH | W | 957 | 105.941 | 40.570 | -0.644 | 0.50 | 48.85 |
| ATOM | 4470 | O | HOH | W | 958 | 63.451 | 36.997 | -4.761 | 1.00 | 41.30 |
| ATOM | 4471 | O | HOH | W | 960 | 49.547 | 14.486 | 2.507 | 1.00 | 12.80 |
| ATOM | 4472 | O | HOH | W | 961 | 56.451 | 12.322 | -1.428 | 1.00 | 21.64 |
| ATOM | 4473 | O | HOH | W | 962 | 57.490 | 11.768 | -6.593 | 1.00 | 24.43 |
| ATOM | 4474 | O | HOH | W | 963 | 64.436 | 5.946 | 4.717 | 1.00 | 23.17 |
| ATOM | 4475 | O | HOH | W | 966 | 52.434 | 11.260 | -11.423 | 1.00 | 32.02 |
| ATOM | 4476 | O | HOH | W | 968 | 44.255 | 13.847 | -5.424 | 1.00 | 28.83 |
| ATOM | 4477 | O | HOH | W | 969 | 46.029 | 1.360 | 4.723 | 1.00 | 31.89 |
| ATOM | 4478 | O | HOH | W | 971 | 64.472 | 24.331 | -18.120 | 1.00 | 41.78 |
| ATOM | 4479 | O | HOH | W | 973 | 67.795 | 10.852 | -10.762 | 1.00 | 45.66 |
| ATOM | 4480 | O | HOH | W | 974 | 66.611 | 6.531 | -5.719 | 1.00 | 27.21 |
| ATOM | 4481 | O | HOH | W | 975 | 68.950 | 6.761 | -3.843 | 1.00 | 20.95 |
| ATOM | 4482 | O | HOH | W | 976 | 67.960 | 9.186 | 3.648 | 1.00 | 17.36 |
| ATOM | 4483 | O | HOH | W | 979 | 76.348 | 12.326 | -3.295 | 1.00 | 66.36 |
| ATOM | 4484 | O | HOH | W | 980 | 74.721 | 21.597 | 1.684 | 1.00 | 30.34 |
| ATOM | 4485 | O | HOH | W | 982 | 99.127 | 17.677 | 2.015 | 1.00 | 63.66 |
| ATOM | 4486 | O | HOH | W | 985 | 98.921 | 12.916 | 10.816 | 1.00 | 31.10 |
| ATOM | 4487 | O | HOH | W | 986 | 97.564 | 14.404 | 12.680 | 1.00 | 28.93 |

FIGURE 3DJ

| | A | B | C | D | E | F | G | H | I | J |
|---|---|---|---|---|---|---|---|---|---|---|
| ATOM | 4488 | O | HOH | W | 987 | 96.625 | 16.161 | 8.711 | 1.00 | 19.04 |
| ATOM | 4489 | O | HOH | W | 989 | 93.994 | 15.040 | -2.196 | 1.00 | 53.87 |
| ATOM | 4490 | O | HOH | W | 990 | 87.215 | 8.976 | 16.104 | 1.00 | 24.16 |
| ATOM | 4491 | O | HOH | W | 991 | 83.005 | 4.846 | 14.184 | 1.00 | 23.79 |
| ATOM | 4492 | O | HOH | W | 992 | 63.511 | 3.359 | 4.539 | 1.00 | 26.59 |
| ATOM | 4493 | O | HOH | W | 995 | 108.440 | 34.321 | 1.851 | 1.00 | 56.55 |
| ATOM | 4494 | O | HOH | W | 996 | 109.895 | 34.694 | -2.669 | 1.00 | 58.84 |
| ATOM | 4495 | O | HOH | W | 997 | 109.680 | 27.155 | -11.971 | 1.00 | 57.23 |
| ATOM | 4496 | O | HOH | W | 1000 | 92.870 | 20.123 | -6.428 | 1.00 | 40.05 |
| ATOM | 4497 | O | HOH | W | 1002 | 89.744 | 31.206 | -5.373 | 1.00 | 34.09 |
| ATOM | 4498 | O | HOH | W | 1003 | 81.077 | 34.761 | -1.992 | 1.00 | 56.91 |
| ATOM | 4499 | O | HOH | W | 1004 | 88.167 | 36.991 | 1.393 | 1.00 | 37.22 |
| ATOM | 4500 | O | HOH | W | 1006 | 88.914 | 34.391 | 10.010 | 1.00 | 34.60 |
| ATOM | 4501 | O | HOH | W | 1008 | 103.961 | 23.249 | 6.378 | 1.00 | 49.61 |
| ATOM | 4502 | O | HOH | W | 1010 | 102.956 | 13.539 | 17.207 | 1.00 | 26.91 |
| ATOM | 4503 | O | HOH | W | 1011 | 101.679 | 11.264 | 15.955 | 1.00 | 33.51 |
| ATOM | 4504 | O | HOH | W | 1012 | 48.058 | 25.838 | -20.572 | 1.00 | 30.39 |
| ATOM | 4505 | O | HOH | W | 1016 | 79.047 | 32.511 | 12.764 | 1.00 | 44.97 |
| ATOM | 4506 | O | HOH | W | 1023 | 94.566 | 38.689 | 10.056 | 1.00 | 51.23 |
| ATOM | 4507 | O | HOH | W | 1027 | 98.526 | 5.811 | 10.377 | 1.00 | 30.46 |
| ATOM | 4508 | O | HOH | W | 1028 | 97.596 | 7.368 | 8.483 | 1.00 | 28.02 |
| ATOM | 4509 | O | HOH | W | 1029 | 85.146 | 11.602 | 4.190 | 1.00 | 30.55 |
| ATOM | 4510 | O | HOH | W | 1036 | 92.641 | 5.738 | 19.065 | 1.00 | 17.60 |
| ATOM | 4511 | O | HOH | W | 1037 | 92.118 | 7.839 | 20.801 | 1.00 | 30.74 |
| ATOM | 4512 | O | HOH | W | 1038 | 95.264 | 4.740 | 19.723 | 1.00 | 37.52 |
| ATOM | 4513 | O | HOH | W | 1039 | 94.176 | -1.440 | 12.817 | 1.00 | 23.79 |
| ATOM | 4514 | O | HOH | W | 1041 | 86.524 | -3.639 | 16.308 | 1.00 | 27.05 |
| ATOM | 4515 | O | HOH | W | 1042 | 78.414 | -3.000 | 13.808 | 1.00 | 54.66 |
| ATOM | 4516 | O | HOH | W | 1044 | 77.136 | 8.491 | 17.756 | 1.00 | 33.11 |
| ATOM | 4517 | O | HOH | W | 1045 | 74.683 | 7.294 | 13.751 | 1.00 | 17.88 |
| ATOM | 4518 | O | HOH | W | 1047 | 86.221 | 20.087 | 30.110 | 1.00 | 39.08 |
| ATOM | 4519 | O | HOH | W | 1048 | 95.006 | 12.481 | 26.813 | 1.00 | 43.63 |
| ATOM | 4520 | O | HOH | W | 1049 | 101.627 | 18.235 | 23.454 | 1.00 | 27.26 |
| ATOM | 4521 | O | HOH | W | 1052 | 75.974 | 29.216 | 11.940 | 1.00 | 24.60 |
| ATOM | 4522 | O | HOH | W | 1054 | 82.596 | 34.568 | 17.085 | 1.00 | 57.00 |
| ATOM | 4523 | O | HOH | W | 1059 | 61.728 | 37.098 | 10.866 | 1.00 | 40.02 |
| ATOM | 4524 | O | HOH | W | 1061 | 64.597 | 40.858 | 3.525 | 1.00 | 48.02 |
| ATOM | 4525 | O | HOH | W | 1062 | 54.478 | 43.960 | 4.616 | 1.00 | 33.73 |
| ATOM | 4526 | O | HOH | W | 1063 | 50.914 | 44.799 | -0.384 | 1.00 | 42.76 |
| ATOM | 4527 | O | HOH | W | 1064 | 49.353 | 20.620 | -4.576 | 1.00 | 28.87 |
| ATOM | 4528 | O | HOH | W | 1066 | 44.092 | 20.490 | -9.161 | 1.00 | 34.53 |
| ATOM | 4529 | O | HOH | W | 1067 | 44.529 | 18.249 | -7.655 | 1.00 | 21.04 |
| ATOM | 4530 | O | HOH | W | 1068 | 40.707 | 31.382 | -11.756 | 1.00 | 58.50 |
| ATOM | 4531 | O | HOH | W | 1069 | 58.573 | 34.313 | -10.230 | 1.00 | 50.00 |
| ATOM | 4532 | O | HOH | W | 1070 | 64.848 | 36.712 | -6.934 | 1.00 | 55.53 |
| ATOM | 4533 | O | HOH | W | 1071 | 71.047 | 33.331 | 2.499 | 1.00 | 50.58 |
| ATOM | 4534 | O | HOH | W | 1072 | 55.031 | 19.765 | 3.794 | 1.00 | 34.69 |
| ATOM | 4535 | O | HOH | W | 1073 | 60.424 | 15.562 | 5.038 | 1.00 | 26.70 |
| ATOM | 4536 | O | HOH | W | 1074 | 51.485 | 9.952 | -9.326 | 1.00 | 16.68 |
| ATOM | 4537 | O | HOH | W | 1075 | 44.631 | 10.490 | 1.216 | 1.00 | 42.30 |
| ATOM | 4538 | O | HOH | W | 1077 | 46.303 | 0.173 | 1.535 | 1.00 | 57.93 |
| ATOM | 4539 | O | HOH | W | 1078 | 57.416 | 11.261 | -17.088 | 1.00 | 32.25 |

FIGURE 3DK

|  | A | B | C | D | E | F | G | H | I | J |
|---|---|---|---|---|---|---|---|---|---|---|
| ATOM | 4540 | O | HOH | W1080 | 64.997 | 20.771 | -20.669 | 1.00 | 37.57 |
| ATOM | 4541 | O | HOH | W1081 | 70.033 | 12.402 | -7.004 | 1.00 | 44.18 |
| ATOM | 4542 | O | HOH | W1082 | 68.208 | 13.155 | 5.432 | 1.00 | 25.46 |
| ATOM | 4543 | O | HOH | W1083 | 78.334 | 20.301 | -1.199 | 1.00 | 25.99 |
| ATOM | 4544 | O | HOH | W1084 | 76.310 | 22.108 | -0.842 | 1.00 | 18.43 |
| ATOM | 4545 | O | HOH | W1085 | 87.926 | 14.907 | 3.836 | 1.00 | 25.63 |
| ATOM | 4546 | O | HOH | W1087 | 78.528 | 3.843 | 5.644 | 1.00 | 20.19 |
| ATOM | 4547 | O | HOH | W1088 | 76.014 | 8.054 | 6.081 | 1.00 | 8.10 |
| ATOM | 4548 | O | HOH | W1089 | 77.063 | 11.683 | 3.664 | 1.00 | 30.13 |
| ATOM | 4549 | O | HOH | W1090 | 103.266 | 10.886 | 13.789 | 1.00 | 45.74 |
| ATOM | 4550 | O | HOH | W1091 | 99.332 | 2.197 | 8.660 | 1.00 | 37.85 |
| ATOM | 4551 | O | HOH | W1093 | 78.745 | 5.048 | 16.088 | 1.00 | 40.57 |
| ATOM | 4552 | O | HOH | W1095 | 75.655 | 13.531 | 15.878 | 1.00 | 32.21 |
| ATOM | 4553 | O | HOH | W1096 | 95.959 | 38.432 | -11.617 | 1.00 | 57.20 |
| ATOM | 4554 | O | HOH | W1097 | 112.119 | 33.242 | -10.604 | 1.00 | 40.54 |
| ATOM | 4555 | O | HOH | W1098 | 107.200 | 43.552 | -1.161 | 1.00 | 51.97 |
| ATOM | 4556 | O | HOH | W1100 | 89.465 | 33.844 | -5.350 | 1.00 | 44.69 |
| ATOM | 4557 | O | HOH | W1101 | 101.754 | 12.440 | 10.925 | 1.00 | 35.89 |
| ATOM | 4558 | O | HOH | W1104 | 104.911 | 18.091 | -0.030 | 1.00 | 60.27 |
| ATOM | 4559 | O | HOH | W1105 | 95.616 | 21.253 | -5.050 | 1.00 | 51.12 |
| ATOM | 4560 | O | HOH | W1106 | 90.938 | 18.666 | -5.768 | 1.00 | 50.02 |
| ATOM | 4561 | O | HOH | W1107 | 89.402 | 20.158 | -9.967 | 1.00 | 46.83 |
| ATOM | 4562 | O | HOH | W1108 | 85.469 | 19.335 | -9.356 | 1.00 | 43.05 |
| ATOM | 4563 | O | HOH | W1110 | 88.403 | 30.835 | -2.965 | 1.00 | 40.04 |
| ATOM | 4564 | O | HOH | W1112 | 83.442 | 35.425 | 1.108 | 1.00 | 43.56 |
| ATOM | 4565 | O | HOH | W1113 | 84.135 | 37.832 | 8.350 | 1.00 | 68.86 |
| ATOM | 4566 | O | HOH | W1115 | 91.672 | 36.448 | 2.789 | 1.00 | 40.09 |
| ATOM | 4567 | O | HOH | W1116 | 97.158 | 35.606 | 3.349 | 1.00 | 45.36 |
| ATOM | 4568 | O | HOH | W1118 | 105.477 | 27.026 | 11.543 | 1.00 | 45.10 |
| ATOM | 4569 | O | HOH | W1119 | 102.363 | 18.473 | 7.534 | 1.00 | 46.31 |
| ATOM | 4570 | O | HOH | W1120 | 105.763 | 16.564 | 11.119 | 1.00 | 58.43 |
| ATOM | 4571 | O | HOH | W1121 | 102.898 | 13.824 | 9.135 | 1.00 | 44.97 |
| ATOM | 4572 | O | HOH | W1122 | 107.035 | 21.948 | 19.567 | 1.00 | 51.45 |
| ATOM | 4573 | O | HOH | W1123 | 106.848 | 20.829 | 12.783 | 1.00 | 47.32 |
| ATOM | 4574 | O | HOH | W1124 | 106.013 | 16.127 | 21.313 | 1.00 | 60.26 |
| ATOM | 4575 | O | HOH | W1125 | 101.419 | 21.641 | 27.218 | 1.00 | 36.87 |
| ATOM | 4576 | O | HOH | W1127 | 94.145 | 36.497 | 20.439 | 1.00 | 61.10 |
| ATOM | 4577 | O | HOH | W1128 | 96.923 | 35.155 | 19.030 | 1.00 | 59.43 |
| ATOM | 4578 | O | HOH | W1129 | 87.646 | 34.340 | 13.359 | 1.00 | 33.35 |
| ATOM | 4579 | O | HOH | W1130 | 76.785 | 21.063 | 6.681 | 1.00 | 19.89 |
| ATOM | 4580 | O | HOH | W1131 | 74.330 | 19.844 | 6.150 | 1.00 | 23.74 |
| ATOM | 4581 | O | HOH | W1132 | 73.428 | 22.294 | 6.291 | 1.00 | 31.77 |
| ATOM | 4582 | O | HOH | W1133 | 71.986 | 23.549 | 8.384 | 1.00 | 22.03 |
| ATOM | 4583 | O | HOH | W1134 | 69.597 | 22.620 | 9.032 | 1.00 | 26.90 |
| ATOM | 4584 | O | HOH | W1135 | 69.855 | 19.769 | 8.568 | 1.00 | 21.32 |
| ATOM | 4585 | O | HOH | W1136 | 72.028 | 18.637 | 8.431 | 1.00 | 39.37 |
| ATOM | 4586 | O | HOH | W1137 | 72.925 | 19.604 | 1.976 | 1.00 | 25.29 |
| ATOM | 4587 | O | HOH | W1138 | 74.848 | 17.644 | 0.292 | 1.00 | 52.75 |
| ATOM | 4588 | O | HOH | W1139 | 77.265 | 17.782 | -0.331 | 1.00 | 22.19 |
| ATOM | 4589 | O | HOH | W1140 | 77.983 | 16.594 | -2.727 | 1.00 | 47.34 |
| ATOM | 4590 | O | HOH | W1141 | 75.540 | 17.510 | -4.068 | 1.00 | 39.46 |
| ATOM | 4591 | O | HOH | W1142 | 96.713 | 15.182 | 1.845 | 1.00 | 49.71 |

FIGURE 3DL

| | A | B | C | D | E | F | G | H | I | J |
|---|---|---|---|---|---|---|---|---|---|---|
| ATOM | 4592 | | O | | HOH W1144 | 93.911 | 26.393 | -2.443 | 1.00 | 40.94 |
| ATOM | 4593 | | O | | HOH W1145 | 77.363 | 5.976 | 7.240 | 1.00 | 23.89 |
| ATOM | 4594 | | O | | HOH W1146 | 78.073 | 1.177 | 5.905 | 1.00 | 35.75 |
| ATOM | 4595 | | O | | HOH W1147 | 81.648 | 0.650 | -2.182 | 1.00 | 46.84 |
| ATOM | 4596 | | O | | HOH W1148 | 64.067 | 2.046 | -3.638 | 1.00 | 39.21 |
| ATOM | 4597 | | O | | HOH W1149 | 64.598 | 1.913 | -0.739 | 1.00 | 40.32 |
| ATOM | 4598 | | O | | HOH W1150 | 83.315 | 0.027 | -0.217 | 1.00 | 23.57 |
| ATOM | 4599 | | O | | HOH W1151 | 78.521 | 0.226 | -1.021 | 1.00 | 42.42 |
| ATOM | 4600 | | O | | HOH W1152 | 74.611 | 3.644 | 4.929 | 1.00 | 37.27 |
| ATOM | 4601 | | O | | HOH W1153 | 72.611 | 1.187 | 5.559 | 1.00 | 56.93 |
| ATOM | 4602 | | O | | HOH W1155 | 77.061 | -0.265 | 3.207 | 1.00 | 44.55 |
| ATOM | 4603 | | O | | HOH W1158 | 93.844 | -2.600 | 15.277 | 1.00 | 47.18 |
| ATOM | 4604 | | O | | HOH W1159 | 95.532 | -4.567 | 13.320 | 1.00 | 36.65 |
| ATOM | 4605 | | O | | HOH W1160 | 89.253 | -3.873 | 14.948 | 1.00 | 40.95 |
| ATOM | 4606 | | O | | HOH W1161 | 62.922 | 7.248 | 15.158 | 1.00 | 53.40 |
| ATOM | 4607 | | O | | HOH W1162 | 78.041 | 1.836 | 14.600 | 1.00 | 44.50 |
| ATOM | 4608 | | O | | HOH W1163 | 76.824 | 6.785 | 15.753 | 1.00 | 24.93 |
| ATOM | 4609 | | O | | HOH W1164 | 79.759 | 9.085 | 21.295 | 1.00 | 48.36 |
| ATOM | 4610 | | O | | HOH W1165 | 86.059 | 4.788 | 24.856 | 1.00 | 52.71 |
| ATOM | 4611 | | O | | HOH W1167 | 60.663 | 16.136 | -21.679 | 1.00 | 59.98 |
| ATOM | 4612 | | O | | HOH W1168 | 91.222 | 16.147 | 27.664 | 1.00 | 31.90 |
| ATOM | 4613 | | O | | HOH W1169 | 87.521 | 17.060 | 30.195 | 1.00 | 55.31 |
| ATOM | 4614 | | O | | HOH W1170 | 73.370 | 4.758 | 12.564 | 1.00 | 45.28 |
| ATOM | 4615 | | O | | HOH W1171 | 73.900 | 13.496 | 5.217 | 1.00 | 49.93 |
| ATOM | 4616 | | O | | HOH W1173 | 66.346 | 14.222 | 12.537 | 1.00 | 40.15 |
| ATOM | 4617 | | O | | HOH W1175 | 76.075 | 32.609 | 10.548 | 1.00 | 45.26 |
| ATOM | 4618 | | O | | HOH W1176 | 75.708 | 29.942 | 9.647 | 1.00 | 36.71 |
| ATOM | 4619 | | O | | HOH W1177 | 72.162 | 30.851 | 13.100 | 1.00 | 40.80 |
| ATOM | 4620 | | O | | HOH W1179 | 76.603 | 31.382 | 12.775 | 1.00 | 37.90 |
| ATOM | 4621 | | O | | HOH W1183 | 52.684 | 38.772 | -8.479 | 1.00 | 50.30 |
| ATOM | 4622 | | O | | HOH W1184 | 55.245 | 39.417 | -14.052 | 1.00 | 44.07 |
| ATOM | 4623 | | O | | HOH W1186 | 37.591 | 38.605 | 8.110 | 1.00 | 49.24 |
| ATOM | 4624 | | O | | HOH W1187 | 43.481 | 29.223 | 6.400 | 1.00 | 53.77 |
| ATOM | 4625 | | O | | HOH W1188 | 40.499 | 26.827 | 9.301 | 1.00 | 54.29 |
| ATOM | 4626 | | O | | HOH W1191 | 57.000 | 44.840 | 4.318 | 1.00 | 50.92 |
| ATOM | 4627 | | O | | HOH W1192 | 56.364 | 42.007 | 1.126 | 1.00 | 49.11 |
| ATOM | 4628 | | O | | HOH W1193 | 64.714 | 38.118 | 12.852 | 1.00 | 48.18 |
| ATOM | 4629 | | O | | HOH W1196 | 67.497 | 40.980 | 9.669 | 1.00 | 51.16 |
| ATOM | 4630 | | O | | HOH W1197 | 63.221 | 36.212 | 8.820 | 1.00 | 37.26 |
| ATOM | 4631 | | O | | HOH W1199 | 61.891 | 41.189 | 2.224 | 1.00 | 44.64 |
| ATOM | 4632 | | O | | HOH W1200 | 59.354 | 41.885 | -1.632 | 1.00 | 43.06 |
| ATOM | 4633 | | O | | HOH W1201 | 65.935 | 35.670 | -4.198 | 1.00 | 58.04 |
| ATOM | 4634 | | O | | HOH W1202 | 56.948 | 33.365 | 8.341 | 1.00 | 51.02 |
| ATOM | 4635 | | O | | HOH W1203 | 62.970 | 39.317 | 10.340 | 1.00 | 50.38 |
| ATOM | 4636 | | O | | HOH W1204 | 112.233 | 15.285 | -24.596 | 1.00 | 79.72 |
| ATOM | 4637 | | O | | HOH W1208 | 45.746 | 32.050 | -0.495 | 1.00 | 42.72 |
| ATOM | 4638 | | O | | HOH W1209 | 45.770 | 26.584 | -0.550 | 1.00 | 42.94 |
| ATOM | 4639 | | O | | HOH W1210 | 50.735 | 22.596 | -0.943 | 1.00 | 18.29 |
| ATOM | 4640 | | O | | HOH W1211 | 45.331 | 34.545 | -5.886 | 1.00 | 40.61 |
| ATOM | 4641 | | O | | HOH W1212 | 41.026 | 54.161 | 11.336 | 1.00 | 64.33 |
| ATOM | 4642 | | O | | HOH W1213 | 41.105 | 24.389 | -9.033 | 1.00 | 56.13 |
| ATOM | 4643 | | O | | HOH W1214 | 38.311 | 24.880 | -9.819 | 1.00 | 71.00 |

FIGURE 3DM

| | A | B | C | D | E | F | G | H | I | J |
|---|---|---|---|---|---|---|---|---|---|---|
| ATOM | 4644 | O | HOH | W1215 | | 42.327 | 22.129 | -8.342 | 1.00 | 67.07 |
| ATOM | 4645 | O | HOH | W1216 | | 45.022 | 20.134 | -2.845 | 1.00 | 38.67 |
| ATOM | 4646 | O | HOH | W1217 | | 44.349 | 21.971 | -1.243 | 1.00 | 41.83 |
| ATOM | 4647 | O | HOH | W1218 | | 43.402 | 31.371 | -14.564 | 1.00 | 51.11 |
| ATOM | 4648 | O | HOH | W1219 | | 60.259 | 26.525 | -21.908 | 1.00 | 45.94 |
| ATOM | 4649 | O | HOH | W1220 | | 57.725 | 25.232 | -27.720 | 1.00 | 43.50 |
| ATOM | 4650 | O | HOH | W1221 | | 100.641 | 16.595 | 21.815 | 1.00 | 42.51 |
| ATOM | 4651 | O | HOH | W1222 | | 58.067 | 35.925 | -18.286 | 1.00 | 50.15 |
| ATOM | 4652 | O | HOH | W1223 | | 50.512 | 38.445 | -10.393 | 1.00 | 53.61 |
| ATOM | 4653 | O | HOH | W1224 | | 58.609 | 32.169 | -19.987 | 1.00 | 32.00 |
| ATOM | 4654 | O | HOH | W1225 | | 59.275 | 36.079 | -12.480 | 1.00 | 45.14 |
| ATOM | 4655 | O | HOH | W1226 | | 69.946 | 31.921 | 0.239 | 1.00 | 24.11 |
| ATOM | 4656 | O | HOH | W1227 | | 69.463 | 35.986 | -6.800 | 1.00 | 51.43 |
| ATOM | 4657 | O | HOH | W1228 | | 78.280 | 28.557 | -6.541 | 1.00 | 40.41 |
| ATOM | 4658 | O | HOH | W1229 | | 76.315 | 27.072 | -4.828 | 1.00 | 25.90 |
| ATOM | 4659 | O | HOH | W1230 | | 74.857 | 29.014 | -3.041 | 1.00 | 27.92 |
| ATOM | 4660 | O | HOH | W1231 | | 74.123 | 30.172 | -6.526 | 1.00 | 37.85 |
| ATOM | 4661 | O | HOH | W1232 | | 74.233 | 28.089 | -5.189 | 1.00 | 19.40 |
| ATOM | 4662 | O | HOH | W1233 | | 73.528 | 28.771 | 11.796 | 1.00 | 28.98 |
| ATOM | 4663 | O | HOH | W1234 | | 60.326 | 17.607 | 6.092 | 1.00 | 41.62 |
| ATOM | 4664 | O | HOH | W1235 | | 57.047 | 17.863 | 4.694 | 1.00 | 34.98 |
| ATOM | 4665 | O | HOH | W1236 | | 58.821 | 19.634 | 4.387 | 1.00 | 26.63 |
| ATOM | 4666 | O | HOH | W1237 | | 57.680 | 16.914 | 7.278 | 1.00 | 46.97 |
| ATOM | 4667 | O | HOH | W1238 | | 53.062 | 21.267 | 9.920 | 1.00 | 52.94 |
| ATOM | 4668 | O | HOH | W1239 | | 50.368 | 22.344 | 6.088 | 1.00 | 45.19 |
| ATOM | 4669 | O | HOH | W1240 | | 47.819 | 19.965 | -2.615 | 1.00 | 29.69 |
| ATOM | 4670 | O | HOH | W1241 | | 48.367 | 21.543 | -0.115 | 1.00 | 31.72 |
| ATOM | 4671 | O | HOH | W1242 | | 45.938 | 22.824 | 0.731 | 1.00 | 49.98 |
| ATOM | 4672 | O | HOH | W1243 | | 56.110 | 27.894 | 13.619 | 1.00 | 51.13 |
| ATOM | 4673 | O | HOH | W1244 | | 56.140 | 25.324 | 13.679 | 1.00 | 53.26 |
| ATOM | 4674 | O | HOH | W1246 | | 56.164 | 11.016 | 0.803 | 1.00 | 29.90 |
| ATOM | 4675 | O | HOH | W1247 | | 45.969 | 13.313 | -1.193 | 1.00 | 25.22 |
| ATOM | 4676 | O | HOH | W1248 | | 47.132 | 14.313 | 1.009 | 1.00 | 36.96 |
| ATOM | 4677 | O | HOH | W1249 | | 65.996 | 7.304 | 2.945 | 1.00 | 18.69 |
| ATOM | 4678 | O | HOH | W1250 | | 78.700 | -5.094 | 11.348 | 1.00 | 44.07 |
| ATOM | 4679 | O | HOH | W1252 | | 74.701 | 15.613 | 2.847 | 1.00 | 24.93 |
| ATOM | 4680 | O | HOH | W1253 | | 73.352 | 18.082 | 4.230 | 1.00 | 24.09 |
| ATOM | 4681 | O | HOH | W1254 | | 71.542 | 13.734 | 4.007 | 1.00 | 45.73 |
| ATOM | 4682 | O | HOH | W1256 | | 62.840 | 7.608 | -4.295 | 1.00 | 27.03 |
| ATOM | 4683 | O | HOH | W1257 | | 60.396 | 6.716 | -3.762 | 1.00 | 25.97 |
| ATOM | 4684 | O | HOH | W1258 | | 64.908 | 8.901 | -11.565 | 1.00 | 53.51 |
| ATOM | 4685 | O | HOH | W1259 | | 66.826 | 8.017 | -7.532 | 1.00 | 38.28 |
| ATOM | 4686 | O | HOH | W1260 | | 50.649 | 12.467 | -13.188 | 1.00 | 34.70 |
| ATOM | 4687 | O | HOH | W1262 | | 45.124 | 19.863 | -13.843 | 1.00 | 50.43 |
| ATOM | 4688 | O | HOH | W1263 | | 48.592 | 9.373 | -9.866 | 1.00 | 33.24 |
| ATOM | 4689 | O | HOH | W1264 | | 43.316 | 10.311 | -3.441 | 1.00 | 49.91 |
| ATOM | 4690 | O | HOH | W1265 | | 43.248 | 11.573 | -1.198 | 1.00 | 47.02 |
| ATOM | 4691 | O | HOH | W1266 | | 48.045 | 4.005 | -2.468 | 1.00 | 52.51 |
| ATOM | 4692 | O | HOH | W1267 | | 42.447 | 4.334 | 1.233 | 1.00 | 45.48 |
| ATOM | 4693 | O | HOH | W1270 | | 58.592 | 2.244 | -9.470 | 1.00 | 58.81 |
| ATOM | 4694 | O | HOH | W1271 | | 54.871 | 7.451 | -11.722 | 1.00 | 49.14 |
| ATOM | 4695 | O | HOH | W1272 | | 56.018 | 17.633 | -19.471 | 1.00 | 51.18 |

FIGURE 3DN

| | A | B | C | D | E | F | G | H | I | J |
|---|---|---|---|---|---|---|---|---|---|---|
| ATOM | 4696 | | O | | HOH W1273 | 46.746 | 23.535 | -16.398 | 1.00 | 50.09 |
| ATOM | 4697 | | O | | HOH W1274 | 62.354 | 19.982 | -22.221 | 1.00 | 40.70 |
| ATOM | 4698 | | O | | HOH W1276 | 62.367 | 8.460 | -16.194 | 1.00 | 61.91 |
| ATOM | 4699 | | O | | HOH W1277 | 73.326 | 7.264 | 6.207 | 1.00 | 38.85 |
| ATOM | 4700 | | O | | HOH W1278 | 53.046 | 29.113 | 11.984 | 1.00 | 62.27 |
| ATOM | 4701 | | O | | HOH W1280 | 107.820 | 23.901 | 3.186 | 1.00 | 52.86 |
| ATOM | 4702 | | O | | HOH W1283 | 95.580 | 19.858 | -10.151 | 1.00 | 56.59 |
| ATOM | 4703 | | O | | HOH W1284 | 85.311 | 36.744 | -4.633 | 1.00 | 48.34 |
| ATOM | 4704 | | O | | HOH W1285 | 86.456 | 38.143 | 10.491 | 1.00 | 62.41 |
| ATOM | 4705 | | O | | HOH W1286 | 90.168 | 40.857 | 8.144 | 1.00 | 62.54 |
| ATOM | 4706 | | O | | HOH W1287 | 89.294 | 40.172 | 5.211 | 1.00 | 67.46 |
| ATOM | 4707 | | O | | HOH W1288 | 90.868 | 37.517 | -2.288 | 1.00 | 58.67 |
| ATOM | 4708 | | O | | HOH W1291 | 104.814 | 12.436 | 11.403 | 1.00 | 52.69 |
| ATOM | 4709 | | O | | HOH W1293 | 90.388 | 26.041 | 28.905 | 1.00 | 39.68 |
| ATOM | 4710 | | O | | HOH W1294 | 97.541 | 28.845 | 31.859 | 1.00 | 52.90 |
| ATOM | 4711 | | O | | HOH W1297 | 83.071 | 35.334 | 12.201 | 1.00 | 52.48 |
| ATOM | 4712 | | O | | HOH W1302 | 83.032 | 9.479 | -5.918 | 1.00 | 66.14 |
| ATOM | 4713 | | O | | HOH W1303 | 91.596 | 14.026 | 4.633 | 1.00 | 42.50 |
| ATOM | 4714 | | O | | HOH W1304 | 95.754 | 36.804 | 8.448 | 1.00 | 38.48 |
| ATOM | 4715 | | O | | HOH W1305 | 88.614 | 12.530 | 4.371 | 1.00 | 45.95 |
| ATOM | 4716 | | O | | HOH W1307 | 83.694 | 7.069 | -5.236 | 1.00 | 55.19 |
| ATOM | 4717 | | O | | HOH W1308 | 79.587 | 11.094 | -3.258 | 1.00 | 36.63 |
| ATOM | 4718 | | O | | HOH W1309 | 71.587 | 15.993 | 5.898 | 1.00 | 26.88 |
| ATOM | 4719 | | O | | HOH W1310 | 96.864 | 11.489 | 22.053 | 1.00 | 48.30 |
| ATOM | 4720 | | O | | HOH W1312 | 97.770 | -1.794 | 16.819 | 1.00 | 58.66 |
| ATOM | 4721 | | O | | HOH W1316 | 85.959 | -9.302 | 15.025 | 1.00 | 47.62 |
| ATOM | 4722 | | O | | HOH W1318 | 77.158 | 1.211 | 12.491 | 1.00 | 59.34 |
| ATOM | 4723 | | O | | HOH W1319 | 78.607 | 0.864 | 17.919 | 1.00 | 67.72 |
| ATOM | 4724 | | O | | HOH W1320 | 84.429 | 4.307 | 21.191 | 1.00 | 40.77 |
| ATOM | 4725 | | O | | HOH W1322 | 94.191 | 8.343 | 22.053 | 1.00 | 38.06 |
| ATOM | 4726 | | O | | HOH W1323 | 85.941 | 6.715 | 22.845 | 1.00 | 58.42 |
| ATOM | 4727 | | O | | HOH W1324 | 89.302 | 4.272 | 25.889 | 1.00 | 52.37 |
| ATOM | 4728 | | O | | HOH W1325 | 87.729 | 9.994 | 26.320 | 1.00 | 46.91 |
| ATOM | 4729 | | O | | HOH W1326 | 59.290 | 19.990 | -22.206 | 1.00 | 57.32 |
| ATOM | 4730 | | O | | HOH W1329 | 74.756 | 4.352 | 7.726 | 1.00 | 37.91 |
| ATOM | 4731 | | O | | HOH W1330 | 70.794 | 6.020 | 12.080 | 1.00 | 54.02 |
| ATOM | 4732 | | O | | HOH W1331 | 71.479 | 16.380 | 11.405 | 1.00 | 52.54 |
| ATOM | 4733 | | O | | HOH W1332 | 66.422 | 9.248 | 14.672 | 1.00 | 53.57 |
| ATOM | 4734 | | O | | HOH W1333 | 71.433 | 19.463 | 12.689 | 1.00 | 33.35 |
| ATOM | 4735 | | O | | HOH W1334 | 73.687 | 32.759 | 11.535 | 1.00 | 56.63 |
| ATOM | 4736 | | O | | HOH W1335 | 77.256 | 31.749 | 18.023 | 1.00 | 69.01 |
| ATOM | 4737 | | O | | HOH W1338 | 47.208 | 49.850 | 23.074 | 1.00 | 62.05 |
| ATOM | 4738 | | O | | HOH W1340 | 42.018 | 34.772 | 2.339 | 1.00 | 49.16 |
| ATOM | 4739 | | O | | HOH W1343 | 63.113 | 42.942 | 7.014 | 1.00 | 62.59 |
| ATOM | 4740 | | O | | HOH W1344 | 45.767 | 43.005 | -0.747 | 1.00 | 56.67 |
| ATOM | 4741 | | O | | HOH W1345 | 45.380 | 35.208 | -8.334 | 1.00 | 54.25 |
| ATOM | 4742 | | O | | HOH W1347 | 41.327 | 26.051 | -7.056 | 1.00 | 62.75 |
| ATOM | 4743 | | O | | HOH W1348 | 42.385 | 29.186 | -13.108 | 1.00 | 42.95 |
| ATOM | 4744 | | O | | HOH W1349 | 100.748 | 23.802 | 28.388 | 1.00 | 50.59 |
| ATOM | 4745 | | O | | HOH W1351 | 61.938 | 38.333 | -8.183 | 1.00 | 57.78 |
| ATOM | 4746 | | O | | HOH W1352 | 72.929 | 32.002 | 2.726 | 1.00 | 39.15 |
| ATOM | 4747 | | O | | HOH W1353 | 54.709 | 19.261 | 9.833 | 1.00 | 56.04 |

FIGURE 3DO

|  | A | B | C | D | E | F | G | H | I | J |
|---|---|---|---|---|---|---|---|---|---|---|
| ATOM | 4748 | O | HOH | W1354 | 58.168 | 42.437 | -4.189 | 1.00 | 56.67 |
| ATOM | 4749 | O | HOH | W1355 | 68.378 | 4.585 | 5.526 | 1.00 | 35.14 |
| ATOM | 4750 | O | HOH | W1356 | 68.287 | 5.087 | 2.627 | 1.00 | 43.60 |
| ATOM | 4751 | O | HOH | W1357 | 70.563 | 7.772 | 3.648 | 1.00 | 53.26 |
| ATOM | 4752 | O | HOH | W1358 | 46.731 | 16.845 | 0.083 | 1.00 | 62.23 |
| ATOM | 4753 | O | HOH | W1359 | 47.843 | 6.876 | -10.653 | 1.00 | 52.70 |
| ATOM | 4754 | O | HOH | W1360 | 45.337 | 1.822 | -2.198 | 1.00 | 39.21 |
| ATOM | 4755 | O | HOH | W1361 | 61.796 | -2.171 | -0.456 | 1.00 | 46.61 |
| ATOM | 4756 | O | HOH | W1362 | 63.872 | -1.882 | -4.093 | 1.00 | 52.48 |
| ATOM | 4757 | O | HOH | W1363 | 58.301 | 5.101 | -10.448 | 1.00 | 42.56 |
| ATOM | 4758 | O | HOH | W1364 | 57.387 | 1.091 | -7.387 | 1.00 | 49.13 |
| ATOM | 4759 | O | HOH | W1365 | 58.097 | 8.251 | -13.060 | 1.00 | 56.00 |
| ATOM | 4760 | O | HOH | W1366 | 64.131 | 11.931 | -16.987 | 1.00 | 43.62 |
| ATOM | 4761 | O | HOH | W1367 | 67.652 | 10.453 | -8.148 | 1.00 | 52.47 |
| ATOM | 4762 | O | HOH | W1368 | 72.481 | 5.092 | -1.958 | 1.00 | 51.59 |
| ATOM | 4763 | O | HOH | W1369 | 58.698 | 46.460 | 6.079 | 1.00 | 52.17 |
| ATOM | 4764 | O | HOH | W1370 | 45.317 | 48.434 | 1.363 | 1.00 | 61.99 |
| ATOM | 4765 | O | HOH | W1371 | 104.807 | 31.365 | 15.334 | 1.00 | 51.72 |
| ATOM | 4766 | O | HOH | W1372 | 91.027 | 28.664 | 28.644 | 1.00 | 46.44 |
| ATOM | 4767 | O | HOH | W1374 | 80.188 | 34.278 | 0.565 | 1.00 | 42.08 |
| ATOM | 4768 | O | HOH | W1375 | 83.492 | 35.406 | -2.555 | 1.00 | 51.75 |
| ATOM | 4769 | O | HOH | W1376 | 100.937 | 14.594 | 7.185 | 1.00 | 42.95 |
| ATOM | 4770 | O | HOH | W1377 | 98.645 | 9.476 | 8.538 | 1.00 | 38.31 |
| ATOM | 4771 | O | HOH | W1378 | 101.135 | 9.593 | 8.163 | 1.00 | 48.94 |
| ATOM | 4772 | O | HOH | W1379 | 79.380 | -1.082 | 1.193 | 1.00 | 46.25 |
| ATOM | 4773 | O | HOH | W1380 | 75.882 | 2.992 | -1.453 | 1.00 | 57.05 |
| ATOM | 4774 | O | HOH | W1386 | 82.944 | 7.676 | 22.254 | 1.00 | 54.55 |
| ATOM | 4775 | O | HOH | W1387 | 60.483 | 24.342 | -23.688 | 1.00 | 54.95 |
| ATOM | 4776 | O | HOH | W1388 | 56.113 | 19.892 | -20.981 | 1.00 | 49.94 |
| ATOM | 4777 | O | HOH | W1389 | 88.603 | 22.146 | 31.353 | 1.00 | 54.01 |
| ATOM | 4778 | O | HOH | W1390 | 83.729 | 17.925 | 32.224 | 1.00 | 63.53 |
| ATOM | 4779 | O | HOH | W1393 | 81.273 | 13.116 | 26.398 | 1.00 | 52.93 |
| ATOM | 4780 | O | HOH | W1394 | 75.145 | 0.959 | 10.571 | 1.00 | 57.41 |
| ATOM | 4781 | O | HOH | W1396 | 54.926 | 37.667 | -17.375 | 1.00 | 58.08 |
| ATOM | 4782 | O | HOH | W1397 | 57.207 | 37.391 | -15.958 | 1.00 | 49.41 |
| ATOM | 4783 | O | HOH | W1398 | 69.357 | 34.500 | -10.940 | 1.00 | 54.39 |
| ATOM | 4784 | O | HOH | W1399 | 94.304 | 36.478 | 6.321 | 1.00 | 48.22 |
| ATOM | 4785 | O | HOH | W1401 | 90.165 | 35.490 | 13.157 | 1.00 | 49.25 |
| ATOM | 4786 | O | HOH | W1402 | 82.158 | 14.788 | -3.661 | 1.00 | 57.77 |
| ATOM | 4787 | O | HOH | W1403 | 102.366 | 9.601 | 11.706 | 1.00 | 67.67 |
| ATOM | 4788 | O | HOH | W1405 | 53.193 | -0.484 | 3.561 | 1.00 | 52.41 |
| ATOM | 4789 | O | HOH | W1406 | 52.880 | 48.512 | 1.648 | 1.00 | 59.14 |
| ATOM | 4790 | O | HOH | W1407 | 70.886 | 37.341 | 9.018 | 1.00 | 58.10 |
| ATOM | 4791 | O | HOH | W1409 | 47.510 | 36.192 | 23.517 | 1.00 | 53.39 |
| ATOM | 4792 | O | HOH | W1410 | 52.085 | 41.838 | -0.695 | 1.00 | 55.67 |
| ATOM | 4793 | O | HOH | W1411 | 42.121 | 25.670 | -3.994 | 1.00 | 51.55 |
| ATOM | 4794 | O | HOH | W1412 | 101.786 | 34.200 | 30.819 | 1.00 | 67.11 |
| ATOM | 4795 | O | HOH | W1413 | 44.082 | 35.477 | -11.999 | 1.00 | 54.86 |
| ATOM | 4796 | O | HOH | W1414 | 72.083 | 32.304 | -6.118 | 1.00 | 37.99 |
| ATOM | 4797 | O | HOH | W1416 | 43.660 | 17.863 | -2.599 | 1.00 | 53.38 |
| ATOM | 4798 | O | HOH | W1418 | 71.475 | 5.884 | 4.990 | 1.00 | 42.67 |
| ATOM | 4799 | O | HOH | W1419 | 74.445 | 15.012 | -3.904 | 1.00 | 53.99 |

FIGURE 3DP

| | A | B | C | D | E | F | G | H | I | J |
|---|---|---|---|---|---|---|---|---|---|---|
| ATOM | 4800 | O | HOH | W1422 | | 54.736 | 33.436 | 9.733 | 1.00 | 67.66 |
| ATOM | 4801 | O | HOH | W1425 | | 88.813 | 11.560 | 2.011 | 1.00 | 49.39 |
| ATOM | 4802 | O | HOH | W1427 | | 70.877 | 14.040 | 15.340 | 1.00 | 50.01 |
| ATOM | 4803 | O | HOH | W1428 | | 69.450 | 14.193 | 12.035 | 1.00 | 53.63 |
| ATOM | 4804 | O | HOH | W1429 | | 113.610 | 25.184 | -2.255 | 1.00 | 58.75 |
| ATOM | 4805 | O | HOH | W1430 | | 108.872 | 19.785 | -0.726 | 1.00 | 65.34 |
| ATOM | 4806 | O | HOH | W1431 | | 103.166 | 23.113 | -14.454 | 1.00 | 56.84 |
| ATOM | 4807 | O | HOH | W1432 | | 82.011 | 33.431 | 6.564 | 1.00 | 48.22 |
| ATOM | 4808 | O | HOH | W1433 | | 90.033 | 36.446 | 8.428 | 1.00 | 51.20 |
| ATOM | 4809 | O | HOH | W1434 | | 91.646 | 35.878 | 5.939 | 1.00 | 51.57 |
| ATOM | 4810 | O | HOH | W1435 | | 106.891 | 24.424 | 20.709 | 1.00 | 44.62 |
| ATOM | 4811 | O | HOH | W1436 | | 103.477 | 29.025 | 28.039 | 1.00 | 55.46 |
| ATOM | 4812 | O | HOH | W1437 | | 94.698 | 33.973 | 23.408 | 1.00 | 46.74 |
| ATOM | 4813 | O | HOH | W1438 | | 79.488 | 31.606 | 16.429 | 1.00 | 57.78 |
| ATOM | 4814 | O | HOH | W1439 | | 83.089 | 35.345 | 8.299 | 1.00 | 72.67 |
| ATOM | 4815 | O | HOH | W1440 | | 78.149 | 31.174 | 3.925 | 1.00 | 39.05 |
| ATOM | 4816 | O | HOH | W1441 | | 89.457 | 14.403 | -4.514 | 1.00 | 66.96 |
| ATOM | 4817 | O | HOH | W1442 | | 93.485 | 33.151 | 17.336 | 1.00 | 61.79 |
| ATOM | 4818 | O | HOH | W1443 | | 101.638 | 9.151 | 19.022 | 1.00 | 56.64 |
| ATOM | 4819 | O | HOH | W1444 | | 100.185 | 5.371 | 20.505 | 1.00 | 47.75 |
| ATOM | 4820 | O | HOH | W1445 | | 100.142 | 3.211 | 13.115 | 1.00 | 46.92 |
| ATOM | 4821 | O | HOH | W1446 | | 98.537 | 3.375 | 4.280 | 1.00 | 51.79 |
| ATOM | 4822 | O | HOH | W1447 | | 89.028 | 19.398 | 30.696 | 1.00 | 52.84 |
| ATOM | 4823 | O | HOH | W1448 | | 80.565 | 18.081 | 30.209 | 1.00 | 56.86 |
| ATOM | 4824 | O | HOH | W1449 | | 83.548 | 22.030 | 28.560 | 1.00 | 38.20 |
| ATOM | 4825 | O | HOH | W1450 | | 70.132 | 35.162 | -0.532 | 1.00 | 69.74 |
| ATOM | 4826 | O | HOH | W1451 | | 61.736 | 40.223 | -1.397 | 1.00 | 60.38 |
| ATOM | 4827 | O | HOH | W1452 | | 50.707 | 17.839 | -14.850 | 1.00 | 22.70 |
| ATOM | 4828 | O | HOH | W1453 | | 70.616 | 17.230 | -10.429 | 1.00 | 55.41 |
| ATOM | 4829 | O | HOH | W1454 | | 61.970 | 25.087 | 17.043 | 1.00 | 44.05 |
| ATOM | 4830 | O | HOH | W1455 | | 69.225 | 26.807 | 14.963 | 1.00 | 44.17 |
| ATOM | 4831 | O | HOH | W1456 | | 47.948 | 33.346 | -22.068 | 1.00 | 54.36 |
| ATOM | 4832 | O | HOH | W1457 | | 54.732 | 41.206 | -22.983 | 1.00 | 64.25 |
| ATOM | 4833 | O | HOH | W1458 | | 63.224 | 39.899 | -3.625 | 1.00 | 47.43 |
| ATOM | 4834 | O | HOH | W1459 | | 40.318 | 29.324 | 20.545 | 1.00 | 64.40 |
| ATOM | 4835 | O | HOH | W1460 | | 53.433 | 43.244 | -21.452 | 1.00 | 76.65 |
| ATOM | 4836 | O | HOH | W1461 | | 46.865 | 28.779 | 18.703 | 1.00 | 69.29 |

SEQUENCE LISTING

```
<160> NUMBER OF SEQ ID NOS: 3

<210> SEQ ID NO 1
<211> LENGTH: 993
<212> TYPE: PRT
<213> ORGANISM: Homo sapien
<220> FEATURE:
<221> NAME/KEY: misc_feature
<223> OTHER INFORMATION: Amino acid sequence for full-length human wild
      type FLT3

<400> SEQUENCE: 1

Met Pro Ala Leu Ala Arg Asp Ala Gly Thr Val Pro Leu Leu Val Val
```

-continued

```
  1               5               10              15
Phe Ser Ala Met Ile Phe Gly Thr Ile Thr Asn Gln Asp Leu Pro Val
                20              25              30
Ile Lys Cys Val Leu Ile Asn His Lys Asn Asn Asp Ser Ser Val Gly
                35              40              45
Lys Ser Ser Ser Tyr Pro Met Val Ser Glu Ser Pro Glu Asp Leu Gly
                50              55              60
Cys Ala Leu Arg Pro Gln Ser Ser Gly Thr Val Tyr Glu Ala Ala Ala
 65             70              75              80
Val Glu Val Asp Val Ser Ala Ser Ile Thr Leu Gln Val Leu Val Asp
                85              90              95
Ala Pro Gly Asn Ile Ser Cys Leu Trp Val Phe Lys His Ser Ser Leu
                100             105             110
Asn Cys Gln Pro His Phe Asp Leu Gln Asn Arg Gly Val Val Ser Met
                115             120             125
Val Ile Leu Lys Met Thr Glu Thr Gln Ala Gly Glu Tyr Leu Leu Phe
                130             135             140
Ile Gln Ser Glu Ala Thr Asn Tyr Thr Ile Leu Phe Thr Val Ser Ile
145             150             155             160
Arg Asn Thr Leu Leu Tyr Thr Leu Arg Arg Pro Tyr Phe Arg Lys Met
                165             170             175
Glu Asn Gln Asp Ala Leu Val Cys Ile Ser Glu Ser Val Pro Glu Pro
                180             185             190
Ile Val Glu Trp Val Leu Cys Asp Ser Gln Gly Glu Ser Cys Lys Glu
                195             200             205
Glu Ser Pro Ala Val Val Lys Lys Glu Glu Lys Val Leu His Glu Leu
                210             215             220
Phe Gly Thr Asp Ile Arg Cys Cys Ala Arg Asn Glu Leu Gly Arg Glu
225             230             235             240
Cys Thr Arg Leu Phe Thr Ile Asp Leu Asn Gln Thr Pro Gln Thr Thr
                245             250             255
Leu Pro Gln Leu Phe Leu Lys Val Gly Glu Pro Leu Trp Ile Arg Cys
                260             265             270
Lys Ala Val His Val Asn His Gly Phe Gly Leu Thr Trp Glu Leu Glu
                275             280             285
Asn Lys Ala Leu Glu Glu Gly Asn Tyr Phe Glu Met Ser Thr Tyr Ser
                290             295             300
Thr Asn Arg Thr Met Ile Arg Ile Leu Phe Ala Phe Val Ser Ser Val
305             310             315             320
Ala Arg Asn Asp Thr Gly Tyr Tyr Thr Cys Ser Ser Ser Lys His Pro
                325             330             335
Ser Gln Ser Ala Leu Val Thr Ile Val Gly Lys Gly Phe Ile Asn Ala
                340             345             350
Thr Asn Ser Ser Glu Asp Tyr Glu Ile Asp Gln Tyr Glu Glu Phe Cys
                355             360             365
Phe Ser Val Arg Phe Lys Ala Tyr Pro Gln Ile Arg Cys Thr Trp Thr
                370             375             380
Phe Ser Arg Lys Ser Phe Pro Cys Glu Gln Lys Gly Leu Asp Asn Gly
385             390             395             400
Tyr Ser Ile Ser Lys Phe Cys Asn His Lys His Gln Pro Gly Glu Tyr
                405             410             415
Ile Phe His Ala Glu Asn Asp Asp Ala Gln Phe Thr Lys Met Phe Thr
                420             425             430
```

-continued

```
Leu Asn Ile Arg Arg Lys Pro Gln Val Leu Ala Glu Ala Ser Ala Ser
        435                 440                 445

Gln Ala Ser Cys Phe Ser Asp Gly Tyr Pro Leu Pro Ser Trp Thr Trp
    450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
            485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
    530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
            565                 570                 575

Gln Met Val Gln Val Thr Gly Ser Ser Asp Asn Glu Tyr Phe Tyr Val
        580                 585                 590

Asp Phe Arg Glu Tyr Glu Tyr Asp Leu Lys Trp Glu Phe Pro Arg Glu
    595                 600                 605

Asn Leu Glu Phe Gly Lys Val Leu Gly Ser Gly Ala Phe Gly Lys Val
610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
            645                 650                 655

Ala Leu Met Ser Glu Leu Lys Met Met Thr Gln Leu Gly Ser His Glu
        660                 665                 670

Asn Ile Val Asn Leu Leu Gly Ala Cys Thr Leu Ser Gly Pro Ile Tyr
    675                 680                 685

Leu Ile Phe Glu Tyr Cys Cys Tyr Gly Asp Leu Leu Asn Tyr Leu Arg
690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
            725                 730                 735

Met Pro Gly Ser Arg Glu Val Gln Ile His Pro Asp Ser Asp Gln Ile
        740                 745                 750

Ser Gly Leu His Gly Asn Ser Phe His Ser Glu Asp Glu Ile Glu Tyr
    755                 760                 765

Glu Asn Gln Lys Arg Leu Glu Glu Glu Glu Asp Leu Asn Val Leu Thr
    770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
            805                 810                 815

Val Leu Val Thr His Gly Lys Val Val Lys Ile Cys Asp Phe Gly Leu
        820                 825                 830

Ala Arg Asp Ile Met Ser Asp Ser Asn Tyr Val Val Arg Gly Asn Ala
    835                 840                 845
```

-continued

```
Arg Leu Pro Val Lys Trp Met Ala Pro Glu Ser Leu Phe Glu Gly Ile
    850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
    930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser
```

<210> SEQ ID NO 2
<211> LENGTH: 987
<212> TYPE: DNA
<213> ORGANISM: Homo sapien
<220> FEATURE:
<221> NAME/KEY: misc_feature
<223> OTHER INFORMATION: Human cDNA sequence encoding of residues 564-713 and 778-954 of FLT3

<400> SEQUENCE: 2

```
cacaagtaca aaaagcaatt taggtatgaa agccagctac agatggtaca ggtgaccggc      60
tcctcagata atgagtactt ctacgttgat ttcagagaat atgaatatga tctcaaatgg     120
gagtttccaa gagaaaattt agagtttggg aaggtactag gatcaggtgc ttttggaaaa     180
gtgatgaacg caacagctta tggaattagc aaaacaggtc tcaatccag gttgccgtc      240
aaaatgctga agaaaaagc agacagctct gaaagagagg cactcatgtc agaactcaag     300
atgatgaccc agctgggaag ccacgagaat attgtgaacc tgctggggc gtgcacactg     360
tcaggaccaa tttacttgat ttttgaatac tgttgctatg gtgatcttct caactatcta     420
agaagtaaaa gagaaaaatt tcacaggact gctagcgagg acttgaatgt gcttacattt     480
gaagatcttc tttgctttgc atatcaagtt gccaaaggaa tggaatttct ggaatttaag     540
tcgtgtgttc acagagacct ggccgccagg aacgtgcttg tcacccacgg gaaagtggtg     600
aagatatgtg actttggatt ggctcgagat atcatgagtg attccaacta tgttgtcagg     660
ggcaatgccc gtctgcctgt aaaatggatg ccccccgaaa gcctgtttga aggcatctac     720
accattaaga gtgatgtctg gtcatatgga atattactgt gggaaatctt ctcacttggt     780
gtgaatcctt accctggcat tccggttgat gctaacttct acaaactgat tcaaaatgga     840
tttaaaatgg atcagccatt ttatgctaca gaagaaatat acattataat gcaatcctgc     900
tgggcttttg actcaaggaa acggccatcc ttccctaatt tgacttcgtt tttaggatgt     960
cagctggcag atgcagaaga agcgatg                                          987
```

<210> SEQ ID NO 3
<211> LENGTH: 360
<212> TYPE: PRT

-continued

<213> ORGANISM: Artificial Sequence
<220> FEATURE:
<223> OTHER INFORMATION: Amino acid sequence for residues 564-713, and
      778-954 of FLT3 with a N-terminal 6x-histidine tag, spacer region,
      rTEV cleavage site, Tyr to Phe mutations and Ala-Ser dipeptide
      inserted in place of the Kinase Insertion Domain

<400> SEQUENCE: 3

```
Met Ser Tyr Tyr His His His His His His Asp Tyr Asp Ile Pro Thr
1               5                   10                  15

Thr Glu Asn Leu Tyr Phe Gln Gly Ala Met Glu Pro Gly Gly Ser His
            20                  25                  30

Lys Tyr Lys Lys Gln Phe Arg Tyr Glu Ser Gln Leu Gln Met Val Gln
        35                  40                  45

Val Thr Gly Ser Ser Asp Asn Glu Phe Phe Val Asp Phe Arg Glu
    50                  55                  60

Tyr Glu Tyr Asp Leu Lys Trp Glu Phe Pro Arg Glu Asn Leu Glu Phe
65                  70                  75                  80

Gly Lys Val Leu Gly Ser Gly Ala Phe Gly Lys Val Met Asn Ala Thr
                85                  90                  95

Ala Tyr Gly Ile Ser Lys Thr Gly Val Ser Ile Gln Val Ala Val Lys
            100                 105                 110

Met Leu Lys Glu Lys Ala Asp Ser Ser Glu Arg Glu Ala Leu Met Ser
        115                 120                 125

Glu Leu Lys Met Met Thr Gln Leu Gly Ser His Glu Asn Ile Val Asn
130                 135                 140

Leu Leu Gly Ala Cys Thr Leu Ser Gly Pro Ile Tyr Leu Ile Phe Glu
145                 150                 155                 160

Tyr Cys Cys Tyr Gly Asp Leu Leu Asn Tyr Leu Arg Ser Lys Arg Glu
                165                 170                 175

Lys Phe His Arg Thr Ala Ser Glu Asp Leu Asn Val Leu Thr Phe Glu
            180                 185                 190

Asp Leu Leu Cys Phe Ala Tyr Gln Val Ala Lys Gly Met Glu Phe Leu
        195                 200                 205

Glu Phe Lys Ser Cys Val His Arg Asp Leu Ala Ala Arg Asn Val Leu
210                 215                 220

Val Thr His Gly Lys Val Val Lys Ile Cys Asp Phe Gly Leu Ala Arg
225                 230                 235                 240

Asp Ile Met Ser Asp Ser Asn Tyr Val Val Arg Gly Asn Ala Arg Leu
                245                 250                 255

Pro Val Lys Trp Met Ala Pro Glu Ser Leu Phe Glu Gly Ile Tyr Thr
            260                 265                 270

Ile Lys Ser Asp Val Trp Ser Tyr Gly Ile Leu Leu Trp Glu Ile Phe
        275                 280                 285

Ser Leu Gly Val Asn Pro Tyr Pro Gly Ile Pro Val Asp Ala Asn Phe
290                 295                 300

Tyr Lys Leu Ile Gln Asn Gly Phe Lys Met Asp Gln Pro Phe Tyr Ala
305                 310                 315                 320

Thr Glu Glu Ile Tyr Ile Ile Met Gln Ser Cys Trp Ala Phe Asp Ser
                325                 330                 335

Arg Lys Arg Pro Ser Phe Pro Asn Leu Thr Ser Phe Leu Gly Cys Gln
            340                 345                 350

Leu Ala Asp Ala Glu Glu Ala Met
        355                 360
```

CRYSTALLIZATION OF FMS-LIKE TYROSINE KINASE 3

FIELD OF THE INVENTION

The present invention relates to a member of a family of type III receptor protein tyrosine kinases (RPTKs) and more specifically to a particular RPTK known as FMS-LIKE TYROSINE KINASE 3 (FLT3). Provided are FLT3 in crystalline form, methods of forming crystals comprising FLT3, methods of using crystals comprising FLT3, a crystal structure of FLT3, and methods of using the crystal structure.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three-dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein. A need thus exists for proteins in crystalline form.

SUMMARY OF THE INVENTION

The present invention is directed to crystals comprising FLT3 and particularly crystals comprising FLT3 that have sufficient size and quality to obtain useful information about the structural properties of FLT3 and molecules or complexes that may associate with FLT3.

In one embodiment, a composition is provided that comprises a protein in crystalline form wherein at least a portion of the protein has 55%, 65%, 75%, 85%, 90%, 95%, 97%, 99% or greater identity with residues 564-713 and 778-954 of SEQ. ID No. 1.

In one variation, the protein has activity characteristic of FLT3. For example, the protein may optionally be inhibited by inhibitors of wild type FLT3. The protein crystal may also diffract X-rays for a determination of structure coordinates to a resolution of 4 Å, 3.5 Å, 3.0 Å or less. In one variation, the protein crystal has a crystal lattice in a $P4_22_12$ space group. The protein crystal may also have a crystal lattice having unit cell dimensions, +/−5%, of a=146.278 Å, b=146.278 Å, c=100.946 Å, $\alpha=\beta=\gamma=90°$.

The present invention is also directed to crystallizing FLT3. The present invention is also directed to the conditions useful for crystallizing FLT3. It should be recognized that a wide variety of crystallization methods can be used in combination with the crystallization conditions to form crystals comprising FLT3 including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein wherein at least a portion of the protein has 55%, 65%, 75%, 85%, 90%, 95%, 97%, 99% or greater identity with residues 564-713 and 778-954 of SEQ. ID No. 1; and storing the crystallization volume under conditions suitable for crystal formation.

In one variation, the crystallization volume comprises the protein at 11.6 mg/ml in 25 mM Tris ph 7.6, 250 mM NaCl, 5 mM DTT, 0.1 mM EDTA, supplemented with 1 mM staurosporine in DMSO, mixed with an equal volume of precipitant solution comprising 2.9 M NaCl, and 100 mM sodium citrate, pH 6.5.

The method may optionally further comprise forming a protein crystal that has a crystal lattice in a $P4_22_12$ space group. The method also optionally further comprises forming a protein crystal that has a crystal lattice having unit cell dimensions, +/−5%, of a=146.278 Å, b=146.278 Å, c=100.946 Å, $\alpha=\beta=\gamma=90°$. The invention also relates to protein crystals formed by these methods.

The present invention is also directed to a composition comprising an isolated protein that comprises or consists of one or more of the protein sequence(s) of FLT3 taught herein for crystallizing FLT3. The present invention is also directed to a composition comprising an isolated nucleic acid molecule that comprises or consists of the nucleotides for expressing the protein sequence of FLT3 taught herein for crystallizing FLT3.

The present invention is also directed to an expression vector that may be used to express the isolated proteins taught herein for crystallizing FLT3. In one variation, the expression vector comprises a promoter that promotes expression of the isolated protein.

The present invention is also directed to a cell line transformed or transfected by an isolated nucleic acid molecule or expression vector of the present invention.

The present invention is also directed to structure coordinates for FLT3 as well as structure coordinates that are comparatively similar to these structure coordinates. It is noted that these comparatively similar structure coordinates may encompass proteins with similar sequences and/or structures, such as other RPTKs. For example, machine-readable data storage media is provided having data storage material encoded with machine-readable data that comprises structure coordinates that are comparatively similar to the structure coordinates of FLT3. The present invention is also directed to a machine readable data storage medium having data storage material encoded with machine readable data, which, when read by an appropriate machine, can display a three dimensional representation of all or a portion of a structure of FLT3 or a model that is comparatively similar to the structure of all or a portion of FLT3.

Various embodiments of machine readable data storage medium are provided that comprise data storage material encoded with machine readable data. The machine readable data comprises: structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1. The amino acids being overlayed and compared need not be identical when the RMSD calculation is performed on alpha carbons and main chain atoms but the amino acids being overlayed and compared must have identical side chains when the RMSD calculation is performed on all non-hydrogen atoms.

For example, in one embodiment where the comparison is based on the 4 Angstrom set of amino acid residues (Column 1) and is based on superimposing alpha-carbon atoms (Column 2), the structure coordinates may have a root mean square deviation equal to or less than 1.43 Å when compared to the structure coordinates of FIG. 3.

TABLE 1

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Table 2 (4 Angstrom set) | alpha-carbon atoms[1] | 1.43 | 0.95 | 0.72 |
|  | main-chain atoms[1] | 1.55 | 1.03 | 0.78 |
|  | all non-hydrogen[2] | 2.03 | 1.35 | 1.01 |
| Table 3 (7 Angstrom set) | alpha-carbon atoms[1] | 1.11 | 0.74 | 0.56 |
|  | main-chain atoms[1] | 1.21 | 0.81 | 0.61 |
|  | all non-hydrogen[2] | 2.03 | 1.35 | 1.01 |
| Table 4 (10 Angstrom set) | alpha-carbon atoms[1] | 0.94 | 0.63 | 0.47 |
|  | main-chain atoms[1] | 1.03 | 0.69 | 0.52 |
|  | all non-hydrogen[2] | 1.25 | 0.83 | 0.63 |
| 564-713 and 778-954 of SEQ. ID No. 1 | alpha-carbon atoms[1] | 1.17 | 0.78 | 0.58 |
|  | main-chain atoms[1] | 1.22 | 0.81 | 0.61 |
|  | all non-hydrogen[2] | 1.37 | 0.91 | 0.68 |

[1]the RMSD computed between the atoms of all amino acids that are common to both the target and the reference in the aligned and superposed structure. The amino acids need not be identical.
[2]the RMSD computed only between identical amino acids, which are common to both the target and the reference in the aligned and superposed structure.

The present invention is also directed to a three-dimensional structure of all or a portion of FLT3. This three-dimensional structure may be used to identify binding sites, to provide mutants having desirable binding properties, and ultimately, to design, characterize, or identify ligands capable of interacting with FLT3. Ligands that interact with FLT3 may be any type of atom, compound, protein or chemical group that binds to or otherwise associates with the protein. Examples of types of ligands include natural substrates for FLT3, inhibitors of FLT3, and heavy atoms. The inhibitors of FLT3 may optionally be used as drugs to treat therapeutic indications by modifying the in vivo activity of FLT3.

In various embodiments, methods are provided for displaying a three dimensional representation of a structure of a protein comprising:

taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

computing a three dimensional representation of a structure based on the structure coordinates; and displaying the three dimensional representation.

The present invention is also directed to a method for solving a three-dimensional crystal structure of a target protein using the structure of FLT3.

In various embodiments, computational methods are provided comprising:

taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

computing phases based on the structural coordinates;

computing an electron density map based on the computed phases; and determining a three-dimensional crystal structure based on the computed electron density map.

In various embodiments, computational methods are provided comprising: taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

These methods may optionally further comprise determining a three-dimensional crystal structure based upon the computed three-dimensional electron density map.

The present invention is also directed to using a crystal structure of FLT3, in particular the structure coordinates of FLT3 and the surface contour defined by them, in methods for screening, designing, or optimizing molecules or other chemical entities that interact with and preferably inhibit FLT3.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of FLT3 and/or its structure coordinates to evaluate the ability of entities to associate with FLT3. The entities may be any entity that may function as a ligand and thus may be any type of atom, compound, protein (such as antibodies) or chemical group that can bind to or otherwise associate with a protein.

In various embodiments, methods are provided for evaluating a potential of an entity to associate with a protein comprising:

creating a computer model of a protein structure using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

performing a fitting operation between the entity and the computer model; and analyzing results of the fitting operation to quantify an association between the entity and the model.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

employing the three-dimensional structure to design or select an entity that can associate with the protein; and contacting the entity with a protein wherein at least a portion of the protein has 55%, 65%, 75%, 85%, 90%, 95%, 97%, 99% or greater identity with residues 564-713 and 778-954 of SEQ. ID No. 1.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1; and employing the three-dimensional structure to design or select an entity that can associate with the protein.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

employing the computer model to design or select an entity that can associate with the protein; and contacting the entity with a protein wherein at least a portion of the protein has 55%, 65%, 75%, 85%, 90%, 95%, 97%, 99% or greater identity with residues 564-713 and 778-954 of SEQ. ID No. 1.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein.

In other embodiments, methods are provided for evaluating the ability of an entity to associate with a protein, the method comprising:

constructing a computer model defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

selecting an entity to be evaluated by a method selected from the group consisting of (i) assembling molecular fragments into the entity, (ii) selecting an entity from a small molecule database, (iii) de novo ligand design of the entity, and (iv) modifying a known ligand for FLT3, or a portion thereof;

performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In other embodiments, methods are provided for evaluating the ability of an entity to associate with a protein, the method comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1);

selecting an entity to be evaluated by a method selected from the group consisting of (i) assembling molecular fragments into the entity, (ii) selecting an entity from a small molecule database, (iii) de novo ligand design of the entity, and (iv) modifying a known ligand for FLT3, or a portion thereof;

performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In regard to each of these embodiments, the protein may optionally have activity characteristic of FLT3. For example, the protein may optionally be inhibited by inhibitors of wild type FLT3.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 564-713 and 778-954 of SEQ. ID No. 1; and performing rational drug design using a three dimensional structure that is based on the obtained structure coordinates.

The protein crystals may optionally have a crystal lattice with a $P4_22_12$ space group and unit cell dimensions, +/−5%, of a=146.278 Å, b=146.278 Å, c=100.946 Å, $\alpha=\beta=\gamma=90°$.

The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1, 2, 3, 4 and 5 referred to in this application.

FIG. 3 lists a set of atomic structure coordinates for FLT3 as derived by X-ray crystallography from a crystal that comprises the protein. The following abbreviations are used in FIG. 3: "X, Y, Z" crystallographically define the atomic position of the element measured; "B" is a thermal factor that measures movement of the atom around its atomic center; "Occ" is an occupancy factor that refers to the fraction of the molecules in which each atom occupies the position specified by the coordinates (a value of "1" indicates that each atom has the same conformation, i.e., the same position, in all molecules of the crystal).

DETAILED DESCRIPTION OF THE INVENTION

Figure 2:
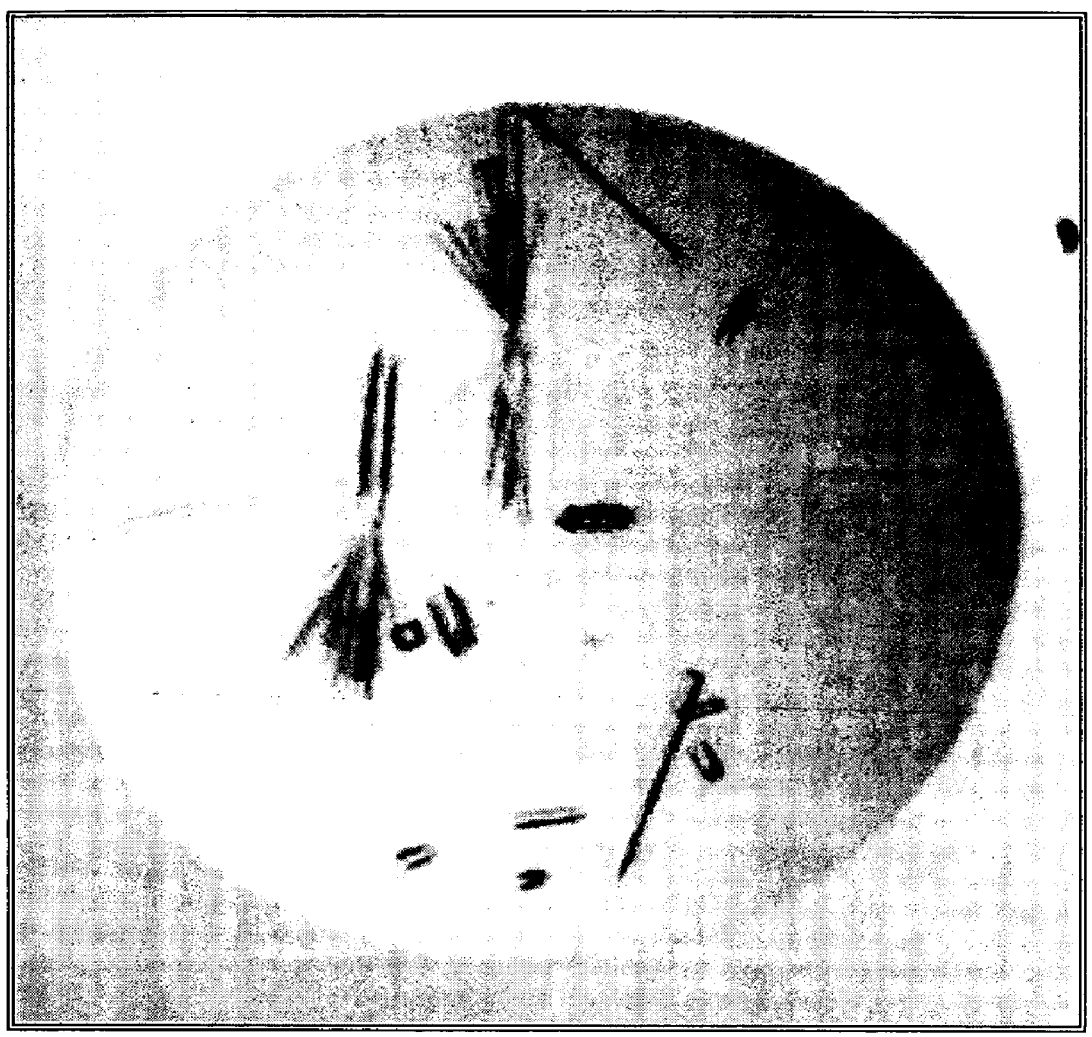
FIG. 2 illustrates a crystal of FLT3 corresponding to SEQ. ID No. 3, having a crystal lattice in a $P4_22_12$ space group and unit cell dimensions, +/−5%, of a=146.278 Å, b=146.278 Å, c=100.946 Å, $\alpha=\beta=\gamma=90°$.

The present invention relates to a member of a family of type III receptor protein tyrosine kinases and more specifically to a particular RPTK known as FMS-like tyrosine kinase 3 (FLT3). Provided is FLT3 in crystalline form, methods of forming crystals comprising FLT3, methods of using crystals comprising FLT3, a crystal structure of FLT3, and methods of using the crystal structure.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=H is=Histidine.

1. FLT3

Fms-like tyrosine kinase 3 (FLT3; FLK-2; STK-1) is a member of the class III receptor tyrosine kinase (RTK) family that includes cFms (CSF1R), cKit and the platelet-derived growth factor receptors PDGFRα and PDGFRβ (Rosnet, O., Schiff, C., Pebusque, M. J., Marchetto, S., Tonnelle, C., Toiron, Y., Birg, F. & Birnbaum, D. (1993) Human FLT3/FLK2 gene: cDNA cloning and expression in hematopoietic cells. *Blood* 82, 1110-9, 1993). Class III RTKs are characterized by having five immunoglobulin-like extracellular domains, a transmembrane and a juxtamembrane domain, and a cytoplasmic split kinase domain that results from an insertion in the C-lobe. Like cKit and cFms, FLT3 is involved in signalling events that regulate the proliferation and differentiation of a variety of haemopoietic cell types (Rosnet, O. & Birnbaum, D. (1993) Hematopoietic receptors of class III receptor-type tyrosine kinases. *Crit. Rev. Oncog.* 4, 595-613; Hannum, C., Culpepper, J., Campbell, D., McClanahan, T., Zurawski, S., Kastelein, R., Bazan, J. F., Hudak, S., Wagner, J., Mattson, J., Luh, J., Duda, G., Martina, N., Peterson, D., Menon, S., Shanafelt, A., Muench, M., Kelner, G., Namikawa, R., Rennick, D., Roncarolo, M.-G., Zlotnik, A., Rosnet, O., Dubreuil, P., Birnbaum D. & Lee, F. (1994) Ligand for FLT3/FLK2 receptor tyrosine kinase regulates growth of haematopoietic stem cells and is encoded by variant RNAs. *Nature* 368, 643-648). The activation of FLT3 by FLT3 ligand, a Type I transmembrane short-chain helical cytokine whose activating N-terminal domain may be released into circulation by proteolytic processing, is believed to occur via ligand-induced receptor dimerization (for reviews see Heldin, C.-H. (1995) Dimerization of cell surface receptors in signal transduction. *Cell* 80, 213-223; Weiss, A. & Schlessinger, J. (1998) Switching signals on or off by receptor dimerization. *Cell* 94, 277-280), that results in cytoplasmic transphosphorylation with concomitant kinase domain activation. The activated kinase stimulates the phosphatidylinositol-3-kinase (PI3K) and RAS signal transduction pathways (see e.g. Zhang, S. & Broxmeyer, H. E. (2000) Flt3 ligand induces tyrosine phosphorylation of gab1 and gab2 and their association with shp-2, grb2, and PI3 kinase. *Biochem. Biophys. Res. Commun.* 277, 195-9).

FLT3 has become a target for therapeutic intervention following the discoveries that the protein is expressed at greater than normal levels in 70-100% of cases of acute myeloid leukemia (AML) and also in a high percentage of cases of acute lymphocytic leukemia (ALL) or myelodysplasia (MDS). In the case of AML, approximately 25% of adult patients and 10%-15% of pediatric patients carry one of a variety of internal tandem duplication (ITD) mutations within the portion of the gene encoding the juxtamembrane region of the protein (Nakao, M., Yokota, S., Iwai, T., Kaneko, H., Horiike, S., Kashima, K., Sonoda, Y., Fujimoto, T. & Misawa, S. (1996) Internal tandem duplication of the flt3 gene found in acute myeloid leukemia. *Leukemia* 10, 1911-8). A second group of AML patients (approx. 7%) contain various point mutations within that segment of the FLT3 gene that encodes the activation loop of the kinase domain, with Asp835Tyr (GAT>TAT) being the most common replacement (Yamamoto, Y., Kiyoi, H., Nakano, Y., Suzuki, R., Kodera, Y., Miyawaki, S., Asou, N., Kuriyama, K., Yagasaki, F., Shimazaki, C., Akiyama, H., Saito, K., Nishimura, M., Motoji, T., Shinagawa, K., Takeshita, A., Saito, H., Ueda, R., Ohno, R. & Naoe, T. (2001) Activating mutation of D835 within the activation loop of FLT3 in human hematologic malignancies. *Blood* 97, 2434-9). Both types of mutation are believed to be important in AML pathogenesis by leading to constitutive activation of the kinase, either through ligand-independent kinase dimerization and subsequent activation, as in the case of ITD mutations, or by promotion of the kinase domain to the activated state, as in the case of activation loop mutations (Kiyoi, H., Towatari, M., Yokota, S., Hamaguchi, M., Ohno, R., Saito, H., & Naoe, T. (1998) Internal tandem duplication of the FLT3 gene is a novel modality of elongation mutation which causes constitutive activation of the product. *Leukemia* 12, 1333-1337). Even in the absence of activating FLT3 gene mutations, an above normal expression of messenger RNA for FLT3 confers an unfavorable prognostic outcome in AML patients (Ozeki, K., Kiyoi, H., Hirose, Y., Iwai, M., Ninomiya, M., Kodera, Y., Miyawaki, S., Kuriyama, K., Shimazaki, C., Akiyama, H., Nishimura, M., Motoji, T., Shinagawa, K., Takeshita, A., Ueda, R., Ohno, R., Emi, N. & Naoe, T. (2003) Biological and clinical significance of the FLT3 transcript level in acute myeloid leukemia. *Blood Nov.* 6, 2003). Thus, therapeutic agents aimed at inhibiting the increased FLT3 kinase activity in various leukemias may block further development of the diseases and potentially lead to remission. The finding that FLT3-knockout mice have relatively normal haematopoiesis (Mackarehtschian, K., Hardin, J. D., Moore, K. A., Boast, S., Goff, S. P. & Lemischka, I. R. (1995) Targeted disruption of the flk2/flt3 gene leads to deficiencies in primitive hematopoietic progenitors. *Immunity* 3, 147-61) suggests that specific FLT3 inhibitors may have minimal side effects in treated patients. FLT3 inhibitors may also have use in combined therapies for the treatment of acute promelocytic leukemia (APL) (Gilliland, D. G. (2003) FLT3-activating mutations in acute promyelocytic leukaemia: a rationale for risk-adapted therapy with FLT3 inhibitors. *Best Pract. Res. Clin. Haematol.* 16, 409-17).

In one embodiment, FLT3 comprises the wild-type form of full length FLT3, set forth herein as SEQ. ID No. 1 (GenBank Accession Number NM 004119; (Rosnet O, Mattei M G, Marchetto S, Birnbaum D., *Genomics* 9:380-385 (1991)).

In another embodiment, FLT3 comprises residues 564-713 and 778-954 of SEQ. ID No. 1 which comprises the active site domain of wild-type FLT3 that is represented in the set of structural coordinates shown in FIG. 3.

It should be recognized that the invention may be readily extended to various variants of wild-type FLT3 and variants of fragments thereof. In another embodiment, FLT3 comprises a sequence wherein at least a portion of the sequence has 55%, 65%, 75%, 85%, 90%, 95%, 97%, 99% or greater identity with SEQ. ID No. 1.

It is also noted that the above sequences of FLT3 are also intended to encompass isoforms, mutants and fusion proteins of these sequences. An example of a fusion protein is provided by SEQ. ID No. 3, which includes a 6 residue N-terminal tag (6 residues are histidine) and a rTEV protease cleavage site that may be used to facilitate purification of the protein.

With the crystal structure provided herein, it is now known where amino acid residues are positioned in the structure. As a result, the impact of different substitutions can be more easily predicted and understood.

For example, based on the crystal structure, applicants have determined that the FLT3 amino acids shown in Table 2 encompass a 4-Angstrom radius around the FLT3 active site and thus are likely to interact with any active site inhibitor of FLT3. Applicants have also determined that the amino acids of Table 3 encompass a 7-Angstrom radius around the FLT3 active site. Further it has been determined that the amino acids of Table 4 encompass a 10-Angstrom radius around the FLT3 active site. It is noted that there is one FLT3 molecule in the asymmetric unit, referred to as chain A. Structural coordinates appear in FIG. 3. It is noted that the sequence and structure of the residues in the active site may also be conserved and hence pertinent to other FLT3 variants and homologs.

One or more of the sets of amino acids set forth in the tables is preferably conserved in a variant of FLT3. Hence, FLT3 may optionally comprise a sequence wherein at least a portion of the sequence has 55%, 65%, 75%, 85%, 90%, 95%, 97%, 99% or greater identity with any one of the above sequences (e.g., all of SEQ. ID No. 1 or residues 564-713 and 778-954 of SEQ. ID No. 1) where at least the residues shown in Tables 2, 3, and/or 4 are conserved with the exception of 0, 1, 2, 3, or 4 residues. It should be recognized that one might optionally vary some of the binding site residues in order to determine the effect such changes have on structure or activity.

TABLE 2

Amino Acids encompassed by a 4-Angstrom radius around the FLT3 active site.

| | | |
|---|---|---|
| LEU 616 | GLY 617 | PHE 621 |
| VAL 624 | ALA 642 | LYS 644 |
| VAL 675 | GLU 692 | TYR 693 |
| CYS 694 | GLY 697 | ASP 698 |
| ARG 815 | ASN 816 | LEU 818 |
| CYS 866 | ASP 867 | HOH 1208 |
| HOH 1278 | HOH 1340 | HOH 1422 |

TABLE 3

Amino Acids encompassed by a 7-Angstrom radius around the FLT3 active site.

| | | |
|---|---|---|
| VAL 615 | LEU 616 | GLY 617 |
| SER 618 | GLY 619 | PHE 621 |
| LYS 623 | VAL 624 | MET 625 |
| ASN 626 | VAL 641 | ALA 642 |
| VAL 643 | LYS 644 | GLU 661 |
| VAL 675 | PHE 691 | GLU 692 |
| TYR 693 | CYS 694 | CYS 695 |
| TYR 696 | GLY 697 | ASP 698 |
| LEU 700 | ASN 701 | ALA 814 |
| ARG 815 | ASN 816 | VAL 817 |
| LEU 818 | VAL 819 | LYS 864 |
| CYS 866 | ASP 867 | PHE 768 |
| HOH 1187 | HOH 1202 | HOH 1208 |
| HOH 1209 | HOH 1239 | HOH 1242 |
| HOH 1278 | HOH 1340 | HOH 1344 |
| HOH 1410 | HOH 1422 | |

TABLE 4

Amino Acids encompassed by a 10-Angstrom radius around the FLT3 active site.

| | | |
|---|---|---|
| LYS 614 | VAL 615 | LEU 616 |
| GLY 617 | SER 618 | GLY 619 |
| ALA 620 | PHE 621 | GLY 622 |
| LYS 623 | VAL 624 | MET 625 |
| ASN 626 | ALA 627 | GLN 640 |
| VAL 641 | ALA 642 | VAL 643 |
| LYS 644 | MET 645 | LEU 658 |
| GLU 661 | MET 665 | ILE 674 |
| VAL 675 | ASN 676 | LEU 677 |
| LEU 678 | LEU 689 | ILE 690 |
| PHE 691 | GLU 692 | TYR 693 |
| CYS 694 | CYS 695 | TYR 696 |
| GLY 697 | ASP 698 | LEU 699 |
| LEU 700 | ASN 701 | TYR 702 |
| HIS 809 | ASP 811 | ALA 813 |
| ALA 814 | ARG 815 | ASN 816 |
| VAL 817 | THR 828 | HIS 829 |
| LYS 864 | ILE 865 | CYS 866 |
| ASP 867 | PHE 768 | GLY 769 |
| LEU 779 | GLU 880 | HOH 1062 |
| HOH 1063 | HOH 1187 | HOH 1188 |
| HOH 1191 | HOH 1192 | HOH 1202 |
| HOH 1208 | HOH 1209 | HOH 1210 |
| HOH 1211 | HOH 1217 | HOH 1238 |
| HOH 1239 | HOH 1240 | HOH 1241 |
| HOH 1242 | HOH 1243 | HOH 1244 |
| HOH 1278 | HOH 1340 | HOH 1344 |
| HOH 1345 | HOH 1410 | HOH 1411 |
| HOH 1422 | | |

With the benefit of the crystal structure and guidance provided by Tables 2, 3 and 4, a wide variety of FLT3 variants (e.g., insertions, deletions, substitutions, etc.) that fall within the above specified identity ranges may be designed and manufactured utilizing recombinant DNA techniques well known to those skilled in the art, particularly in view of the knowledge of the crystal structure provided herein. These modifications can be used in a number of combinations to produce the variants. The present invention is useful for crystallizing and then solving the structure of the range of variants of FLT3.

Variants of FLT3 may be insertional variants in which one or more amino acid residues are introduced into a predetermined site in the FLT3 sequence. For instance, insertional variants can be fusions of heterologous proteins or polypeptides to the amino or carboxyl terminus of the subunits.

Variants of FLT3 also may be substitutional variants in which at least one residue has been removed and a different residue inserted in its place. Non-natural amino acids (i.e., amino acids not normally found in native proteins), as well as isosteric analogs (amino acid or otherwise), may optionally be employed in substitutional variants. Examples of suitable substitutions are well known in the art, such as Glu→Asp, Asp→Glu, Ser→Cys, and Cys→Ser for example.

Another class of variants is deletional variants, which are characterized by the removal of one or more amino acid residues from the FLT3 sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution of bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea; 2,4-pentanedione; transaminase catalyzed reaction with glyoxylate; and N-hydroxysuccinamide esters of polyethylene glycol or other bulky substitutions.

Arginyl residues may be modified by reaction with a number of reagents, including phenylglyoxal; 2,3-butanedione; 1,2-cyclohexanedione; and ninhydrin. Modification of arginine residues requires that the reaction be performed in alkaline conditions because of the high $pK_\alpha$ of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming O-acetyl tyrosyl species and 3-nitro derivatives, respectively. Tyrosyl residues may also be iodinated using $^{125}$I or $^{131}$I to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic sequence encoding FLT3 may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for their affect on a variety of different properties including, for example, solubility, crystallizability and a modification to the protein's structure and activity.

In one variation, the variant and/or fragment of wild-type FLT3 is functional in the sense that the resulting protein is capable of associating with at least one same chemical entity that is also capable of selectively associating with a protein comprising the wild-type FLT3 (e.g., residues 564-713 and 778-954 of SEQ. ID No. 1) since this common associative ability evidences that at least a portion of the native structure has been conserved.

It is noted that the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of FLT3, and the atomic structure coordinates obtained therefrom, can be used to identify compounds that bind to the native domain. These compounds may affect the activity of the native domain.

Amino acid substitutions, deletions and additions that do not significantly interfere with the three-dimensional structure of FLT3 will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine; isoleucine; valine; glycine; alanine; asparagine; glutamine; serine; threonine; phenylalanine; and tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of FLT3 will be apparent to those having skills in the art, particularly in view of the three dimensional structure of FLT3 provided herein.

2. Cloning, Expression and Purification of FLT3

The gene encoding FLT3 can be isolated from RNA, cDNA or cDNA libraries. In this case, the portion of the gene encoding amino acid residues 564-713 and 778-954 (SEQ. ID No. 1), corresponding to the juxtamembrane and kinase domains, was isolated and is shown as SEQ. ID No. 2.

Construction of expression vectors and recombinant proteins from the DNA sequence encoding FLT3 may be performed by various methods well known in the art. For example, these techniques may be performed according to Sambrook et al., Molecular Cloning-A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of FLT3. Example 1 provides one such expression system.

Once expressed, purification steps are employed to produce FLT3 in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

FLT3 may optionally be affinity labeled during cloning, preferably with a N-terminal six-histidine tag and a rTEV protease cleavage site, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization & Crystals Comprising FLT3

One aspect of the present invention relates to methods for forming crystals comprising FLT3 as well as crystals comprising FLT3.

In one embodiment, a method for forming crystals comprising FLT3 is provided comprising forming a crystallization volume comprising FLT3, one or more precipitants, optionally a buffer, optionally a monovalent and/or divalent salt and optionally an organic solvent; and storing the crystallization volume under conditions suitable for crystal formation.

In yet another embodiment, a method for forming crystals comprising FLT3 is provided comprising forming a crystallization volume comprising FLT3 in solution comprising the components shown in Table 5; and storing the crystallization volume under conditions suitable for crystal formation.

TABLE 5

| Precipitant |
| --- |
| 0.1M to 6M of precipitant wherein the precipitant comprises one or more members of the group consisting of sodium chloride or other salt such as ammonium sulfate or sodium, potassium or ammonium phosphate. |
| pH |
| pH 4-10. Buffers that may be used include, but are not limited to tris, bicine, phosphate, cacodylate, acetate, citrate, HEPES, PIPES, MES and combinations thereof. |

TABLE 5-continued

Additives

Optionally 1 to 30% additives wherein the additives comprise a small organic molecule such as glycerol, ethylene glycol, PEG, PEG-MME, or monovalent and/or divalent salt (for example, sodium, lithium, magnesium, calcium, and the like)

Protein Concentration 1 mg/ml-50 mg/ml

Temperature

1° C.-25° C.

In yet another embodiment, a method for forming crystals comprising FLT3 is provided comprising forming a crystallization volume comprising FLT3; introducing crystals comprising FLT3 as nucleation sites; and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro, macro and/or streak seeding of crystals may also be performed to facilitate crystallization.

It should be understood that forming crystals comprising FLT3 and crystals comprising FLT3 according to the invention are not intended to be limited to the wild type, full length FLT3 shown in SEQ. ID No. 1 and fragments comprising residues 564-713 and 778-954 of SEQ. ID No. 1. Rather, it should be recognized that the invention may be extended to various other fragments and variants of wild-type FLT3 as described above.

It should also be understood that forming crystals comprising FLT3 and crystals comprising FLT3 according to the invention may be such that FLT3 is optionally complexed with one or more ligands and one or more copies of the same ligand. The ligand used to form the complex may be any ligand capable of binding to FLT3. In one variation, the ligand is a natural substrate. In another variation, the ligand is an inhibitor.

In one particular embodiment, FLT3 crystals have a crystal lattice in the $P4_22_12$ space group. FLT3 crystals may also optionally have unit cell dimensions, +/−5%, of a=146.278 Å, b=146.278 Å, c=100.946 Å, $\alpha=\beta=\gamma=90°$. FLT3 crystals also preferably are capable of diffracting X-rays for determination of atomic coordinates to a resolution of 4 Å, 3.5 Å, 3.0 Å or better.

Crystals comprising FLT3 may be formed by a variety of different methods known in the art. For example, crystallizations may be performed by batch, dialysis, and vapor diffusion (sitting drop and hanging drop) methods. A detailed description of basic protein crystallization setups may be found in McRee, D., *Practical Protein Crystallography*, $2^{nd}$ Ed. (1999), Academic Press Inc. Further descriptions regarding performing crystallization experiments are provided in Stevens et al. (2000) *Curr. Opin. Struct. Biol.*: 10(5):558-63, and U.S. Pat. Nos. 6,296,673; 5,419,278; and 5,096,676.

In one variation, crystals comprising FLT3 are formed by mixing substantially pure FLT3 with an aqueous buffer containing a precipitant at a concentration just below a concentration necessary to precipitate the protein. One suitable precipitant for crystallizing FLT3 is polyethylene glycol (PEG), which combines some of the characteristics of the salts and other organic precipitants (see, for example, Ward et al., J. Mol. Biol. 98:161, 1975, and McPherson, J. Biol. Chem. 251:6300, 1976).

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of a FLT3 complex were obtained. In order to accomplish this, systematic broad screen crystallization trials were performed on an FLT3 complex using the sitting drop technique. In each experiment, a 100 nL mixture of FLT3 complex and precipitant was placed on a platform positioned over a well containing 100 μL of the precipitating solution. Precipitate and crystal formation was detected in the sitting drops. Fine screening was then carried out for those crystallization conditions that appeared to produce precipitate and/or crystal in the drops.

Based on the crystallization experiments that were performed, a thorough understanding of how different crystallization conditions affect FLT3 crystallization was obtained. Based on this understanding, a series of crystallization conditions were identified that may be used to form crystals comprising FLT3. These conditions are summarized in Table 5. A particular example of crystallization conditions that may be used to form diffraction quality crystals of the FLT3 complex is detailed in Example 2. FIG. 2 illustrates crystals of the FLT3 complex formed using the crystallization conditions provided in Table 5.

One skilled in the art will recognize that the crystallization conditions provided in Table 5 and Example 2 can be varied and still yield protein crystals comprising FLT3. For example, it is noted that variations on the crystallization conditions described herein can be readily determined by taking the conditions provided in Table 5 and performing fine screens around those conditions by varying the type and concentration of the components in order to determine additional suitable conditions for crystallizing FLT3, variants of FLT3, and ligand complexes thereof.

Crystals comprising FLT3 have a wide range of uses. For example, now that crystals comprising FLT3 have been produced, it is noted that crystallizations may be performed using such crystals as a nucleation site within a concentrated protein solution. According to this variation, a concentrated protein solution is prepared and crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising FLT3 according to the present invention, the crystals so formed can be used by this crystallization technique to initiate crystal growth of other FLT3 comprising crystals, including FLT3 complexed to other ligands.

As will be described herein in greater detail, crystals may also be used to perform X-ray or neutron diffraction analysis in order to determine the three-dimensional structure of FLT3 and, in particular, to assist in the identification of its active site. Knowledge of the binding site region allows rational design and construction of ligands including inhibitors. Crystallization and structural determination of FLT3 mutants having altered bioactivity allows the evaluation of whether such changes are caused by general structure deformation or by side chain alterations at the substitution site.

4. X-Ray Data Collection and Structure Determination

Crystals comprising FLT3 may be obtained as described above in Section 3. As described herein, these crystals may then be used to perform X-ray data collection and for structure determination.

In one embodiment, described in Example 2, crystals of FLT3 were obtained where FLT3 has the sequence of residues shown in SEQ. ID No. 3. These particular crystals were used to determine the three dimensional structure of FLT3. However, it is noted that other crystals comprising FLT3 including different FLT3 variants, fragments, and complexes thereof may also be used.

Diffraction data were collected from cryocooled crystals (100 K) of FLT3 at the Advanced Light Source (ALS) beam line 5.0.3 using an ADSC Quantum CCD detector. The diffraction pattern of the FLT3 crystals displayed symmetry consistent with space group $P4_22_12$ with unit cell dimensions a=146.278 Å, b=146.278 Å, c=100.946 Å, $\alpha=\beta=\gamma=90°$ (+/−5%). Data were collected and integrated to 2.45 Å with the HKL2000 program package (Otwinowski, Z. and Minor, W., *Meth. Enzymol.* 276:307 (1997)).

The structure solution for FLT3 in the space group $P4_22_12$ with unit cell dimensions a=146.278 Å, b=146.278 Å, c=100.946 Å, $\alpha=\beta=\gamma=90°$ (+/−5%) was obtained by the molecular replacement method using the program AMoRE (Navaza, J. *Acta Crystallogr. A*50: 157 (1994)), with the coordinates for autoinhibited cKit receptor kinase (Mol, C. D., et al., *J. Biol. Chem.* 279:31655 (2004); PDB code 1T45) used as a search model. Using data in the resolution range 15.0 to 3.6 Å, the correct solutions were obtained yielding a correlation coefficient of 0.368 and an R-value of 0.468. All subsequent crystallographic calculations were performed using the CCP4 program package (Collaborative Computational Project, N. The CCP4 Suite: Programs for Protein Crystallography. *Acta Crystallogr. D*50, 760-763 (1994)). The molecular replacement solutions were subjected to rigid body refinement followed by restrained least-squares refinement using the maximum likelihood method as implemented in REFMAC (Murshudov, G. N., Vagin, A. A. and Dodson E. J. *Acta Crystallogr D*53:240 (1997)). The initial refinement resulted in an R-value of 0.300 and an $R_{free}$ value of 0.363 from which differences between the FLT3 structure and the molecular replacement model could be discerned. Multiple rounds of manual fitting of the FLT3 sequence and ordered regions not present in the initial model were performed with Xfit (McRee, D. E., *J. Struct. Biol.* 125:156 (1999)). Manual fitting was interspersed with restrained least-squares refinement in REFMAC against data from 30.0 to 2.45 Å, and which employed non-crystallographic symmetry restraints between the two molecules in the earlier stages. All stages of refinement were carried out with bulk solvent corrections and anisotropic scaling, and excluded 5% of $R_{free}$ reflections for cross-validation. The data collection and data refinement statistics are given in Table 6.

TABLE 6

| Crystal data | |
|---|---|
| Space group | $P4_22_12$ |
| Unit cell dimensions | a = 146.278Å |
| | b = 146.278Å |
| | c = 100.946Å |
| | $\alpha = \beta = \gamma = 90°$ |
| Data collection | |
| X-ray source | ALS BL 5.0.3 |
| Wavelength [Å] | 1.00 |
| Resolution [Å] | 2.45 |
| Observations (unique) | 40491 |
| Redundancy | 3.95 |
| Completeness overall (outer shell) | 98.8 (98.0)% |
| I/σ(I) overall (outer shell) | 9.9 (3.2) |
| $R_{symm}^1$ overall (outer shell) | 0.074 (.456) |
| Refinement | |
| Reflections used | 38270 |
| R-factor | 18.94% |
| $R_{free}$ | 23.10% |
| r.m.s bonds | 0.009Å |
| r.m.s angles | 1.70° |

During structure determination, where the unit cell dimensions were a=146.278 Å, b=146.278 Å, c=100.946 Å, $\alpha=\beta=\gamma=90°$, it was realized that the asymmetric unit comprised two FLT3 molecules. Structure coordinates were determined for this complex and the resultant set of structural coordinates from the refinement are presented in FIG. 3.

It is noted that the sequence of the structure coordinates presented in FIG. 3 differ in some regards from the sequence shown in SEQ. ID No. 3. Structure coordinates are not reported for residues 564-598, 836-850, and 946-954 in molecule A and residues 564-595, 836-849, and 946-954 in molecule B because the electron density obtained was insufficient to identify their position.

Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of ligands that could associate with those pockets. The term "binding pocket" as used herein refers to a region of the protein that, as a result of its shape, favorably associates with a ligand.

These variations in coordinates may be generated because of mathematical manipulations of the FLT3 structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that binds to the active site binding pocket of FLT3 would also be expected to bind to another binding pocket whose structure coordinates defined a shape that fell within the acceptable error.

Various computational methods may be used to determine whether a particular protein or a portion thereof (referred to here as the "target protein"), typically the binding pocket, has a high degree of three-dimensional spatial similarity to another protein (referred to here as the "reference protein") against which the target protein is being compared.

The process of comparing a target protein structure to a reference protein structure may generally be divided into three steps: 1) defining the equivalent residues and/or atoms for the target and reference proteins, 2) performing a fitting operation between the proteins; and 3) analyzing the results. These steps are described in more detail below. All structure comparisons reported herein and the structure comparisons claimed are intended to be based on the particular comparison procedure described below.

Equivalent residues or atoms can be determined based upon an alignment of primary sequences of the proteins, an alignment of their structural domains or as a combination of both. Sequence alignments generally implement the dynamic programming algorithm of Needleman and Wunsch [*J. Mol. Biol.* 48: 442-453, 1970]. For the purpose of this invention the sequence alignment was performed using the publicly available software program MOE (Chemical Computing Group Inc.) package version 2002.3. When using the MOE program, alignment was performed in the sequence editor window using the ALIGN option utilizing the following program parameters: Initial pairwise Build-up: ON, Substitution Matrix: Blosum62, Round Robin: ON, Gap Start: 7, Gap Extend: 1, Iterative Refinement: ON, Build-up: TREE-BASED, Secondary Structure: NONE, Structural Alignment: ENABLED, Gap Start: 1, Gap Extend: 0.1

Once aligned, a rigid body fitting operation is performed where the structure for the target protein is translated and rotated to obtain an optimum fit relative to the structure of the reference protein. The fitting operation uses an algorithm that computes the optimum translation and rotation to be applied to the moving structure, such that the root mean square deviation of the fit over the specified pairs of equivalent atoms is an absolute minimum. For the purpose of fitting operations made herein, the publicly available software program MOE (Chemical Computing Group Inc.) v. 2002.3 was used.

The results from this process are typically reported as an RMSD value between two sets of atoms. The term "root mean square deviation" means the square root of the arithmetic mean of the squares of deviations. It is a way to express the deviation or variation from a trend or object. As used herein, an RMSD value refers to a calculated value based on variations in the atomic coordinates of a target protein from the atomic coordinates of a reference protein or portions of thereof. The structure coordinates for FLT3, provided in FIG. 3, are used as the reference protein in these calculations.

The same set of atoms was used for initial fitting of the structures and for computing root mean square deviation values. For example, if a root mean square deviation (RMSD) between Cα atoms of two proteins is needed, the proteins in question should be superposed only on the Cα atoms and not on any other set of atoms. Similarly, if an RMSD calculation for all atoms is required, the superposition of two structures should be performed on all atoms.

Based on a review of protein structures deposited in the Protein Databank (PDB), 1RJB was identified as having the smallest RMSD values relative to the structure coordinates provided herein. Table 7 below provides a series of RMSD values that were calculated by the above described process using the structure coordinates in FIG. 3 as the reference protein and the structure coordinates from PDB code: 1RJB (Human Flt3 autoinhibited catalytic domain) as the target protein.

TABLE 7

| AA RESIDUES USED TO PERFORM RMSD COMPARISON WITH PDB:1VR2 | PORTION OF EACH AA RESIDUE USED TO PERFORM RMSD COMPARISON WITH PDB:1RJB | RMSD [Å] |
|---|---|---|
| Table 2 (4 Angstrom set) | alpha-carbon atoms[1] | 2.85 |
| | main-chain atoms[1] | 3.10 |
| | all non-hydrogen[2] | 4.05 |
| Table 3 (7 Angstrom set) | alpha-carbon atoms[1] | 2.22 |
| | main-chain atoms[1] | 2.42 |
| | all non-hydrogen[2] | 4.05 |
| Table 4 (10 Angstrom set) | alpha-carbon atoms[1] | 1.88 |
| | main-chain atoms[1] | 2.06 |
| | all non-hydrogen[2] | 2.50 |
| 564-713 and 778-954 of SEQ. ID No. 1 | alpha-carbon atoms[1] | 2.33 |
| | main-chain atoms[1] | 2.43 |
| | all non-hydrogen[2] | 2.73 |

[1]the RMSD computed between the atoms of all amino acids that are common to both the target and the reference in the aligned and superposed structure. The amino acids need not be identical.
[2]the RMSD computed only between identical amino acids, which are common to both the target and the reference in the aligned and superposed structure.

It is noted that mutants and variants of FLT3, as well as other RPTKs, are likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3 or structure coordinates having a root mean square deviation (RMSD) equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

As noted, there are many different ways to express the surface contours of the FLT3 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

5. FLT3 Structure

The present invention is also directed to a three-dimensional crystal structure of FLT3. This crystal structure may be used to identify binding sites, to provide mutants having desirable binding properties, and ultimately, to design, characterize, or identify ligands that interact with FLT3 as well as other structurally similar proteins.

The three-dimensional crystal structure of FLT3 may be generated, as is known in the art, from the structure coordinates shown in FIG. 3 and similar such coordinates.

During the course of structure solution it became evident that the crystals of FLT3 of the present invention contained two FLT3 molecules in the asymmetric unit. The final refined coordinates include amino acid residues 599-713, 776-835, and 851-945 in molecule A, and residues 596-713, 776-835, 850-945 in molecule B (FIG. 3). Structure coordinates are not reported for residues 564-598, 836-850, 946-954 in molecule A and residues 564-595, 836-849, 946-954 in molecule B because the electron density obtained was insufficient to identify their position. The final coordinate set additionally includes 384 solvent molecules modeled as water, and two molecules of the inhibitor staurosporine.

Figure 4:
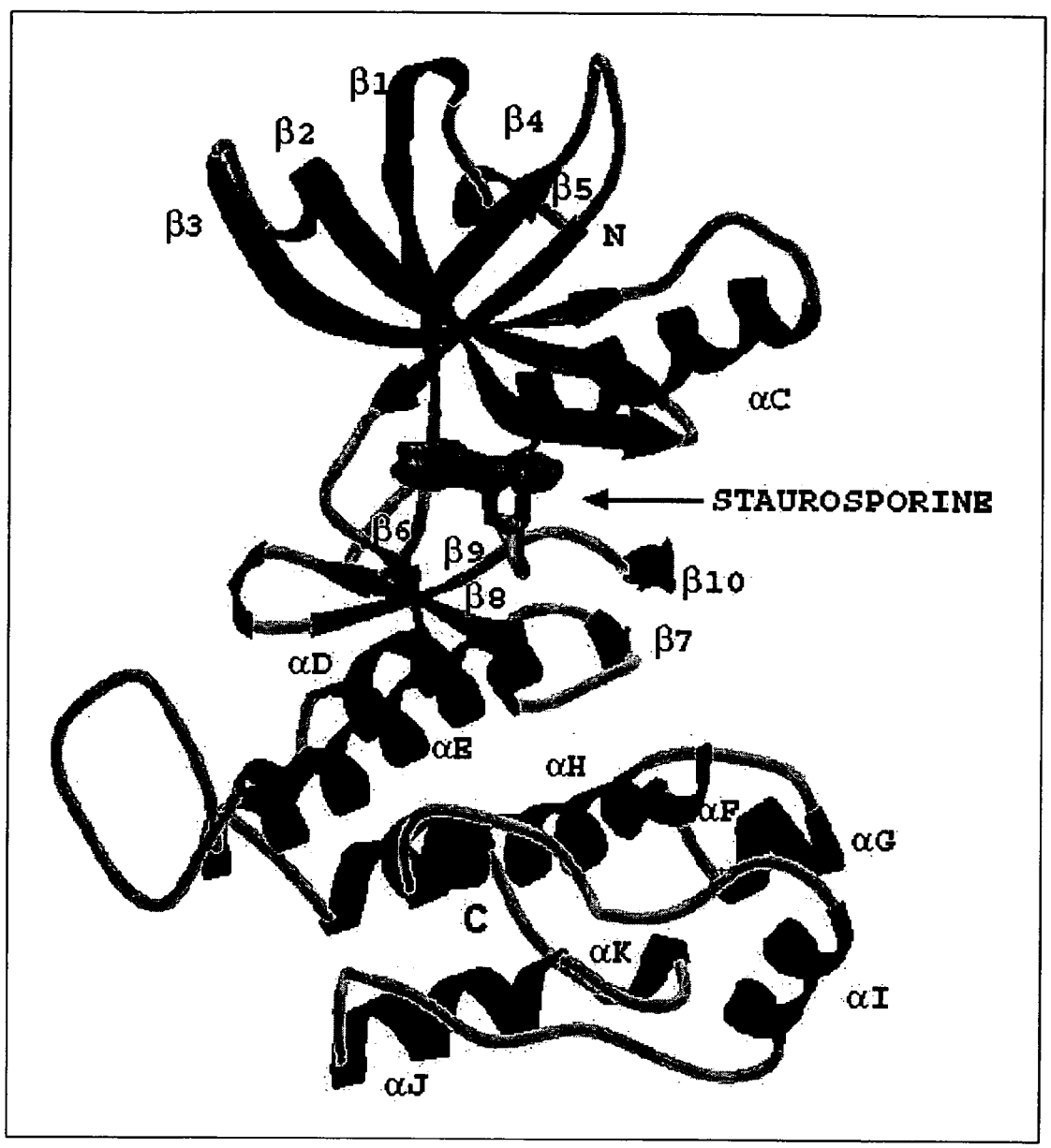
FIG. 4 illustrates a ribbon diagram overview of the structure of FLT3, highlighting secondary structural elements of the protein.

FIG. 4 illustrates a ribbon diagram overview of the structure of FLT3, highlighting the secondary structural elements of the protein. As can be seen, the structure exhibits bilobal architecture typical of protein kinase catalytic domains. The smaller N-terminal lobe (residues 596-673) contains a five-stranded anti-parallel β-sheet (β1-β5) and one α-helix (αC). The C-terminal lobe (residues 674-945) contains five short β-strands (β6 and β10) and eight α-helices (αD-αK).

Kinases show considerable variability in the relative orientation of the N and C lobes, in the position and orientation of the αC, and in the conformation of the activation loop. This relative orientation of the N- and C-terminal lobes is important in kinase function. A catalytically active conformation is generally a closed structure in which the two lobes clamp together bringing conserved residues into catalytically optimal positions. In particular, in the active conformation, the αC helix becomes parallel with the cleft between the lobes and makes tertiary contacts with the C-lobe. In the inactive conformation observed in several unphosphorylated kinase structures the two lobes are spaced apart at a much higher angle and the αC helix is rotated away from the C-lobe.

For FLT3, the activation segment (also known as the activation loop) comprising residues 829-855 is partially disordered in molecule A and B. Residues 836-850 in molecule A and residues 836-849 of molecule B were not included in the coordinates of FIG. 3.

Figure 5:
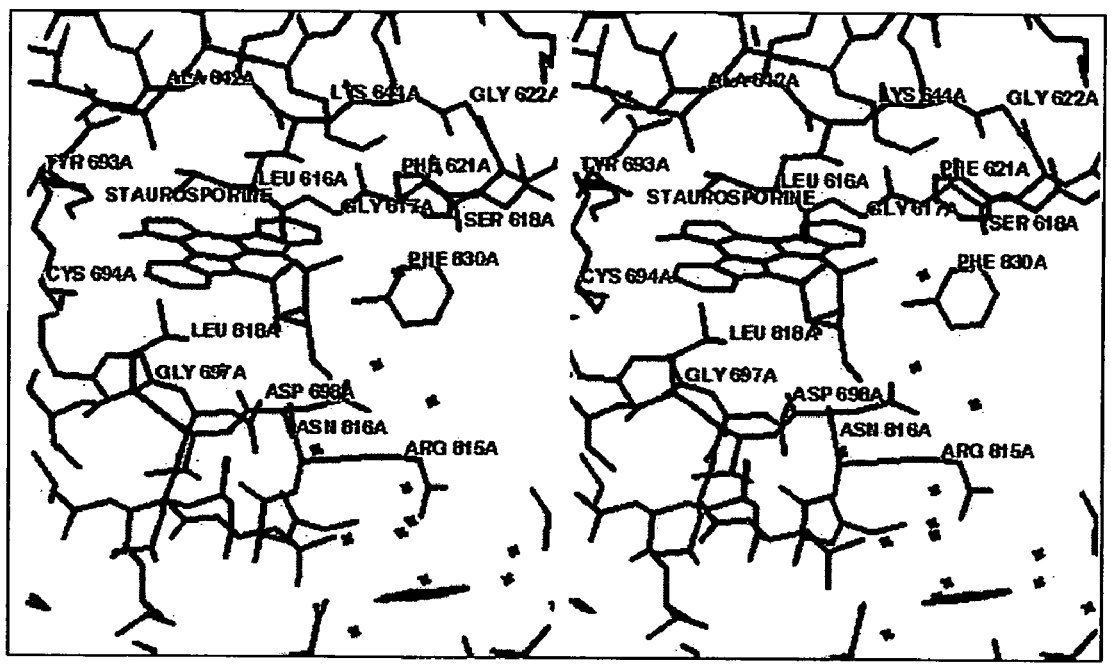
FIG. 5 illustrates the FLT3 binding site of FLT3 based on the determined crystal structure for the molecule in the asymmetric unit corresponding to the coordinates shown in FIG. 3.

FIG. 5 illustrates the binding site of FLT3 based on the determined crystal structure corresponding to the coordinates shown in FIG. 3.

6. FLT3 Active Site and Ligand Interaction

The terms "binding site" or "binding pocket", as used herein, refer to a region of a protein that, as a result of its shape, favorably associates with a ligand or substrate. The term "FLT3-like binding pocket" refers to a portion of a molecule or molecular complex whose shape is sufficiently similar to the FLT3 binding pockets as to bind common ligands. This commonality of shape may be quantitatively defined based on a comparison to a reference point, that reference point being the structure coordinates provided herein. For example, the commonality of shape may be quantitatively defined based on a root mean square deviation (RMSD) from the structure coordinates of the backbone atoms of the amino acids that make up the binding pockets in FLT3 (as set forth in FIG. 3).

The "active site binding pockets" or "active site" of FLT3 refers to the area on the surface of FLT3 where the substrate binds.

FIG. 5 illustrates the staurosporine inhibitor binding site of FLT3 based on the determined crystal structure for the molecule in the asymmetric unit corresponding to the structure coordinates shown in FIG. 3. The inhibitor binding site for staurosporine is located at the interface of the two lobes (FIG. 5).

The ATP binding site of protein kinases is a primary target for the design of small molecule inhibitors. The ATP binding site appears well conserved among protein kinases and involves residues protruding from the β1-β2-β3 sheet, helix C, the loop region linking β5 and the C-lobe, and the catalytic loop. The structure of the ATP binding pocket in the FLT3 complex shows considerable sequence variability with other kinases, which is reflective of diversity among kinase sub-families. The ATP binding cleft shows subtle differences in ATP site architecture that may be explored to confer specificity of inhibition.

In resolving the crystal structure of FLT3, Applicants determined that FLT3 amino acids shown in Table 2 (above) are encompassed within a 4-Angstrom radius around the FLT3 active site and therefore are likely close enough to interact with an active site inhibitor of FLT3. Applicants have also determined that the amino acids shown in Table 3 (above) are encompassed within a 7-Angstrom radius around the FLT3 active site. Further, the amino acids shown in Table 4 (above) are encompassed within a 10-Angstrom radius around the FLT3 active site. Due to their proximity to the active site, the amino acids in the 4, 7, and/or 10 Angstrom sets are preferably conserved in variants of FLT3. While it is desirable to largely conserve these residues, it should be recognized however that variants may also involve varying 1, 2, 3, 4 or more of the residues set forth in Tables 2, 3 and 4 in order, for example, to evaluate the roles these amino acids play in the binding pocket.

With the knowledge of the FLT3 crystal structure provided herein, Applicants are able to know the contour of an FLT3 binding pocket based on the relative positioning of the 4, 7, and/or 10 Angstroms sets of amino acids. Again, it is noted that it may be desirable to form variants where 1, 2, 3, 4 or more of the residues set forth in Tables 2, 3 and 4 are varied in order to evaluate the roles these amino acids play in the binding pocket. Accordingly, any set of structure coordinates for a protein from any source shall be considered within the scope of the present invention if the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

Accordingly, in various embodiments, the invention relates to data, computer readable media comprising data, and uses of the data where the data comprises structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

As noted above, there are many different ways to express the surface contours of the FLT3 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

It will be readily apparent to those of skill in the art that the numbering of amino acids in other isoforms of FLT3 may be different than that set forth for FLT3. Corresponding amino acids in other isoforms of FLT3 are easily identified by visual inspection of the amino acid sequences or by using commercially available homology software programs, as further described below.

7. System Splaying the Three Dimensional Structure of FLT3

The present invention is also directed to machine-readable data storage media having data storage material encoded with machine-readable data that comprises structure coordinates for FLT3. The present invention is also directed to a machine readable data storage media having data storage material encoded with machine readable data, which, when read by an appropriate machine, can display a three dimensional representation of a structure of FLT3.

All or a portion of the FLT3 coordinate data shown in FIG. 3, when used in conjunction with a computer programmed with software to translate those coordinates into the three-dimensional structure of FLT3 may be used for a variety of purposes, especially for purposes relating to drug discovery. Software for generating three-dimensional graphical representations are known and commercially available. The ready use of the coordinate data requires that it be stored in a computer-readable format. Thus, in accordance with the present invention, data capable of being displayed as the three-dimensional structure of FLT3 and/or portions thereof and/or their structurally similar variants may be stored in a machine-readable storage medium, which is capable of displaying a graphical three-dimensional representation of the structure.

For example, in various embodiments, a computer is provided for producing a three-dimensional representation of at least an FLT3-like binding pocket, the computer comprising:

machine readable data storage medium comprising a data storage material encoded with machine-readable data, the machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1;

a working memory for storing instructions for processing the machine-readable data;

a central-processing unit coupled to the working memory and to the machine-readable data storage medium, for processing the machine-readable data into the three-dimensional representation; and an output hardware coupled to the central processing unit, for receiving the three dimensional representation.

Another embodiment of this invention provides a machine-readable data storage medium, comprising a data storage material encoded with machine readable data which, when used by a machine programmed with instructions for using said data, displays a graphical three-dimensional representation comprising FLT3 or a portion or variant thereof.

In various variations, the machine readable data comprises data for representing a protein based on structure coordinates where the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1.

According to another embodiment, the machine-readable data storage medium comprises a data storage material encoded with a first set of machine readable data which comprises the Fourier transform of structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other FLT3-like enzymes, and isoforms of FLT3.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

Figure 6:
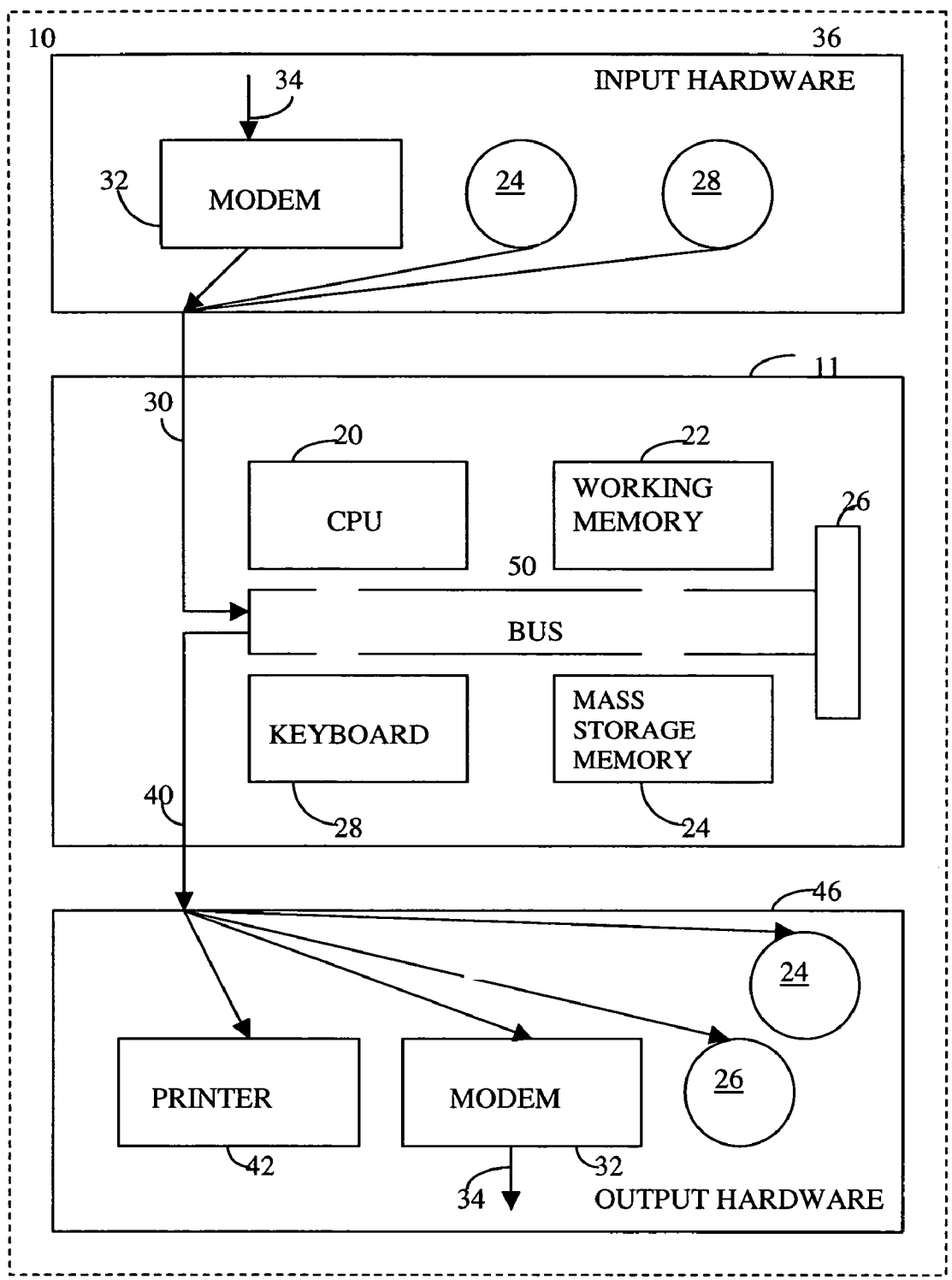
FIG. 6 illustrates a system that may be used to carry out instructions for displaying a crystal structure of FLT3 encoded on a storage medium.

FIG. 6 illustrates an example of a computer system that may be used in combination with storage media according to the present invention. As illustrated, the computer system 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices, coupled to computer 11 by output lines 40, may similarly implement output hardware 46. By way of example, output hardware 46 may include CRT display terminal 26 for displaying a graphical representation of a binding pocket of this invention using a program such as MOE as described herein. Output hardware might also include a printer 42, so that hard copy output may be produced, or a disk drive 24, to store system output for later use.

In operation, CPU 20 coordinates the use of the various input and output devices 36, 46; coordinates data accesses from mass storage 24 and accesses to and from working memory 22; and determines the sequence of data processing steps. A number of programs may be used to process the machine-readable data of this invention. Such programs are discussed in reference to using the three dimensional structure of FLT3 described herein.

The storage medium encoded with machine-readable data according to the present invention can be any conventional data storage device known in the art. For example, the storage medium can be a conventional floppy diskette or hard disk. The storage medium can also be an optically readable data storage medium, such as a CD-ROM or a DVD-ROM, or a rewritable medium such as a magneto-optical disk that is optically readable and magneto-optically writable.

8. Uses of the Three Dimensional Structure of FLT3

The three-dimensional crystal structure of the present invention may be used to identify FLT3 binding sites, be used as a molecular replacement model to solve the structure of unknown crystallized proteins, to design mutants having desirable binding properties, and ultimately, to design, characterize, and identify entities capable of interacting with FLT3 and other structurally similar proteins as well as other uses that would be recognized by one of ordinary skill in the art. Such entities may be chemical entities or proteins. The term "chemical entity," as used herein, refers to chemical compounds, complexes of at least two chemical compounds, and fragments of such compounds.

The FLT3 structure coordinates provided herein are useful for screening and identifying drugs that inhibit FLT3 and other structurally similar proteins. For example, the structure encoded by the data may be computationally evaluated for its ability to associate with putative substrates or ligands. Such compounds that associate with FLT3 may inhibit FLT3, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with FLT3 or a fragment or variant thereof by using all or a portion of the structure coordinates provided in FIG. 3 or functional equivalents thereof. A method is also provided for evaluating the potential of an entity to associate with FLT3 or a fragment or variant thereof by using structure coordinates similar to all or a portion of the structure coordinates provided in FIG. 3 or functional equivalents thereof.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 2, 3 and 4 that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising an FLT3-like binding pocket. One embodiment of the method comprises: using all or a portion of the structure coordinates provided herein to generate a three-dimensional structure of an FLT3-like binding pocket; employing the three-dimensional structure to design or select a potential ligand; synthesizing the potential ligand; and contacting the synthesized potential ligand with a protein comprising an FLT3-like binding pocket to determine the ability of the potential ligand to interact with the protein. According to this method, the structure coordinates used may have a root mean square deviation equal to or less than the RMSD values specified in Columns 3, 4 or 5 of Table 1 when compared to the structure coordinates of FIG. 3 according to the RMSD calculation method set forth herein, provided that the portion of amino acid residues specified in Column 2 of Table 1 of each set of structure coordinates are superimposed and the root mean square deviation is calculated based only on those amino acid residues in the structure coordinates that are also present in the portion of the protein specified in Column 1 of Table 1. The portion of the protein structure used optionally comprises all of the amino acids listed in Tables 2, 3, and/or 4 that are present.

As noted previously, the three-dimensional structure of an FLT3-like binding pocket need not be generated directly from structure coordinates. Rather, a computer model can be formed that defines a surface contour that is the same or similar to the surface contour defined by the structure coordinates.

A method is also provided for evaluating the ability of an entity, such as a compound or a protein to associate with an FLT3-like binding pocket, the method comprising: constructing a computer model of a binding pocket defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in Column 1 of Table 1; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for FLT3, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

The computer model of a binding pocket used in this embodiment need not be generated directly from structure coordinates. Rather, a computer model can be formed that defines a surface contour that is the same or similar to the surface contour defined by the structure coordinates.

Also according to the method, the method may further include synthesizing the entity and contacting a protein having an FLT3-like binding pocket with the synthesized entity.

With the structure provided herein, the present invention for the first time permits the use of molecular design techniques to identify, select or design potential inhibitors of FLT3, based on the structure of an FLT3-like binding pocket. Such a predictive model is valuable in light of the high costs associated with the preparation and testing of the many diverse compounds that may possibly bind to the FLT3 protein.

According to this invention, a potential FLT3 inhibitor may now be evaluated for its ability to bind an FLT3-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of an FLT3-like binding pocket may be computationally evaluated using a series of steps in which chemical entities or fragments are screened and selected for their ability to associate with the FLT3-like binding pockets.

One skilled in the art may use one of several methods to screen entities (whether chemical or protein) for their ability to associate with an FLT3-like binding pocket. This process may begin by visual inspection of, for example, an FLT3-like binding pocket on a computer screen based on the FLT3 structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849-857 (1985)) available from Oxford University, Oxford, UK; MCSS (A. Miranker et al., "Functionality Maps of Binding Sites: A Multiple Copy Simultaneous Search Method." Proteins: Structure, Function and Genetics, 11, pp. 29-34 (1991)) available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195-202 (1990)) available from Scripps Research Institute, La Jolla, Calif.; and DOCK (I. D. Kuntz et al., "A Geometric Approach to Macromolecule-Ligand Interactions", J. Mol. Biol., 161, pp. 269-288 (1982)) available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of FLT3. This may then be followed by manual model building using software such as MOE, QUANTA or Sybyl [Tripos Associates, St. Louis, Mo].

Useful programs to aid one of skill in the art in connecting the individual chemical entities or fragments include: CAVEAT (P. A. Bartlett et al., "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); G. Lauri and P. A. Bartlett, "CAVEAT: a Program to Facilitate the Design of Organic Molecules", J. Comput. Aided Mol. Des., 8, pp. 51-66 (1994)) available from the University of California, Berkeley, Calif.; 3D Database systems such as ISIS (MDL Information Systems, San Leandro, Calif.) reviewed in Y. C. Martin, "3D Database Searching in Drug Design", J. Med. Chem., 35, pp. 2145-2154 (1992); and HOOK (M. B. Eisen et al., "HOOK: A Program for Finding Novel Molecular Architectures that Satisfy the Chemical and Steric Requirements of a Macromolecule Binding Site", Proteins: Struct., Funct., Genet., 19, pp. 199-221 (1994)) available from Molecular Simulations, San Diego, Calif.

Instead of proceeding to build an inhibitor of an FLT3-like binding pocket in a step-wise fashion one fragment or entity at a time as described above, inhibitory or other FLT3 binding compounds may be designed as a whole or "de novo" using either an empty binding site or optionally including some portion(s) of a known inhibitor(s). There are many de novo ligand design methods including: LUDI (H.-J. Bohm, "The Computer Program LUDI: A New Method for the De Novo Design of Enzyme Inhibitors", J. Comp. Aid. Molec. Design, 6, pp. 61-78 (1992)) available from Molecular Simulations Incorporated, San Diego, Calif.; LEGEND (Y. Nishibata et al., Tetrahedron, 47, p. 8985 (1991)) available from Molecular Simulations Incorporated, San Diego, Calif.; LEAPFROG available from Tripos Associates, St. Louis, Mo.; and SPROUT (V. Gillet et al., "SPROUT: A Program for Structure Generation)", J. Comput. Aided Mol. Design, 7, pp. 127-153 (1993)) available from the University of Leeds, UK.

Other molecular modeling techniques may also be employed in accordance with this invention (see, e.g., Cohen et al., "Molecular Modeling Software and Methods for Medicinal Chemistry", J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modem Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once an entity has been designed or selected, for example, by the above methods, the efficiency with which that entity may bind to an FLT3 binding pocket may be tested and optimized by computational evaluation. For example, an effective FLT3 binding pocket inhibitor preferably demonstrates a relatively small difference in energy between its bound and free states (i.e., a small deformation energy of binding). Thus, the most efficient FLT3 binding pocket inhibitors should preferably be designed with deformation energy of binding of not greater than about 10 kcal/mole, and more preferably, not greater than 7 kcal/mole. FLT3 binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to an FLT3 binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. COPYRGT. 1995); AMBER, version 4.1 (P. A. Kollman, University of California at San Francisco, COPYRGT 1995); QUANTA/CHARMM (Molecular Simulations, Inc., San Diego, Calif. COPYRGT.1995); Insight II/Discover (Molecular Simulations, Inc., San Diego, Calif. COPYRGT.1995); DelPhi (Molecular Simulations, Inc., San Diego, Calif. COPYRGT.1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by this invention, is the computational screening of small molecule databases for chemical entities or compounds that can bind in whole, or in part, to an FLT3 binding pocket. In this screening, the quality of fit of such entities to the binding site may be judged either by shape complementarities or by estimated interaction energy [E. C. Meng et al., J. Comp. Chem., 13, 505-524 (1992)].

According to another embodiment, the invention provides compounds that associate with an FLT3-like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 3 as a molecular replacement model.

By using molecular replacement, all or part of the structure coordinates of the FLT3 provided by this invention (and set forth in FIG. 3) can be used to determine the structure of another crystallized molecule or molecular complex more quickly and efficiently than attempting an ab initio structure determination. One particular use includes use with other structurally similar proteins. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of FLT3 according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55-77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of FLT3 can be resolved by this method.

In one embodiment, the method of molecular replacement is utilized to obtain structural information about the present invention and any other FLT3-like molecule. The structure coordinates of FLT3, as provided by this invention, are particularly useful in solving the structure of other isoforms of FLT3 or FLT3 complexes.

The structure coordinates of FLT3 as provided by this invention are useful in solving the structure of FLT3 variants that have amino acid substitutions, additions and/or deletions (referred to collectively as "FLT3 mutants", as compared to naturally occurring FLT3). These FLT3 mutants may optionally be crystallized in co-complex with a ligand, such as an inhibitor, substrate analogue or a suicide substrate. The crystal structures of a series of such complexes may then be solved by molecular replacement and compared with that of FLT3. Potential sites for modification within the various binding sites of the enzyme may thus be identified. This information provides an additional tool for determining the most efficient binding interactions such as, for example, increased hydrophobic interactions, between FLT3 and a ligand. It is noted that the ligand may be the protein's natural ligand or may be a potential agonist or antagonist of a protein.

All of the complexes referred to above may be studied using well-known X-ray diffraction techniques and may be refined versus 1.5-3 Å resolution X-ray data to an R value of about 0.22 or less using computer software, such as X-PLOR [Yale University, COPYRIGHT. 1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known FLT3 inhibitors, and more importantly, to design new FLT3 inhibitors.

The structure coordinates described above may also be used to derive the dihedral angles, phi and psi, that define the conformation of the amino acids in the protein backbone. As will be understood by those skilled in the art, the phin angle refers to the rotation around the bond between the alpha-carbon and the nitrogen, and the PSin angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of FLT3

Crystals, crystallization conditions and the diffraction pattern of FLT3 that can be generated from the crystals also have a range of uses. One particular use relates to screening entities that are not known ligands of FLT3 for their ability to bind to FLT3. For example, with the availability of crystallization conditions, crystals and diffraction patterns of FLT3 provided according to the present invention, it is possible to take a crystal of FLT3; expose the crystal to one or more entities that may be a ligand of FLT3; and determine whether a ligand/FLT3 complex is formed. The crystals of FLT3 may be exposed to potential ligands by various methods, including but not limited to, soaking a crystal in a solution of one or more potential ligands or co-crystallizing FLT3 in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligand/FLT3 complex(es) may be used to design new ligands that bind tighter, bind more specifically, have better biological activity or have better safety profiles than known ligands.

In one embodiment, a method is provided for identifying a ligand that binds to FLT3 comprising: (a) attempting to crystallize a protein that comprises a sequence wherein at least a portion of the sequence has 55%, 65%, 75%, 85%, 90%, 95%, 97%, 99% or greater identity with SEQ. ID No. 3 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to FLT3 comprising: soaking a crystal of a protein wherein at least a portion of the protein has 55%, 65%, 75%, 85%, 90%, 95%, 97%, 99% or greater identity with SEQ. ID No. 3 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-FLT3 complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression and Purification of FLT3

This example describes cloning, expression and purification of FLT3. It should be noted that a variety of other expression systems and hosts are also suitable for the expression of FLT3, as would be readily appreciated by one of skill in the art.

The portion of the gene encoding residues 564-954 (from SEQ. ID No. 1), which corresponds to the catalytic domain of human FLT3, was cloned into a modified pFastBacHTc vector (also known as pSXB1) at the BamHI and XbaI sites. The region corresponding to amino acid residues 714-777 (SEQ. ID No. 1) was deleted by using inverse PCR, which generated additional Ala and Ser residues at positions 175-176, respectively (SEQ. ID No. 3). The two tyrosine residues at positions 589 and 591 were additionally mutated to phenylalanine residues. Expression from this vector produced the recombinant FLT3 catalytic domain with a 6×-histidine tag at the N-terminus followed by a rTEV protease cleavage sequence to facilitate tag removal (the excised 6×-Histidine tag and rTev cleavage site sequences are underlined in SEQ. ID No. 3). Recombinant baculovirus genomic DNAs incorporating the FLT3 catalytic domain cDNA sequences were generated by transposition using the Bac-to-Bac system (Invitrogen). Infectious viral particles were obtained by transfection of a 2 ml adherent culture of Spodoptera frugiperda Sf21 insect cells with the recombinant viral genomic DNA. Growth in ESF 921 protein free medium (Expression Systems) was for 3 days at 27° C. The resulting Passage 0 viral supernatant was used to obtain Passage 1 high titer viral stock (HTS) by infection of a 30 ml adherent culture of Spodoptera frugiperda Sf21 insect cells grown under similar conditions. Passage 1 HTS was used in turn to infect a 100 ml suspension culture of Spodoptera frugiperda Sf21 insect cells in order to generate Passage 2 HTS.

Passage 2 HTS was used to infect a 5-liter culture of Spodoptera frugiperda Sf21 insect cells (at a density of approx. 3×10$^6$ cells/ml) in a 10 liter Wave BioReactor grown in ESF-921 serum-free medium at a multiplicity of infection (moi) of approximately 5 (empirical value based on usual HTS viral counts). Cell growth/infection proceeded for two days after which time the cells were pelleted by centrifugation and the cell pellet stored at −80 C until required. Frozen cell pellets from two such 5-liter cultures were removed from the −80 C freezer and each suspended in 150 ml of Lysis Buffer (50 mM Tris-HCl, pH 7.9, 200 mM NaCl, 0.25 mM TCEP, 1 mM PMSF and 2 'Complete-EDTA' Roche Protease Inhibitor tablets). The suspensions were stirred for 45 min at 4 C followed by centrifugation at 7,000 g for 1 h. To each supernatant were added 8 ml of a 50% slurry of ProBond (InVitrogen) resin that had been equilibrated in Lysis Buffer without protease inhibitors. The suspensions were mixed for 90 min followed by centrifugation at 640 g for 5 min. The supernatants were discarded and the resin pellets washed three times with 50 mM potassium phosphate, pH 7.9, 400 mM NaCl, 0.25 mM TCEP and 1 ug/mL leupeptin. Each resin sample was transferred to an OmniFit chromatography column (10 cm×1.5 cm diameter) at 4 C and washed with 50 column volumes of 50 mM potassium phosphate, pH 7.9, 400 mM NaCl, 20 mM imidazole-HCl, pH 7.9, 0.25 mM TCEP and 1 ug/mL leupeptin. The columns were subsequently washed with 5 column volumes of 50 mM Tris-HCl, pH 7.9, 400 mM NaCl, 0.25 mM TCEP and 1 ug/mL leupeptin. Target elution was effected by the addition of 50 mM Tris-HCl, pH 7.9, 400 mM NaCl, 200 mM imidazole-HCl, pH 7.9, 0.25 mM TCEP, 1 ug/mL leupeptin. The eluates were pooled and the polyhistidine purification tag removed by cleavage overnight with 100 u/ml TEV protease during dialysis against 50 mM Tris-HCl, pH 7.9, 400 mM NaCl, 20 mM imidazole-HCl, pH 7.9, 0.25 mM TCEP and 1 ug/mL leupeptin at 4 C. The TEV-treated sample was passed by gravity flow through an 8 ml bed volume of ProBond chelating resin charged with Ni that had been equilibrated in 50 mM Tris-HCl, pH 7.9, 400 mM NaCl, 20 mM imidazole-HCl, pH 7.9, 0.25 mM TCEP and 1 ug/mL leupeptin at 4 C. The unbound flow-through material was concentrated and buffer-exchanged into 25 mM Tris-HCl buffer, pH 7.6, 250 mM NaCl, 5 mM DTT and 1 mM EDTA-NaOH, pH 8.0, by using Millipore centrifugal concentrators. Following three five-fold dilution buffer-exchanges, the purified FLT3 was concentrated to 11.6 mg/ml with a total volume of 1.08 ml (12.5 mg purified FLT3). The purified protein had the correct molecular mass (38,439) as determined by Mass Spectrograph (MS) analysis, was monomeric by analytical size-exclusion chromatography (SEC) and exhibited a major band by both isoelectric focusing (IEF) and by sodium-dodecyl-sulfate polyacrylamide gel electrophoresis (SDS-PAGE) analyses.

Example 2

Crystallization of the FLT3:Staurosporine Complex

This example describes the crystallization of FLT3. It is noted that the precise crystallization conditions used may be further varied, for example by performing a fine screen based on these crystallization conditions.

FLT3 protein samples (corresponding to SEQ. ID No. 3) were incubated with 1 mM staurosporine before setting crystallization trials. Crystals were obtained after an extensive and broad screen of conditions, followed by optimization. Crystals were obtained after an extensive and broad screen of conditions, followed by optimization. Diffraction quality crystals were grown in 100 nl sitting droplets using the vapor diffusion method. 50 nl comprising the FLT3-staurosporine complex (11 mg/ml) was mixed with 50 nL from a reservoir solution (100 µl) comprising: 2.9M NaCl; and 0.1M sodium citrate buffer pH=6.5. The resulting solution was incubated over a period of 10 days at 4° C. Crystals typically appeared after 3-5 days and grew to a maximum size within 7-10 days. Single crystals were transferred, briefly, into a cryoprotecting solution containing the reservoir solution supplemented with 25% v/v glycerol. Crystals were then flash frozen by direct immersion in liquid nitrogen and then stored under liquid nitrogen. Crystals of the FLT3-staurosporine complex produced as described is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, patent applications, papers, and books cited in this application are incorporated herein in their entirety.

What is claimed is:

1. A composition comprising a protein in crystalline form wherein the protein consists of SEQ ID NO:3, wherein said protein is in complex with a kinase inhibitor ligand, and wherein the protein crystal has a crystal lattice in a $P4_22_12$ space group and unit cell dimensions, +/−5%, of a=146.278 Å, b=146.278 Å, c=100.946 Å, $\alpha=\beta=\gamma=90°$.

2. A composition according to claim 1 wherein the crystal diffracts X-rays for a determination of structure coordinates to a resolution greater than 3.0 Angstroms.

3. A method for forming a crystal of a protein comprising:
   forming a crystallization volume comprising: a precipitant solution and a protein wherein the protein consists of SEQ ID NO:3, wherein said protein is in complex with a kinase inhibitor ligand, and wherein the protein crystal has a crystal lattice in a $P4_22_12$ space group and unit cell dimensions, +/−5%, of a=146.278 Å, b=146.278 Å, c=100.946 Å, $\alpha=\beta=\gamma=90°$; and
   storing the crystallization volume under conditions suitable for crystal formation of the protein.

4. A method according to claim 3 wherein the crystal diffracts X-rays for a determination of structure coordinates to a resolution greater than 3.0 Angstroms.

5. A method according to claim 3, the method further comprising diffracting the protein crystal to produce a diffraction protein and solving the structure of the protein from the diffraction pattern.

6. An isolated soluble protein consisting of residues 564-713 and 778-954 of SEQ ID NO:1.

7. The protein according to claim 6 where the protein is expressed from a nucleic acid molecule that consists of SEQ ID NO:2.

8. A soluble protein consisting of SEQ ID NO:3.

9. An isolated non-crystalline protein consisting of amino acids 564-713 and 778-954 of SEQ ID NO:1.

10. A non-crystalline protein consisting of SEQ ID NO:3.

* * * * *